United States Patent
Verhoeven et al.

(10) Patent No.: US 11,059,850 B2
(45) Date of Patent: Jul. 13, 2021

(54) SPIROBICYCLIC ANALOGUES

(71) Applicant: Janssen Pharmaceutica NV, Beerse (BE)

(72) Inventors: Jonas Verhoeven, Brussels (BE); Guido Alfons F. Verniest, Beerse (BE); Johannes Wilhelmus John F. Thuring, Beerse (BE); Tongfei Wu, Hever (BE); Vineet Pande, Beerse (BE); Lieven Meerpoel, Beerse (BE); Dirk Brehmer, Beerse (BE); Weimei Sun, Raritan, NJ (US); Scott E. Denmark, Champaign, IL (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 16/769,793

(22) PCT Filed: Dec. 6, 2018

(86) PCT No.: PCT/EP2018/083808
§ 371 (c)(1),
(2) Date: Jun. 4, 2020

(87) PCT Pub. No.: WO2019/110734
PCT Pub. Date: Jun. 13, 2019

(65) Prior Publication Data
US 2020/0369707 A1    Nov. 26, 2020

Related U.S. Application Data

(60) Provisional application No. 62/596,441, filed on Dec. 8, 2017.

(30) Foreign Application Priority Data

Mar. 26, 2018    (EP) .................................... 18163867

(51) Int. Cl.
C07H 19/167        (2006.01)
(52) U.S. Cl.
CPC .................................. *C07H 19/167* (2013.01)
(58) Field of Classification Search
None
See application file for complete search history.

(56) References Cited

U.S. PATENT DOCUMENTS

| 4,224,438 | A | | 9/1980 | Fauland et al. |
|---|---|---|---|---|
| 6,143,749 | A | * | 11/2000 | Bhagwat ............... A61P 9/00 514/262.1 |
| 2003/0225205 | A1 | | 12/2003 | Epple et al. |
| 2004/0043959 | A1 | | 3/2004 | Bloom et al. |
| 2006/0167241 | A1 | | 7/2006 | Hayakawa |
| 2008/0132525 | A1 | | 6/2008 | Wahhab et al. |
| 2011/0159111 | A1 | | 6/2011 | Curry et al. |
| 2012/0035115 | A1 | | 2/2012 | Manoharan et al. |
| 2013/0023491 | A1 | | 1/2013 | Annes et al. |
| 2013/0310333 | A1 | | 11/2013 | Chesworth et al. |
| 2013/0310334 | A1 | | 11/2013 | Chesworth et al. |
| 2014/0100184 | A1 | | 4/2014 | Song et al. |
| 2014/0221345 | A1 | | 8/2014 | Duncan et al. |
| 2014/0228343 | A1 | | 8/2014 | Duncan et al. |
| 2014/0329794 | A1 | | 11/2014 | Duncan et al. |
| 2016/0009744 | A1 | | 1/2016 | Duffey et al. |
| 2016/0244475 | A1 | | 8/2016 | Tatlock et al. |
| 2017/0198006 | A1 | | 7/2017 | Duncan et al. |
| 2018/0243328 | A1 | | 8/2018 | Wu et al. |

FOREIGN PATENT DOCUMENTS

| WO | 96/40686 | A1 | 12/1996 |
|---|---|---|---|
| WO | 03/39523 | A2 | 5/2003 |
| WO | 03/70739 | | 8/2003 |
| WO | 03/74083 | | 9/2003 |
| WO | 2004/022572 | A1 | 3/2004 |
| WO | 2005/065150 | A2 | 7/2005 |

(Continued)

OTHER PUBLICATIONS

Alinari et al., "Selective inhibition of progen agrinine methyltransferase 5 blocks initiation and maintenance of B-cell transformation.", Blood, Apr. 16, 2015, pp. 2530-2543, vol. 125(16).

Andreu-Perez, P. et al., "Protein Arginine Methyltransferase 5 Regulates ERK 1/2 Signal Transduction Amplitude and Cell Fate Through CRAF", Sci. Signal, (2011), p. ra58, vol. 4, No. 190.

Antonysamy, S., et al., "Crystal structure of the human PRMT5:MEP50 complex", Proc. Natl Acad Sci, (2012), pp. 17960-17965, vol. 109, No. 44.

Barbash, O., et al., "Abstract LB-248: Protein arginine methyltransferase 5 (PRMT5) inhibition as a therapeutic strategy in B-cell lymphoma", Cancer Research, (2015), see Abstract.

Bezzi, M., et al., "Regulation of constitutive and alternative splicing by PRMT5 reveals a role for Mdm4 pre-mRNA in sensing defects in the spliceosomal machinery", Genes & Development, (2013), pp. 1903-1916, vol. 27, No. 17.

(Continued)

*Primary Examiner* — Traviss C McIntosh, III
(74) *Attorney, Agent, or Firm* — BakerHostetler

(57) ABSTRACT

The present invention relates to novel spirobicyclic analogues of Formula (I) wherein the variables have the meaning defined in the claims. The compounds according to the present invention are useful as PRMT5 inhibitors. The invention further relates to pharmaceutical compositions comprising said compounds as an active ingredient as well as the use of said compounds as a medicament.

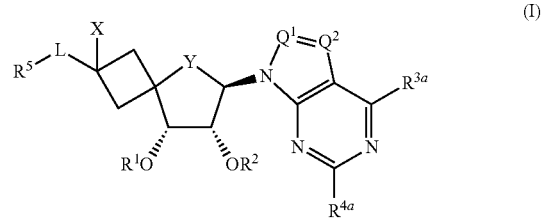

21 Claims, No Drawings

(56) References Cited

FOREIGN PATENT DOCUMENTS

| | | |
|---|---|---|
| WO | 2006/078752 A2 | 7/2006 |
| WO | 2010/039548 A2 | 4/2010 |
| WO | 2011/075665 A2 | 6/2011 |
| WO | 2012/075500 A2 | 6/2012 |
| WO | 2012/082436 A2 | 6/2012 |
| WO | 2012/083170 A1 | 6/2012 |
| WO | 2012/138530 A1 | 10/2012 |
| WO | 2013/151975 A1 | 10/2013 |
| WO | 2014/035140 A2 | 3/2014 |
| WO | 2014/100695 A1 | 6/2014 |
| WO | 2014/100719 A2 | 6/2014 |
| WO | 2014/100730 A1 | 6/2014 |
| WO | 2015/106025 A1 | 7/2015 |
| WO | 2015/200680 A2 | 12/2015 |
| WO | 2016/135582 A1 | 9/2016 |
| WO | 2017/032840 A1 | 3/2017 |
| WO | 2017/153186 A1 | 9/2017 |
| WO | 2018/065365 A1 | 4/2018 |
| WO | 2018/154104 A1 | 8/2018 |

OTHER PUBLICATIONS

Braun, C.J., et al., "Coordinated Splicing of Regulatory Detained Intrans within Oncogenic Transcripts Creates an Exploitable Vulnerability in Malignant Glioma", Cancer Cell, (2017), pp. 411-426, vol. 32, No. 4.

Bundegaard, H., "Design of Prodrugs", Elsevier, New York-Oxford, (1985), pp. 1-92.

Chan-Penebre, E., et al., "A selective inhibitor of PRMT5 with in vivo and in vitro potency in MCL models", Nature Chemical Biology, (2015), pp. 432-437, vol. 11, No. 6.

Crane et al., Journal of Organic Chemistry, 45(19), 1980, pp. 3827-3831.

Deady, L.W., "Ring Nitrogen Oxidation of Amino Substituted Nitrogen Heterocycles with m-Chloroperbenzoic Acid", Synthetic Communications, (1977), pp. 509-514, vol. 7, No. 8.

Devkota, K., et al., "Analogues of the Natural Product Sinefungin as Inhibitors of EHMT1 and EHMT2", ACS Med Chem Lett, (2014), pp. 293-297, vol. 5.

Di Lorenzo, A., et al., "Histone arginine methylation", FEBS Letters, (2011), pp. 2024-2031, vol. 585, No. 13.

European Search Report; EP Patent Application No. EP Patent Application No. 15184011.3; Issuance of Report dated Oct. 22, 2015.

Friesen, W.J., et al., "The Methylosome, a 20S Complex Containing JBP1 and pICln, Produces Dimethylarginine-Moditied Sm Proteins", Molecular and Cellular Biology, (2001), pp. 8289-8300, vol. 21, No. 24.

Geoghegan, V., et al., "Comprehensive identification of arginine methylation in primary T cells reveals regulatory roles in cell signaling", Nature Communications, (2015), p. 6758, vol. 6.

Gu, Z., et al., "Protein arginine methyltransferase 5 is essential for growth of lung cancer cells", Biochem J., (2012), pp. 235-241, vol. 446, No. 2.

Guo, Fang, Yanxinig Han, Xuesen Zhao, Jianghua Wang, Fei Liu, Chunxiao Xu, Lai Wei et al. "STING agonists induce an innate antiviral Immune response against hepatitis B virus." Antimicrobial agents and chemotherapy 59, No. 2 (2015): 1273-1281.

Hsu, J.M., et al., "Crosstalk between Arg 1175 methylation and Tyr 1173 phosphorylation negatively modulates EGFR-mediated ERK activation", Nature Cell Biology, (2011), pp. 174-181, vol. 13, No. 2.

Hu, H., et al., "Small Molecule Inhibitors of Protein Arginine Methyltransferase", Expert Opinion on Investigational Drugs, (2016), pp. 335-358, vol. 25, No. 3.

International Report on Patentability; International Patent Application No. PCT/EP2016/070097; Issuance of Report dated Feb. 27, 2018.

International Search Report relating to International Patent Application No. PCT/EP2016/070097, filed on Aug. 25, 2016. International Search Report dated Oct. 12, 2016.

International Search Report relating to International Patent Application No. PCT/EP2017/054324, filed on Feb. 24, 2017. International Search Report dated May 2, 2017.

International Search Report relating to International Patent Application No. PCT/EP2017/074983, filed on Oct. 2, 2017. International Search Report dated Nov. 16, 2017.

International Search Report relating to International Patent Application No. PCT/EP2018/054644, filed on Feb. 26, 2018. International Search Report dated May 3, 2018.

Jansson, M., et al., "Arginine methylation regulates the p53 response", Nature Cell Biology, (2008), pp. 1431-1439, vol. 10, No. 12.

Karkhanis, V., et al., "Versatility of PRMT5-induced methylation in growth control and development", Trends in Biochemical Sciences, (2011), pp. 633-641, vol. 36, No. 12.

Kung, P.P., et al., "Design, synthesis, and biological evaluation of novel human 5'-deoxy-5'-methylthioadenosine phosphorylase (MTAP) substrates", Bioorganic & Medicinal Chemistry Letters, (2005), pp. 2829-2833, vol. 15.

March, J., "Advanced Organic Chemistry—Reactions, Mechanisms, and Structure", John Wiley & Sons, Inc., (2002), 4th Edition, A Wiley-Interscience Publication, see Table of Contents.

Matsubara, S., et al., "[2+1] Cycloaddition reaction of bis(iodozincio)methane with 1,2-diketones: face-to-face complex of bis(iodozincio)methane and 1,2- diketones as a reaction intermediate", Tetrahedron, (2002), pp. 8255-8262, vol. 58.

Moukha-Chafiq, O., et al., "Synthesis and General Biological Activity of a Small Adenosine-5'-(Carboxamide and Sulfanilamide) Library", Nucleosides, Nucleotides and NucleicAcids, (2014), pp. 709-729, vol. 33, No. 11.

Pal, S., et al., "Low levels of miR-92b/96 induce PRMT5 translation and H3R3 methylation in mantle cell lymphoma", The EMBO Journal, (2007), pp. 3558-3569, vol. 26, No. 15.

Penebre, E., et al., "Identification of a First-in-Class PRMT5 Inhibitor with Potent in Vitro and in Vivo Activity in Preclinical Models of Mantle Cell Lymphoma", Blood, (2014), see Abstract.

Prasad, R.N., et al., "Modification of the 5' Position of Purine Nucleosides. 2. Synthesis and Some Cardiovascular Properties of Adenosine-5'-(N-substituted)carboxamides1,2", J. Med. Chem., (1980), pp. 313-319, vol. 23, No. 3.

Schmidt, R.R., et al., "Synthese 5'-modifizierter Adenosinderivate", Chemische Berichte, (1968), pp. 590-594, vol. 101, No. 2.

Shendure, J., et al., "Next-generation DNA sequencing", Nature Biotechnolgoy, (2008), pp. 1135-1145, vol. 26, No. 10.

Shilo, K., et al., "Cellular localization of protein arginine methyltransferase-5 correlates with grade of lung tumors", Diagnostic Pathology, (2013), pp. 1-9, vol. 8, No. 201.

Stahl, P.H., et al., "Handbook of Pharmaceutical Salts: Properties, Selection, and Use", Journal of Medicinal Chemistry, Book Reviews, (2003), pp. 1277-1278, vol. 46, No. 7.

Stopa, N., et al., "The PRMT5 arginine methyltransferase: many roles in development, cancer and beyond", Cell. Mol. Life Sci., (2015), pp. 2041-2059, vol. 72, No. 11.

Tiwari et al. Nucleosides, Nucleotides and Nucleic Acids (2009), vol. 28, Nos. 5-7, pp. 657-677.

Vuilhorgne, M., et al., "New Synthetic S-Adenosyl-Homocysteine Analogues with Oncostatic and Antiviral Activity", Heterocylces, 1978, pp. 495-520, vol. 11, XP009112700.

Wang, L., et al., "Protein Arginine Methyltransrerase 5 Suppresses the Transcription of the RB Family of Tumor Suppressors in Leukemia and Lymphoma Cells", Molecular and Cellular Biology, (2008), pp. 6262-6277, vol. 28, No. 20.

Wang, Q., et al., "Identification of a Novel Protein Arginine Methyltransferase 5 Inhibitor in Non-small Cell Lung Cancer by Structure-Based Virtual Screening", Frontiers in Pharmacology, (2018), pp. 1-10, vol. 9, article 173.

Wei, H., et al., "PRMT5 dimethylates R30 of the p65 subunit to activate NF-KB", Proc Natl Acad Sci USA, (2013), pp. 13516-13521, vol. 110, No. 33.

(56) References Cited

OTHER PUBLICATIONS

Wei, T.Y.W., et al., "Methylosome protein 50 promotes androgen- and estrogen-independent tumorigenesis", Cellular Signaling, (2014), pp. 2940-2950, vol. 26.
Written Opinion of the International Search Authority relating to International Patent Application No. PCT/EP2017/054324, filed on Feb. 24, 2017. Written Opinion dated May 2, 2017.
Written Opinion PCT/EP2017/074983, dated Nov. 16, 2017.
Zhao, Q., et al., "PRMT5-mediated methylation of histone H4R3 recruits DNMT3A, coupling histone and DNA methylation in gene silencing", Nat Struct Mol Biol, (2009), pp. 304-311, vol. 16, No. 3.
Dermer, "Another Anniversary for the War on Cancer", Biotechnology, 1994, vol. 12, p. 320.
Evans, et al., "Pharmacogenomics: Translating Functional Genomics into Rational Therapeutics", Science, 1999, vol. 286, pp. 487-491.
Graubert, et al., "Recurrent mutations in the U2AF 1 splicing factor in myelodysplastic syndromes", Nature Genetics, Jan. 1, 2012, vol. 44, pp. 53-59.
HUGO Gene Nomenclature Committee (HGNC) reports for the Major Spliceosome found online at https://www.genenames.org/data/genegroup/#!/group/1518 and accessed Apr. 20, 2021.
Li, et al., A patent review of arginine methyltransferase inhibitors, Expert Opinion on Therapeutic Patents, 2019, vol. 29, No. 2, pp. 97-114.
Xiong, et al., Driver Genes as Targets for Lung Cancer Prevention and Treatment Progress in Chemistry, Sep. 9, 2013, vol. 25, pp. 1517-1525.

\* cited by examiner

SPIROBICYCLIC ANALOGUES

CROSS-REFERENCE TO RELATED APPLICATIONS

This application is the National Stage of International Patent Application No. PCT/EP2018/083808, filed Dec. 6, 2018, which claims the benefit of U.S. Provisional Application No. 62/596,441, filed Dec. 8, 2017 and EP Application No. 18163867.7, filed Mar. 26, 2018, the contents of which are incorporated herein by reference.

FIELD OF THE INVENTION

The present invention relates to novel spirobicyclic analogues useful as PRMT5 inhibitors. The invention further relates to pharmaceutical compositions comprising said compounds as an active ingredient as well as the use of said compounds as a medicament.

BACKGROUND OF THE INVENTION

PRMT5, also described as Hsl7, Jbp1, Skb1, Capsuleen or Dart5, is one of the major methyltransferases responsible for mono- and symmetric dimethylation of arginines. Post-translational arginine methylation on histones and non-histone proteins seems to be crucial for a variety of biological processes, like genome organisation, transcription, differentiation, spliceosome function, signal transduction and regulation of cell-cycle progression, stem cells and T-cell fate[Stopa, N. et al., Cell Mol Life Sci, 2015. 72(11): p. 2041-59] [Geoghegan, V. et al., Nat Commun, 2015. 6: p. 6758]. Metazoan PRMT5 forms a functional complex with the methylosome protein 50 (MEP50) also named as Wdr77, androgen receptor coactivator p44 and Valois. Both, elevated PRMT5-MEP50 protein level and cytoplasmic accumulation are implicated in cancer tumorigenesis and have recently been correlated with poor clinical outcome [Shilo, K. et al., Diagn Pathol, 2013. 8: p. 201]. Cellular rescue experiments that addressed both the catalytic and scaffold function of the PRMT5-MEP50 complex, beside comprehensive enzymological studies have substantiate the oncogenic link between protein level, localisation and enzymatic function[Gu, Z. et al., Biochem J, 2012. 446(2): p. 235-41] [Di Lorenzo, A. et. al., FEBS Lett, 2011. 585(13): p. 2024-31] [Chan-Penebre, E. et al., Nat Chem Biol, 2015. 11(6): p. 432-7]. This correlation turns PRMT5 into an essential small molecule drug target against cancer and other diseases[Stopa, N. et al., Cell Mol Life Sci, 2015. 72(11): p. 2041-59].

PRMT5 is a member of the type II PRMT subfamily that utilises S-adenosylmethionine (SAM) to generate symmetric dimethylated arginine on histones and non-histone protein substrates and S-adenosylhomocysteine (SAH). The crystal structure of the human hetereo-octameric complex $(PRMT5)_4(MEP50)_4$ co-crystalised with SAH and a histone H4 peptide substrate illustrated the mechanism of methylation and substrate recognition[Antonysamy, S. et al., Proc Natl Acad Sci USA, 2012. 109(44): p. 17960-5]. The regulation of PRMT5 activity occurs through a vast number of different binding partners, post-translational modification cross talk, miRNAs and subcellular localisation.

Methylation of histones H2A and H4 on Arg3 and histone H3 on Arg8 regulate chromatin organisation for specific repression of gene transcripts that are involved in differentiation, transformation, cell-cycle progression and tumour suppression [Karkhanis, V. et al., Trends Biochem Sci, 2011. 36(12): p. 633-41]. Furthermore, PRMT5-mediated methylation of histone H4 on Arg3 might recruit the DNA-methyltransferase DNMT3A to couple histone and DNA methylation for long-term gene silencing [Zhao, Q. et al., Nat Struct Mol Biol, 2009. 16(3): p. 304-11].

Non-histone methylation can occur either in the cytoplasm or nucleus dependent on the cellular localisation of PRMT5. The methylation of the Sm proteins D1 and D3, which are required for the assembly of the nuclear spliceosome, takes place in the cytoplasm as part of the PRMT5 containing "methylosome" [Friesen, W. J. et al., Mol Cell Biol, 2001. 21(24): p. 8289-300]. Further evidence for PRMT5 involved in splicing has been provided by the conditional PRMT5 knockout in mouse neural stem cells. Cells that lack PRMT5 showed a selective retention of introns and skipping of exons with weak 5' donor sites [Bezzi, M. et al., Genes Dev, 2013. 27(17): p. 1903-16].

In addition to a role in splicing, PRMT5 influences key pathways involved in cell fate and homeostasis by direct methylation of key signalling nodules like p53 [Jansson, M. et al., Nat Cell Biol, 2008. 10(12): p. 1431-9], EGFR [Hsu, J. M. et al., Nat Cell Biol, 2011. 13(2): p. 174-81], CRAF [Andreu-Perez, P. et al., Sci Signal, 2011. 4(190): p. ra58], PI3K/AKT [Wei, T. Y. et al., Cell Signal, 2014. 26(12): p. 2940-50], NFκB [Wei, H. et al., Proc Natl Acad Sci USA, 2013. 110(33): p. 13516-21].

Since PRMT5 is one of the major sym-Arg methyltransferases and involved in a multitude of cellular processes, an increased protein expression appears to be an important factor in its tumourigenicity. Interestingly, the translation of PRMT5 in mantle cell lymphoma (MCL) seems to be regulated by miRNAs. Although MCL cells show less mRNA and a slower transcription rate of PRMT5 than normal B lymphocytes, the PRMT5 level and the methylation of H3R8 and H4R3 are significantly increased [Pal, S. et al., EMBO J, 2007. 26(15): p. 3558-69]. Re-expression of miRNAs that binds the 3'UTR region of PRMT5 decreases PRMT5 protein level [Wang, L. et al., Mol Cell Biol, 2008. 28(20): p. 6262-77]. Strikingly, a prmt5 antisense RNA has been found within the human prmt5 gene that supports the hypothesis of a specific translational regulation rather than high mRNA expression level [Stopa, N. et al., Cell Mol Life Sci, 2015. 72(11): p. 2041-59].

Although PRMT5 is considered as a clinical relevant target, very few selective PRMT5 inhibitors have been published, yet. Very recently, a novel sub-nanomolar potent PRMT5 inhibitor (EPZ015666) with anti-tumour activity in multiple MCL xenograft models has been described to be the first chemical probe suitable for further validation of PRMT5's biology and role in cancer [Chan-Penebre, E. et al., Nat Chem Biol, 2015. 11(6): p. 432-7].

Further development of specific small molecule inhibitors of PRMT5 may lead to novel chemotherapeutic approaches for cancer.

WO2016135582 and US20160244475 describe substituted nucleoside derivatives useful as anticancer agents.

WO2014100695A1 discloses compounds useful for inhibiting PRMT5 activity; Methods of using the compounds for treating PRMT5-mediated disorders are also described.

WO2014100730A1 discloses PRMT5 inhibitors containing a dihydro- or tetrahydroisoquinoline and uses thereof.

Devkota, K. et al., ACS Med Chem Lett, 2014. 5: p. 293-297, describes the synthesis of a series of analogues of the natural product sinefungin and the ability of these analogues to inhibit EHMT1 and EHMT2.

WO2003070739 discloses partial and full agonists of A1 adenosine receptors, their preparation, and their therapeutic use.

WO2012082436 discloses compounds and compositions as modulators of histone methyltransferases, and for treating diseases influenced by modulation of histone methyltransferase activity.

WO2014100719 discloses PRMT5 inhibitors and uses thereof.

WO03074083 discloses combination therapies that selectively kill methylthioadenosine phosphorylase deficient cells. Analogs of MTA are described herein as anti-toxicity agents.

Kung, P.-P. et al., Bioorg Med Chem Lett, 2005. 15: p. 2829-2833, describes the design, synthesis, and biological evaluation of novel human 5'-deoxy-5'-methylthioadenosine phosphorylase (MTAP) substrates.

WO2012075500 discloses 7-deazapurine modulators of histone methyltransferase.

WO2014035140 discloses compounds and compositions for modulating histone methyltransferase activity.

WO2015200680 describes PRMT5 inhibitors and uses thereof.

WO9640686 describes heterocyclic substituted cyclopentane compounds and methods of using such compounds for inhibiting adenosine kinase.

WO2017032840 relates to novel 6-6 bicyclic aromatic ring substituted nucleoside analogues useful as PRMT5 inhibitors.

WO2017153186 relates to novel compounds useful as PRMT5 inhibitors.

There is thus a strong need for novel PRMT5 inhibitors thereby opening new avenues for the treatment or prevention of cancer, such as e.g. mantle cell lymphoma. It is accordingly an object of the present invention to provide such compounds.

The compounds of the present invention are structurally different and may have improved properties such as for example improved potency, or improved pharmacokinetics (PK) and oral bioavailability, compared with compounds disclosed in the prior art.

SUMMARY OF THE INVENTION

It has been found that the compounds of the present invention are useful as PRMT5 inhibitors. The compounds according to the invention and compositions thereof, may be useful for the treatment or prevention, in particular for the treatment, of diseases such as a blood disorder, metabolic disorders, autoimmune disorders, cancer, inflammatory diseases, cardiovascular diseases, neurodegenerative diseases, pancreatitis, multiorgan failure, kidney diseases, platelet aggregation, sperm motility, transplantation rejection, graft rejection, lung injuries, and the like.

The present invention concerns novel compounds of Formula (I):

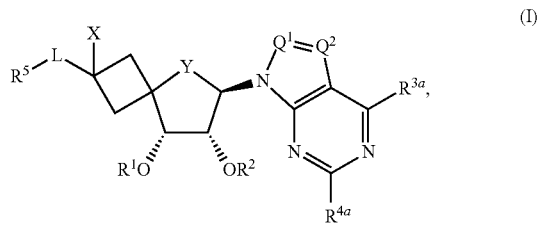

(I)

wherein
$R^1$ represents hydrogen or —C(=O)—$C_{1-4}$alkyl;
$R^2$ represents hydrogen or —C(=O)—$C_{1-4}$alkyl;
X represents hydrogen;
Y represents —O—, —$CH_2$— or —$CF_2$—;
$Q^1$ represents $CR^{6a}$;
$Q^2$ represents N or $CR^{6b}$;
$R^{6a}$ and $R^{6b}$ each independently represent hydrogen, halogen, $C_{1-4}$alkyl, —$NR^{9a}R^{9b}$, or $C_{1-4}$alkyl substituted with one, two or three halo atoms;
$R^{9a}$ and $R^{9b}$ each independently represent hydrogen or $C_{1-4}$alkyl;
$R^{3a}$ represents hydrogen, halo, —$NR^{7a}R^{7b}$, $C_{1-4}$alkyl, $C_{2-4}$alkenyl, $C_{3-6}$cycloalkyl, —OH, or —O—$C_{1-4}$alkyl;
$R^{7a}$ represents hydrogen;
$R^{7b}$ represents hydrogen, $C_{3-6}$cycloalkyl, or $C_{1-4}$alkyl;
$R^{4a}$ represents hydrogen, halo, —$NR^{8a}R^{8b}$, or $C_{1-4}$alkyl;
L represents —$CH_2$—, —O—$CH_2$—, —$CH_2$—O—, or —O—;
$R^5$ represents Ar or Het; and in case L represents —O— or —O—$CH_2$—, $R^5$ can also represent hydrogen;
Ar represents phenyl optionally substituted with one or more halo substituents;
Het represents a monocyclic or bicyclic ring system selected from the group consisting of (a-1), (a-2), (a-3), (a-4), (a-5), (a-6) and (a-7):

(a-1)

(a-2)

(a-3)

(a-4)

(a-5)

(a-6)

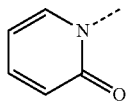
(a-7)

wherein said monocyclic or bicyclic aromatic ring system is optionally substituted with one or more substituents each independently selected from the group consisting of halo and —NH$_2$;

and pharmaceutically acceptable addition salts, and solvates thereof.

The present invention also concerns methods for the preparation of compounds of the present invention and pharmaceutical compositions comprising them.

The compounds of the present invention were found to inhibit PRMT5 per se or can undergo metabolism to a (more) active form in vivo (prodrugs), and therefore may be useful in the treatment or prevention, in particular in the treatment, of diseases such as a blood disorder, metabolic disorders, autoimmune disorders, cancer, inflammatory diseases, cardiovascular diseases, neurodegenerative diseases, pancreatitis, multiorgan failure, kidney diseases, platelet aggregation, sperm motility, transplantation rejection, graft rejection, lung injuries, and the like.

In view of the aforementioned pharmacology of the compounds of Formula (I) and pharmaceutically acceptable addition salts, and solvates thereof, it follows that they may be suitable for use as a medicament.

In particular the compounds of Formula (I) and pharmaceutically acceptable addition salts, and solvates thereof, may be suitable in the treatment or prevention, in particular in the treatment, of any one of the diseases or conditions mentioned hereinbefore or hereinafter, in particular cancer.

The present invention also concerns the use of compounds of Formula (I) and pharmaceutically acceptable addition salts, and solvates thereof, for the manufacture of a medicament for the inhibition of PRMT5, for the treatment or prevention of any one of the diseases or conditions mentioned hereinbefore or hereinafter, in particular cancer.

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

DETAILED DESCRIPTION

When describing the compounds of the invention, the terms used are to be construed in accordance with the following definitions, unless a context dictates otherwise.

When any variable occurs more than one time in any constituent or in any formula (e.g. Formula (I)), its definition in each occurrence is independent of its definition at every other occurrence.

Whenever the term "substituted" is used in the present invention, it is meant, unless otherwise is indicated or is clear from the context, to indicate that one or more hydrogens, in particular from 1 to 3 hydrogens, preferably 1 or 2 hydrogens, more preferably 1 hydrogen, on the atom or radical indicated in the expression using "substituted" are replaced with a selection from the indicated group, provided that the normal valency is not exceeded, and that the substitution results in a chemically stable compound, i.e. a compound that is sufficiently robust to survive isolation to a useful degree of purity from a reaction mixture, and formulation into a therapeutic agent.

When two or more substituents are present on a moiety they may, unless otherwise is indicated or is clear from the context, replace hydrogens on the same atom or they may replace hydrogen atoms on different atoms in the moiety.

The prefix "$C_{x-y}$" (where x and y are integers) as used herein refers to the number of carbon atoms in a given group. Thus, a $C_{1-4}$alkyl group contains from 1 to 4 carbon atoms, a $C_{1-3}$alkyl group contains from 1 to 3 carbon atoms and so on.

The term "halo" as a group or part of a group is generic for fluoro, chloro, bromo, iodo unless otherwise is indicated or is clear from the context.

The term "$C_{1-4}$alkyl" as a group or part of a group refers to a hydrocarbyl radical of Formula $C_nH_{2n+1}$ wherein n is a number ranging from 1 to 4. $C_{1-4}$alkyl groups comprise from 1 to 4 carbon atoms, preferably from 1 to 3 carbon atoms, more preferably 1 to 2 carbon atoms. $C_{1-4}$alkyl groups may be linear or branched and may be substituted as indicated herein. When a subscript is used herein following a carbon atom, the subscript refers to the number of carbon atoms that the named group may contain. $C_{1-4}$alkyl includes all linear, or branched alkyl groups with between 1 and 4 carbon atoms, and thus includes methyl, ethyl, n-propyl, i-propyl, 2-methyl-ethyl, butyl and its isomers (e.g. n-butyl, isobutyl and tert-butyl), and the like.

The skilled person will realize that non-limiting examples of suitable —O—$C_{1-4}$alkyl include methyloxy (also methoxy), ethyloxy (also ethoxy), propyloxy, isopropyloxy, butyloxy, isobutyloxy, sec-butyloxy and tert-butyloxy.

The term "$C_{2-4}$alkenyl" as used herein as a group or part of a group represents a straight or branched chain hydrocarbon group containing from 2 to 4 carbon atoms and containing a carbon carbon double bond such as, but not limited to, ethenyl, propenyl, butenyl, 1-propen-2-yl, and the like.

The term '$C_{3-6}$cycloalkyl' as used herein as a group or part of a group represents cyclic saturated hydrocarbon radicals having from 3 to 6 carbon atoms such as cyclopropyl, cyclobutyl, cyclopentyl or cyclohexyl.

In case L represents —O—CH$_2$—, it is intended that oxygen (O) is attached to R$^5$.

In case L represents —CH$_2$—O—, it is intended that oxygen (O) is attached to the spiro moiety.

Whenever substituents are represented by chemical structure, "---" represents the bond of attachment to the remainder of the molecule of Formula (I).

The term "subject" as used herein, refers to an animal, preferably a mammal (e.g. cat, dog, primate or human), more preferably a human, who is or has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medicinal doctor or other clinician, which includes alleviation or reversal of the symptoms of the disease or disorder being treated.

The term "composition" is intended to encompass a product comprising the specified ingredients in the specified amounts, as well as any product which results, directly or indirectly, from combinations of the specified ingredients in the specified amounts.

The term "treatment", as used herein, is intended to refer to all processes wherein there may be a slowing, interrupting, arresting or stopping of the progression of a disease, but does not necessarily indicate a total elimination of all symptoms.

The term "compounds of the (present) invention" as used herein, is meant to include the compounds of Formula (I) and pharmaceutically acceptable addition salts, and solvates thereof.

Some of the compounds of Formula (I) may also exist in their tautomeric form. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerisations. Valence tautomers include interconversions by reorganisation of some of the bonding electrons.

Such forms in so far as they may exist, although not explicitly indicated in the above Formula (I), are intended to be included within the scope of the present invention.

As used herein, any chemical formula with bonds shown only as solid lines and not as solid wedged or hashed wedged bonds, or otherwise indicated as having a particular configuration (e.g. R, S) around one or more atoms, contemplates each possible stereoisomer, or mixture of two or more stereoisomers. Where the stereochemistry of any particular chiral atom is not specified in the structures shown herein, then all stereoisomers are contemplated and included as the compounds of the invention, either as a pure stereoisomer or as a mixture of two or more stereoisomers.

Hereinbefore and hereinafter, the term "compound of Formula (I)" is meant to include the stereoisomers thereof and the tautomeric forms thereof. However where stereochemistry, as mentioned in the previous paragraph, is specified by bonds which are shown as solid wedged or hashed wedged bonds, or are otherwise indicated as having a particular configuration (e.g. R, S), then that stereoisomer is so specified and defined. It will be clear this also applies to subgroups of Formula (I).

It follows that a single compound may, where possible, exist in both stereoisomeric and tautomeric form.

The terms "stereoisomers", "stereoisomeric forms" or "stereochemically isomeric forms" hereinbefore or hereinafter are used interchangeably.

Enantiomers are stereoisomers that are non-superimposable mirror images of each other. A 1:1 mixture of a pair of enantiomers is a racemate or racemic mixture.

Atropisomers (or atropoisomers) are stereoisomers which have a particular spatial configuration, resulting from a restricted rotation about a single bond, due to large steric hindrance. All atropisomeric forms of the compounds of Formula (I) are intended to be included within the scope of the present invention.

Diastereomers (or diastereoisomers) are stereoisomers that are not enantiomers, i.e. they are not related as mirror images. If a compound contains a double bond, the substituents may be in the E or the Z configuration. Substituents on bivalent cyclic (partially) saturated radicals may have either the cis- or trans-configuration; for example if a compound contains a disubstituted cycloalkyl group, the substituents may be in the cis or trans configuration. Therefore, the invention includes enantiomers, atropisomers, diastereomers, racemates, E isomers, Z isomers, cis isomers, trans isomers and mixtures thereof, whenever chemically possible.

The meaning of all those terms, i.e. enantiomers, atropisomers, diastereomers, racemates, E isomers, Z isomers, cis isomers, trans isomers and mixtures thereof are known to the skilled person.

The absolute configuration is specified according to the Cahn-Ingold-Prelog system. The configuration at an asymmetric atom is specified by either R or S. Resolved stereoisomers whose absolute configuration is not known can be designated by (+) or (−) depending on the direction in which they rotate plane polarized light. For instance, resolved enantiomers whose absolute configuration is not known can be designated by (+) or (−) depending on the direction in which they rotate plane polarized light.

When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other stereoisomers. Thus, when a compound of Formula (I) is for instance specified as (R), this means that the compound is substantially free of the (S) isomer; when a compound of Formula (I) is for instance specified as E, this means that the compound is substantially free of the Z isomer; when a compound of Formula (I) is for instance specified as cis, this means that the compound is substantially free of the trans isomer.

For therapeutic use, salts of the compounds of Formula (I) and solvates thereof, are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

Pharmaceutically-acceptable salts include acid addition salts and base addition salts. Such salts may be formed by conventional means, for example by reaction of a free acid or a free base form with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of the invention in the form of a salt with another counter-ion, for example using a suitable ion exchange resin.

The pharmaceutically acceptable addition salts as mentioned hereinabove or hereinafter are meant to comprise the therapeutically active non-toxic acid and base addition salt forms which the compounds of Formula (I) and solvates thereof, are able to form.

Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds of Formula (I) and solvates thereof containing an acidic proton may also be converted into their non-toxic metal or amine addition salt forms by treatment with appropriate organic and inorganic bases.

Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline; the benzathine, N-methyl-D-glucamine, hydrabamine salts, and salts with amino acids such as, for example, arginine, lysine and the like. Conversely the salt form can be converted by treatment with acid into the free acid form.

For the purposes of this invention prodrugs are also included within the scope of the invention.

The term "prodrug" of a relevant compound of the invention includes any compound that, following oral or parenteral administration, in particular oral administration, is metabolised in vivo to a form that compound in an experimentally-detectable amount, and within a predetermined time (e.g. within a dosing interval of between 6 and 24 hours (i.e. once to four times daily)). For the avoidance of doubt, the term "parenteral" administration includes all forms of administration other than oral administration, in particular intravenous (IV), intramuscular (IM), and subcutaneous (SC) injection. Prodrugs may be prepared by modifying functional groups present on the compound in such a way that the modifications are cleaved, in vivo when such prodrug is administered to a mammalian subject. The modifications typically are achieved by synthesising the parent compound with a prodrug substituent. In general, prodrugs include compounds of the invention wherein a hydroxyl, amino, sulfhydryl, carboxy or carbonyl group in a compound of the invention is bonded to any group that may be cleaved in vivo to regenerate the free hydroxyl, amino, sulfhydryl, carboxy or carbonyl group, respectively; in particular wherein a hydroxyl group in a compound of the invention is bonded to any group (e.g. —C(=O)—$C_{1-4}$ alkyl) that may be cleaved in vivo to regenerate the free hydroxyl. Within the context of this invention, prodrugs in particular are compounds of Formula (I) or subgroups thereof wherein $R^1$ and/or $R^2$ represent —C(=O)—$C_{1-4}$ alkyl.

Examples of prodrugs include, but are not limited to, esters and carbamates of hydroxy functional groups, esters groups of carboxyl functional groups, N-acyl derivatives and N-Mannich bases. General information on prodrugs may be found e.g. in Bundegaard, H. "Design of Prodrugs" p. 1-92, Elesevier, N.Y.-Oxford (1985).

The term solvate comprises the hydrates and solvent addition forms which the compounds of Formula (I) are able to form, as well as pharmaceutically acceptable addition salts thereof. Examples of such forms are e.g. hydrates, alcoholates and the like.

The compounds of the invention as prepared in the processes described below may be synthesized in the form of mixtures of enantiomers, in particular racemic mixtures of enantiomers, that can be separated from one another following art-known resolution procedures. A manner of separating the enantiomeric forms of the compounds of Formula (I), and pharmaceutically acceptable addition salts, and solvates thereof, involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound would be synthesized by stereospecific methods of preparation. These methods will advantageously employ enantiomerically pure starting materials.

The present invention also embraces isotopically-labeled compounds of the present invention which are identical to those recited herein, but for the fact that one or more atoms are replaced by an atom having an atomic mass or mass number different from the atomic mass or mass number usually found in nature (or the most abundant one found in nature).

All isotopes and isotopic mixtures of any particular atom or element as specified herein are contemplated within the scope of the compounds of the invention, either naturally occurring or synthetically produced, either with natural abundance or in an isotopically enriched form. Exemplary isotopes that can be incorporated into compounds of the invention include isotopes of hydrogen, carbon, nitrogen, oxygen, phosphorus, sulfur, fluorine, chlorine and iodine, such as $^2H$, $^3H$, $^{11}C$, $^{13}C$, $^{14}C$, $^{13}N$, $^{15}O$, $^{17}O$, $^{18}O$, $^{32}P$, $^{33}P$, $^{35}S$, $^{18}F$, $^{36}Cl$, $^{122}I$, $^{123}I$, $^{125}I$, $^{131}I$, $^{75}Br$, $^{76}Br$, $^{77}Br$ and $^{82}Br$. Preferably, the radioactive isotope is selected from the group of $^2H$, $^3H$, $^{11}C$ and $^{18}F$. More preferably, the radioactive isotope is $^2H$. In particular, deuterated compounds are intended to be included within the scope of the present invention.

Certain isotopically-labeled compounds of the present invention (e.g., those labeled with $^3H$ and $^{14}C$) are useful for substrate tissue distribution assays. Tritiated ($^3H$) and carbon-14 ($^{14}C$) isotopes are useful for their ease of preparation and detectability. Further, substitution with heavier isotopes such as deuterium (i.e., $^2H$ may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$ and $^{18}F$ are useful for positron emission tomography (PET) studies to examine substrate receptor occupancy.

In an embodiment, the present invention concerns novel compounds of Formula (I), wherein $R^1$ represents hydrogen;

$R^2$ represents hydrogen;

X represents hydrogen;

Y represents —O—, —$CH_2$— or —$CF_2$—;

$Q^1$ represents $CR^{6a}$;

$Q^2$ represents N or $CR^{6b}$;

$R^{6a}$ and $R^{6b}$ each independently represent hydrogen, halogen, $C_{1-4}$alkyl, —$NR^{9a}R^{9b}$, or $C_{1-4}$alkyl substituted with one, two or three halo atoms;

$R^{9a}$ and $R^{9b}$ each independently represent hydrogen or $C_{1-4}$alkyl;

$R^{3a}$ represents hydrogen, halo, —$NR^{7a}R^{7b}$, $C_{1-4}$alkyl, $C_{2-4}$alkenyl, $C_{3-6}$cycloalkyl, —OH, or —O—$C_{1-4}$alkyl:

$R^{7a}$ represents hydrogen;

$R^{7b}$ represents hydrogen, $C_{3-6}$cycloalkyl, or $C_{1-4}$alkyl;

$R^{4a}$ represents hydrogen, halo, —$NR^{8a}R^{8b}$, or $C_{1-4}$alkyl;

L represents —$CH_2$—, —O—$CH_2$—, —$CH_2$—O—, or —O—;

$R^5$ represents Ar or Het; and in case L represents —O— or —O—$CH_2$—, $R^5$ can also represent hydrogen;

Ar represents phenyl optionally substituted with one or more halo substituents; Het represents a monocyclic or bicyclic ring system selected from the group consisting of (a-1), (a-2), (a-3), (a-4), (a-5), (a-6) and (a-7):

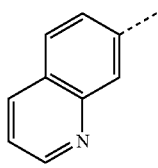
(a-1)

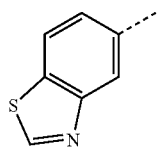
(a-2)

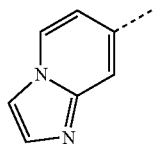
(a-3)

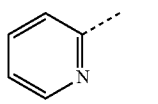
(a-4)

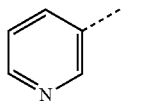
(a-5)

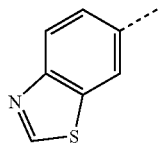
(a-6)

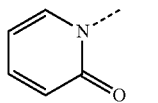
(a-7)

wherein said monocyclic or bicyclic aromatic ring system is optionally substituted with one or more substituents each independently selected from the group consisting of halo and —NH$_2$;

and pharmaceutically acceptable addition salts, and solvates thereof.

In an embodiment, the present invention concerns novel compounds of Formula (I),
wherein
$R^1$ represents —C(=O)—C$_{1-4}$alkyl;
$R^2$ represents —C(=O)—C$_{1-4}$alkyl;
X represents hydrogen;
Y represents —O—, —CH$_2$— or —CF$_2$—;
$Q^1$ represents CR$^{6a}$;
$Q^2$ represents N or CR$^{6b}$;
$R^{6a}$ and $R^{6b}$ each independently represent hydrogen, halogen, C$_{1-4}$alkyl, —NR$^{9a}$R$^{9b}$, or C$_{1-4}$alkyl substituted with one, two or three halo atoms;
$R^{9a}$ and $R^{9b}$ each independently represent hydrogen or C$_{1-4}$alkyl;
$R^{3a}$ represents hydrogen, halo, —NR$^{7a}$R$^{7b}$, C$_{1-4}$alkyl, C$_{2-4}$alkenyl, C$_{3-6}$cycloalkyl, —OH, or —O—C$_{1-4}$alkyl;
$R^{7a}$ represents hydrogen;
$R^{7b}$ represents hydrogen, C$_{3-6}$cycloalkyl, or C$_{1-4}$alkyl;
$R^{4a}$ represents hydrogen, halo, —NR$^{8a}$R$^{8b}$, or C$_{1-4}$alkyl;

L represents —CH$_2$—, —O—CH$_2$—, —CH$_2$—O—, or —O—;
$R^5$ represents Ar or Het; and in case L represents —O— or —O—CH$_2$—, $R^5$ can also represent hydrogen;
Ar represents phenyl optionally substituted with one or more halo substituents;
Het represents a monocyclic or bicyclic ring system selected from the group consisting of (a-1), (a-2), (a-3), (a-4), (a-5), (a-6) and (a-7):

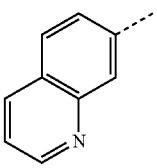
(a-1)

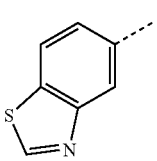
(a-2)

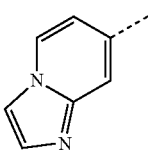
(a-3)

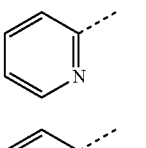
(a-4)

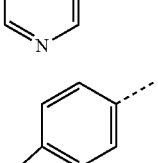
(a-5)

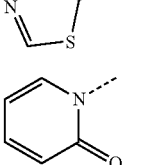
(a-6)

(a-7)

wherein said monocyclic or bicyclic aromatic ring system is optionally substituted with one or more substituents each independently selected from the group consisting of halo and —NH$_2$;

and pharmaceutically acceptable addition salts, and solvates thereof.

In an embodiment, the present invention concerns novel compounds of Formula (I),
wherein
$R^1$ represents hydrogen or —C(=O)—C$_{1-4}$alkyl;
$R^2$ represents hydrogen or —C(=O)—C$_{1-4}$alkyl;
X represents hydrogen;
Y represents —O—, —CH$_2$— or —CF$_2$—;
$Q^1$ represents CR$^{6a}$;
$Q^2$ represents N or CR$^{6b}$;

$R^{6a}$ and $R^{6b}$ represent hydrogen;
$R^3$ represents hydrogen, halo, —NR$^{7a}$R$^{7b}$, $C_{1-4}$alkyl, $C_{2-4}$alkenyl, $C_{3-6}$cycloalkyl, —OH, or —O—$C_{1-4}$alkyl;
$R^{7a}$ represents hydrogen;
$R^{7b}$ represents hydrogen, $C_{3-6}$cycloalkyl, or $C_{1-4}$alkyl;
$R^{4a}$ represents hydrogen;
L represents —CH$_2$—, —O—CH$_2$—, —CH$_2$—O—, or —O—;
$R^5$ represents Ar or Het; and in case L represents —O— or —O—CH$_2$—, $R^5$ can also represent hydrogen;
Ar represents phenyl optionally substituted with one or more halo substituents;
Het represents a monocyclic or bicyclic ring system selected from the group consisting of (a-1), (a-2), (a-3), (a-4), (a-5), (a-6) and (a-7):

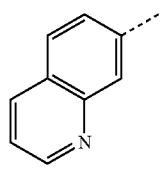
(a-1)

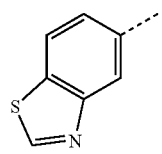
(a-2)

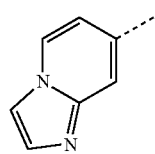
(a-3)

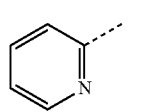
(a-4)

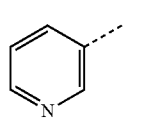
(a-5)

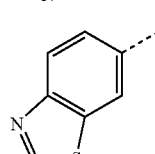
(a-6)

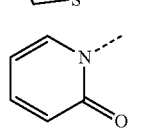
(a-7)

wherein said monocyclic or bicyclic aromatic ring system is optionally substituted with one or more substituents each independently selected from the group consisting of halo and —NH$_2$;
and pharmaceutically acceptable addition salts, and solvates thereof.

In an embodiment, the present invention concerns novel compounds of Formula (I), wherein
$R^1$ represents hydrogen or —C(=O)—$C_{1-4}$alkyl;
$R^2$ represents hydrogen or —C(=O)—$C_{1-4}$alkyl;
X represents hydrogen;
Y represents —O— or —CH$_2$—;
$Q^1$ represents CR$^{6a}$;
$Q^2$ represents N or CR$^{6b}$;
$R^{6a}$ and $R^{6b}$ represent hydrogen;
$R^3$ represents halo or —NR$^{7a}$R$^{7b}$;
$R^{7a}$ represents hydrogen;
$R^{7b}$ represents hydrogen;
$R^{4a}$ represents hydrogen;
L represents —CH$_2$—, —O—CH$_2$—, —CH$_2$—O—, or —O—;
$R^5$ represents Ar or Het; and in case L represents —O— or —O—CH$_2$—, $R^5$ can also represent hydrogen;
Ar represents phenyl;
Het represents a monocyclic or bicyclic ring system selected from the group consisting of (a-1), (a-2), (a-3), (a-4), (a-5), (a-6) and (a-7):

wherein said monocyclic or bicyclic aromatic ring system is optionally substituted with one or more substituents each independently selected from the group consisting of halo and —NH$_2$;
and pharmaceutically acceptable addition salts, and solvates thereof.

In an embodiment, the present invention concerns novel compounds of Formula (I),
wherein
$R^1$ represents hydrogen or —C(=O)—$C_{1-4}$alkyl; in particular hydrogen;
$R^2$ represents hydrogen or —C(=O)—$C_{1-4}$alkyl; in particular hydrogen;
X represents hydrogen;
Y represents —O—;
$Q^1$ represents $CR^{6a}$;
$Q^2$ represents N;
$R^{6a}$ represents hydrogen;
$R^{3a}$ represents —$NR^{7a}R^{7b}$;
$R^{7a}$ represents hydrogen;
$R^{7b}$ represents hydrogen;
$R^{4a}$ represents hydrogen;
L represents —O—;
$R^5$ represents Het;
Het represents (a-1), optionally substituted with one or more substituents each independently selected from the group consisting of halo and —$NH_2$;
and pharmaceutically acceptable addition salts, and solvates thereof.

Another embodiment of the present invention relates to those compounds of Formula (I), and pharmaceutically acceptable addition salts, and solvates thereof, or any subgroup thereof as mentioned in any of the other embodiments, wherein one or more of the following restrictions apply:
(i) Y represents —O— or —$CH_2$—;
(ii) $R^{6a}$ and $R^{6b}$ represent hydrogen;
(iii) $R^{3a}$ represents halo or —$NR^{7a}R^{7b}$;
(iv) $R^{7a}$ represents hydrogen; $R^{7b}$ represents hydrogen;
(v) $R^{4a}$ represents hydrogen;
(vi) Ar represents phenyl.

In an embodiment, the present invention relates to those compounds of Formula (I) and pharmaceutically acceptable addition salts, and solvates thereof, or any subgroup thereof as mentioned in any of the other embodiments, wherein $R^1$ and $R^2$ represent hydrogen.

In an embodiment, the present invention relates to those compounds of Formula (I) and pharmaceutically acceptable addition salts, and solvates thereof, or any subgroup thereof as mentioned in any of the other embodiments, wherein
$R^1$ represents-C(=O)—$C_{1-4}$alkyl; $R^2$ represents-C(=O)—$C_{1-4}$alkyl.

In an embodiment, the present invention relates to those compounds of Formula (I) and pharmaceutically acceptable addition salts, and solvates thereof, or any subgroup thereof as mentioned in any of the other embodiments, wherein Y represents —$CH_2$—.

In an embodiment, the present invention relates to those compounds of Formula (I) and pharmaceutically acceptable addition salts, and solvates thereof, or any subgroup thereof as mentioned in any of the other embodiments, wherein Y represents —$CH_2$— or —$CF_2$—.

In an embodiment, the present invention relates to those compounds of Formula (I) and pharmaceutically acceptable addition salts, and solvates thereof, or any subgroup thereof as mentioned in any of the other embodiments, wherein Y represents —O—.

In an embodiment, the present invention relates to those compounds of Formula (I) and pharmaceutically acceptable addition salts, and solvates thereof, or any subgroup thereof as mentioned in any of the other embodiments, wherein $R^{3a}$ represents halo, —$NR^{7a}R^{7b}$, $C_{1-4}$alkyl, $C_{2-4}$alkenyl, $C_{3-6}$cycloalkyl, —OH, or —O—$C_{1-4}$alkyl.

In an embodiment, the present invention relates to those compounds of Formula (I) and pharmaceutically acceptable addition salts, and solvates thereof, or any subgroup thereof as mentioned in any of the other embodiments, wherein $R^{3a}$ represents halo or —$NR^{7a}R^{7b}$.

In an embodiment, the present invention relates to those compounds of Formula (I) and pharmaceutically acceptable addition salts, and solvates thereof, or any subgroup thereof as mentioned in any of the other embodiments, wherein $R^{3a}$ represents Cl or —$NR^{7a}R^{7b}$.

In an embodiment, the present invention relates to those compounds of Formula (I) and pharmaceutically acceptable addition salts, and solvates thereof, or any subgroup thereof as mentioned in any of the other embodiments, wherein $R^{3a}$ represents Cl or —$NR^{7a}R^{7b}$;
$R^{7a}$ and $R^{7b}$ represent hydrogen.

In an embodiment, the present invention relates to those compounds of Formula (I) and pharmaceutically acceptable addition salts, and solvates thereof, or any subgroup thereof as mentioned in any of the other embodiments, wherein $R^{3a}$ represents halo; in particular wherein $R^{3a}$ represents chloro.

In an embodiment, the present invention relates to those compounds of Formula (I) and pharmaceutically acceptable addition salts, and solvates thereof, or any subgroup thereof as mentioned in any of the other embodiments, wherein $R^{3a}$ represents —$NR^{7a}R^{7b}$; $R^{7a}$ and $R^{7b}$ represent hydrogen.

In an embodiment, the present invention relates to those compounds of Formula (I) and pharmaceutically acceptable addition salts, and solvates thereof, or any subgroup thereof as mentioned in any of the other embodiments, wherein $R^1$ and $R^2$ represent —C(=O)—$C_{1-4}$alkyl; and $R^{3a}$ represents halo.

In an embodiment, the present invention relates to those compounds of Formula (I) and pharmaceutically acceptable addition salts, and solvates thereof, or any subgroup thereof as mentioned in any of the other embodiments, wherein $R^1$ and $R^2$ represent —C(=O)—$C_{1-4}$alkyl; and $R^{3a}$ represents chloro.

In an embodiment, the present invention relates to those compounds of Formula (I) and pharmaceutically acceptable addition salts, and solvates thereof, or any subgroup thereof as mentioned in any of the other embodiments, wherein $R^1$ and $R^2$ represent H; and $R^{3a}$ represents —$NR^{7a}R^{7b}$; $R^{7a}$ and $R^{7b}$ represent hydrogen.

In an embodiment, the present invention relates to those compounds of Formula (I) and pharmaceutically acceptable addition salts, and solvates thereof, or any subgroup thereof as mentioned in any of the other embodiments, wherein
Y represents O;
$Q^2$ represents N.

In an embodiment, the present invention relates to those compounds of Formula (I) and pharmaceutically acceptable addition salts, and solvates thereof, or any subgroup thereof as mentioned in any of the other embodiments, wherein
when Y represents —$CH_2$— or —$CF_2$—; $Q^2$ represents N or $CR^{6b}$;
when Y represents —O—; $Q^2$ represents N.

In an embodiment, the present invention relates to those compounds of Formula (I) and pharmaceutically acceptable addition salts, and solvates thereof, or any subgroup thereof as mentioned in any of the other embodiments, wherein
when Y represents —$CH_2$— or —$CF_2$—; $Q^2$ represents N or $CR^{6b}$; $R^{6b}$ represents hydrogen;
when Y represents —O—; $Q^2$ represents N.

In an embodiment, the present invention relates to those compounds of Formula (I) and pharmaceutically acceptable addition salts, and solvates thereof, or any subgroup thereof as mentioned in any of the other embodiments, wherein $Q^2$ represents N.

In an embodiment, the present invention relates to those compounds of Formula (I) and pharmaceutically acceptable addition salts, and solvates thereof, or any subgroup thereof as mentioned in any of the other embodiments, wherein $Q^2$ represents $CR^{6b}$.

In an embodiment, the present invention relates to those compounds of Formula (I) and pharmaceutically acceptable addition salts, and solvates thereof, or any subgroup thereof as mentioned in any of the other embodiments, wherein
$Q^2$ represents $CR^{6b}$;
$R^{6b}$ represents hydrogen.

In an embodiment, the present invention relates to those compounds of Formula (I) and pharmaceutically acceptable addition salts, and solvates thereof, or any subgroup thereof as mentioned in any of the other embodiments, wherein
$R^5$ represents Ar or Het.

In an embodiment, the present invention relates to those compounds of Formula (I) and pharmaceutically acceptable addition salts, and solvates thereof, or any subgroup thereof as mentioned in any of the other embodiments, wherein
$R^5$ represents Het.

In an embodiment, the present invention relates to those compounds of Formula (I) and pharmaceutically acceptable addition salts, and solvates thereof, or any subgroup thereof as mentioned in any of the other embodiments, wherein
Het represents (a-1); optionally substituted as defined in any of the other embodiments.

In an embodiment, the present invention relates to those compounds of Formula (I) and pharmaceutically acceptable addition salts, and solvates thereof, or any subgroup thereof as mentioned in any of the other embodiments, wherein
Het represents (a-2); optionally substituted as defined in any of the other embodiments.

In an embodiment, the present invention relates to those compounds of Formula (I) and pharmaceutically acceptable addition salts, and solvates thereof, or any subgroup thereof as mentioned in any of the other embodiments, wherein
Het represents (a-3); optionally substituted as defined in any of the other embodiments.

In an embodiment, the present invention relates to those compounds of Formula (I) and pharmaceutically acceptable addition salts, and solvates thereof, or any subgroup thereof as mentioned in any of the other embodiments, wherein
Het represents (a-4); optionally substituted as defined in any of the other embodiments.

In an embodiment, the present invention relates to those compounds of Formula (I) and pharmaceutically acceptable addition salts, and solvates thereof, or any subgroup thereof as mentioned in any of the other embodiments, wherein
Het represents (a-5); optionally substituted as defined in any of the other embodiments.

In an embodiment, the present invention relates to those compounds of Formula (I) and pharmaceutically acceptable addition salts, and solvates thereof, or any subgroup thereof as mentioned in any of the other embodiments, wherein
Het represents (a-6); optionally substituted as defined in any of the other embodiments.

In an embodiment, the present invention relates to those compounds of Formula (I) and pharmaceutically acceptable addition salts, and solvates thereof, or any subgroup thereof as mentioned in any of the other embodiments, wherein
Het represents (a-7); optionally substituted as defined in any of the other embodiments.

In an embodiment, the present invention relates to those compounds of Formula (I) and pharmaceutically acceptable addition salts, and solvates thereof, or any subgroup thereof as mentioned in any of the other embodiments, wherein L represents —$CH_2$—.

In an embodiment, the present invention relates to those compounds of Formula (I) and pharmaceutically acceptable addition salts, and solvates thereof, or any subgroup thereof as mentioned in any of the other embodiments, wherein L represents —O—$CH_2$—.

In an embodiment, the present invention relates to those compounds of Formula (I) and pharmaceutically acceptable addition salts, and solvates thereof, or any subgroup thereof as mentioned in any of the other embodiments, wherein L represents —$CH_2$—O—.

In an embodiment, the present invention relates to those compounds of Formula (I) and pharmaceutically acceptable addition salts, and solvates thereof, or any subgroup thereof as mentioned in any of the other embodiments, wherein L represents —O—.

In an embodiment, the present invention relates to those compounds of Formula (I) and pharmaceutically acceptable addition salts, and solvates thereof, or any subgroup thereof as mentioned in any of the other embodiments, wherein
L represents —$CH_2$— or —O—$CH_2$—.

In an embodiment, the present invention relates to those compounds of Formula (I) and pharmaceutically acceptable addition salts, and solvates thereof, or any subgroup thereof as mentioned in any of the other embodiments, wherein
L represents —$CH_2$—O— or —O—.

In an embodiment, the present invention relates to those compounds of Formula (I) and pharmaceutically acceptable addition salts, and solvates thereof, or any subgroup thereof as mentioned in any of the other embodiments, wherein
L represents —$CH_2$—, —O—$CH_2$—, —$CH_2$—O—, or —O—.

In an embodiment, the present invention relates to those compounds of Formula (I) and pharmaceutically acceptable addition salts, and solvates thereof, or any subgroup thereof as mentioned in any of the other embodiments, wherein the compounds of Formula (I) are restricted to compounds of Formula (I-x):

(I-x)

It will be clear that all variables in the structure of Formula (I-x), may be defined as defined for the compounds of Formula (I) or any subgroup thereof as mentioned in any of the other embodiments.

In an embodiment, the present invention relates to those compounds of Formula (I) and pharmaceutically acceptable addition salts, and solvates thereof, or any subgroup thereof as mentioned in any of the other embodiments, wherein the compounds of Formula (I) are restricted to compounds of Formula (I-y):

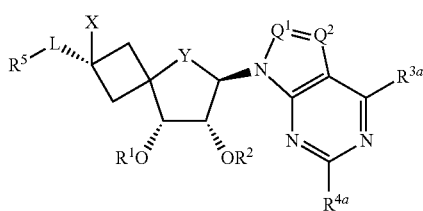

(I-y)

It will be clear that all variables in the structure of Formula (I-y), may be defined as defined for the compounds of Formula (I) or any subgroup thereof as mentioned in any of the other embodiments.

In an embodiment, the present invention relates to a subgroup of Formula (I) as defined in the general reaction schemes.

In an embodiment the compound of Formula (I) is selected from the group consisting of compounds 2, 5 and 6.

In an embodiment the compound of Formula (I) is selected from the group consisting of compounds 2, 5 and 6, and pharmaceutically acceptable addition salts, and solvates thereof.

In an embodiment the compound of Formula (I) is selected from the group consisting of any of the exemplified compounds, and the free bases, the pharmaceutically acceptable addition salts, and the solvates thereof.

All possible combinations of the above-indicated embodiments are considered to be embraced within the scope of this invention.

In another embodiment, the present invention relates to intermediates of Formula (XXX)

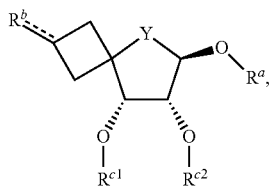

(XXX)

wherein
Y represents —O—, —CH$_2$— or —CF$_2$—;
R$^a$ represents hydrogen or a hydroxyl protecting group such as for example C$_{1-4}$alkyl, t-butyldimethylsilyl, C$_{1-4}$alkyl-O—C$_{1-4}$alkyl, tetrahydropyranyl, allyl, t-butyldiphenylsilyl, benzyl, —C(=O)—C$_{1-4}$alkyl, or —C(=O)-phenyl;
R$^b$ represents —OH, =O, —CH$_2$—OH, or =CH$_2$;
wherein the bond towards R$^b$ ⚌ represents a single bond in case R represents —OH or —CH$_2$—OH, or a double bond in case R$^b$ represents =O or =CH$_2$;
R$^{c1}$ and R$^{c2}$ represent —C(=O)—C$_{1-4}$alkyl, benzoyl optionally substituted with one or two substituents each independently selected from —CH$_3$ and —OCH$_3$, benzyl optionally substituted with one or two substituents each independently selected from —CH$_3$ and —OCH$_3$, or —CH$_2$-napthyl optionally substituted with one or two substituents each independently selected from —CH$_3$ and —OCH$_3$;
or R$^{c1}$ and R$^{c2}$ taken together represent —C(C$_{1-4}$alkyl)$_2$-;
and pharmaceutically acceptable addition salts, and solvates thereof.

In another embodiment, the present invention relates to intermediates of Formula (XXX), wherein
Y represents —O—, —CH$_2$— or —CF$_2$—;
R$^a$ represents hydrogen or a hydroxyl protecting group such as for example C$_{1-4}$alkyl, t-butyldimethylsilyl, C$_{1-4}$alkyl-O—C$_{1-4}$alkyl, tetrahydropyranyl,
allyl, t-butyldiphenylsilyl, benzyl, —C(=O)—C$_{1-4}$alkyl, or —C(=O)-phenyl;
R$^b$ represents —OH, =O, —CH$_2$—OH, or =CH$_2$;
wherein the bond towards R$^b$ ⚌ represents a single bond in case R$^b$ represents —OH or —CH$_2$—OH, or a double bond in case R$^b$ represents =O or =CH$_2$;
R$^{c1}$ and R$^{c2}$ represent —C(=O)—C$_{1-4}$alkyl;
or R$^{c1}$ and R$^{c2}$ taken together represent —C(C$_{1-4}$alkyl)$_2$-;
and pharmaceutically acceptable addition salts, and solvates thereof.

Similar as for compounds of Formula (I), the term "intermediates of Formula (XXX)" is meant to include the stereoisomers thereof and the tautomeric forms thereof.

The skilled person will understand that in case R$^{c1}$ and R$^{c2}$ taken together represent —C(C$_{1-4}$alkyl)$_2$-, the intermediates of Formula (XXX) are restricted to the intermediates of Formula (XXX-A)

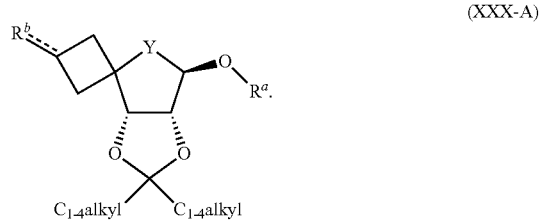

(XXX-A)

The skilled person will understand that in case R$^{c1}$ and R$^{c2}$ represent —C(=O)—C$_{1-4}$alkyl, the intermediates of Formula (XXX) are restricted to the intermediates of Formula (XXX-B)

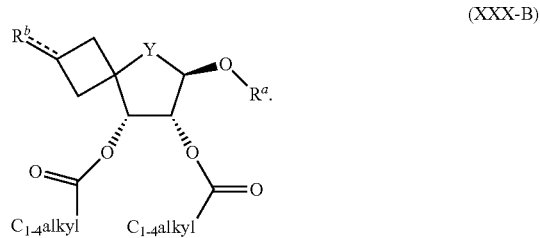

(XXX-B)

In an embodiment, the present invention relates to those intermediates of Formula (XXX) and pharmaceutically acceptable addition salts, and solvates thereof, or any subgroup thereof as mentioned in any of the other embodiments, wherein the intermediates of Formula (XXX) are restricted to intermediates of Formula (XXX-C), (XXX-D), (XXX-E), (XXX-F), (XXX-G), (XXX-H), (XXX-I), and (XXX-J):

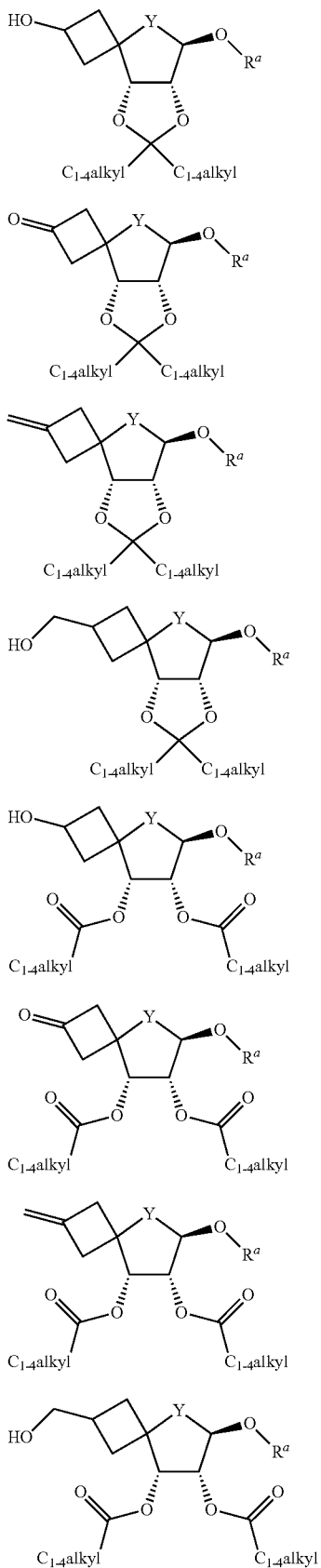

It will be clear that all variables in the structures of Formula (XXX-A), (XXX-B), (XXX-C), (XXX-D), (XXX-E), (XXX-F), (XXX-G), (XXX-H), (XXX-I), and (XXX-J) may be defined as defined for the intermediates of Formula (XXX) or any subgroup thereof as mentioned in any of the other embodiments.

In an embodiment, the present invention relates to those intermediates of Formula (XXX) and pharmaceutically acceptable addition salts, and solvates thereof, or any subgroup thereof as mentioned in any of the other embodiments, wherein Y represents —O—.

In an embodiment, the present invention relates to those intermediates of Formula (XXX) and pharmaceutically acceptable addition salts, and solvates thereof, or any subgroup thereof as mentioned in any of the other embodiments, wherein Y represents —CH$_2$— or —CF$_2$—.

In an embodiment, the present invention relates to those intermediates of Formula (XXX) and pharmaceutically acceptable addition salts, and solvates thereof, or any subgroup thereof as mentioned in any of the other embodiments, wherein R$^a$ represents hydrogen, C$_{1-4}$alkyl, t-butyldimethylsilyl, C$_{1-4}$alkyl-O—C$_{1-4}$alkyl, tetrahydropyranyl, allyl, t-butyldiphenylsilyl, benzyl, —C(=O)—C$_{1-4}$alkyl, or —C(=O)-phenyl.

In an embodiment, the present invention relates to those intermediates of Formula (XXX) and pharmaceutically acceptable addition salts, and solvates thereof, or any subgroup thereof as mentioned in any of the other embodiments, wherein R$^a$ represents hydrogen, C$_{1-4}$alkyl, or t-butyldimethylsilyl.

All possible combinations of the above-indicated embodiments are considered to be embraced within the scope of this invention.

In an embodiment, the invention relates to the use of intermediates of Formula (XXX) and pharmaceutically acceptable addition salts, and solvates thereof, in the synthesis of compounds of Formula (I) and pharmaceutically acceptable addition salts, and solvates thereof.

Methods for the Preparation

In this section, as in all other sections unless the context indicates otherwise, references to Formula (I) also include all other sub-groups and examples thereof as defined herein.

The general preparation of some typical examples of the compounds of Formula (I) is described hereunder and in the specific examples. Compounds of Formula (I) are generally prepared from starting materials which are either commercially available, prepared by standard synthetic processes commonly used by those skilled in the art, or prepared as described in the specific examples. The following schemes are only meant to represent examples of the invention and are in no way meant to be a limit of the invention.

Alternatively, compounds of the present invention may also be prepared by analogous reaction protocols as described in the general schemes below, combined with standard synthetic processes commonly used by those skilled in the art of organic chemistry, or combined with synthetic processes as described in WO2017/153186 and WO2017/032840.

The skilled person will understand that compounds wherein "Y represents —CF$_2$—" can in general be prepared according to analogous reaction protocols as described in the general schemes wherein "Y represents —CH$_2$—".

The skilled person will realize that in the reactions described in the Schemes, it may be necessary to protect reactive functional groups, for example hydroxy, amino, or carboxy groups, where these are desired in the final product, to avoid their unwanted participation in the reactions. Conventional protecting groups can be used in accordance with standard practice. This is illustrated in the specific examples. For example the skilled person will realize that for some reactions (such as e.g. Scheme 3 step 4) the amino group has to be protected first by using N,N-dimethylformamide dimethyl acetal, and is deprotected again after reaction. Typical reaction conditions are described in the specific examples.

The skilled person will realize that in the reactions described in the Schemes, it may be advisable or necessary to perform the reaction under an inert atmosphere, such as for example under $N_2$-gas atmosphere, for example when NaH is used in the reaction.

It will be apparent for the skilled person that it may be necessary to cool the reaction mixture before reaction work-up (refers to the series of manipulations required to isolate and purify the product(s) of a chemical reaction such as for example quenching, column chromatography, extraction).

The skilled person will realize that heating the reaction mixture under stirring may enhance the reaction outcome. In some reactions microwave heating may be used instead of conventional heating to shorten the overall reaction time.

The skilled person will realize that another sequence of the chemical reactions shown in the Schemes below, may also result in the desired compound of Formula (I).

The skilled person will realize that intermediates and compounds shown in the schemes below may be further functionalized according to methods well-known by the person skilled in the art. For example, compounds wherein $R^{3a}$ represents Cl, can be converted into compounds wherein $R^{3a}$ represents $NH_2$ by reaction with $NH_3$ (e.g. 25% in water) in a typical solvent such as for example dioxane, at a typical temperature of about 100° C. For example, compounds of Formula (I) wherein $R^1$ and $R^2$ represent hydrogen can be converted into compounds of Formula (I) wherein $R^1$ and $R^2$ represent —C(=O)—$C_{1-4}$alkyl.

The skilled person will realize that more Compounds of Formula (I) can be prepared by using similar synthetic protocols as described in the Schemes below.

In case one of the starting materials is available as a salt form, the skilled person will realize that it may be necessary to first treat the salt with a base, such as for example N,N-diisopropylethylamine (DIPEA).

All variables are defined as mentioned hereabove unless otherwise is indicated or is clear from the context.

In general, compounds of Formula (I-a) and (I-b) can be prepared according to Scheme 1:

General scheme 1

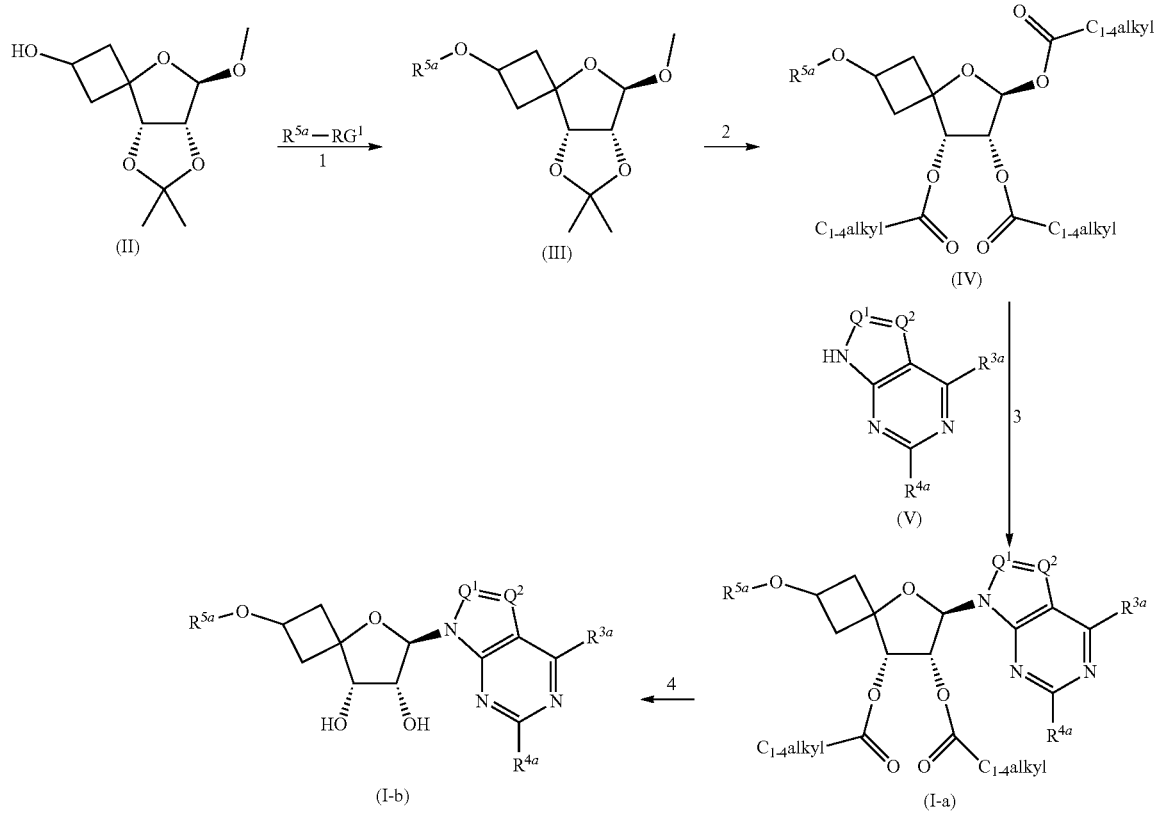

In scheme 1, 'RG$^1$' is defined as a suitable reactive group such as for example hydroxy; 'R$^{5a}$' is defined as Ar or Het; and all other variables in Scheme 1 are defined according to the scope of the present invention.

In scheme 1, the following reaction conditions typically apply:

1: An intermediate of Formula (II) is reacted with $R^{5a}$-RG$^1$; typically in the presence of triphenylphosphine (PPh$_3$), diisopropyl azodicarboxylate (DIAD) or diethyl azodicarboxylate (DEAD), in a suitable solvent such as for example anhydrous THF at a suitable temperature such as for example room temperature (r.t.);

2: first in the presence of a suitable acid, such as for example HCl (e.g. 37% in H$_2$O; 1M solution; or 2M solution; each optionally in the presence of an organic co-solvent such as methanol), at a suitable temperature such as for example between room temperature and 90° C.; subsequently in the presence of suitable acid anhydride of formula (C$_4$alkylC=O)$_2$O with a suitable solvent such as pyridine at a suitable temperature such as for example room temperature;

3: An intermediate of Formula (IV) is reacted with an intermediate of Formula (V), typically in the presence of a reagent such as for example N,O-bis(trimethylsilyl)acet-amide (BSA), a reagent such as for example trimethylsilyl trifluoromethanesulfonate (TMSOTf), in a solvent such as for example anhydrous CH$_3$CN; typically at a temperature between r.t. and 100° C.;

4: A Compound of Formula (I-a) can be reacted to a Compound of Formula (I-b) in the presence of a base such as for example NH$_3$ (e.g. 25% in H$_2$O) optionally in the presence of a solvent such as dioxane at a suitable temperature such as for example between 0° C.-140° C. In particular, when R$^{3a}$ represents Cl, the reaction conditions described in step 4 at lower temperatures within the temperature range will preserve Cl in the R$^{3a}$ position, while the reaction conditions described in step 4 at higher temperatures within the temperature range will convert the Cl to an amino group.

The starting materials in scheme 1 are commercially available or can be prepared by standard means obvious to those skilled in the art or as described in following general schemes or specific examples.

In general, compounds of Formula (I-c), (I-d) and (I-e) can be prepared according to Scheme 2:

General scheme 2

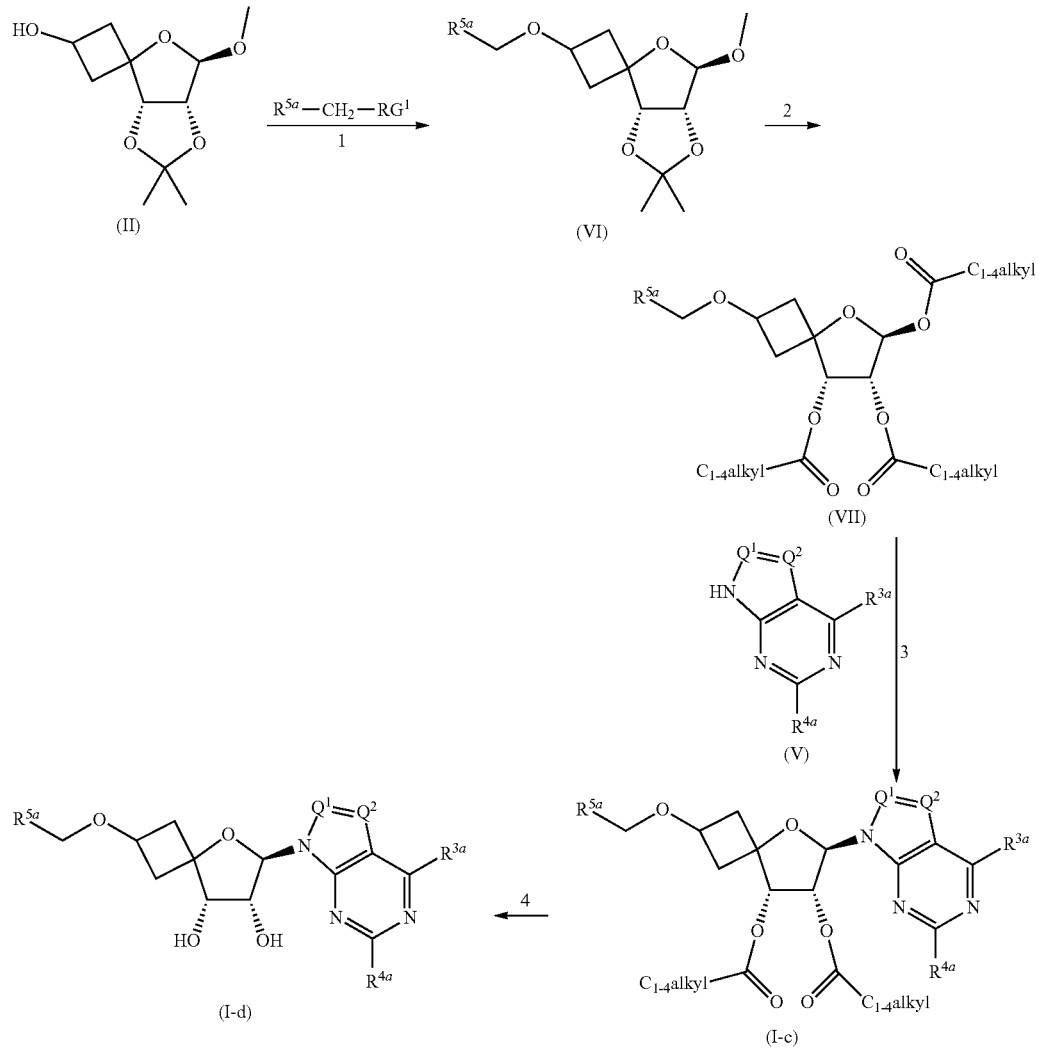

In scheme 2, 'RG$^1$' is defined as a suitable reactive group such as for example bromo; 'R$^{5a}$' is defined as Ar or Het; and all other variables in Scheme 2 are defined according to the scope of the present invention.

In scheme 2, the following reaction conditions typically apply:

1: An intermediate of Formula (II) is reacted with $R^{5a}$—$CH_2$—$RG^1$; typically in the presence of a base such as NaH or potassium tert-butoxide (KOtBu), in a suitable solvent such as for example anhydrous N,N-dimethylformamide (DMF) or THF at a suitable temperature such as for example room temperature;

2: first in the presence of a suitable acid, such as for example HCl (e.g. 37% in $H_2O$; 1M solution; or 2M solution; each optionally in the presence of an organic co-solvent such as methanol), at a suitable temperature such as for example between room temperature and 90° C.;

as for example $NH_3$ (e.g. 25% in $H_2O$) optionally in the presence of a solvent such as dioxane at a suitable temperature such as for example between 0° C.-140° C. In particular, when $R^{3a}$ represents Cl, the reaction conditions described in step 4 at lower temperatures within the temperature range will preserve Cl in the $R^{3a}$ position, while the reaction conditions described in step 4 at higher temperatures within the temperature range will convert the Cl to an amino group.

Alternatively compounds of Formula (I-b) can be prepared according to Scheme 3 via compounds of Formula (I-f):

General scheme 3

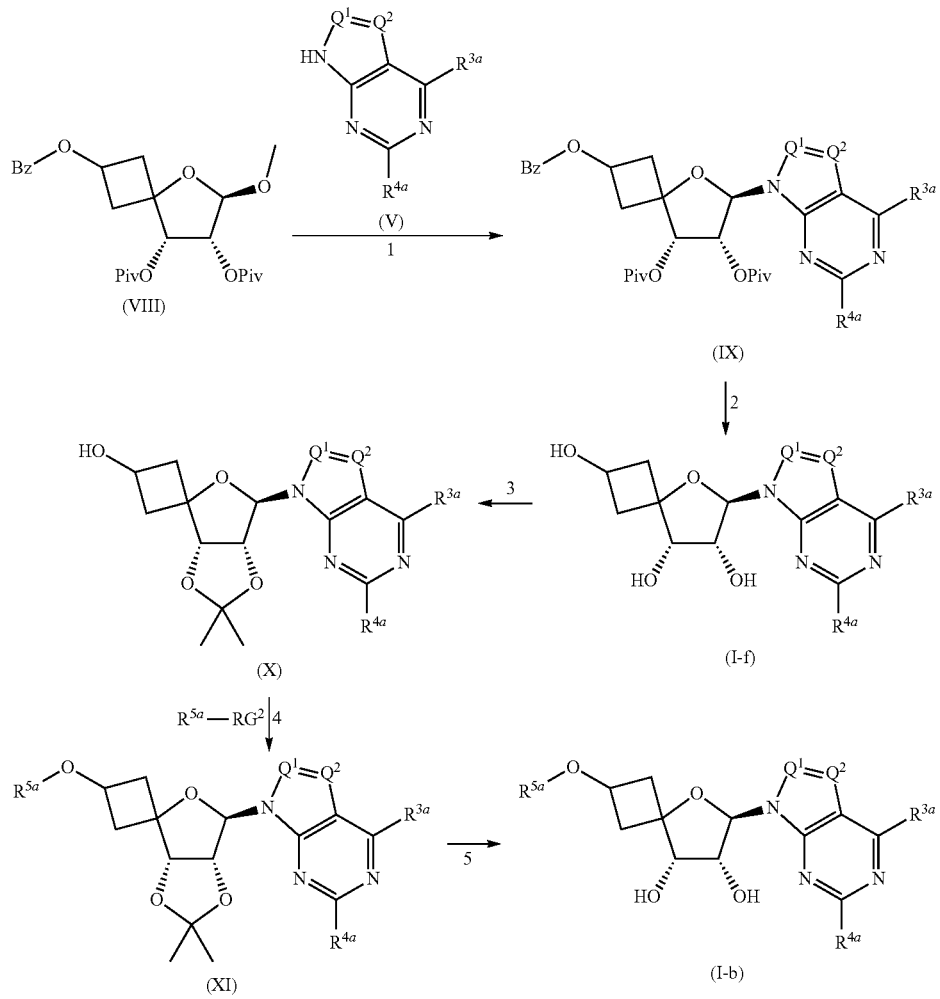

subsequently in the presence of suitable acid anhydride of formula $(C_{1-4}alkylC=O)_2O$ with a suitable solvent such as pyridine at a suitable temperature such as for example room temperature;

3: An intermediate of Formula (VII) is reacted with an intermediate of Formula (V), typically in the presence of a reagent such as for example BSA, a reagent such as for example TMSOTf, in a solvent such as for example anhydrous $CH_3CN$; typically at a temperature between r.t. and 100° C.;

4: A Compound of Formula (I-c) can be reacted to a Compound of Formula (I-d) in the presence of a base such In scheme 3, '$RG^2$' is defined as a suitable reactive group such as for example hydroxy; '$R^{5a}$' is defined as Ar or Het; 'Piv' means pivaloyl, 'Bz' means benzoyl; and all other variables in Scheme 3 are defined according to the scope of the present invention.

In scheme 3, the following reaction conditions apply:

1: An intermediate of Formula (VIII) can be reacted with an intermediate of Formula (V), typically in the presence of a reagent such as for example BSA, reagent such as for example TMSOTf, in a solvent such as for example anhydrous $CH_3CN$; typically at a temperature between r.t. and 100° C.;

2: An intermediate of Formula (IX) can be reacted to a Compound of Formula (I-f) in the presence of abase such as for example NH₃ (e.g. 25% in H₂O) optionally in the presence of a solvent such as dioxane at a suitable temperature such as for example between 0° C.-140° C. In particular, when $R^{3a}$ represents Cl, the reaction conditions described in step 2 at lower temperatures within the temperature range will preserve Cl in the $R^{3a}$ position, while the reaction conditions described in step 2 at higher temperatures within the temperature range will convert the Cl to an amino group.

3: A Compound of Formula (I-f) can be reacted to an intermediate of Formula (X), typically in the presence of 4-methylbenzenesulfonic acid (p-TsOH), in a solvent such as for example acetone; typically at r.t.;

4: typically in the presence of triphenylphosphine (PPh₃), diisopropyl azodicarboxylate (DIAD) or diethyl azodicarboxylate (DEAD), in a suitable solvent such as for example anhydrous THF at a suitable temperature such as for example room temperature (r.t.);

5: in the presence of a suitable acid, such as for example 4M HCl in dioxane or 4M HCl in MeOH, with a suitable solvent such as for example MeOH at a suitable temperature such as for example room temperature; or alternatively in the presence of a suitable acid such as for example trifluoroacetic acid (TFA) in dichloromethane (DCM) at a suitable temperature, or acetic acid in THF and water at a suitable temperature such as for example room temperature.

In general, compounds of Formula (I-h) can be prepared according to Scheme 4:

General scheme 4

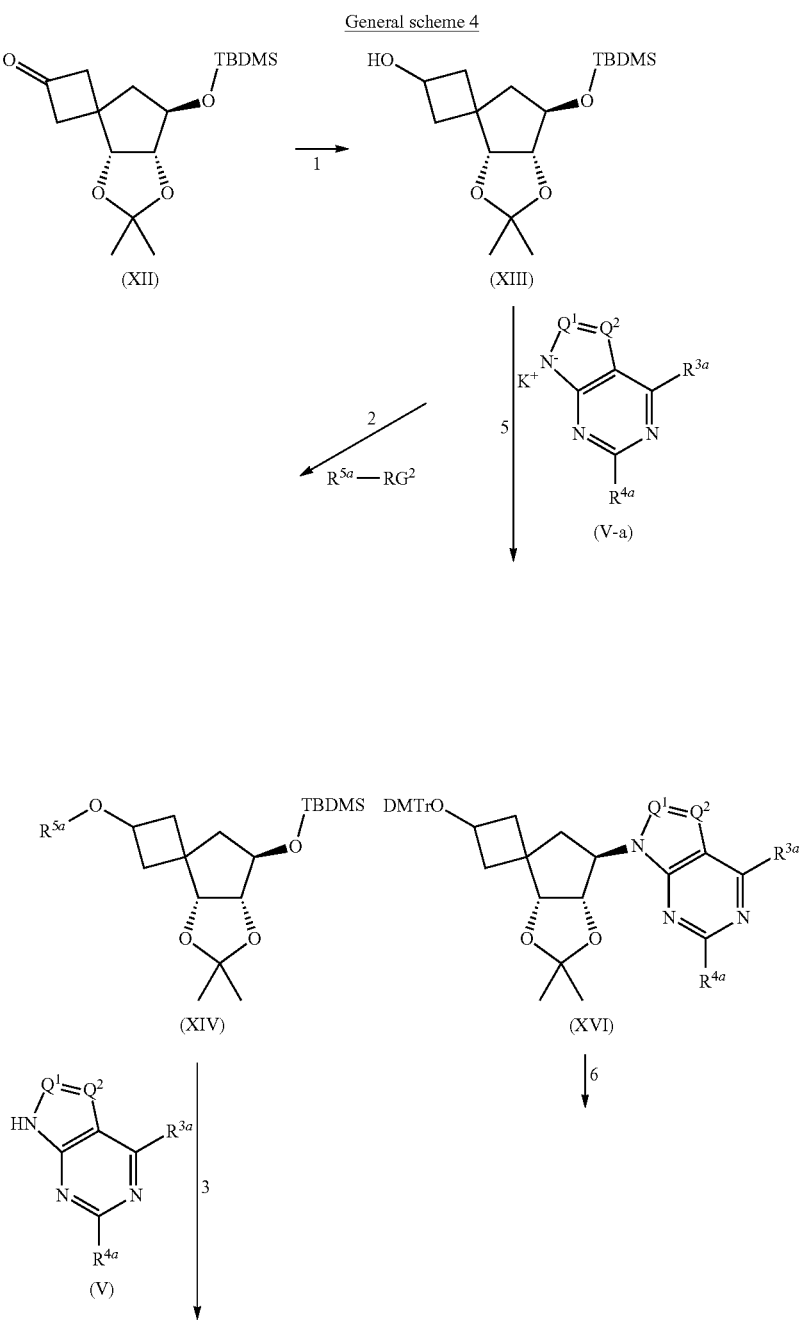

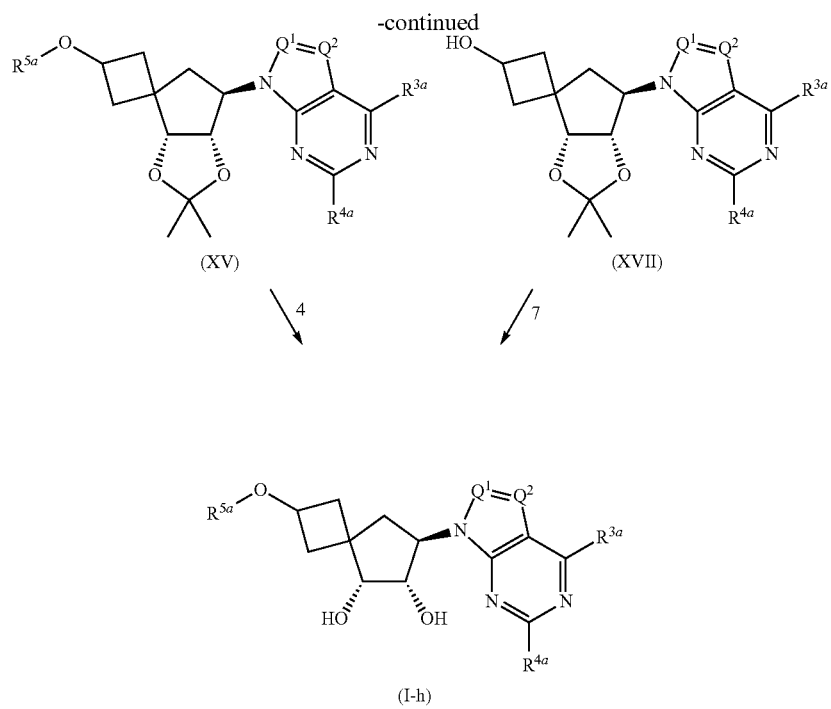

In scheme 4, 'RG²' is defined as a suitable reactive group such as for example hydroxy; 'TBDMS' is defined as t-butyldimethylsilyl; 'DMTr' is defined as dimethoxytrityl; 'R$^{5a}$' is defined as Ar or Het; and all other variables in Scheme 4 are defined according to the scope of the present invention.

In scheme 4, the following reaction conditions apply:

1: In the presence of a suitable reducing agent such as for example NaBH$_4$, in a suitable solvent such as for example methanol (MeOH), at a suitable temperature such as for example 0° C.;

2: typically in the presence of triphenylphosphine (PPh), diisopropyl azodicarboxylate (DIAD) or diethyl azodicarboxylate (DEAD), in a suitable solvent such as for example anhydrous THF at a suitable temperature such as for example room temperature (r.t.):

3: typically first silyl deprotection in the presence of a reagent such as for example tetrabutylammonium fluoride (TBAF); in a suitable solvent such as for example THF; at a suitable temperature such as for example r.t.;

subsequently, reaction with a suitable reagent such as for example Tf$_2$O (triflic anhydride or trifluoromethanesulfonic anhydride), in a suitable solvent such as for example dichloromethane (DCM) at a suitable temperature such as for example 0° C.; finally reaction with an intermediate of Formula (V) in the presence of a base such as for example potassium tert-butoxide, in a suitable solvent such as for example DMF, at a suitable temperature such as for example between −10° C. and 0° C.;

4: in the presence of a suitable acid, such as for example HCl aqueous 1M, or 4M HCl in MeOH, with a suitable solvent such as for example MeOH or ethanol (EtOH) at a suitable temperature such as for example room temperature; or alternatively in the presence of a suitable acid such as for example trifluoroacetic acid (TFA) in dichloromethane (DCM) at a suitable temperature, or acetic acid in THF and water at a suitable temperature such as for example room temperature;

5: typically first silyl deprotection in the presence of a reagent such as for example tetrabutylammonium fluoride (TBAF); in a suitable solvent such as for example THF; at a suitable temperature such as for example r.t.;

subsequently typically in the presence of DMTrCl (dimethoxytrityl chloride) in a solvent such as for example pyridine at a temperature such as room temperature; subsequently, reaction with a suitable reagent such as for example Tf$_2$O (triflic anhydride or trifluoromethanesulfonic anhydride), in a suitable solvent such as for example pyridine at a suitable temperature such as for example 0° C.;

finally reaction with an intermediate of Formula (V-a) in the presence of a suitable solvent such as for example dimetylacetamide (DMA), at a suitable temperature such as for example between 0° C. and r.t.;

6: dimethoxytrityl deprotection in the presence of an acid such as for example formic acid (typically 80% in H$_2$O) in a suitable solvent such as for example CH$_3$CN, at a suitable temperature such as for example r.t.;

7: typically first in the presence of triphenylphosphine (PPh$_3$), diisopropyl azodicarboxylate (DIAD) or diethyl azodicarboxylate (DEAD), in a suitable solvent such as for example anhydrous THF at a suitable temperature such as for example room temperature (r.t.);

and then typically a second step in the presence of a suitable acid, such as for example HCl aqueous 1M, or 4M HCl in MeOH, with a suitable solvent such as for example MeOH or ethanol (EtOH) at a suitable temperature such as for example room temperature; or alternatively in the presence of a suitable acid such as for example trifluoroacetic acid (TFA) in dichloromethane (DCM) at a suitable temperature, or acetic acid in THF and water at a suitable temperature such as for example room temperature.

In general, compounds of Formula (I-g) can be prepared according to Scheme 6:

General scheme 5

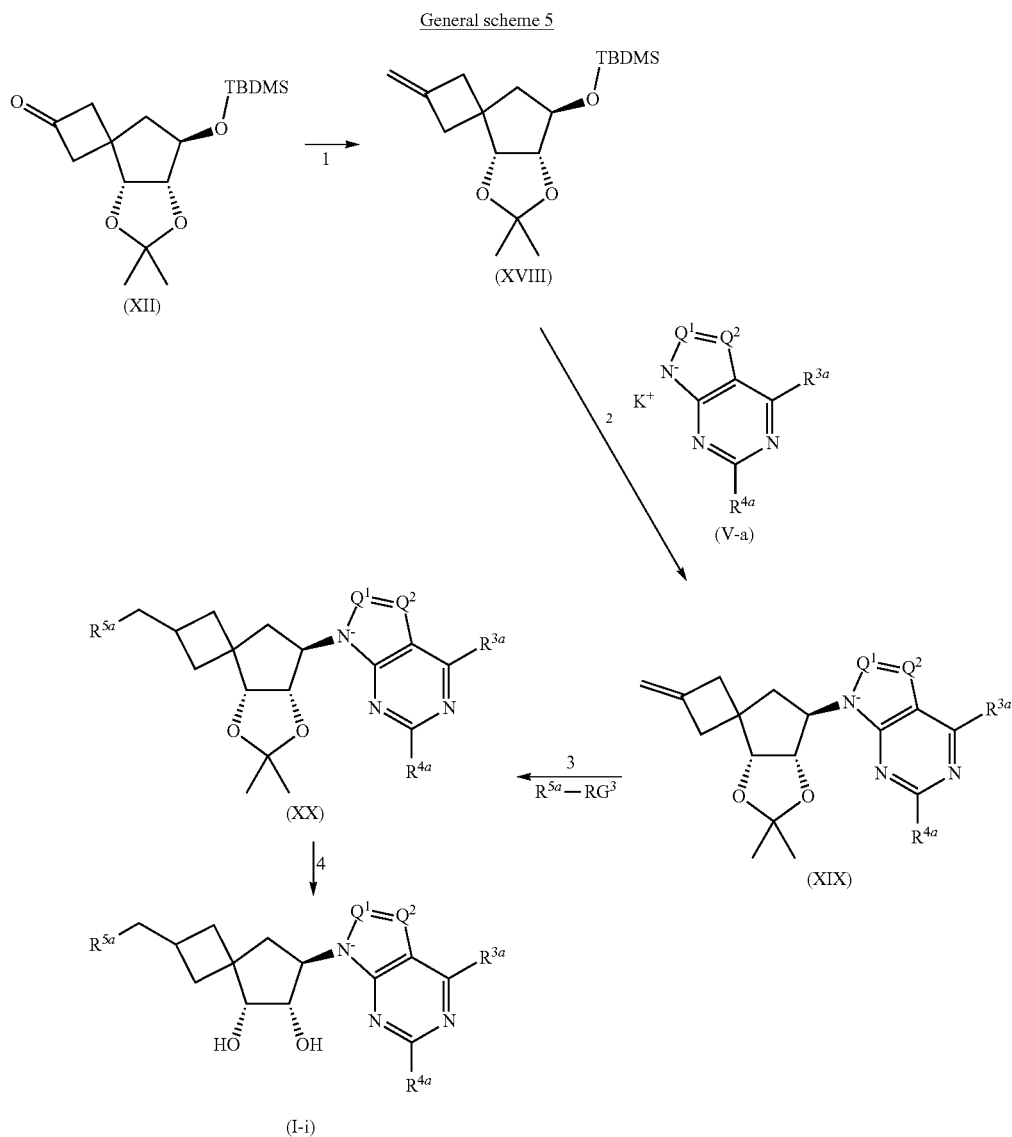

In scheme 5, 'RG³' is defined as a suitable reactive group such as for example iodo or bromo; 'TBDMS' is defined as t-butyldimethylsilyl; 'DMTr' is defined as dimethoxytrityl; '$R^{5a}$' is defined as Ar or Het; and all other variables in Scheme 5 are defined according to the scope of the present invention.

In scheme 5, the following reaction conditions apply:

1: In the presence of a reagent such as for example methyltriphenylphosphonium bromide (MePPh$_3$⁺Br⁻), in the presence of a base such as for example potassium tert-butoxide (KOtBu), in a solvent such as for example THF, at a suitable temperature such as for example between 0° C. and r.t.;

2: typically first silyl deprotection in the presence of a reagent such as for example tetrabutylammonium fluoride (TBAF); in a suitable solvent such as for example THF; at a suitable temperature such as for example r.t.;

subsequently, reaction with a suitable reagent such as for example Tf$_2$O (triflic anhydride or trifluoromethanesulfonic anhydride), in a suitable solvent such as for example dichloromethane (DCM) at a suitable temperature such as for example 0° C.; finally reaction with an intermediate of Formula (V-a) in a suitable solvent such as for example DMF, at a suitable temperature such as for example between –0° C. and r.t.;

3: in a first step in the presence of an alkene precursor of formula (XIX) and a 9-BBN solution 0.5 M in THF typically under nitrogen atmosphere at a temperature between room temperature and reflux and a reaction time between 30 minutes to 3 hours. In a second step in the presence of suitable $R^{5a}$-RG³ ('RG³' is defined as a suitable reactive group such as for example iodo or bromo) and a suitable catalyst as for example 1,1'-bis(diphenylphosphino)ferrocene]dichloropalladium(II) or 1,1'-bis(di-tert-butylphosphino)ferrocene palladium dichloride, and in the presence of a suitable base as for example potassium phosphate tribasic in a suitable solvent mixture as for example THF, at a suitable temperature between 50° C. and reflux and a suitable reaction time between 1 and 3 hours;

4: typically in the presence of a suitable acid, such as for example HCl aqueous 1M, or 4M HCl in MeOH, with a suitable solvent such as for example MeOH or ethanol (EtOH) at a suitable temperature such as for example room temperature; or alternatively in the presence of a suitable acid such as for example trifluoroacetic acid (TFA) in dichloromethane (DCM) at a suitable temperature, or acetic acid in THF and water at a suitable temperature such as for example room temperature.

In general, compounds of Formula (I-g) can be prepared according to Scheme 6:

3: typically in the presence of a suitable acid, such as for example HCl aqueous 1M, or 4M HCl in MeOH, with a suitable solvent such as for example MeOH or ethanol (EtOH) at a suitable temperature such as for example room temperature; or alternatively in the presence of a suitable acid such as for example trifluoroacetic acid (TFA) in dichloromethane (DCM) at a suitable temperature, or acetic acid in THF and water at a suitable temperature such as for example room temperature.

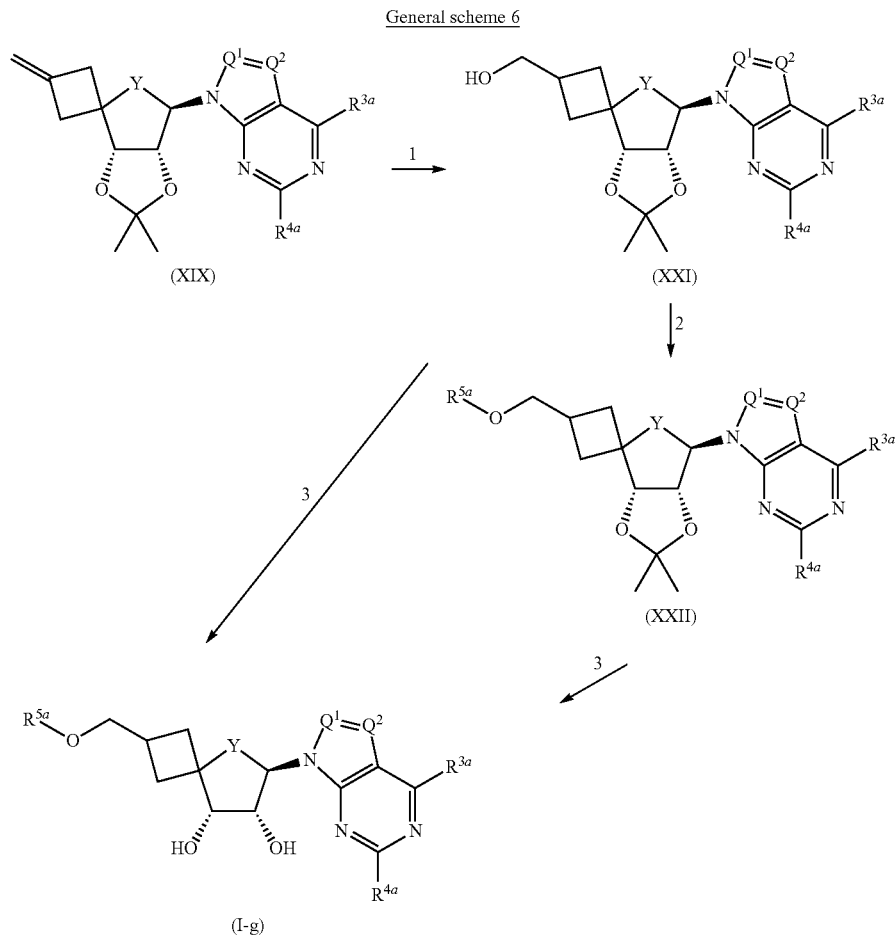

In scheme 6, '$R^5$' is defined according to the scope, '$R^5$' is defined as Ar or Het; and all other variables in Scheme 6 are defined according to the scope of the present invention.

In scheme 6, the following reaction conditions apply:

1: in a first step in the presence of an alkene precursor of formula (XIX) and a 9-BBN solution 0.5 M in THF typically under nitrogen atmosphere at a temperature between room temperature and reflux and a reaction time between 30 minutes to 3 hours. In a second step in the presence of an aqueous base such as for example aqueous NaOH, in the presence of an oxidizing agent such as for example $H_2O_2$, typically at a temperature between 0° C. to r.t.;

2: typically in the presence of triphenylphosphine ($PPh_3$), diisopropyl azodicarboxylate (DIAD) or diethyl azodicarboxylate (DEAD), in a suitable solvent such as for example anhydrous THF at a suitable temperature such as for example room temperature (r.t.);

In general, intermediates of Formula (XXIV) and (XXV) can be prepared according to Scheme 7:

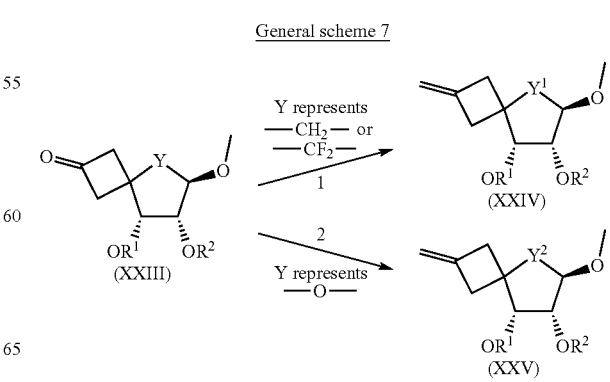

In scheme 7, 'Y$^1$' represents —CH$_2$— or —CF$_2$—, 'Y$^2$' represents —O—, and all other variables are defined according to the scope of the present invention.

1: (when Y is limited to Y$^1$) in the presence of methyltriphenylphosphonium bromide, a suitable base such as for example KOtBu, in a typical solvent such as for example THF, at r.t.

2: (when Y is limited to Y$^2$) in the presence of bis(cyclopentadienyl)dimethyltitanium (CAS: 1271-66-5), in a typical solvent such as for example THF, at a typical temperature such as 70° C.

The skilled person will realize that intermediates of Formula (XXIV) and (XXV) can be used in the synthesis of compounds of Formula (I), and can be used directly or indirectly (first conversion to other intermediate) in reactions such as any of the other General schemes, in particular reactions of General schemes 5 and 6.

In all these preparations, the reaction products may be isolated from the reaction medium and, if necessary, further purified according to methodologies generally known in the art such as, for example, extraction, crystallization, trituration and chromatography.

The chirally pure forms of the compounds of Formula (I) form a preferred group of compounds. It is therefore that the chirally pure forms of the intermediates and their salt forms are particularly useful in the preparation of chirally pure compounds of Formula (I). Also enantiomeric mixtures of the intermediates are useful in the preparation of compounds of Formula (I) with the corresponding configuration.

Pharmacology

It has been found that the compounds of the present invention inhibit PRMT5 activity.

In particular compounds of the present invention bind to the PRMT5 enzyme, and competitively with natural substrate SAM (S-adenosyl-L-methionine), to inhibit such enzyme.

It is therefore anticipated that the compounds according to the present invention or pharmaceutical compositions thereof may be useful for treating or preventing, in particular treating, of diseases such as a blood disorder, metabolic disorders, autoimmune disorders, cancer, inflammatory diseases, cardiovascular diseases, neurodegenerative diseases, pancreatitis, multiorgan failure, kidney diseases, platelet aggregation, sperm motility, transplantation rejection, graft rejection, lung injuries and the like.

In particular the compounds according to the present invention or pharmaceutical compositions thereof may be useful for treating or preventing, in particular treating, of diseases such as allergy, asthma, hematopoietic cancer, lung cancer, prostate cancer, melanoma, metabolic disorder, diabetes, obesity, blood disorder, sickle cell anemia, and the like.

The compounds according to the present invention or pharmaceutical compositions thereof may be useful for treating or preventing, in particular treating, of diseases such as a proliferative disorder, such as an autoimmune disease, cancer, a benign neoplasm, or an inflammatory disease.

The compounds according to the present invention or pharmaceutical compositions thereof may be useful for treating or preventing, in particular treating, of diseases such as a metabolic disorder comprising diabetes, obesity; a proliferative disorder comprising cancer, hematopoietic cancer, lung cancer, prostate cancer, melanoma, or pancreatic cancer; blood disorder; hemoglobinopathy; sickle cell anemia; β-thalassemia, an inflammatory disease, and autoimmune disease e.g. rheumatoid arthritis, systemic lupus erythematosus, Sjogren's syndrome, diarrhea, gastroesophageal reflux disease, and the like.

In some embodiments, the inhibition of PRMT5 by a provided compound may be useful in treating or preventing, in particular treating, the following non-limiting list of cancers: breast cancer, lung cancer, esophageal cancer, bladder cancer, hematopoietic cancer, lymphoma, medulloblastoma, rectum adenocarcinoma, colon adenocarcinoma, gastric cancer, pancreatic cancer, liver cancer, adenoid cystic carcinoma, lung adenocarcinoma, head and neck squamous cell carcinoma, brain tumors, hepatocellular carcinoma, renal cell carcinoma, melanoma, oligodendroglioma, ovarian clear cell carcinoma, and ovarian serous cystadenoma.

Examples of metabolic disorders which may be treated or prevented, in particular treated, include, but are not limited to, diabetes or obesity.

Examples of blood disorders which may be treated or prevented, in particular treated, include, but are not limited to, hemoglobinopathy, such as sickle cell disease or 3-thalassemia.

Examples of cancers which may be treated or prevented, in particular treated, include, but are not limited to, acoustic neuroma, adenocarcinoma, adrenal gland cancer, anal cancer, angiosarcoma (e.g., lymphangio sarcoma, lymphangioendothelio sarcoma, hemangio sarcoma), appendix cancer, benign monoclonal gammopathy, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), bronchus cancer, carcinoid tumor, cervical cancer (e.g., cervical adenocarcinoma), chordoma, choriocarcinoma, craniopharyngioma, colorectal cancer (e.g., colon cancer, rectal cancer, colorectal adenocarcinoma), epithelial carcinoma, ependymoma, endothelio sarcoma (e.g., Kaposi's sarcoma, multiple idiopathic hemorrhagic sarcoma), endometrial cancer (e.g., uterine cancer, uterine sarcoma), esophageal cancer (e.g., adenocarcinoma of the esophagus, Barrett's adenocarinoma), Ewing sarcoma, eye cancer (e.g., intraocular melanoma, retinoblastoma), familiar hypereosinophilia, gall bladder cancer, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC), throat cancer (e.g., pharyngeal cancer, laryngeal cancer, nasopharyngeal cancer, oropharyngeal cancer)), hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., "Waldenstrom's macro globulinemia"), immunoblastic large cell lymphoma, hairy cell leukemia (HCL), precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, anaplastic large cell lymphoma); a mixture of one or more leukemia/lymphoma as described above; and multiple myeloma (MM)), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, non-small cell lung cancer (NSCLC), squamous lung cancer (SLC), adenocarcinoma of the lung, Lewis lung carcinoma, lung neuroendocrine tumors: typical carcinoid, atypical carcinoid, small cell lung cancer (SCLC), and large cell neuroendocrine carcinoma), leiomyosarcoma (LMS), mastocytosis (e.g., systemic mastocytosis), myelodysplastic syndromes (MDS), mesothelioma, myeloproliferative disorder (MPD) (e.g., polycythemia Vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendoctrine tumor (GEP-NET), carcinoid tumor), osteosarcoma, ovarian cancer (e.g., cystadenocarcinoma, ovarian embryonal carcinoma, ovarian adenocarcinoma), papillary adenocarcinoma, pancreatic cancer (e.g., pancreatic andenocarcinoma, intraductal papillary mucinous neoplasm (IPMN), Islet cell tumors), penile cancer (e.g., Paget's disease of the penis and scrotum), pinealoma, primitive neuroectodermal tumor (PNT), prostate cancer (e.g., prostate adenocarcinoma), rectal cancer, rhabdomyosarcoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), urethral cancer, vaginal cancer, and vulvar cancer (e.g., Paget's disease of the vulva).

Examples of neurodegenerative diseases which may be treated or prevented, in particular treated, include, but are not limited to, motor neurone disease, progressive supranuclear palsy, corticobasal degeneration, Pick's disease, Alzheimer's disease, AIDS-related dementia, Parkinson's disease, amyotropic lateral sclerosis, retinitis pigmentosa, spinal muscular atropy, and cerebellar degeneration.

Examples of cardiovascular diseases which may be treated or prevented, in particular treated, include, but are not limited to, cardiac hypertrophy, restenosis, atherosclerosis, and glomerulonephritis.

Examples of inflammatory diseases which may be treated or prevented, in particular treated, include, but are not limited to, inflammation associated with acne, anemia (e.g., aplastic anemia, haemolytic autoimmune anaemia), rhinitis, asthma, arteritis (e.g., polyarteritis, temporal arteritis, periarteritis nodosa, Takayasu's arteritis), arthritis (e.g., crystalline arthritis, osteoarthritis, psoriatic arthritis, gouty arthritis, reactive arthritis, rheumatoid arthritis and Reiter's arthritis), upper respiratory tract disease, ankylosing spondylitis, amylosis, amyotrophic lateral sclerosis, autoimmune diseases, allergies or allergic reactions, atherosclerosis, bronchitis, bursitis, chronic prostatitis, conjunctivitis, Chagas disease, chronic obstructive pulmonary disease, diverticulitis, cermatomyositis, diabetes (e.g., type I diabetes mellitus, type 2 diabetes mellitus), a skin condition (e.g., psoriasis, eczema, eczema hypersensitivity reactions, burns, dermatitis, pruritus (itch)), endometriosis, Guillain-Barre syndrome, infection, ischaemic heart disease, Kawasaki disease, glomerulonephritis, gingivitis, hypersensitivity, headaches (e.g., migraine headaches, tension headaches), ileus (e.g., postoperative ileus and ileus during sepsis), idiopathic thrombocytopenic purpura, interstitial cystitis (painful bladder syndrome), gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)), lupus, morphea, myeasthenia gravis, myocardial ischemia, multiple sclerosis, nephrotic syndrome, pemphigus vulgaris, pernicious aneaemia, peptic ulcers, polymyositis, primary biliary cirrhosis, neuroinflammation associated with brain disorders (e.g., Parkinson's disease, Huntington's disease, and Alzheimer's disease), prostatitis, chronic inflammation associated with cranial radiation injury, pelvic inflammatory disease, reperfusion injury, regional enteritis, rheumatic fever, systemic lupus erythematosus, scheroderma, scierodoma, sarcoidosis, spondyloarthopathies, Sjogren's syndrome, thyroiditis, transplantation rejection, tendonitis, trauma or injury (e.g., frostbite, chemical irritants, toxins, scarring, burns, physical injury), vasculitis, vitiligo and Wegener's granulomatosis.

In particular the inflammatory disease is an acute inflammatory disease (e.g., for example, inflammation resulting from infection). In particular the inflammatory disease is a chronic inflammatory disease (e.g., conditions resulting from asthma, arthritis and inflammatory bowel disease). The compounds may also be useful in treating inflammation associated with trauma and non-inflammatory myalgia. The compounds may also be useful in treating inflammation associated with cancer.

Examples of autoimmune diseases which may be treated or prevented, in particular treated, include, but are not limited to, arthritis (including rheumatoid arthritis, spondyloarthopathies, gouty arthritis, degenerative joint diseases such as osteoarthritis, systemic lupus erythematosus, Sjogren's syndrome, ankylosing spondylitis, undifferentiated spondylitis, Behcet's disease, haemolytic autoimmune anaemias, amyotrophic lateral sclerosis, amylosis, multiple sclerosis, acute painful shoulder, psoriatic, and juvenile arthritis), asthma, atherosclerosis, osteoporosis, bronchitis, tendonitis, bursitis, skin condition (e.g., psoriasis, eczema, eczema hypersensitivity reactions, burns, dermatitis, pruritus (itch)), enuresis, eosinophilic disease, gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)), and disorders ameliorated by a gastroprokinetic agent (e.g., ileus, postoperative ileus and ileus during sepsis; gastroesophageal reflux disease (GORD, or its synonym GERD); eosinophilic esophagitis, gastroparesis such as diabetic gastroparesis; food intolerances and food allergies and other functional bowel disorders, such as non-ulcerative dyspepsia (NUD) and non-cardiac chest pain (NCCP, including costo-chondritis)).

In a particular embodiment, a provided compound may be useful in somatic cell reprogramming, such as reprogramming somatic cells into stem cells. In a particular embodiment, a provided compound may be useful in germ cell development, and are thus envisioned useful in the areas of reproductive technology and regenerative medicine.

Other diseases which may be treated or prevented, in particular treated, include, but are not limited to, ischemic injury associated myocardial infarctions, immunological diseases, stroke, arrhythmia, toxin-induced or alcohol related liver diseases, aspirin-sensitive rhinosinusitis, cystic fibrosis, cancer pain, and haematological diseases, for example chronic anemia and aplastic anemia.

The compounds of the present invention may also have therapeutic applications in sensitising tumour cells for radiotherapy and chemotherapy.

Hence the compounds of the present invention may be used as "radiosensitizer" and/or "chemosensitizer" or can be given in combination with another "radiosensitizer" and/or "chemosensitizer".

The term "radiosensitizer", as used herein, is defined as a molecule, preferably a low molecular weight molecule, administered to animals in therapeutically effective amounts to increase the sensitivity of the cells to ionizing radiation and/or to promote the treatment of diseases which are treatable with ionizing radiation.

The term "chemosensitizer", as used herein, is defined as a molecule, preferably a low molecular weight molecule, administered to animals in therapeutically effective amounts to increase the sensitivity of cells to chemotherapy and/or promote the treatment of diseases which are treatable with chemotherapeutics.

Several mechanisms for the mode of action of radiosensitizers have been suggested in the literature including: hypoxic cell radiosensitizers (e.g., 2-nitroimidazole compounds, and benzotriazine dioxide compounds) mimicking oxygen or alternatively behave like bioreductive agents under hypoxia; non-hypoxic cell radiosensitizers (e.g., halogenated pyrimidines) can be analogoues of DNA bases and preferentially incorporate into the DNA of cancer cells and thereby promote the radiation-induced breaking of DNA molecules and/or prevent the normal DNA repair mechanisms; and various other potential mechanisms of action have been hypothesized for radiosensitizers in the treatment of disease.

Many cancer treatment protocols currently employ radiosensitizers in conjunction with radiation of x-rays. Examples of x-ray activated radiosensitizers include, but are not limited to, the following: metronidazole, misonidazole, desmethylmisonidazole, pimonidazole, etanidazole, nimorazole, mitomycin C, RSU 1069, SR 4233, EO9, RB 6145, nicotinamide, 5-bromodeoxyuridine (BUdR), 5-iododeoxyuridine (IUdR), bromodeoxycytidine, fluorodeoxyuridine (FudR), hydroxyurea, cisplatin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, Photofrin, benzoporphyrin derivatives, tin etioporphyrin, pheoborbide-a, bacteriochlorophyll-a, naphthalocyanines, phthalocyanines, zinc phthalocyanine, and therapeutically effective analogs and derivatives of the same.

Radiosensitizers may be administered in conjunction with a therapeutically effective amount of one or more other compounds, including but not limited to: compounds which promote the incorporation of radiosensitizers to the target cells; compounds which control the flow of therapeutics, nutrients, and/or oxygen to the target cells; chemotherapeutic agents which act on the tumour with or without additional radiation; or other therapeutically effective compounds for treating cancer or other diseases.

Chemosensitizers may be administered in conjunction with a therapeutically effective amount of one or more other compounds, including but not limited to: compounds which promote the incorporation of chemosensitizers to the target cells; compounds which control the flow of therapeutics, nutrients, and/or oxygen to the target cells; chemotherapeutic agents which act on the tumour or other therapeutically effective compounds for treating cancer or other disease. Calcium antagonists, for example verapamil, are found useful in combination with antineoplastic agents to establish chemosensitivity in tumor cells resistant to accepted chemotherapeutic agents and to potentiate the efficacy of such compounds in drug-sensitive malignancies.

The compounds of the present invention might also reduce the risk of cancer recurrence.

The invention relates to compounds of Formula (I) and pharmaceutically acceptable addition salts, and solvates thereof, for use as a medicament.

In an embodiment, the invention relates to intermediates of Formula (XXX) and pharmaceutically acceptable addition salts, and solvates thereof, for use as a medicament.

The invention relates to compounds of Formula (I) and pharmaceutically acceptable addition salts, and solvates thereof, for use in the inhibition of PRMT5 activity.

The compounds of the present invention can be "anti-cancer agents", which term also encompasses "anti-tumor cell growth agents" and "anti-neoplastic agents".

The invention relates to compounds of Formula (I) and pharmaceutically acceptable addition salts, and solvates thereof, for use in the treatment of diseases mentioned above.

The invention relates to compounds of Formula (I) and pharmaceutically acceptable addition salts, and solvates thereof, for the treatment or prevention, in particular for the treatment, of said diseases.

The invention relates to compounds of Formula (I) and pharmaceutically acceptable addition salts, and solvates thereof, for the treatment or prevention, in particular in the treatment, of PRMT5 mediated diseases or conditions.

The invention relates to compounds of Formula (I) and pharmaceutically acceptable addition salts, and solvates thereof, for the manufacture of a medicament.

The invention relates to compounds of Formula (I) and pharmaceutically acceptable addition salts, and solvates thereof, for the manufacture of a medicament for the inhibition of PRMT5.

The invention relates to compounds of Formula (I) and pharmaceutically acceptable addition salts, and solvates thereof, for the manufacture of a medicament for the treatment or prevention, in particular for the treatment, of any one of the disease conditions mentioned hereinbefore.

The invention relates to compounds of Formula (I) and pharmaceutically acceptable addition salts, and solvates thereof, for the manufacture of a medicament for the treatment of any one of the disease conditions mentioned hereinbefore.

The invention relates to compounds of Formula (I) and pharmaceutically acceptable addition salts, and solvates thereof, can be administered to mammals, preferably humans, for the treatment or prevention of any one of the diseases mentioned hereinbefore.

In view of the utility of the compounds of Formula (I) and pharmaceutically acceptable addition salts, and solvates thereof, there is provided a method of treating warm-blooded animals, including humans, suffering from or a method of preventing warm-blooded animals, including humans, to suffer from any one of the diseases mentioned hereinbefore.

Said methods comprise the administration, i.e. the systemic or topical administration, preferably oral administration, of an effective amount of a compound of Formula (I) or a pharmaceutically acceptable addition salt, or a solvate thereof, to warm-blooded animals, including humans.

Those of skill in the treatment of such diseases could determine the effective therapeutic daily amount from the test results presented hereinafter. An effective therapeutic daily amount would be from about 0.005 mg/kg to 50 mg/kg, in particular 0.01 mg/kg to 50 mg/kg body weight, more in particular from 0.01 mg/kg to 25 mg/kg body weight, preferably from about 0.01 mg/kg to about 15 mg/kg, more preferably from about 0.01 mg/kg to about 10 mg/kg, even more preferably from about 0.01 mg/kg to about 1 mg/kg, most preferably from about 0.05 mg/kg to about 1 mg/kg body weight. A particular effective therapeutic daily amount might be from about 0.01 to 1.00 g twice a day (BID), more in particular 0.30 to 0.85 g BID; even more in particular 0.40 g BID. The amount of a compound according to the present invention, also referred to here as the active ingredient, which is required to achieve a therapeutically effect will of course, vary on case-by-case basis, for example with the particular compound, the route of administration, the age and condition of the recipient, and the particular disorder or disease being treated.

A method of treatment may also include administering the active ingredient on a regimen of between one and four intakes per day. In these methods of treatment the compounds according to the invention are preferably formulated prior to administration. As described herein below, suitable pharmaceutical formulations are prepared by known procedures using well known and readily available ingredients.

The compounds of the present invention, that can be suitable to treat or prevent cancer or cancer-related conditions, may be administered alone or in combination with one or more additional therapeutic agents. Combination therapy includes administration of a single pharmaceutical dosage formulation which contains a compound of Formula (I), a pharmaceutically acceptable addition salt, or a solvate thereof, and one or more additional therapeutic agents, as well as administration of the compound of Formula (I), a pharmaceutically acceptable addition salt, or a solvate thereof, and each additional therapeutic agents in its own separate pharmaceutical dosage formulation. For example, a compound of Formula (I), a pharmaceutically acceptable addition salt, or a solvate thereof, and a therapeutic agent may be administered to the patient together in a single oral dosage composition such as a tablet or capsule, or each agent may be administered in separate oral dosage formulations.

While it is possible for the active ingredient to be administered alone, it is preferable to present it as a pharmaceutical composition.

Accordingly, the present invention further provides a pharmaceutical composition and, as active ingredient, a therapeutically effective amount of a compound of Formula (I), a pharmaceutically acceptable addition salt, or a solvate thereof.

Accordingly, the present invention further provides a pharmaceutical composition comprising a pharmaceutically acceptable carrier and, as active ingredient, a therapeutically effective amount of a compound of Formula (I), a pharmaceutically acceptable addition salt, or a solvate thereof.

The carrier or diluent must be "acceptable" in the sense of being compatible with the other ingredients of the composition and not deleterious to the recipients thereof.

For ease of administration, the subject compounds may be formulated into various pharmaceutical forms for administration purposes. The compounds according to the invention, in particular the compounds of Formula (I) and pharmaceutically acceptable addition salts, and solvates thereof, or any subgroup or combination thereof may be formulated into various pharmaceutical forms for administration purposes. As appropriate compositions there may be cited all compositions usually employed for systemically administering drugs.

To prepare the pharmaceutical compositions of this invention, an effective amount of the particular compound as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration orally, rectally, percutaneously, by parenteral injection or by inhalation. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable solutions containing a compound of Formula (I), a pharmaceutically acceptable addition salt, or a solvate thereof, may be formulated in an oil for prolonged action. Appropriate oils for this purpose are, for example, peanut oil, sesame oil, cottonseed oil, corn oil, soybean oil, synthetic glycerol esters of long chain fatty acids and mixtures of these and other oils. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. Acid or base addition salts of compounds of Formula (I) due to their increased water solubility over the corresponding base or acid form, are more suitable in the preparation of aqueous compositions.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

In order to enhance the solubility and/or the stability of the compounds of Formula (I) and pharmaceutically acceptable addition salts, and solvates thereof, in pharmaceutical compositions, it can be advantageous to employ α—, β- or γ-cyclodextrins or their derivatives, in particular hydroxyalkyl substituted cyclodextrins, e.g. 2-hydroxypropyl-β-cyclodextrin or sulfobutyl-β-cyclodextrin. Also co-solvents such as alcohols may improve the solubility and/or the stability of the compounds according to the invention in pharmaceutical compositions.

Depending on the mode of administration, the pharmaceutical composition will preferably comprise from 0.05 to 99% by weight, more preferably from 0.1 to 70% by weight, even more preferably from 0.1 to 50% by weight of the compound of Formula (I), a pharmaceutically acceptable addition salt, or a solvate thereof, and from 1 to 99.95% by weight, more preferably from 30 to 99.9% by weight, even more preferably from 50 to 99.9% by weight of a pharmaceutically acceptable carrier, all percentages being based on the total weight of the composition.

As another aspect of the present invention, a combination of a compound of the present invention with another anti-cancer agent is envisaged, especially for use as a medicine, more specifically for use in the treatment of cancer or related diseases.

For the treatment of the above conditions, the compounds of the invention may be advantageously employed in combination with antibody based immune cell redirection, for example T-cell/neutrophil redirection. This can be achieved for example by the use of bispecific monoclonal antibodies or artificial T-cell receptors.

For the treatment of the above conditions, the compounds of the invention may be advantageously employed in combination with one or more other medicinal agents, more particularly, with other anti-cancer agents or adjuvants in cancer therapy. Examples of anti-cancer agents or adjuvants (supporting agents in the therapy) include but are not limited to:

platinum coordination compounds for example cisplatin optionally combined with amifostine, carboplatin or oxaliplatin;

taxane compounds for example paclitaxel, paclitaxel protein bound particles (Abraxane™) or docetaxel;

topoisomerase I inhibitors such as camptothecin compounds for example irinotecan, SN-38, topotecan, topotecan hcl;

topoisomerase II inhibitors such as anti-tumour epipodophyllotoxins or podophyllotoxin derivatives for example etoposide, etoposide phosphate or teniposide;

anti-tumour vinca alkaloids for example vinblastine, vincristine or vinorelbine;

anti-tumour nucleoside derivatives for example 5-fluorouracil, leucovorin, gemcitabine, gemcitabine hcl, capecitabine, cladribine, fludarabine, nelarabine;

alkylating agents such as nitrogen mustard or nitrosourea for example cyclophosphamide, chlorambucil, carmustine, thiotepa, mephalan (melphalan), lomustine, altretamine, busulfan, dacarbazine, estramustine, ifosfamide optionally in combination with mesna, pipobroman, procarbazine, streptozocin, temozolomide, uracil;

anti-tumour anthracycline derivatives for example daunorubicin, doxorubicin optionally in combination with dexrazoxane, doxil, idarubicin, mitoxantrone, epirubicin, epirubicin hcl, valrubicin;

molecules that target the IGF-1 receptor for example picropodophilin;

tetracarcin derivatives for example tetrocarcin A;

glucocorticoids for example prednisone;

antibodies for example trastuzumab (HER2 antibody), rituximab (CD20 antibody), gemtuzumab, gemtuzumab ozogamicin, cetuximab, pertuzumab, bevacizumab, alemtuzumab, eculizumab, ibritumomab tiuxetan, nofetumomab, panitumumab, tositumomab, CNTO 328;

estrogen receptor antagonists or selective estrogen receptor modulators or inhibitors of estrogen synthesis for example tamoxifen, fulvestrant, toremifene, droloxifene, faslodex, raloxifene or letrozole;

aromatase inhibitors such as exemestane, anastrozole, letrazole, testolactone and vorozole;

differentiating agents such as retinoids, vitamin D or retinoic acid and retinoic acid metabolism blocking agents (RAMBA) for example accutane;

DNA methyl transferase inhibitors for example azacytidine or decitabine;

antifolates for example premetrexed disodium;

antibiotics for example antinomycin D, bleomycin, mitomycin C, dactinomycin, carminomycin, daunomycin, levamisole, plicamycin, mithramycin;

antimetabolites for example clofarabine, aminopterin, cytosine arabinoside or methotrexate, azacitidine, cytarabine, floxuridine, pentostatin, thioguanine;

apoptosis inducing agents and antiangiogenic agents such as Bcl-2 inhibitors for example YC 137, BH 312, ABT 737, gossypol, HA 14-1, TW 37 or decanoic acid;

tubuline-binding agents for example combrestatin, colchicines or nocodazole;

kinase inhibitors (e.g. EGFR (epithelial growth factor receptor) inhibitors, MTKI (multi target kinase inhibitors), mTOR inhibitors) for example flavoperidol, imatinib mesylate, erlotinib, gefitinib, dasatinib, lapatinib, lapatinib ditosylate, sorafenib, sunitinib, sunitinib maleate, temsirolimus;

farnesyltransferase inhibitors for example tipifarnib;

histone deacetylase (HDAC) inhibitors for example sodium butyrate, suberoylanilide hydroxamic acid (SAHA), depsipeptide (FR 901228), NVP-LAQ824, R306465, JNJ-26481585, trichostatin A, vorinostat;

Inhibitors of the ubiquitin-proteasome pathway for example PS-341, MLN 0.41 or bortezomib;

Yondelis;

Telomerase inhibitors for example telomestatin;

Matrix metalloproteinase inhibitors for example batimastat, marimastat, prinostat or metastat.

Recombinant interleukins for example aldesleukin, denileukin diftitox, interferon alfa 2a, interferon alfa 2b, peginterferon alfa 2b MAPK inhibitors Retinoids for example alitretinoin, bexarotene, tretinoin Arsenic trioxide Asparaginase Steroids for example dromostanolone propionate, megestrol acetate, nandrolone (decanoate, phenpropionate), dexamethasone Gonadotropin releasing hormone agonists or antagonists for example abarelix, goserelin acetate, histrelin acetate, leuprolide acetate Thalidomide, lenalidomide Mercaptopurine, mitotane, pamidronate, pegademase, pegaspargase, rasburicase BH3 mimetics for example ABT-737

MEK inhibitors for example PD98059, AZD6244, CI-1040 colony-stimulating factor analogs for example filgrastim, pegfilgrastim, sargramostim; erythropoietin or analogues thereof (e.g. darbepoetin alfa); interleukin 11; oprelvekin; zoledronate, zoledronic acid; fentanyl; bisphosphonate; palifermin a steroidal cytochrome P450 17alpha-hydroxylase-17,20-lyase inhibitor (CYP17), e.g. abiraterone, abiraterone acetate Glycolysis inhibitors, such as 2-deoxyglucose mTOR inhibitors such as rapamycins and rapalogs, and mTOR kinase inhibitors PI3K inhibitors and dual mTOR/PI3K inhibitors autophagy inhibitors, such as chloroquine and hydroxychloroquine antibodies that re-activate the immune response to tumors, for example nivolumab (anti-PD-1), lambrolizumab (anti-PD-1), ipilimumab (anti-CTLA4), and MPDL3280A (anti-PD-L1).

The present invention further relates to a product containing as first active ingredient a compound according to the invention and as further active ingredient one or more anticancer agents, as a combined preparation for simultaneous, separate or sequential use in the treatment of patients suffering from cancer.

The one or more other medicinal agents and the compound according to the present invention may be administered simultaneously (e.g. in separate or unitary compositions) or sequentially in either order. In the latter case, the two or more compounds will be administered within a period and in an amount and manner that is sufficient to ensure that an advantageous or synergistic effect is achieved. It will be appreciated that the preferred method and order of administration and the respective dosage amounts and regimes for each component of the combination will depend on the particular other medicinal agent and compound of the present invention being administered, their route of administration, the particular tumour being treated and the particular host being treated. The optimum method and order of administration and the dosage amounts and regime can be readily determined by those skilled in the art using conventional methods and in view of the information set out herein.

The weight ratio of the compound according to the present invention and the one or more other anticancer agent(s) when given as a combination may be determined by the person skilled in the art. Said ratio and the exact dosage and frequency of administration depends on the particular compound according to the invention and the other anticancer agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compounds of the instant invention. A particular weight ratio for the present compound of Formula (I) and another anticancer agent may range from 1/10 to 10/1, more in particular from 1/5 to 5/1, even more in particular from 1/3 to 3/1.

The platinum coordination compound is advantageously administered in a dosage of 1 to 500 mg per square meter (mg/m$^2$) of body surface area, for example 50 to 400 mg/m$^2$ particularly for cisplatin in a dosage of about 75 mg/m$^2$ and for carboplatin in about 300 mg/i per course of treatment.

The taxane compound is advantageously administered in a dosage of 50 to 400 mg per square meter (mg/m$^2$) of body surface area, for example 75 to 250 mg/m$^2$, particularly for paclitaxel in a dosage of about 175 to 250 mg/m$^2$ and for docetaxel in about 75 to 150 mg/m$^2$ per course of treatment.

The camptothecin compound is advantageously administered in a dosage of 0.1 to 400 mg per square meter (mg/m$^2$) of body surface area, for example 1 to 300 mg/m$^2$, particularly for irinotecan in a dosage of about 100 to 350 mg/m$^2$ and for topotecan in about 1 to 2 mg/m$^2$ per course of treatment.

The anti-tumour podophyllotoxin derivative is advantageously administered in a dosage of 30 to 300 mg per square meter (mg/m$^2$) of body surface area, for example 50 to 250 mg/m$^2$, particularly for etoposide in a dosage of about 35 to 100 mg/m$^2$ and for teniposide in about 50 to 250 mg/m$^2$ per course of treatment.

The anti-tumour vinca alkaloid is advantageously administered in a dosage of 2 to 30 mg per square meter (mg/m$^2$) of body surface area, particularly for vinblastine in a dosage of about 3 to 12 mg/m$^2$, for vincristine in a dosage of about 1 to 2 mg/m$^2$, and for vinorelbine in dosage of about 10 to 30 mg/m$^2$ per course of treatment.

The anti-tumour nucleoside derivative is advantageously administered in a dosage of 200 to 2500 mg per square meter (mg/m$^2$) of body surface area, for example 700 to 1500 mg/m$^2$, particularly for 5-FU in a dosage of 200 to 500 mg/m$^2$, for gemcitabine in a dosage of about 800 to 1200 mg/m$^2$ and for capecitabine in about 1000 to 2500 mg/m$^2$ per course of treatment.

The alkylating agents such as nitrogen mustard or nitrosourea is advantageously administered in a dosage of 100 to 500 mg per square meter (mg/m$^2$) of body surface area, for example 120 to 200 mg/m$^2$, particularly for cyclophosphamide in a dosage of about 100 to 500 mg/m$^2$, for chlorambucil in a dosage of about 0.1 to 0.2 mg/kg, for carmustine in a dosage of about 150 to 200 mg/m$^2$, and for lomustine in a dosage of about 100 to 150 mg/m$^2$ per course of treatment.

The anti-tumour anthracycline derivative is advantageously administered in a dosage of 10 to 75 mg per square meter (mg/m$^2$) of body surface area, for example 15 to 60 mg/m², particularly for doxorubicin in a dosage of about 40 to 75 mg/m², for daunorubicin in a dosage of about 25 to 45 mg/m², and for idarubicin in a dosage of about 10 to 15 mg/m² per course of treatment.

The antiestrogen agent is advantageously administered in a dosage of about 1 to 100 mg daily depending on the particular agent and the condition being treated. Tamoxifen is advantageously administered orally in a dosage of 5 to 50 mg, preferably 10 to 20 mg twice a day, continuing the therapy for sufficient time to achieve and maintain a therapeutic effect. Toremifene is advantageously administered orally in a dosage of about 60 mg once a day, continuing the therapy for sufficient time to achieve and maintain a therapeutic effect. Anastrozole is advantageously administered orally in a dosage of about 1 mg once a day. Droloxifene is advantageously administered orally in a dosage of about 20-100 mg once a day. Raloxifene is advantageously administered orally in a dosage of about 60 mg once a day. Exemestane is advantageously administered orally in a dosage of about 25 mg once a day.

Antibodies are advantageously administered in a dosage of about 1 to 5 mg per square meter (mg/m²) of body surface area, or as known in the art, if different. Trastuzumab is advantageously administered in a dosage of 1 to 5 mg per square meter (mg/m²) of body surface area, particularly 2 to 4 mg/m² per course of treatment.

These dosages may be administered for example once, twice or more per course of treatment, which may be repeated for example every 7, 14, 21 or 28 days.

The following examples illustrate the present invention. In case no specific stereochemistry is indicated for a stereocenter of a compound, this means that a mixture of the R and the S enantiomers was obtained. In case more than 1 stereocenter is present in a structure, each stereocenter for which no specific stereochemistry is indicated was obtained as a mixture of R and S.

The skilled person will realize that typically after a column purification, the desired fractions were collected and the solvent was evaporated to obtain the desired compound or intermediate.

Examples

Hereinafter, the term "rt", "r.t." or "RT" means room temperature; "Me" means methyl; "MeOH" means methanol; "Et" means ethyl; "EtOH" means ethanol; "EtOAc" means ethyl acetate; "Ac" means acetyl; "Ac₂O" means acetic anhydride; "AcOH" means acetic acid; "Et₂O" means di-ethylether; "Int." means intermediate; "DMF" means N,N-dimethyl formamide; "THF" means tetrahydrofuran; "LC" means liquid chromatography; "Celite®" means diatomaceous earth; "LCMS" means Liquid Chromatography/Mass spectrometry; "HPLC" means high-performance liquid chromatography; "TFA" means trifluoroacetic acid; "h" means hour(s); "Me₂S" means dimethyl sulphide; "DMSO" means dimethyl sulfoxide; "DMSO-d6" means deuterated dimethyl sulfoxide; "DIPE" means diisopropyl ether; "PPh₃" means triphenylphosphine; "TBAF" means tetrabutylammonium fluoride; "DBU" means 1,8-diazabicyclo[5.4.0]undecene-7; "eq." means equivalent(s); "KOtBu" means potassium tert-butoxide; "TBDMSCl" means tert-butyldimethylsilyl chloride; "Bn" means benzyl; "9-BBN" means 9-Borabicyclo[3.3.1]nonane; "Tf₂O" means triflic anhydride; "TBDMS" means tert-butyl dimethylsilyl or t-butyl dimethylsilyl; "aq." means aqueous; "Ts" or "Tos" means tosyl (p-toluenesulfonyl); "DEAD" means diethyl azodicarboxylate; "Bz" means benzoyl; "BnBr" means benzyl bromide; "Bn" means benzyl; "PhMgBr" means phenylmagnesium bromide; "anhyd." means anhydrous; "Rh(acac)(eth)₂" means acetylacetonatobis(ethylene)rhodium (I); "p-TsOH" means 4-methylbenzenesulfonic acid; "(R)-MonoPhos" means (R)—N,N-dimethyldinaphtho[2,1-D:1',2'-F][1,3,2]dioxaphosphepin-4-amine; "DMF-DMA" means N,N-Dimethylformamide dimethyl acetal; "BSA" means N,O-bis(trimethylsilyl)acetamide; "TMSOTf" means trimethylsilyl trifluoromethanesulfonate; "Prep SFC" means Preparative Supercritical Fluid Chromatography; "Piv" means pivaloyl; "PivCl" means pivaloyl chloride; "MePPh₃⁺Br⁻" means methyltriphenylphosphonium bromide; "iPrNH₂" means isopropylamine; "sat." means saturated; "DMA" means dimethyl acetamide.

In some cases, a stereobond is indicated as 'a wavy bond'. This means the stereochemical configuration at the stereocenter is a mixture. In this case, a comment next to the wavy bond will further detail what type of mixture is obtained.

For example, intermediate 10:

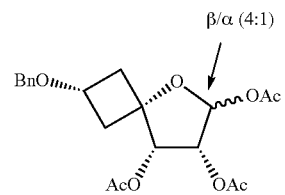

The wavy bond in intermediate 10 indicates that the stereochemical configuration at the stereocenter is a mixture, and the comment next to the wavy bond details that this is a β/α (4:1) anomer. (4:1) indicates that the ratio of β/α is 4/1. The β anomer corresponds with the structure wherein the wavy bond is a wedged bond when the bonds in position 2 and 3 of the sugar ring are drawn as dashed bonds:

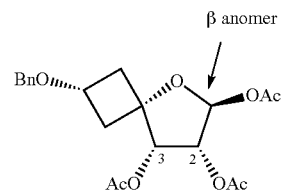 [SMILES: CC(=O)O[C@@H]1O[C@]2(C[C@@H](OCc3ccccc3)C2)[C@@H](OC(C)=O)[C@H]1OC(C)=O]

The α anomer corresponds with the structure wherein the wavy bond is a dashed bond when the bonds in position 2 and 3 of the sugar ring are drawn as dashed bonds:

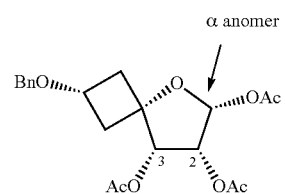

It will be clear that the same rule applies to other intermediates which are indicated as a β/α anomers.

For example, intermediate 45:

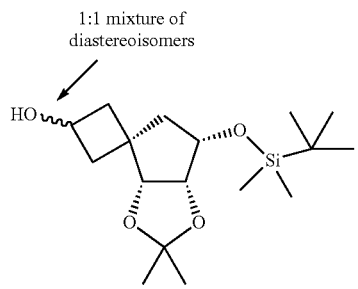

The wavy bond in intermediate 45 indicates that the stereochemical configuration at the stereocenter is a mixture, and the comment next to the wavy bond details that this is a 1:1 mixture of diastereoisomers.

It will be clear that the same rule applies to other intermediates which are indicated as a 1:1 mixture of diastereoisomers.

Preparation of the Intermediates and Compounds

Preparation of Intermediate 1

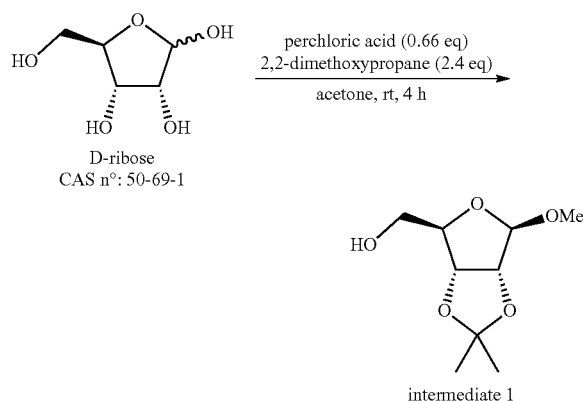

D-ribose (67.2 mmol, 10.1 g, 1.00 eq) was added to a solution of 2,2-dimethoxypropane (163 mmol, 20 ml, 2.40 eq) in acetone (80 ml). After 15 minutes, a homogenous solution was obtained and the mixture was cooled to 0° C. followed by the dropwise addition of perchloric acid (aq. 70%, 46.0 mmol, 4.00 ml) over 10 minutes. Subsequently, the mixture was stirred for 2 h at room temperature after which methanol (345 mmol; 14.0 ml) was added and the bright yellow solution was stirred for an additional 2 hours at room temperature. The mixture was cooled again to 0° C. and NaHCO$_3$ (6.42 g) dissolved in water (20 ml) was carefully added (over 20 minutes) to precipitate the perchloric salts, which were then filtered off. The filtrate was evaporated to a volume of 40 ml and extracted with diethylether (2×200 ml). Combined organic fractions were washed with brine (1×100 ml), dried (MgSO$_4$), filtered and the filtrate was concentrated in vacuo to give the desired intermediate 1(142 mmol, 11.9 g, 87% yield) as a pale yellow oil which was used without additional purification.

$^1$H NMR (250 MHz, CDCl$_3$) δ 4.98 (s, 1H), 4.84 (d, J=6.3 Hz, 1H), 4.59 (d, J=6.0 Hz, 1H), 4.44 (m, 1H), 3.75-3.56 (m, 2H), 3.44 (s, 3H), 1.49 (s, 3H), 1.32 ppm (s, 3H).

Preparation of Intermediate 2

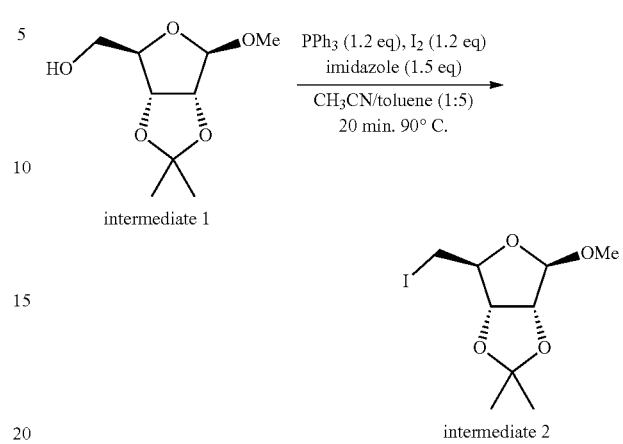

To a round-bottomed flask equipped with stirring bar and reflux condensor was added intermediate 1 (10.0 g, 49.0 mmol, 1.00 eq) and a mixture of toluene/acetonitrile (5:1) (300 ml). Subsequently, imidazole (5.00 g, 74.0 mmol, 1.50 eq) and triphenylphospine (13.4 g, 59.0 mmol, 1.20 eq) were added. After dissolution, iodine (14.9 g, 59.0 mmol, 1.20 eq) was added portionwise over a period of 15 minutes (exothermal). After complete addition, the reaction was heated to 90° C. for 20 minutes and cooled to room temperature before work-up was initiated. The reaction mixture was diluted in Et$_2$O (200 ml) and washed with a saturated solution of Na$_2$S$_2$O$_3$ (2×200 ml), water (2×200 ml) and brine (1×200 ml). The organic phase was dried (MgSO$_4$), filtered and the filtrate was concentrated in vacuo. Triphenylphosphine-oxides were precipitated with pentane and removed by filtration. The filtrate was concentrated in vacuo to give intermediate 2(13.3 g, crude) used without purification.

$^1$H NMR (250 MHz, CDCl$_3$) δ 5.04 (s, 1H), 4.76 (d, J=6.0 Hz, 1H), 4.62 (d, J=6.0 Hz, 1H), 4.43 (dd, J=10.0, 6.1 Hz, 1H), 3.36 (s, 3H) 3.28 (dd, J=10.0, 6.1 Hz, 1H), 3.17 (d, J=10.0 Hz, 1H), 1.47 (s, 3H), 1.32 ppm (s, 3H)

Preparation of Intermediate 3

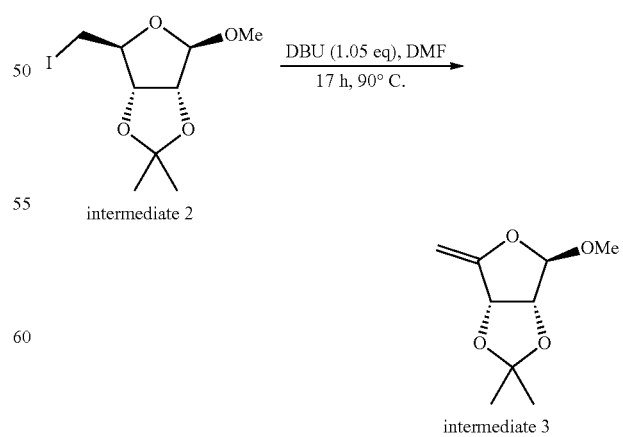

To a two-necked round-bottomed flask equipped with stirring bar and reflux condenser was added intermediate 2

(30.0 g, 95.5 mmol, 1.00 eq) and DMF (250 ml). The mixture was heated to 90° C. during which distilled DBU (15.7 ml, 10.5 mmol, 1.1 eq) was added over 2 minutes. The mixture was heated for 17 hours at 90° C. after which full conversion was observed by NMR. The solution was cooled to room temperature, diluted in EtOAc (300 ml) and washed with brine (3×300 ml). The organic phase was dried (MgSO$_4$), filtered and the filtrate was concentrated in vacuo. The resulting oil (19.1 g, crude) was purified by vacuum distillation at 55° C. to give the desired intermediate 3 (10.8 g, 61% yield over 2 steps from intermediate 1) as a liquid colorless oil.

$^1$H NMR (250 MHz, CDCl$_3$) δ 5.11 (s, 1H), 5.02 (d, J=5.9 Hz, 1H), 4.60 (m, 1H), 4.50 (d, J=5.9, 1H), 4.38 (m, 1H), 3.41 (s, 3H), 1.47 (s, 3H), 1.35 ppm (s, 3H) $^{13}$C NMR (63 MHz, CDCl$_3$) δ 161.4, 113.4, 108.8, 88.9, 82.8, 78.9, 55.9, 26.9, 25.9 ppm Preparation of Intermediate 4

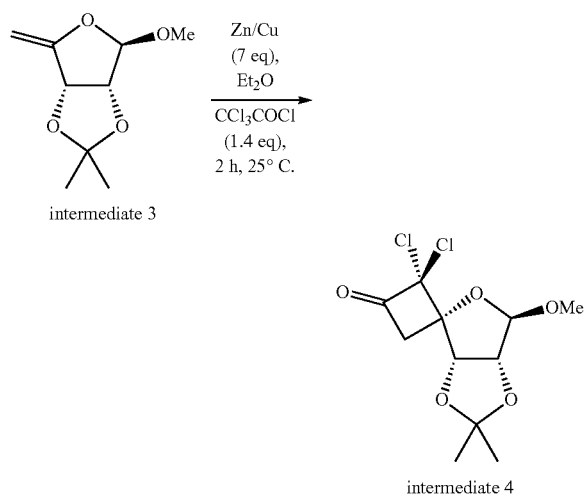

Zinc powder (25.0 g, 0.380 mol) was added to a two-necked round bottomed flask (500 ml) containing demineralized water (100 ml) and the solution was degassed with nitrogen for 15 minutes. Subsequently, copper(II)sulfate (1.85 g, 11.5 mmol) was added and the stirring solution was degassed for 45 minutes. The mixture was filtered and the solids were washed with degassed water (250 ml) and degassed acetone (250 ml), respectively. The zinc-copper couple was dried in vacuo for 12 hours. A solution of intermediate 3 (5.00 g, 26.9 mmol, 1.00 eq) in anhydrous Et$_2$O (150 ml, dried over 4 Å molecular sieves) was added to the zinc-copper couple (12.2 g, 186 mmol, 7.00 eq) in a flame-dried flask under inert argon atmosphere. Subsequently, a solution of trichloroacetylchloride (4.29 ml, 37.7 mmol, 1.40 eq) in anhydrous Et$_2$O (30 ml) was added dropwise to the stirring mixture over a period of 3 hours at 25° C. After complete addition, stirring was stopped and the organic layer was decanted from precipitated zinc salts and washed with pentane/Et$_2$O (100 ml). The organic phase was washed with NaHCO$_3$ (aq. sat. 3×150 ml) and brine (3×100 ml), dried (MgSO$_4$), filtered and the filtrate was concentrated in vacuo to give the desired intermediate 4 (7.20 g, crude)

$^1$H NMR (250 MHz, CDCl$_3$) δ 5.10 (d, J=5.7 Hz, 1H), 5.07 (s, 1H), 4.68 (d, J=5.7 Hz), 3.61 (dd, J=28.2, 18.7, 2H), 3.52 (s, 1H), 1.43 (s, 3H), 1.34 ppm (s, 3H).

$^{13}$C NMR (63 MHz, CDCl$_3$) δ 191.6, 113.5, 110.0, 91.1, 87.6, 85.3, 81.2, 57.3, 50.0, 26.5, 25.5 ppm Preparation of Intermediate 5

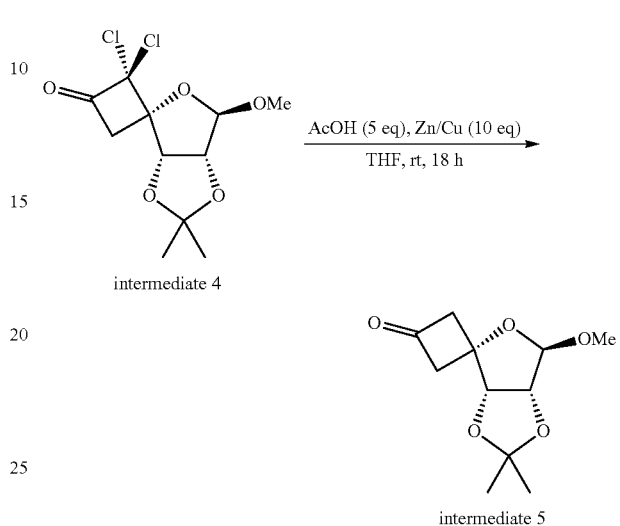

Intermediate 4 (6.77 g, 22.8 mmol, 1.00 eq) was dissolved in THF (90 ml) and glacial acetic acid (6.52 ml, 11.4 mmol, 5 eq) was added followed by the portionwise addition of the zinc-copper couple (14.9 g, 0.228 mol, 10.0 eq). The reaction mixture was stirred for 18 hours at room temperature. The mixture was filtered over celite, rinsed with THF (50 ml) and the filtrate was concentrated to a minimal volume in vacuo. The resulting oil was redissolved in EtOAc (300 ml) and washed with NaHCO$_3$ (aq. sat. 2×100 ml) and brine (3×90 ml) and the organic phase was dried (MgSO$_4$), filtered and the filtrate was concentrated in vacuo to give intermediate 5 (3.66 g, 15.9 mmol; 70% yield over 2 steps from intermediate 3).

$^1$H NMR (500 MHz, CDCl$_3$) δ 4.94 (s, 1H), 4.67 (d, J=5.8 Hz, 1H), 4.65 (d, J=5.8 Hz, 1H), 3.48 (dd, J=18.7, 5.7 Hz, 1H), 3.34 (s, 3H), 3.31 (dd, J=19.5, 5.4 Hz, 1H), 3.10 (dd, J=18.3, 4.7 Hz, 1H), 3.04 (dd, J=18.3, 5.7 Hz, 1H), 1.41 (s, 3H), 1.31 ppm (s, 3H)

$^{13}$C NMR (125 MHz, CDCl$_3$) δ 204.7, 113.1, 108.7, 85.7, 84.5, 78.5, 59.2, 55.2, 54.7, 26.5, 25.4 ppm Preparation of Intermediate 6

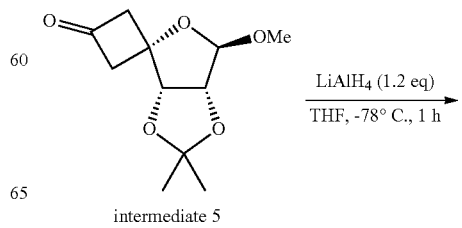

-continued

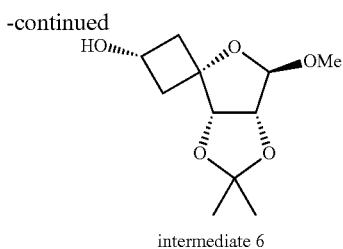

intermediate 6

Intermediate 5 (1.00 g, 4.38 mmol, 1.00 eq) was dissolved in anhydrous THF (30 ml) and cooled to −78° C. Lithiumaluminium hydride (199 mg; 5.70 mmol; 1.20 eq) was added portionwise over 10 minutes to the cooled reaction mixture. After 1 hour at −78° C., the mixture was warmed to room temperature, filtered over celite and the filtrate was concentrated in vacuo to a minimal volume. The residue was redissolved in EtOAc (300 ml) and washed with HCl (aq. 0.5M, 2×100 ml), NaHCO$_3$ (aq. sat. 1×100 ml) and brine (2×100 ml). The organic layer was dried (MgSO$_4$), filtered and the filtrate was concentrated in vacuo. The residue was purified by column chromatography over silica gel (gradient elution: n-heptane/EtOAc from 99:1 to 95:5). The fractions containing the product were collected and the solvent was evaporated to give the desired intermediate 6 (702 mg, 3.07 mmol, 71% yield) as a colorless oil.

$^1$H NMR (250 MHz, CDCl$_3$) δ 4.79 (s, 1H), 4.56 (d, J=5.8 Hz, 1H), 4.41 (d, J=5.8 Hz, 1H), 4.02 (quin., J=7.2 Hz, 1H), 3.31 (s, 3H), 2.85 (dt, J=12.5, 6.6 Hz, 1H), 2.43 (dt, J=12.4, 6.2 Hz, 1H), 2.24 (dd, J=10.6, 6.2 Hz, 1H), 2.04 (dd, J=11.0, 6.5 Hz), 1.39 (s, 3H), 1.29 ppm (s, 3H)

$^{13}$C NMR (63 MHz, CDCl$_3$) δ 112.7, 107.6, 85.5, 84.6, 78.3, 60.1, 55.0, 46.5, 40.4, 26.5, 25.4 ppm Preparation of Intermediate 7

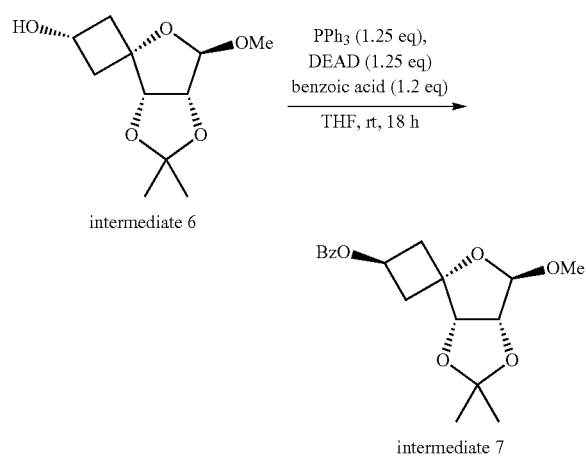

Intermediate 6 (2.00 g, 8.70 mmol, 1.00 eq) was dissolved in THF (50 ml) and benzoic acid (1.33 g, 10.9 mmol, 1.25 eq) was added followed by triphenylphosphine (2.85 g, 10.9 mmol, 1.25 eq) and diethyl azadicarboxylate (1.70 ml, 10.9 mmol, 1.25 eq). The mixture was stirred at room temperature for 18 hours and then concentrated in vacuo to a minimal volume. The slurry was dissolved in EtOAc (100 ml) and NaHCO$_3$ (aq. sat. 50 ml) was added. The product was extracted with EtOAc (3×100 ml) and combined organic phases were dried (MgSO$_4$), filtered and the filtrate was concentrated in vacuo to give intermediate 7 (2.53 g, crude)

$^1$H NMR (500 MHz, CDCl$_3$) δ 8.04 (d, J=7.5 Hz, 2H), 7.56 (t, J=7.4 Hz, 1H), 7.44 (t, J=7.7 Hz, 2H), 5.40 (m, 1H), 4.90 (s, 1H), 4.68 (d, J=5.8 Hz, 1H), 4.59 (d, J=5.8 Hz, 1H), 3.38 (s, 3H), 2.75 (m, 2H), 2.64 (ddd, J=13.2, 7.4, 3.3 Hz, 1H), 2.31 (ddd, J=13.8, 4.7, 2.9 Hz, 1H), 1.42 (s, 3H), 1.33 ppm (s, 3H)

$^{13}$C NMR (125 MHz, CDCl$_3$) δ 166.4, 133.2, 130.5, 129.8, 128.6, 112.6, 108.4, 85.8, 85.4, 84.0, 66.5, 55.1, 43.2, 37.5, 26.6, 25.6 ppm Preparation of Intermediate 8

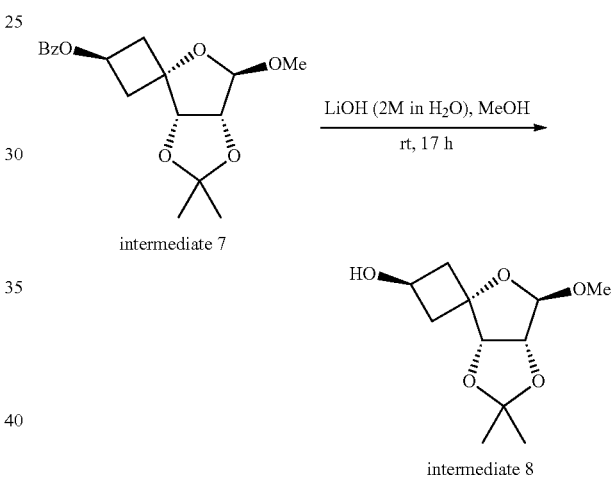

Intermediate 7 (2.91 g, 8.70 mmol, 1.00 eq) was dissolved in methanol (45 ml) and lithiumhydroxide (5.00 ml, 2M in H$_2$O) was added. The mixture was stirred at room temperature for 18 h followed by removal of the solvent in vacuo to a minimal volume. The slurry was dissolved in EtOAc (100 ml) and brine (50 ml) was added. The product was extracted with EtOAc (3×100 ml) and combined organic phases were dried (MgSO$_4$), filtered and the filtrate was concentrated in vacuo. The residue was purified by column chromatography over silica gel (gradient elution: n-heptane/EtOAc from 99:1 to 95:5). The fractions containing the product were collected and the solvent was evaporated to give the desired intermediate 8 (1.08 g, 4.70 mmol, 54% yield from intermediate 6) as a colorless oil.

$^1$H NMR (500 MHz, CDCl$_3$) δ 4.86 (s, 1H), 4.67 (d, J=5.8 Hz, 1H), 4.57 (d, J=5.8 Hz, 1H), 4.53 (m, 1H), 3.34 (s, 3H), 2.53 (m, 1H), 2.42 (m, 2H), 2.05 (m, 1H), 1.41 (s, 3H), 1.33 ppm (s, 3H)

$^{13}$C NMR (125 MHz, CDCl$_3$) δ 112.5, 108.4, 86.0, 85.4, 83.8, 63.5, 55.0, 45.2, 40.2, 26.6, 25.5 ppm

Preparation of Intermediate 9

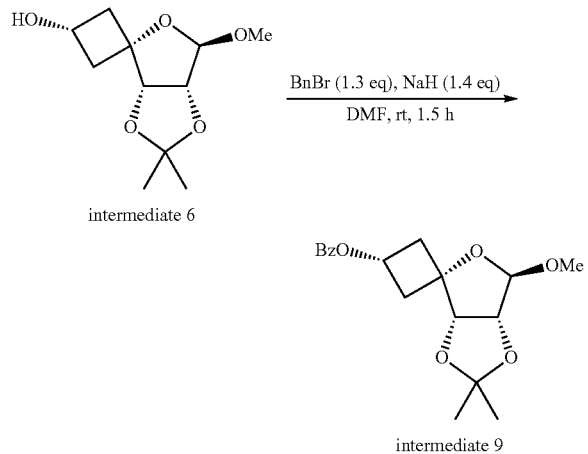

intermediate 6 intermediate 9

To a flame dried flask was added sodium hydride (277 mg, 6.93 mmol, 1.40 eq) and anhydrous DMF (10 ml, dried over 4 Å molecular sieves) under inert argon atmosphere. The mixture was cooled to 0° C. and intermediate 6 (1.14 g; 4.95 mmol, 1.00 eq) dissolved in anhydrous DMF (12.0 ml) was added dropwise over 5 minutes. After stirring for 15 minutes, benzylbromide (0.77 ml, 6.44 mmol, 1.30 eq) was added dropwise at 0° C. and the mixture was further stirred at room temperature for 1.5 hours. Subsequently, the reaction was cooled to 0° C. and carefully quenched by adding brine (100 ml). The product was extracted in EtOAc (3×120 ml) and combined organic layers were washed with brine (2×100 ml), dried (MgSO$_4$), filtered and the filtrate was concentrated in vacuo to give the desired intermediate 9 (890 mg, crude).

$^1$H NMR (250 MHz, CDCl$_3$) δ 7.37-7.25 (m, 5H), 4.83 (s, 1H), 4.59 (d, J=5.8 Hz, 1H), 4.42 (m, 3H), 3.80 (quin. J=7.1 Hz, 1H), 3.33 (s, 1H), 2.84 (dt, J=12.1, 6.1 Hz, 1H), 2.40 (dt, J=12.1, 6.1 Hz, 1H), 2.43 (dd, J=10.9, 6.6 Hz, 1H), (dd, J=11.9, 7.6 Hz, 1H), 1.42 (s, 3H), 1.32 ppm (s, 3H)

$^{13}$C NMR (63 MHz, CDCl$_3$) δ 138.2, 128.6, 128.0, 127.9, 112.6, 107.7, 85.6, 84.7, 78.8, 70.6, 65.6, 54.9, 43.9, 37.7, 26.5, 25.5 ppm

Preparation of Intermediate 10

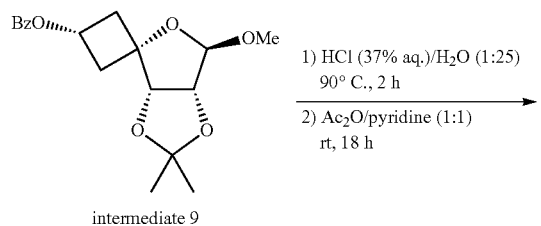

intermediate 9

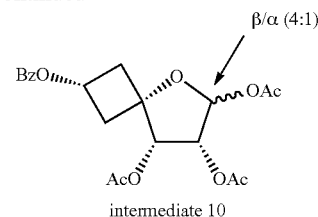

intermediate 10

To a suspension of intermediate 9 (300 mg, 0.94 mmol, 1.00 eq) in water (4.8 ml) was added HCl (37% aq., 0.18 ml) and the mixture was heated to 90° C. for 3 h. Subsequently, the solution was cooled to room temperature and carefully quenched with NaOH (aq. 1M, 5 ml). The mixture was extracted with EtOAc (3×10 ml) and combined organic layers were dried (MgSO$_4$), filtered and the filtrate was concentrated in vacuo. The obtained powder was dissolved in pyridine (1.5 ml) followed by the addition of acetic anhydride (1.5 ml) and stirred at room temperature for 22 h. The mixture was diluted in EtOAc (30 ml), washed with brine (3×10 ml) and the organic layer was dried (MgSO$_4$), filtered and the filtrate was concentrated in vacuo. The residue was purified by column chromatography over silica gel (gradient elution: n-heptane/EtOAc from 95:5 to 0:100). The fractions containing the product were collected and the solvent was evaporated to give the desired intermediate 10 (150 mg, 0.38 mmol, 41% yield) as a 4:1 mixture of β:α isomers.

Preparation of Compound 39

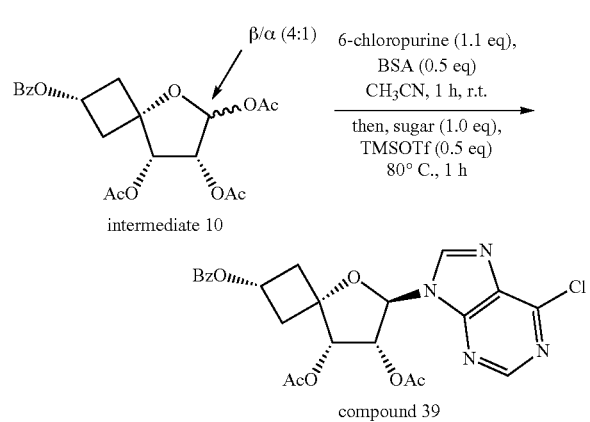

intermediate 10 compound 39

6-Chloropurine (130 mg, 0.84 mmol; 1.10 eq) was weighed in an oven dried vial and anhydrous acetonitrile (2.5 ml, dried over 4 Å molecular sieves) was added followed by N,O-bis(trimethylsilyl)acetamide (0.10 ml, 0.39 mmol, 0.50 eq). The mixture was stirred for 30 minutes at room temperature during which a homogeneous solution was obtained. Subsequently, the sugar moiety intermediate 10 (306 mg; 0.78 mmol, 1.00 eq) dissolved in anhydrous acetonitrile (2.2 ml) was added to the mixture followed by the dropwise addition of TMSOTf (0.07 ml, 0.39 mmol, 0.50 eq). The solution was heated to 80° C. for 2 h, then cooled to room temperature and diluted in EtOAc (80 ml). NaHCO$_3$ (aq. sat. 50 ml) was added and the product was extracted in EtOAc (3×80 ml). Combined organic fractions were dried (MgSO$_4$), filtered and the filtrate was concentrated in vacuo.

The residue was purified by column chromatography over silica gel (gradient elution: n-heptane/EtOAc from 95:5 to 0:100). The fractions containing the product were collected and the solvent was evaporated to give the desired Compound 39 (344 mg, 0.71 mmol, 91% yield)

¹H NMR (500 MHz, CDCl₃) δ 8.67 (s, 1H), 8.11 (s, 1H), 7.28-7.19 (m, 5H), 6.21 (m, 1H), 6.06 (d, J=6.8 Hz, 1H), 5.43 (d, J=4.3 Hz, 1H), 4.36 (s, 2H), 3.70 (quin., J=6.9 Hz, 1H), 2.79 (dt, J=12.4, 6.2 Hz, 1H), 2.63 (dt, J=12.5, 6.2 Hz, 1H), 2.35 (dd, J=11.7, 6.6 Hz, 1H), 2.25 (dd, J=11.9, 6.7 Hz, 1H), 2.13 (s, 3H), 1.94 ppm (s, 3H)

¹³C NMR (125 MHz, CDCl₃) δ 170.0, 169.4, 152.3, 151.7, 151.5, 144.4, 137.8, 132.8, 128.6, 128.0, 86.4, 79.4, 75.4, 72.9, 71.0, 64.1, 43.4, 39.0, 20.7, 20.5 ppm Preparation of Compound 1

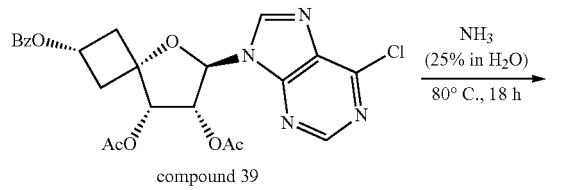

compound 39

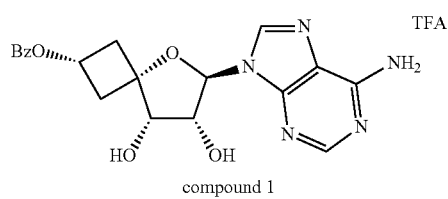

compound 1

Compound 39 (45 mg, 0.09 mmol; 1.00 eq) was suspended in aqueous ammonia (1.5 ml) and heated to 80° C. for 17 h. The mixture was cooled to room temperature and extracted in EtOAc (3×15 ml) with brine (10 ml). The organic layer was dried (MgSO₄), filtered and the filtrate was concentrated in vacuo. The residue was purified by preparative-HPLC (gradient elution: 0.1% TFA in CH₃CN/ 0.1% TFA in H₂O). The desired fractions were combined and lyophilized to yield Compound 1 (8.0 mg; a TFA salt, number of equivalents not determined) as a white powder.

¹H NMR (500 MHz, MeOD) δ 8.33 (s, 1H), 8.29 (s, 1H), 7.27-7.18 (m, 5H), 5.94 (d, J=6.7 Hz, 1H), 4.90 (dd, J=5.9, 3.6 Hz, 1H), 4.38 (s, 2H), 3.96 (d, J=4.3 Hz, 1H), 3.73 (quin., J=6.9 Hz, 1H), 2.91 (dt, J=12.2, 6.1 Hz, 1H), 2.63 (dt, J=12.2, 6.1 Hz, 1H), 2.24 (dd, J=11.2, 6.4 Hz, 1H), 2.05 ppm (dd, J=11.3, 6.5 Hz, 1H)

¹³C NMR (125 MHz, MeOD) δ 161.6 (q, J=34.4 Hz, TFA), 152.0, 149.2, 146.0, 142.5, 138.2, 128.2, 127.8, 127.5, 119.6 (TFA), 88.6, 80.0, 75.6, 74.3, 70.3, 64.6, 43.0, 38.2 ppm Preparation of Intermediate 12

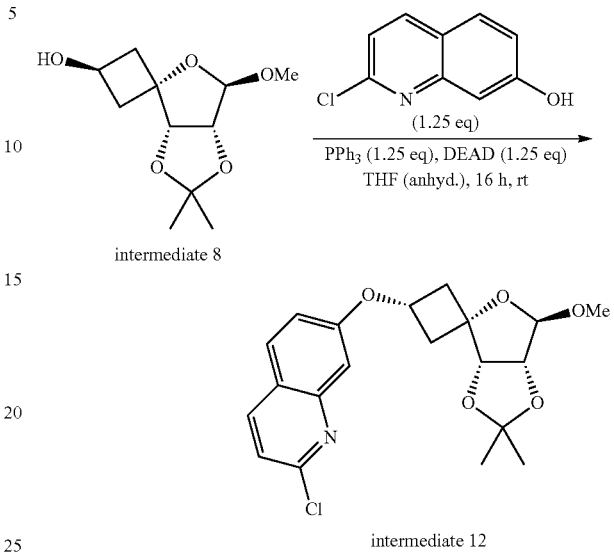

intermediate 8 intermediate 12

Intermediate 8 (90.0 mg, 0.391 mmol, 1.00 eq) was dissolved in anhydrous THF (5.00 ml) and triphenylphosphine (128 mg, 0.489 mmol, 1.25 eq) was added followed by the portionwise addition of 2-chloro-7-quinolinol (87.8 mg, 0.489 mmol, 1.25 eq). Diethyl azodicarboxylate (0.08 ml, 0.489 mmol, 1.25 eq) was added dropwise and the mixture was stirred at room temperature for 16 hours. Subsequently, the solution was concentrated to a minimal volume in vacuo and the residue was purified by column chromatography over silica gel (gradient elution: n-heptane/EtOAc from 95:5 to 1:1). The fractions containing the product were collected and the solvent was evaporated to give the desired intermediate 12 (142 mg, 93% yield) as a colorless oil.

¹H NMR (360 MHz, CDCl₃): δ=8.01 (d, J=8.4 Hz, 1H), 7.70 (d, J=9.1 Hz, 1H), 7.26 (d, J=1.8 Hz, 1H), 7.16-7.25 (m, 2H), 4.87 (s, 1H), 4.65 (d, J=5.9 Hz, 1H), 4.48-4.59 (m, 2H), 3.34 (s, 3H), 3.17-3.28 (m, 1H), 2.75 (dt, J=12.4, 6.2 Hz, 1H), 2.53 (dd, J=12.6, 7.5 Hz, 1H), 2.38 (dd, J=12.4, 7.3 Hz, 1H), 1.45 (s, 3H), 1.37 ppm (s, 3H)

¹³C NMR (91 MHz, CDCl₃): δ=159.1, 151.0, 149.5, 138.3, 128.6, 122.0, 120.1, 119.8, 112.6, 108.2, 107.5, 85.3, 84.4, 79.0, 64.9, 54.7, 43.7, 37.6, 26.3, 25.2 ppm Preparation of Intermediate 13

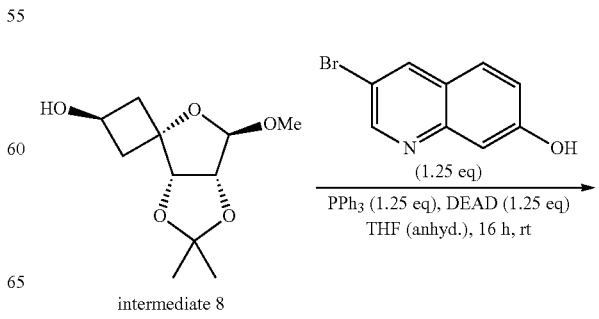

intermediate 8

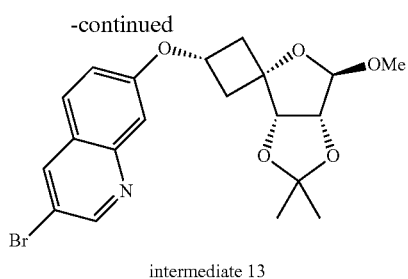

intermediate 13

Intermediate 8 (112 mg, 0.486 mmol, 1.00 eq) was dissolved in anhydrous THF (3.50 ml) and triphenylphosphine (159 mg, 0.608 mmol, 1.25 eq) was added followed by the portionwise addition of 3-bromo-7-quinolinol (136 mg, 0.608 mmol, 1.25 eq). Diethyl azodicarboxylate (0.10 ml, 0.608 mmol, 1.25 eq) was added dropwise and the mixture was stirred at room temperature for 16 hours. Subsequently, the solution was concentrated to a minimal volume in vacuo and the residue was purified by column chromatography over silica gel (gradient elution: n-heptane/EtOAc from 95:5 to 1:1). The fractions containing the product were collected and the solvent was evaporated to give the desired intermediate 13 (184 mg, 87% yield) as a colorless oil.

$^1$H NMR (360 MHz, CDCl$_3$): δ=8.79 (d, J=2.2 Hz, 1H), 8.17 (d, J=2.2 Hz, 1H), 7.59 (d, J=9.1 Hz, 1H), 7.15-7.25 (m, 2H), 4.85 (s, 1H), 4.64 (d, J=5.9 Hz, 1H), 4.50-4.58 (m, 2H), 3.33 (s, 3H), 3.20 (dt, J=12.4, 6.2 Hz, 1H), 2.74 (dt, J=12.4, 6.2 Hz, 1H), 2.53 (dd, J=12.4, 7.3 Hz, 1H), 2.37 (dd, J=12.4, 7.3 Hz, 1H), 1.43 (s, 3H), 1.35 ppm (s, 3H)

$^{13}$C NMR (91 MHz, CDCl$_3$): δ=158.4, 151.4, 147.8, 136.8, 128.0, 124.3, 121.0, 114.6, 112.6, 108.8, 107.5, 85.3, 84.4, 79.0, 64.9, 54.8, 43.8, 37.6, 26.3, 25.2 ppm Preparation of Intermediate 14

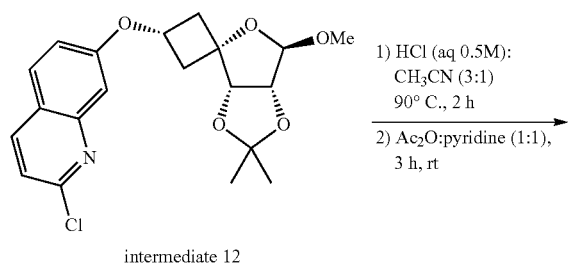

intermediate 12

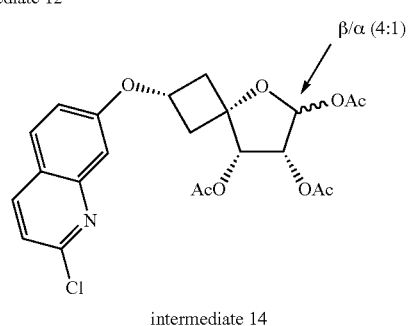

intermediate 14

Intermediate 12 (143 mg, 0.369 mmol, 1.00 eq) was dissolved in CH$_3$CN (2.00 ml) and HCl (0.5M in H$_2$O, 6.00 ml) was added. The solution was heated to 90° C. for 2 hours and a homogeneous solution was obtained. The mixture was concentrated in vacuo and coevaporated with toluene to obtain a white solid that was directly dissolved in pyridine (4.00 ml) and acetic anhydride (4.00 ml) and stirred at room temperature for 3 hours. The mixture was concentrated to a minimal volume in vacuo and coevaporated with toluene to dryness. The residue was purified by column chromatography over silica gel (gradient elution: n-heptane/EtOAc from 95:5 to 0:1). The fractions containing the product were collected and the solvent was evaporated to give the desired intermediate 14 (107 mg, 62% yield over 2 steps) as a 4:1 mixture of β:α isomers.

Preparation of Intermediate 15

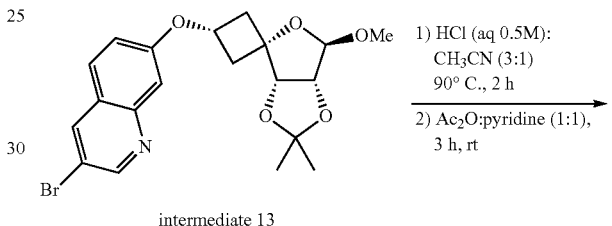

intermediate 13

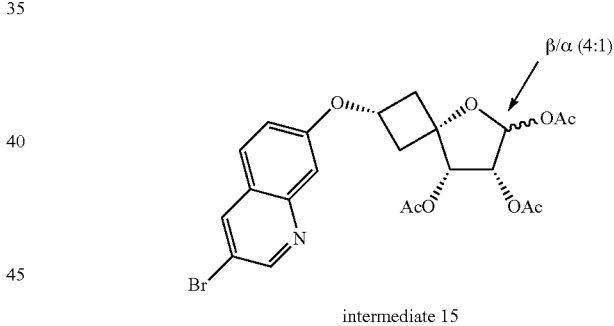

intermediate 15

Intermediate 13 (209 mg, 0.479 mmol, 1.00 eq) was dissolved in CH$_3$CN (3.00 ml) and HCl (0.5M in H$_2$O, 9.00 ml) was added. The solution was heated to 90° C. for 2 hours and a homogeneous solution was obtained. The mixture was concentrated in vacuo and coevaporated with toluene to obtain a white solid that was directly dissolved in pyridine (6.00 ml) and acetic anhydride (6.00 ml) and stirred at room temperature for 3 hours. The mixture was concentrated to a minimal volume in vacuo and coevaporated with toluene to dryness. The residue was purified by column chromatography over silica gel (gradient elution: n-heptane/EtOAc from 95:5 to 0:1). The fractions containing the product were collected and the solvent was evaporated to give the desired intermediate 15 (199 mg, 82% yield over 2 steps) as a 4:1 mixture of β:α isomers.

Preparation of Compound 40

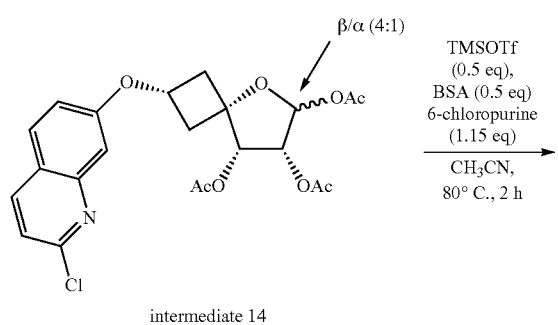

Preparation of Compound 41

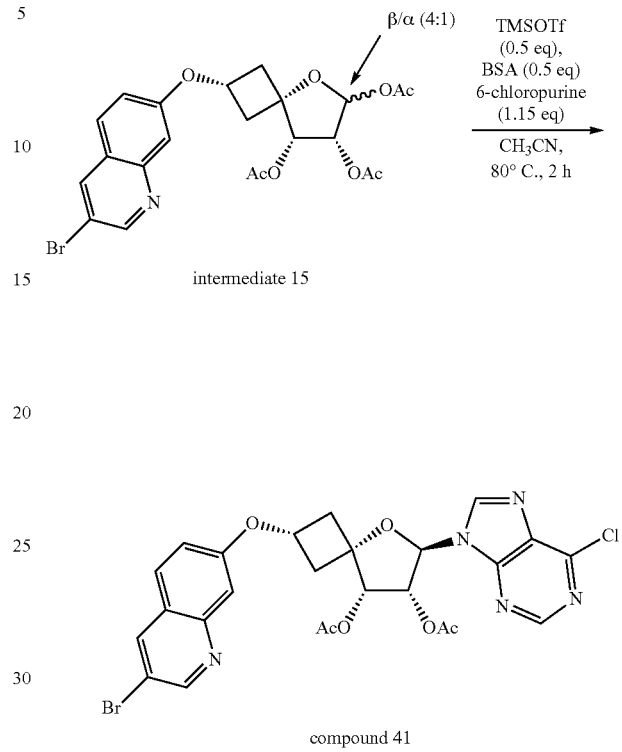

6-Chloropurine (40.9 mg, 0.265 mmol, 1.15 eq) was added to an oven dried vial and dissolved in CH₃CN (1.00 ml) followed by the addition of N,O-bis(trimethylsilyl) acetamide (0.03 ml, 0.115 mmol, 0.50 eq). The mixture was stirred for 30 minutes at room temperature and intermediate 14 (107 mg, 0.230 mmol, 1.00 eq) dissolved in CH₃CN (1.50 ml) was added followed by the dropwise addition of trimethylsilyl trifluoromethanesulfonate (0.02 ml, 0.115 mmol, 0.50 eq). The solution was heated to 80° C. for 1 hour, cooled to room temperature, diluted with EtOAc (20 ml) and NaHCO₃ (aq. sat. 10 ml) was added. The phases were separated and the aqueous phase was extracted with EtOAc (2×20 ml). Combined organic layers were dried (MgSO₄), filtered and the filtrate was concentrated in vacuo to yield Compound 40 (140 mg, crude).

$^{1}$H NMR (360 MHz, CDCl₃): δ=8.68 (s, 1H), 8.17 (s, 1H), 7.93 (d, J=8.8 Hz, 1H), 7.60 (d, J=8.8 Hz, 1H), 7.17 (d, J=8.4 Hz, 1H), 7.03-7.09 (m, 2H), 6.29 (dd, J=6.0, 4.6 Hz, 1H), 6.09 (d, J=6.2 Hz, 1H), 5.63 (d, J=4.4 Hz, 1H), 4.46 (quin, J=6.8 Hz, 1H), 3.18 (dt, J=13.0, 6.3 Hz, 1H), 3.07 (dt, J=12.7, 6.3 Hz, 1H), 2.67 (dd, J=13.0, 6.8 Hz, 1H), 2.42 (dd, J=12.8, 7.0 Hz, 1H), 2.22 (s, 3H), 1.99 ppm (s, 3H)

$^{13}$C NMR (91 MHz, CDCl₃): δ=169.8, 169.3, 158.7, 152.1, 151.4, 151.1, 151.0, 149.3, 144.4, 138.4, 132.5, 128.8, 122.0, 120.1, 120.0, 107.9, 86.6, 79.3, 74.7, 72.6, 63.1, 42.6, 39.0, 20.6, 20.3 ppm 6-Chloropurine (69.5 mg, 0.450 mmol, 1.15 eq) was added to an oven dried vial and dissolved in CH₃CN (1.20 ml) followed by the addition of N,O-bis(trimethylsilyl) acetamide (0.05 ml, 0.196 mmol, 0.50 eq). The mixture was stirred for 30 minutes at room temperature and intermediate 15 (199 mg, 0.391 mmol, 1.00 eq) dissolved in CH₃CN (2.00 ml) was added followed by the dropwise addition of trimethylsilyl trifluoromethanesulfonate (0.04 ml, 0.196 mmol, 0.50 eq). The solution was heated to 80° C. for 1 hour, cooled to room temperature, diluted with EtOAc (20 ml) and NaHCO₃ (aq. sat. 10 ml) was added. The phases were separated and the aqueous phase was extracted with EtOAc (2×20 ml). Combined organic layers were dried (MgSO₄), filtered and the filtrate was concentrated in vacuo to yield Compound 41 (272 mg, crude).

$^{1}$H NMR (360 MHz, CDCl₃): δ=8.80 (d, J=2.2 Hz, 1H), 8.75 (s, 1H), 8.21 (s, 1H), 8.19 (d, J=1.8 Hz, 1H), 7.60 (d, J=9.1 Hz, 1H), 7.09-7.24 (m, 2H), 6.36 (dd, J=6.2, 4.8 Hz, 1H), 6.15 (d, J=6.2 Hz, 1H), 5.69 (d, J=4.8 Hz, 1H), 4.54 (quin, J=6.8 Hz, 1H), 3.18-3.31 (m, 1H), 3.01-3.18 (m, 1H), 2.73 (dd, J=12.8, 7.0 Hz, 1H), 2.50 (dd, J=12.8, 7.0 Hz, 1H), 2.26 (s, 3H), 2.04 ppm (s, 3H)

$^{13}$C NMR (91 MHz, CDCl₃): δ=169.8, 169.2, 158.1, 152.1, 151.5, 151.4, 151.1, 147.6, 144.4, 137.0, 132.6, 128.2, 124.5, 121.0, 114.7, 108.5, 86.5, 79.4, 74.9, 72.5, 63.1, 60.3, 42.7, 39.0, 20.6, 20.3 ppm Preparation of Compounds 2 and 3

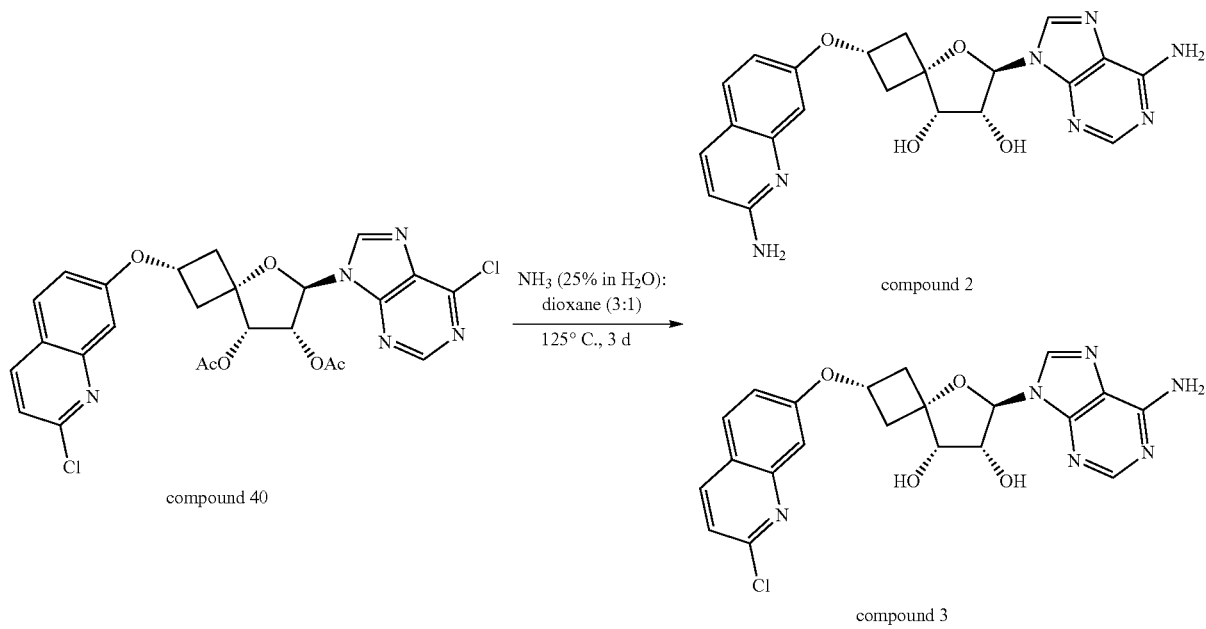 [SMILES: CC(=O)O[C@H]1[C@H](n2cnc3c(Cl)ncnc32)O[C@]2(C[C@@H](Oc3ccc4ccc(Cl)nc4c3)C2)[C@H]1OC(C)=O ; Nc1ccc2ccc(O[C@H]3C[C@]4(C3)O[C@@H](n3cnc5c(N)ncnc53)[C@H](O)[C@@H]4O)cc2n1 ; Nc1ncnc2c1ncn2[C@@H]1O[C@]2(C[C@@H](Oc3ccc4ccc(Cl)nc4c3)C2)[C@@H](O)[C@H]1O]

compound 40 compound 2 compound 3

Compound 40 (140 mg, crude) was dissolved in 1,4-dioxane (10.0 ml), and ammonia (30.0 ml, 25% in H$_2$O) was added. The mixture was heated to 125° C. in a pressure reactor for 3 days, cooled to room temperature and concentrated to a minimal volume in vacuo. The residue was coevaporated with toluene to dryness and a purification was performed via Prep SFC (Stationary phase: Chiralpak Diacel AD 20×250 mm, Mobile phase: CO$_2$, iPrOH+0.4 iPrNH$_2$) yielding the desired compound 2 (21.7 mg, 21% yield over 2 steps) and compound 3 (17.8 mg, 17% yield over 2 steps)

$^1$H NMR Compound 2 (400 MHz, DMSO-d$_6$): δ=8.27-8.34 (m, 1H), 8.14 (s, 1H), 7.78 (d, J=8.8 Hz, 1H), 7.50 (d, J=8.8 Hz, 1H), 7.24 (s, 2H), 6.80 (s, 1H), 6.74 (dd, J=8.7, 2.1 Hz, 1H), 6.59 (d, J=8.6 Hz, 1H), 6.33 (br s, 2H), 5.89 (d, J=6.8 Hz, 1H), 5.55 (br s, 1H), 5.49 (s, 1H), 5.49 (br s, 1H), 5.04 (br s, 1H), 4.46 (quin, J=6.5 Hz, 1H), 4.00-4.20 (m, 2H), 3.14-3.23 (m, 3H), 2.92-3.03 (m, 1H), 2.22-2.34 (m, 1H), 2.12 ppm (dd, J=12.1, 7.0 Hz, 1H)

$^{13}$C NMR Compound 2 (101 MHz, DMSO-d$_6$): δ=158.4, 157.9, 156.0, 152.5, 149.6, 149.2, 140.0, 136.6, 128.6, 119.4, 117.5, 112.7, 109.7, 106.4, 87.0, 79.1, 74.8, 72.7, 63.2, 48.6, 43.2, 38.4 ppm $^1$H NMR Compound 3 (400 MHz, DMSO-d$_6$): δ=8.34 (d, J=8.6 Hz, 1H), 8.31 (s, 1H), 8.14 (s, 1H), 7.94 (d, J=9.0 Hz, 1H), 7.42 (d, J=8.4 Hz, 1H), 7.21-7.32 (m, 4H), 5.90 (d, J=6.8 Hz, 1H), 5.56 (br d, J=4.0 Hz, 1H), 5.52 (br d, J=6.4 Hz, 1H), 5.06 (br q, J=4.2 Hz, 1H), 4.59 (quin, J=6.8 Hz, 1H), 4.12-4.20 (m, 1H), 3.24 (dt, J=12.1, 6.1 Hz, 1H), 3.07 (dt, J=11.9, 5.9 Hz, 1H), 2.29 (dd, J=12.2, 6.9 Hz, 1H), 2.17 ppm (dd, J=12.0, 7.2 Hz, 1H)

$^{13}$C NMR Compound 3 (101 MHz, DMSO-d$_6$): δ=158.9, 156.0, 155.9, 152.5, 150.1, 149.6, 149.0, 140.0, 139.5, 129.3, 121.8, 119.9, 119.8, 119.3, 107.8, 87.0, 79.0, 74.7, 72.6, 63.8, 43.0, 38.1 ppm Preparation of Compound 4

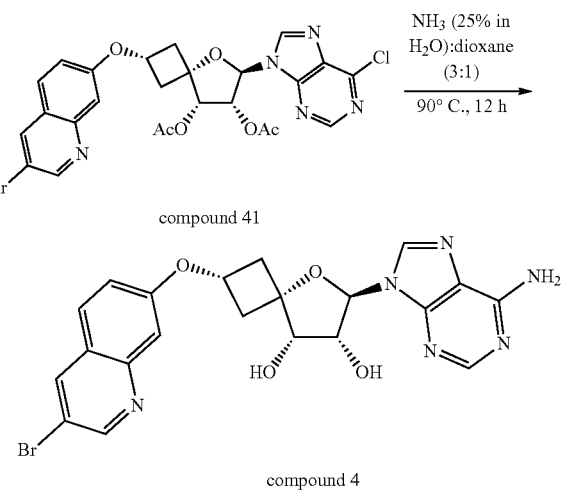

compound 41 compound 4

Compound 41 (270 mg, crude) was dissolved in 1,4-dioxane (1.5 ml), and ammonia (4.5 ml, 25% in H$_2$O) was added. The mixture was heated to 90° C. in a pressure reactor for 12 hours, cooled to room temperature and concentrated to a minimal volume in vacuo. The residue was coevaporated with toluene to dryness and a purification was performed via Prep SFC (Stationary phase: Chiralcel Diacel OJ 20×250 mm, Mobile phase: CO$_2$, iPrOH+0.4 iPrNH$_2$) yielding the desired compound 4 (85.8 mg, 44% yield over 2 steps).

$^1$H NMR (400 MHz, DMSO-d$_6$): δ=8.86 (d, J=2.2 Hz, 1H), 8.60 (d, J=2.2 Hz, 1H), 8.30 (s, 1H), 8.13 (s, 1H), 7.87 (d, J=9.0 Hz, 1H), 7.18-7.38 (m, 3H), 5.90 (d, J=6.8 Hz, 1H), 5.49-5.60 (m, 1H), 5.04 (dd, J=6.6, 4.2 Hz, 1H), 4.59 (quin, J=6.7 Hz, 1H), 4.15 (d, J=4.2 Hz, 1H), 3.28-3.34 (m, 1H), 3.23 (dt, J=12.0, 6.0 Hz, 1H), 3.05 (dt, J=11.9, 5.9 Hz, 1H), 2.30 (br dd, J=12.1, 6.8 Hz, 1H), 2.17 ppm (dd, J=12.1, 7.0 Hz, 1H)

$^{13}$C NMR (101 MHz, DMSO-$d_6$): δ=158.7, 156.5, 156.4, 153.0, 151.5, 150.1, 148.0, 137.6, 129.3, 124.6, 121.2, 119.8, 119.8, 114.6, 109.0, 87.5, 79.5, 75.2, 73.1, 64.3, 43.5, 38.6 ppm Preparation of Intermediate 18

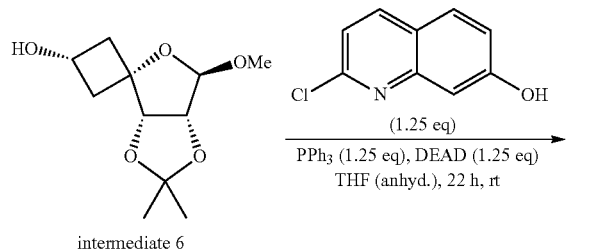

intermediate 6

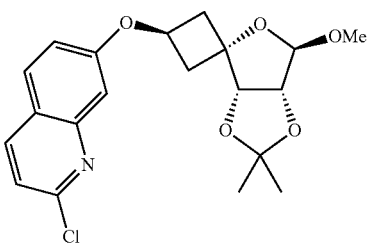

intermediate 18

Intermediate 6 (250 mg, 1.09 mmol, 1.00 eq) was dissolved in anhydrous THF (7.50 ml) and triphenylphosphine (342 mg, 1.30 mmol, 1.25 eq) was added followed by the portionwise addition of 2-chloro-7-quinolinol (234 mg, 1.30 mmol, 1.25 eq). Diethyl azodicarboxylate (0.20 ml, 1.30 mmol, 1.25 eq) was added dropwise and the mixture was stirred at room temperature for 22 hours. Subsequently, the solution was concentrated to a minimal volume in vacuo and the residue was purified by column chromatography over silica gel (gradient elution: n-heptane/EtOAc from 99:1 to 1:1). The fractions containing the product were collected and the solvent was evaporated to give the desired intermediate 18 (224 mg, 53% yield) as a colorless oil.

$^1$H NMR (360 MHz, CDCl$_3$): δ=8.00 (d, J=8.8 Hz, 1H), 7.69 (d, J=9.1 Hz, 1H), 7.09-7.33 (m, 3H), 4.92-5.01 (m, 1H), 4.91 (s, 1H), 4.68 (d, J=5.9 Hz, 1H), 4.59 (d, J=5.9 Hz, 1H), 3.40 (s, 3H), 2.76-2.86 (m, 2H), 2.63-2.73 (m, 1H), 2.35 (dt, J=12.0, 1.9 Hz, 1H), 1.41 (s, 3H), 1.33 (s, 3H), 1.21-1.21 ppm (m, 1H)

$^{13}$C NMR (91 MHz, CDCl$_3$): δ=159.3, 151.0, 149.5, 138.4, 128.6, 122.0, 120.4, 119.8, 112.3, 108.3, 108.2, 85.6, 85.1, 83.5, 68.3, 54.9, 42.6, 36.9, 26.3, 25.3 ppm Preparation of Intermediate 19

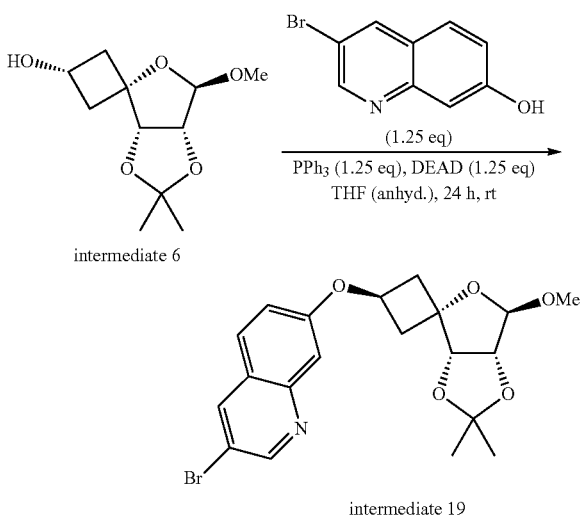

intermediate 6 intermediate 19

Intermediate 6 (250 mg, 1.09 mmol, 1.00 eq) was dissolved in anhydrous THF (7.50 ml) and triphenylphosphine (342 mg, 1.30 mmol, 1.25 eq) was added followed by the portionwise addition of 3-bromo-7-quinolinol (292 mg, 1.30 mmol, 1.25 eq). Diethyl azodicarboxylate (0.20 ml, 1.30 mmol, 1.25 eq) was added dropwise and the mixture was stirred at room temperature for 24 hours. Subsequently, the solution was concentrated to a minimal volume in vacuo and the residue was purified by column chromatography over silica gel (gradient elution: n-heptane/EtOAc from 99:1 to 1:1). The fractions containing the product were collected and the solvent was evaporated to give the desired intermediate 19 (270 mg, 57% yield) as a colorless oil.

$^1$H NMR (400 MHz, CDCl$_3$): δ=8.79 (d, J=2.2 Hz, 1H), 8.17 (d, J=2.2 Hz, 1H), 7.59 (d, J=8.6 Hz, 1H), 7.14-7.23 (m, 2H), 4.92-5.01 (m, 1H), 4.89 (s, 1H), 4.66 (d, J=5.7 Hz, 1H), 4.58 (d, J=5.7 Hz, 1H), 3.38 (s, 3H), 2.79 (dt, J=5.6, 1.4 Hz, 1H), 2.62-2.72 (m, 2H), 2.35 (ddd, J=13.8, 3.7, 1.9 Hz, 1H), 1.40 (s, 3H), 1.31 ppm (s, 3H)

$^{13}$C NMR (101 MHz; CDCl$_3$): δ=158.6, 151.3, 147.8, 136.8, 128.0, 124.3, 121.2, 114.5, 112.3, 108.9, 108.2, 85.6, 85.1, 83.6, 68.2, 54.9, 42.6, 37.0, 26.3, 25.3 ppm Preparation of Intermediate 20

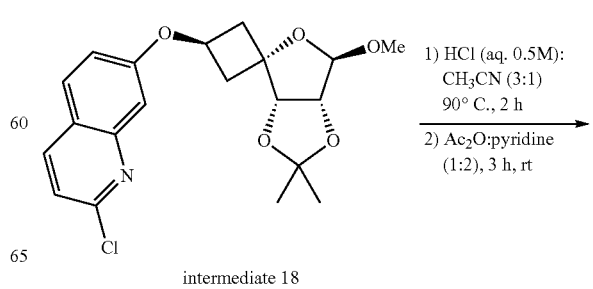

intermediate 18

-continued

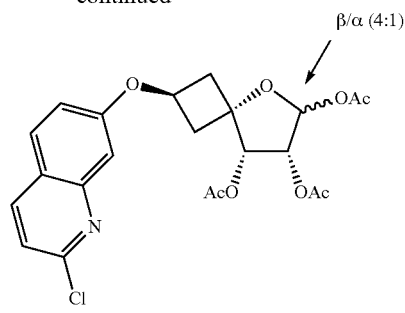

intermediate 20

Intermediate 18 (218 mg, 0.557 mmol, 1.00 eq) was dissolved in CH$_3$CN (3.00 ml) and HCl (0.5M in H$_2$O, 9.00 ml) was added. The solution was heated to 90° C. for 2 hours and a homogeneous solution was obtained. The mixture was concentrated in vacuo and coevaporated with toluene to obtain a white solid that was directly dissolved in pyridine (6.00 ml) and acetic anhydride (3.00 ml) and stirred at room temperature for 3 hours. The mixture was concentrated to a minimal volume in vacuo and coevaporated with toluene to dryness. The residue was purified by column chromatography over silica gel (gradient elution: n-heptane/EtOAc from 95:5 to 1:4). The fractions containing the product were collected and the solvent was evaporated to give the desired intermediate 20 (130 mg, 50% yield over 2 steps) as a 4:1 mixture of: isomers.

Preparation of Intermediate 21

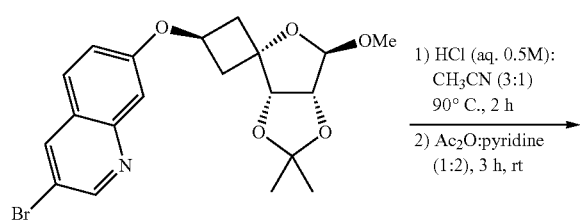

intermediate 21

Intermediate 19 (268 mg, 0.615 mmol, 1.00 eq) was dissolved in CH$_3$CN (3.00 ml) and HCl (0.5M in H$_2$O, 9.00 ml) was added. The solution was heated to 90° C. for 2 hours and a homogeneous solution was obtained. The mixture was concentrated in vacuo and coevaporated with toluene to obtain a white solid that was directly dissolved in pyridine (6.00 ml) and acetic anhydride (3.00 ml) and stirred at room temperature for 3 hours. The mixture was concentrated to a minimal volume in vacuo and coevaporated with toluene to dryness. The residue was purified by column chromatography over silica gel (gradient elution: n-heptane/EtOAc from 95:5 to 1:4). The fractions containing the product were collected and the solvent was evaporated to give the desired intermediate 21 (200 mg, 64% yield over 2 steps) as a 4:1 mixture of β:α isomers.

Preparation of Compound 42 intermediate 20 compound 42

6-Chloropurine (49.4 mg, 0.320 mmol, 1.15 eq) was added to an oven dried vial and dissolved in CH$_3$CN (1.20 ml) followed by the addition of N,O-bis(trimethylsilyl)acetamide (0.03 ml, 0.139 mmol, 0.50 eq). The mixture was stirred for 30 minutes at room temperature and intermediate 20 (129 mg, 0.278 mmol, 1.00 eq) dissolved in CH$_3$CN (1.80 ml) was added followed by the dropwise addition of trimethylsilyl trifluoromethanesulfonate (0.03 ml, 0.139 mmol, 0.50 eq). The solution was heated to 80° C. for 2 hours, cooled to room temperature, diluted with EtOAc (20 ml) and NaHCO$_3$ (aq. sat. 15 ml) was added. The phases were separated and the aqueous phase was extracted with EtOAc (2×20 ml). Combined organic layers were dried (MgSO$_4$), filtered and the filtrate was concentrated in vacuo to yield the desired Compound 42 (164 mg, crude).

$^1$H NMR (360 MHz, CDCl$_3$): δ=8.80 (s, 1H), 8.20 (s, 1H), 8.03 (d, J=8.4 Hz, 1H), 7.73 (d, J=8.8 Hz, 1H), 7.28-7.30 (m, 1H), 7.11-7.23 (m, 3H), 6.36 (dd, J=6.4, 4.6 Hz, 1H), 6.13 (d, J=6.2 Hz, 1H), 5.77-5.83 (m, 1H), 4.93 (dq, J=7.1, 3.6 Hz, 1H), 3.02 (ddd, J=13.6, 7.0, 3.5 Hz, 1H), 2.75-2.87 (m, 2H), 2.63-2.73 (m, 1H), 2.18 (s, 3H), 2.02 ppm (s, 3H)

Preparation of Compound 43

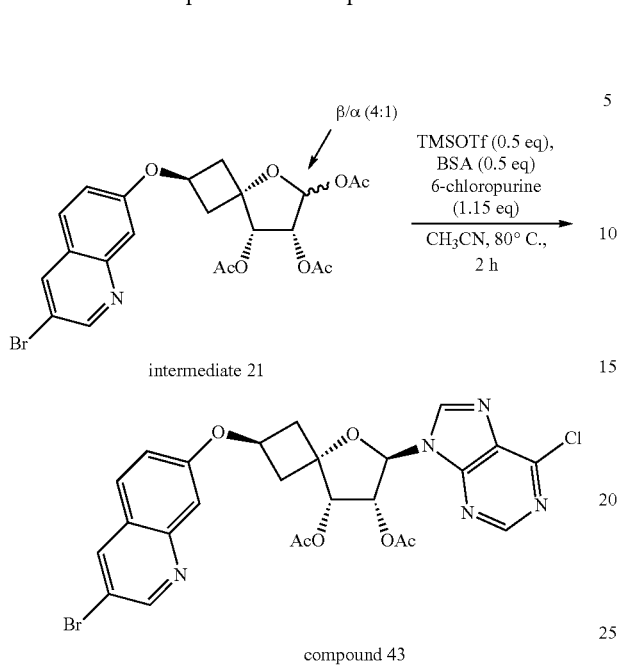

intermediate 21 compound 43

6-Chloropurine (69.9 mg, 0.452 mmol, 1.15 eq) was added to an oven dried vial and dissolved in CH$_3$CN (1.50 ml) followed by the addition of N,O-bis(trimethylsilyl) acetamide (0.05 ml, 0.197 mmol, 0.50 eq). The mixture was stirred for 30 minutes at room temperature and intermediate 21 (200 mg, 0.393 mmol, 1.00 eq) dissolved in CH$_3$CN (2.50 ml) was added followed by the dropwise addition of trimethylsilyl trifluoromethanesulfonate (0.04 ml, 0.197 mmol, 0.50 eq). The solution was heated to 80° C. for 2 hours, cooled to room temperature, diluted with EtOAc (30 ml) and NaHCO$_3$ (aq. sat. 15 ml) was added. The phases were separated and the aqueous phase was extracted with EtOAc (2×30 ml). Combined organic layers were dried (MgSO$_4$), filtered and the filtrate was concentrated in vacuo to yield the desired Compound 43 (250 mg, crude).

$^1$H NMR (360 MHz, CDCl$_3$): δ=8.82-8.85 (m, 1H), 8.80 (s, 1H), 8.24 (d, J=1.8 Hz, 1H), 8.20 (s, 1H), 7.66 (d, J=9.1 Hz, 1H), 7.16-7.24 (m, 2H), 6.35 (dd, J=6.2, 4.8 Hz, 1H), 6.14 (d, J=6.2 Hz, 1H), 5.80 (d, J=4.4 Hz, 1H), 4.96 (dq, J=7.1, 3.6 Hz, 1H), 3.03 (ddd, J=13.5, 6.8, 3.5 Hz, 1H), 2.65-2.94 (m, 3H), 2.18 (s, 3H), 2.02 ppm (s, 3H)

Preparation of Compound 5

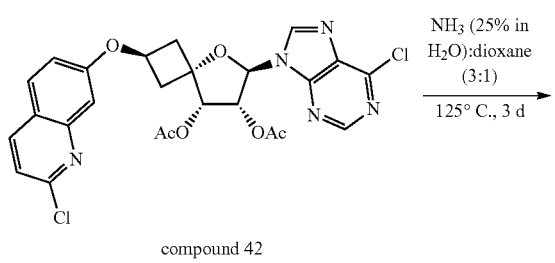

compound 42

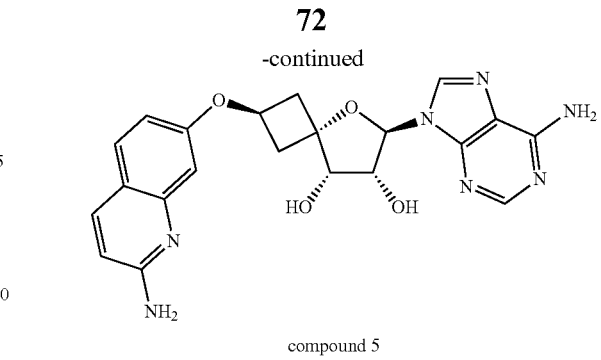

compound 5

Compound 42 (164 mg, crude) was dissolved in 1,4-dioxane (10.0 ml), and ammonia (30.0 ml, 25% in H$_2$O) was added. The mixture was heated to 125° C. in a pressure reactor for 3 days, cooled to room temperature and concentrated to a minimal volume in vacuo. The residue was coevaporated with toluene to dryness and a purification was performed via Prep SFC (Stationary phase: Chiralpak Diacel AS 20×250 mm, Mobile phase: CO$_2$, EtOH+0.4 iPrNH$_2$) yielding the desired Compound 5 (12.9 mg, 11% yield over 2 steps from intermediate 20)

$^1$H NMR (400 MHz, DMSO-d$_6$): δ=8.34 (s, 1H), 8.16 (s, 1H), 7.78 (d, J=8.6 Hz, 1H), 7.51 (d, J=8.8 Hz, 1H), 7.26 (s, 2H), 6.75 (dd, J=8.6, 2.4 Hz, 1H), 6.67 (d, J=2.4 Hz, 1H), 6.58 (d, J=8.8 Hz, 1H), 6.28-6.39 (m, 2H), 5.90 (d, J=6.8 Hz, 1H), 4.99 (dd, J=6.8, 4.2 Hz, 1H), 4.79-4.88 (m, 1H), 4.09 (d, J=4.2 Hz, 1H), 2.77 (ddd, J=13.2, 7.0, 3.5 Hz, 1H), 2.63-2.71 (m, 1H), 2.54 (dd, J=7.2, 3.9 Hz, 1H), 2.43 ppm (dt, J=13.4, 3.8 Hz, 1H) $^{13}$C NMR (101 MHz, DMSO-d$_6$): δ=158.5, 157.9, 156.0, 152.5, 149.6, 149.3, 140.2, 136.5, 128.6, 119.4, 117.4, 112.7, 109.7, 106.6, 87.1, 83.3, 75.6, 72.5, 66.6, 41.2, 37.0 ppm

Preparation of Compound 6

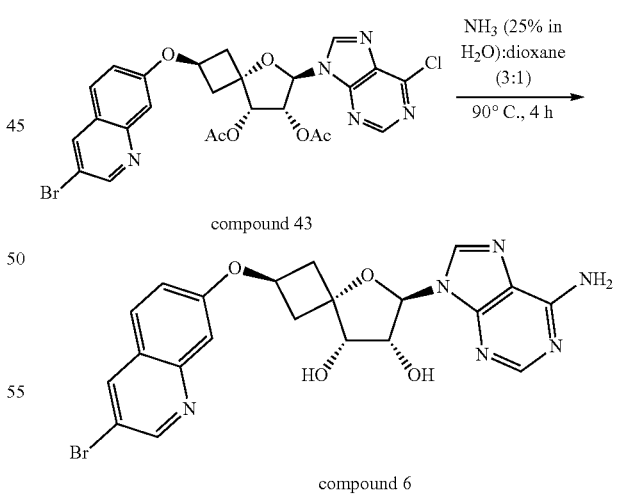

compound 43 compound 6

Compound 43 (250 mg, crude) was dissolved in 1,4-dioxane (1.5 ml), and ammonia (4.5 ml, 25% in H$_2$O) was added. The mixture was heated to 80° C. in a pressure reactor for 4 hours, cooled to room temperature and concentrated to a minimal volume in vacuo. The residue was coevaporated with toluene to dryness and a purification was performed via Prep SFC (Stationary phase: Chiralpak Diacel AS 20×250 mm, Mobile phase: $CO_2$, EtOH+0.4 $iPrNH_2$) yielding the desired compound 6 (113 mg, 58% yield from intermediate 21)

$^1$H NMR (400 MHz, DMSO-$d_6$): δ=8.85 (d, J=2.4 Hz, 1H), 8.62 (d, J=2.4 Hz, 1H), 8.35 (s, 1H), 8.17 (s, 1H), 7.90 (d, J=9.2 Hz, 1H), 7.18-7.36 (m, 4H), 5.92 (d, J=6.8 Hz, 1H), 5.33-5.55 (m, 2H), 4.80-5.11 (m, 1H), 4.68-4.80 (m, 1H), 4.12 (t, J=4.3 Hz, 1H), 2.85 (ddd, J=13.3, 7.0, 3.4 Hz, 1H), 2.69-2.76 (m, 1H), 2.60 (ddd, J=13.6, 7.0, 3.4 Hz, 1H), 2.44-2.50 ppm (m, J=3.7, 3.7 Hz, 1H)

$^{13}$C NMR (101 MHz, DMSO-$d_6$): δ=158.3, 156.0, 152.5, 151.0, 149.6, 147.4, 140.1, 137.0, 128.8, 124.1, 120.7, 119.4, 114.0, 108.7, 87.2, 83.2, 75.5, 72.5, 67.3, 41.0, 36.9 ppm Preparation of Intermediate 24

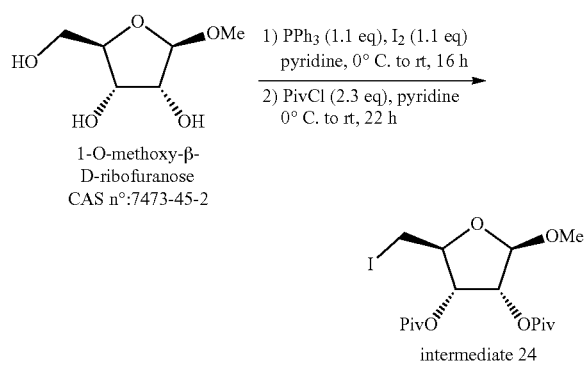

1-O-methoxy-β-D-ribofuranose (25.3 g, 154 mmol, 1.00 eq) was dissolved in pyridine (253 ml) and triphenylphosphine (44.4 g, 169 mmol, 1.10 eq) was added portionwise. The solution was cooled to 0° C. and iodine (42.9 g, 169 mmol, 1.10 eq) was added portionwise over a period of 40 minutes. The solution was cooled at 0° C. for an additional 20 minutes after addition of the reagents before it was stirred at room temperature for 24 hours. Subsequently, the reaction mixture was cooled to 0° C. and pivaloyl chloride (43.5 ml, 354 mmol, 2.30 eq) was added dropwise via a pressure equalized dropping funnel over a period of 1.5 hours to the stirring mixture. After addition of the reagent, the mixture was warmed to room temperature and stirred for 22 hours. The mixture was concentrated to a minimal volume in vacuo and coevaporated with toluene (2×300 ml).

To the remaining brown slurry was added n-heptane (1 L) upon which triphenylphosphine-oxides precipitated. The mixture was sonicated for 1 hour and the solid material was filtered and washed with n-heptane (300 ml). The filtrate was concentrated in vacuo to a minimal volume to yield a yellow syrup. Subsequently, the syrup was redissolved in EtOAc (500 ml) and washed with a solution of sodiumthiosulfate (aq. sat. 1×250 ml) and brine (1×250 ml). The organic phase was dried ($MgSO_4$), filtered and the filtrate was concentrated in vacuo to yield intermediate 24 (49.0 g, 72% crude yield) which solidified upon standing at room temperature.

$^1$H NMR (400 MHz, $CDCl_3$) δ 5.27 (d, J=4.8 Hz, 1H), 5.20 (dd, J=6.3, 4.8 Hz, 1H), 4.85 (s, 1H), 4.24 (q, J=6.6 Hz, 1H), 3.41 (s, 3H), 3.33 (dd, J=6.5, 4.9 Hz, 2H), 1.22 (s, 9H), 1.21 ppm (s, 9H)

$^{13}$C NMR (101 MHz, $CDCl_3$) δ 177.0, 176.8, 106.1, 80.3, 75.2, 74.9, 55.3, 38.8, 38.6, 27.1, 6.7 ppm Preparation of Intermediate 25

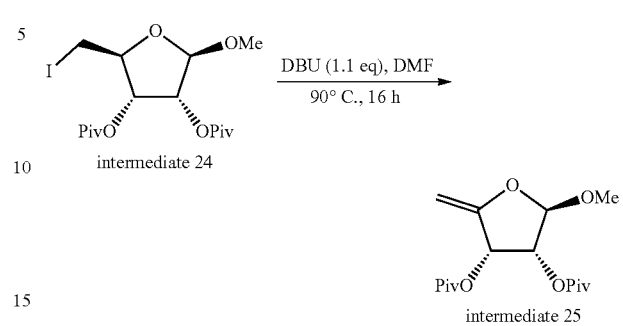

Intermediate 24 (47.8 g, 108 mmol, 1.00 eq) was dissolved in DMF (500 ml) and DBU (17.8 ml, 119 mmol, 1.10 eq) was added at once to the stirring mixture which was heated to 90° C. for 18 hours. The mixture was cooled to room temperature and concentrated in vacuo to approximately 250 ml. Subsequently, the brown solution was diluted in n-heptane (1.5 l) and washed with brine (3×750 ml). The resulting organic phase was dried ($MgSO_4$), filtered and the filtrate was concentrated in vacuo. The residue was purified by column chromatography over silica gel (gradient elution: n-heptane/EtOAc from 99:1 to 9:1). The fractions containing the product were collected and the solvent was evaporated to give the desired intermediate 25 (30.2 g, 96.1 mmol, 89% yield) as a colorless liquid.

$^1$H NMR (360 MHz, $CDCl_3$) δ 5.76 (dt, J=5.1, 1.9 Hz, 1H), 5.16 (d, J=5.1 Hz, 1H), 5.02 (s, 1H), 4.51 (t, J=1.8 Hz, 1H), 4.08 (t, J=2.0 Hz, 1H), 3.46 (s, 3H), 1.23 (s, 9H), 1.21 ppm (s, 9H)

$^{13}$C NMR (101 MHz, $CDCl_3$) δ 177.3, 177.2, 157.2, 106.2, 84.6, 73.2, 69.7, 56.3, 39.1, 39.0, 27.4, 27.3 ppm Preparation of Intermediate 26

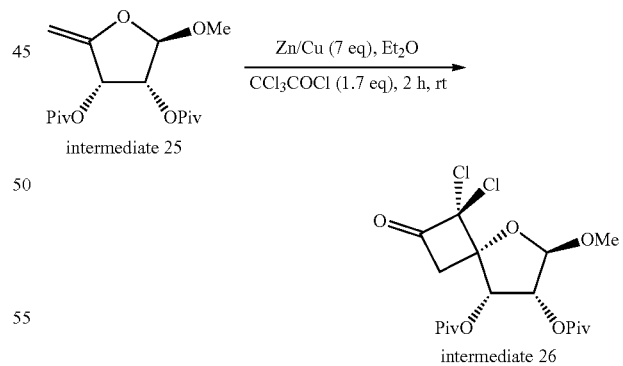

Zinc powder (25.0 g, 0.38 mol, 1.00 eq) was added to a two-necked round bottomed flask (500 ml) containing demineralized water (100 ml) and the solution was degassed with nitrogen during 15 minutes. Subsequently, copper(II) sulfate (1.85 g, 11.5 mmol, 0.03 eq) was added and the stirring solution was degassed and stirred for 45 minutes. The mixture was filtered and the black solids were washed with degassed water (250 ml) and degassed acetone (250 ml), respectively. The zinc-copper couple was dried in vacuo for 12 hours. Intermediate 25 (10.0 g, 31.8 mmol, 1.00 eq) was weighed in an oven dried flask and dissolved in anhydrous diethylether (300 ml, dried over 4 Å molecular sieves). Subsequently, zinc-copper couple (14.6 g, 223 mmol, 7.00 eq) was added at once to the stirring solution in diethylether. An oven dried pressure equalized dropping funnel was installed and charged with anhydrous diethylether (100 ml) and trichloroacetyl chloride (6.10 ml, 54.1 mmol, 1.70 eq). The reagent was added dropwise over a period of 2.5 hours and the temperature was monitored carefully in order not to exceed 25° C. After addition, zinc-copper couple was decanted, rinsed with diethylether (100 ml) and the organic layer was diluted with n-heptane (500 ml) before it was washed with NaHCO$_3$ (aq. sat. 3×300 ml) and brine (2×250 ml). The organic phase was dried (MgSO$_4$), filtered and the filtrate was concentrated in vacuo at 40° C. to give intermediate 26 (13.2 g, crude).

$^1$H NMR (360 MHz, CDCl$_3$) δ 5.84 (d, J=4.0 Hz, 1H), 5.35 (d, J=4.4 Hz, 1H), 4.98 (s, 1H), 3.92 (d, J=18.7 Hz, 1H), 3.51 (s, 1H), 3.40 (d, J=18.7 Hz, 1H), 1.19 ppm (s, 18H) $^{13}$C NMR (91 MHz, CDCl$_3$) δ 191.0, 176.3, 175.4, 106.0, 91.4, 83.2, 74.6, 71.2, 55.9, 52.0, 38.5, 26.8 ppm Preparation of Intermediate 27

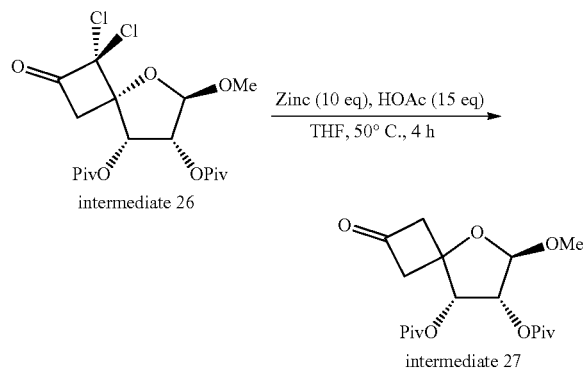

Intermediate 26 (2.64 g, 6.21 mmol, 1.00 eq) was dissolved in THF (45.0 ml) and acetic acid (5.33 ml, 93.1 mmol, 15.0 eq) was added followed by the portionwise addition of zinc powder (4.06 g, 62.1 mmol, 10.0 eq) and the mixture was heated to 50° C. for 5 hours. Subsequently, the solution was cooled to room temperature and filtered over celite. The filtrate was concentrated to a minimal volume in vacuo, redissolved in EtOAc (200 ml), washed with brine (2×75 ml), dried (MgSO$_4$), filtered and concentrated in vacuo. The residue was purified by column chromatography over silica gel (gradient elution: n-heptane/EtOAc from 99:1 to 1:1). The fractions containing the product were collected and the solvent was evaporated to give the desired intermediate 27 (1.48 g, 4.16 mmol, 67% yield) as a colorless oil.

$^1$H NMR (360 MHz, CDCl$_3$) δ 5.56 (d, J=4.4 Hz, 1H), 5.26 (dd, J=4.4, 0.7 Hz, 1H), 4.91 (s, 1H), 3.43-3.51 (m, 2H), 3.42 (s, 3H), 3.33-3.41 (m, 1H), 3.14-3.25 (m, 1H), 1.22 (s, 9H), 1.21 ppm (s, 9H)

$^{13}$C NMR (101 MHz, CDCl$_3$) δ 203.2, 177.2, 176.8, 105.7, 75.7, 75.1, 74.0, 58.3, 55.7, 55.5, 39.0, 38.8, 27.1 ppm Preparation of Intermediate 28

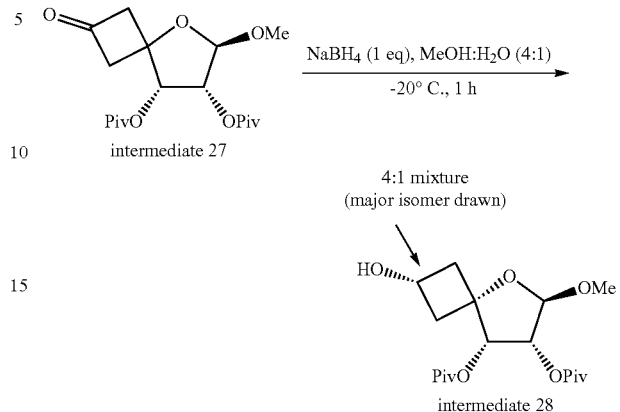

Intermediate 27 (1.04 g, 2.92 mmol, 1.00 eq) was dissolved in MeOH (20 ml) and water (5 ml) was added. The mixture was cooled to −20° C. and sodiumborohydride (110 mg, 2.92 mmol, 1.00 eq) was added portionwise. The mixture was stirred for 1 hour at −20° C. and then warmed to room temperature, diluted in EtOAc (100 ml). Brine (40 ml) was added and the product was extracted in EtOAc (3×100 ml). Combined organic fractions were dried (MgSO$_4$), filtered and the filtrate was concentrated in vacuo to give intermediate 28 (1.06 g, crude, 4:1 mixture of diastereoisomers).

Preparation of Intermediate 29

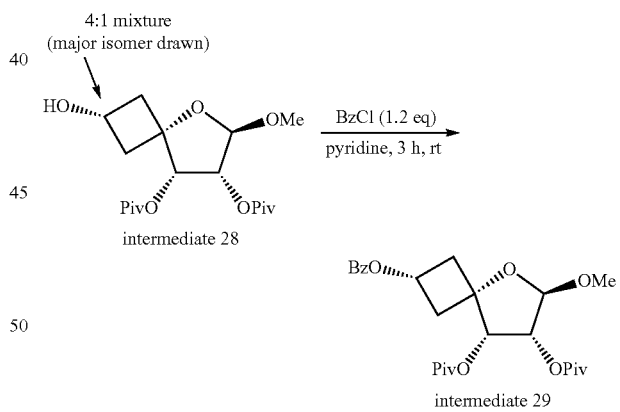

Intermediate 28 (4.00 g, 11.4 mmol, 1.00 eq) was dissolved in pyridine (50 ml) and cooled to 0° C. Subsequently, benzoyl chloride (1.58 ml, 13.6 mmol, 1.20 eq) was added dropwise over a period of 5 minutes and the mixture was stirred for 3 hours at room temperature. The solution was concentrated in vacuo to a minimal volume and redissolved in EtOAc (500 ml) and brine (150 ml) was added. The product was extracted in EtOAc (1×500 ml, 2×250 ml) and combined organic phases were dried (MgSO$_4$), filtered and the filtrate was concentrated in vacuo. The residue was purified by column chromatography over silica gel (gradient elution: n-heptane/EtOAc from 99:1 to 4:1). The fractions containing intermediate 29 were collected and the solvent was evaporated to give intermediate 29 (3.52 g, 7.62 mmol, 68% yield) as a colorless oil.

¹H NMR (360 MHz, CDCl₃) δ 8.03 (dd, J=8.5, 1.2 Hz, 2H), 7.51-7.61 (m, 1H), 7.39-7.48 (m, 2H), 5.37 (d, J=4.4 Hz, 1H), 5.20 (dd, J=4.4, 1.3 Hz, 1H), 4.78-4.88 (m, 2H), 3.40 (s, 3H), 3.10 (dt, J=12.9, 6.3 Hz, 1H), 2.89 (dt, J=12.9, 6.4 Hz, 1H), 2.73 (dd, J=13.0, 7.3 Hz, 1H), 2.44 (dd, J=12.9, 7.4 Hz, 1H), 1.28 (s, 9H), 1.21 ppm (s, 9H)

¹³C NMR (101 MHz, CDCl₃) δ 117.2, 177.0, 166.0, 133.0, 129.9, 129.6, 128.4, 105.4, 77.6, 75.1, 74.5, 61.5, 55.3, 43.2, 40.2, 39.1, 38.8, 27.3, 27.1 ppm Preparation of Intermediate 30

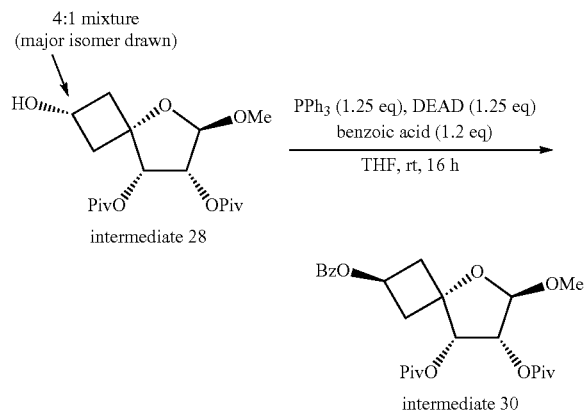

Intermediate 28 (2.28 g, 6.36 mmol, 1.00 eq) was dissolved in THF (60 ml) and benzoic acid (932 mg, 7.63 mmol, 1.20 eq) was added followed by triphenylphosphine (2.01 g, 7.63 mmol, 1.20 eq). The mixture was cooled to 0° C. and diethyl azodicarboxylate (1.15 ml, 7.31 mmol, 1.20 eq) was added. The mixture was warmed to room temperature after the addition and stirred for 16 hours followed by adding pentane (120 ml) to precipitate triphenylphosphine-oxides. The solids were filtered and rinsed with heptane (30 ml). To the filtrate was added brine (50 ml) and the product was extracted in heptane (1×150 ml, 2×100 ml). Combined organic layers were dried (MgSO₄), filtered and the filtrate was concentrated in vacuo. The residue was purified by column chromatography over silica gel (gradient elution: n-heptane/EtOAc from 99:1 to 4:1). The fractions containing intermediate 30 were collected and the solvent was evaporated to give intermediate 30 (1.79 g, 3.88 mmol, 61% yield) as a colorless oil.

¹H NMR (400 MHz, CDCl₃) δ 7.98-8.04 (m, 2H), 7.52-7.60 (m, 1H), 7.39-7.47 (m, 2H), 5.44 (m, 1H), 5.37 (d, J=4.4 Hz, 1H), 5.18 (dd, J=4.4, 1.5 Hz, 1H), 4.88 (d, J=1.5 Hz, 1H), 3.42 (s, 3H), 2.81 (ddd, J=13.4, 7.5, 4.4 Hz, 1H), 2.62-2.72 (m, 2H), 2.52-2.62 (m, 1H), 1.21 (s, 9H), 1.20 ppm (s, 9H)

¹³C NMR (101 MHz, CDCl₃) δ 177.2, 177.0, 166.1, 133.0, 130.0, 129.6, 128.4, 105.7, 81.1, 75.1, 74.3, 65.5, 55.4, 41.3, 39.3, 39.0, 38.8, 27.2, 27.1 ppm Preparation of Intermediate 31

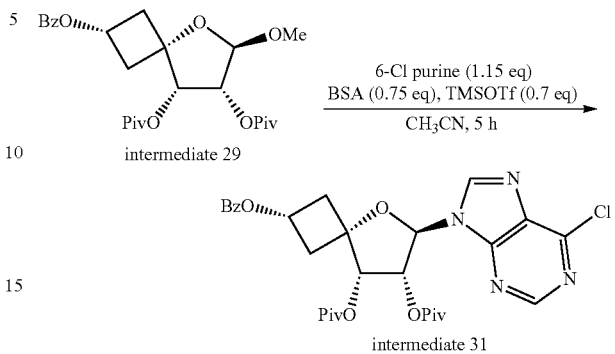

6-Chloropurine (76.9 mg, 0.497 mmol, 1.15 eq) was weighed in an oven dried microwave vial and dissolved in anhydrous acetonitrile (1.00 ml, dried over 3 Å molecular sieves). The vial was sealed and N,O-bis(trimethylsilyl)acetamide (0.084 ml, 0.324 mmol, 0.75 eq) was added and the mixture was stirred at room temperature for 45 minutes. Subsequently, intermediate 29 (200 mg, 0.432 mmol, 1.00 eq) was dissolved in anhydrous acetonitrile (1.75 ml) and added to the stirring mixture of the silylated purine base. TMSOTf (0.06 ml, 0.303 mmol, 0.70 eq) was added drop-wise at room temperature to the mixture which was heated to 90° C. for 5 hours. The mixture was cooled to room temperature and diluted in CH₂Cl₂ (50 ml). NaHCO₃ (aq. sat. 20 ml) was added and the product was extracted in CH₂Cl₂ (2×50 ml, 1×30 ml). Combined organic fractions were dried (MgSO₄), filtered and the filtrate was concentrated in vacuo. The residue was purified by column chromatography over silica gel (gradient elution: n-heptane/EtOAc from 95:5 to 1:4). The fractions containing the product were collected and the solvent was evaporated to give the desired intermediate 31 (240 mg, 0.410 mmol, 95% yield) as a white foam.

Preparation of Intermediate 76

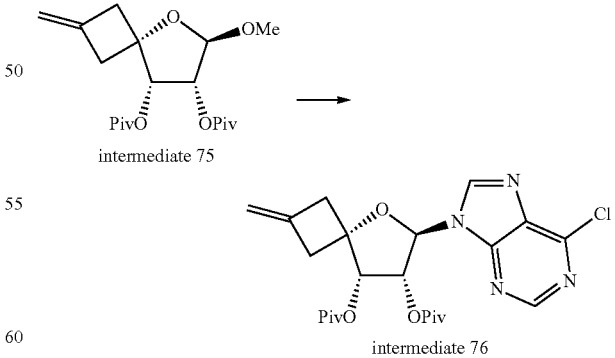

Intermediate 76 was prepared according to analogous reaction protocol as described for intermediate 31. Intermediate 76: 71% yield, 525 mg, 1.09 mmol, off-white foam.

¹H NMR (400 MHz, CDCl₃): δ 8.77 (s, 1H), 8.20 (s, 1H), 6.19 (dd, J=5.7, 4.5 Hz, 1H), 6.09 (d, J=5.7 Hz, 1H), 5.72 (d,

J=4.5 Hz, 1H), 4.96 (dt, J=4.8, 2.3 Hz, 2H), 3.10-3.25 (m, 2H), 2.96-3.10 (m, 2H), 1.31 (s, 9H), 1.14 ppm (s, 9H).

$^{13}$C NMR (101 MHz, CDCl$_3$): δ 176.9, 152.2, 151.5, 151.3, 143.9, 143.9, 137.2, 132.6, 108.8, 87.4, 82.8, 74.1, 73.3, 44.3, 40.4, 39.2, 38.8, 27.3, 27.0 ppm.

Preparation of Intermediate 32

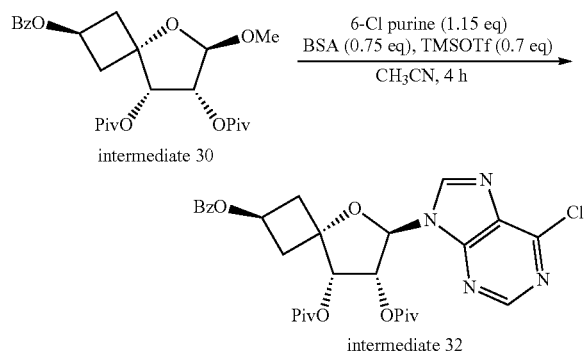

6-Chloropurine (154, 0.994 mmol, 1.15 eq) was weighed in an oven dried microwave vial and dissolved in anhydrous acetonitrile (2.00 ml, dried over 3 Å molecular sieves). The vial was sealed and N,O-bis(trimethylsilyl)acetamide (0.16 ml, 0.648 mmol, 0.75 eq) was added and the mixture was stirred at room temperature for 45 minutes. Subsequently, intermediate 30 (400 mg, 0.864 mmol, 1.00 eq) was dissolved in anhydrous acetonitrile (3.50 ml) and added to the stirring mixture of the silylated purine base. TMSOTf (0.11 ml, 0.606 mmol, 0.70 eq) was added dropwise at room temperature to the mixture which was heated to 90° C. for 4 hours. The mixture was cooled to room temperature and diluted in CH$_2$Cl$_2$ (100 ml). NaHCO$_3$ (aq. sat. 50 ml) was added and the product was extracted in CH$_2$Cl$_2$ (3×100 ml). Combined organic fractions were dried (MgSO$_4$), filtered and the filtrate was concentrated in vacuo. The residue was purified by column chromatography over silica gel (gradient elution: n-heptane/EtOAc from 95:5 to 1:4). The fractions containing the product were collected and the solvent was evaporated to give the desired intermediate 32 (460 mg, 0.786 mmol, 91% yield) as a white foam.

Preparation of Compound 7

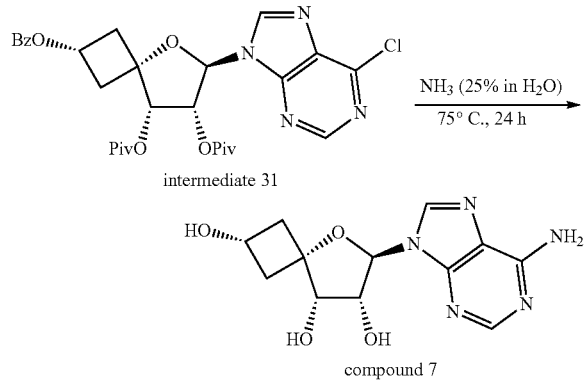

Intermediate 31 (320 mg, 0.547 mmol, 1.00 eq) was dissolved in 1,4-dioxane (2.00 ml) and NH$_3$ (8.00 ml, 25% in H$_2$O) was added. The mixture was heated to 75° C. for 24 h in a pressure reactor, then cooled to room temperature and concentrated in vacuo followed by coevaporation with toluene (3×70 ml). Subsequently, the solids were washed by stirring with CH$_3$CN for 1 hour followed by centrifugation and decantation of the solvent. This procedure was repeated three times to remove impurities from protective groups. The resulting solids were dried in vacuo at 50° C. for 18 h to give compound 7 (153 mg, 80% yield) as a white powder.

$^1$H NMR (500 MHz, MeOD) δ 8.40 (s, 1H), 8.38 (s, 1H), 6.00 (d, J=6.7 Hz, 1H), 4.96 (t, J=5.3 Hz, 1H), 4.03 (d, J=4.0 Hz, 1H), 3.92 (quin., J=7.1 Hz, 1H), 2.98 (dt, J=12.3, 6.1 Hz, 1H), 2.70 (dt, J=12.2, 6.1 Hz, 1H), 2.25 (dd, J=10.7, 6.5 Hz, 1H), 2.07 ppm (dd, J=10.9, 6.6 Hz, 1H)

$^{13}$C NMR (125 MHz, MeOD) δ 152.8, 150.5, 146.5, 143.9, 120.9, 89.8, 80.7, 76.7, 75.6, 59.0, 46.6, 41.7 ppm Preparation of Intermediate 77

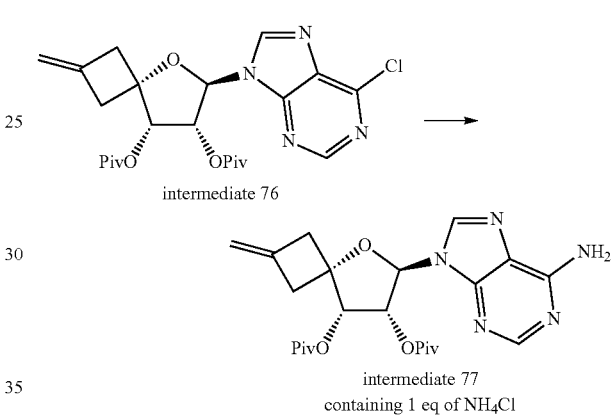

Intermediate 77 was prepared according to an analogous reaction protocol as was described for the synthesis of compound 7. Intermediate 77: 90% yield, 270 mg, 0.789 mmol, off-white salt (containing 1 eq of NH$_4$Cl).

$^1$H NMR (DMSO-d$_6$, 400 MHz): δ=8.31 (s, 1H), 8.15 (s, 1H), 5.85-5.94 (m, 1H), 5.47 (br s, 2H), 5.05 (br s, 1H), 4.87 (br d, J=1.6 Hz, 2H), 3.98 (br d, J=3.7 Hz, 1H), 3.13 (br d, J=15.9 Hz, 1H), 2.89 (br d, J=2.0 Hz, 2H), 2.69 ppm (br dd, J=16.3, 2.4 Hz, 1H).

Preparation of Compound 8

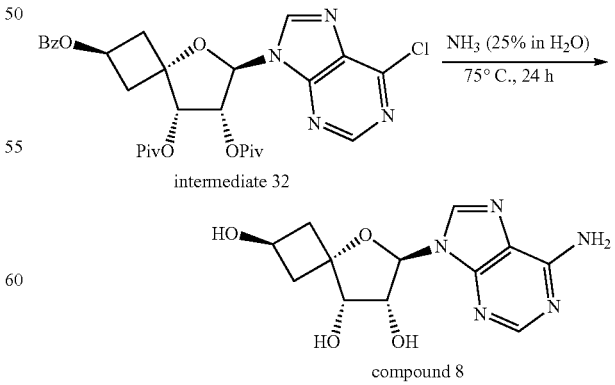

Intermediate 32 (340 mg, 0.581 mmol, 1.00 eq) was dissolved in 1,4-dioxane (2.00 ml) and NH$_3$ (8.00 ml, 25% in H$_2$O) was added. The mixture was heated to 75° C. for 24 h in a pressure reactor, then cooled to room temperature and concentrated in vacuo followed by coevaporation with toluene (3×70 ml). Subsequently, the solids were washed by stirring with CH$_3$CN for 1 hour followed by centrifugation and decantation of the solvent. This procedure was repeated three times to remove impurities from protective groups. The resulting solids were dried in vacuo at 50° C. for 18 h to give compound 8 (169 mg, 84% yield) as a white powder.

$^1$H NMR (500 MHz, MeOD) δ 8.42 (s, 1H), 8.37 (s, 1H), 6.02 (d, J=6.3 Hz, 1H), 4.90 (dd, J=5.4, 3.6 Hz, 1H), 4.37 (m, 1H), 4.21 (d, J=4.5 Hz, 1H), 2.64 (dt, J=12.3, 6.5 Hz, 1H), 2.70 (ddd, J=13.3, 5.5, 3.1 Hz, 1H), 2.40 (m, 1H), 2.23 ppm (ddd, J=12.9, 5.3, 3.1 Hz, 1H)

$^{13}$C NMR (125 MHz, MeOD) δ 153.0, 150.3, 147.0, 143.9, 120.8, 90.1, 85.7, 77.2, 75.4, 62.7, 44.6, 40.8 ppm Preparation of Intermediate 33

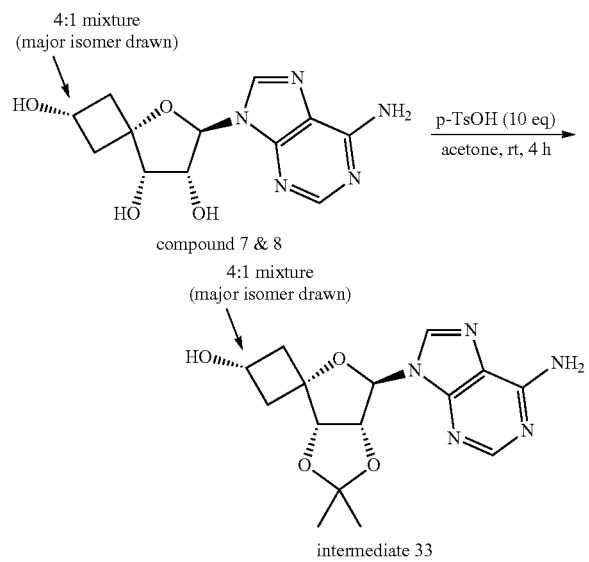

A 4:1 mixture of compound 7 & 8 (500 mg, 1.44 mmol, 1.00 eq) (mixture prepared via an analogous reaction protocol as used for int. 29) was suspended in acetone (75 ml) and 4-methylbenzenesulfonic acid (2.74 g, 14.4 mmol, 10.0 eq) was added all at once. The yellow mixture was stirred for 4 hours at room temperature before ice cold NaHCO$_3$ (aq. sat. 45 ml) was added. The solution was concentrated to a minimal volume, coevaporated to dryness with toluene followed by the addition of acetone (50 ml). The suspension was stirred for 17 hours at room temperature and subsequently filtered to remove the salts. The filtrate was concentrated to a minimal volume in vacuo. The residue was purified by column chromatography over silica gel (gradient elution: CH$_2$Cl$_2$/MeOH from 100:0 to 7:3). The fractions containing the product were collected and the solvent was evaporated to give the desired intermediate 33 (264 mg, 52% yield) as a white solid Preparation of Intermediate 78

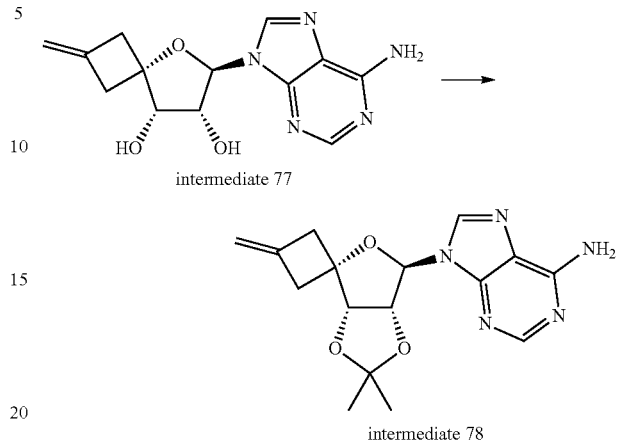

Intermediate 78 was prepared according to an analogous reaction protocol as described for intermediate 33. Intermediate 78: 90% yield, 475 mg, 1.38 mmol, yellow sticky solid.

$^1$H NMR (400 MHz, CDCl$_3$): δ 8.32 (s, 1H), 7.86 (s, 1H), 6.15 (br. s. 2H), 6.04 (s, 1H, 1'), 5.87 (d, J=5.9 Hz, 1H, 2'), 5.07 (d, J=5.9 Hz, 1H, 3'), 4.88 (quin, J=2.4 Hz, 1H, —CH$_2$), 4.80 (quin, J=2.4 Hz, 1H, —CH$_2$), 3.22 (ddq, J=16.4, 4.3, 2.2 Hz, 1H), 2.98 (dq, J=16.4, 2.8 Hz, 1H), 2.76 (ddq, J=15.8, 4.2, 2.7 Hz, 1H), 2.35 (dq, J=15.8, 2.7 Hz, 1H), 1.54 (s, 3H), 1.43 ppm (s, 3H). $^{13}$C NMR (101 MHz, CDCl$_3$): δ 155.8, 153.0, 149.3, 140.4, 139.1, 120.0, 113.3, 107.9, 90.9, 85.4, 85.3, 84.0, 45.3, 39.9, 27.6, 26.6, 25.4 ppm.

Preparation of Intermediate 34

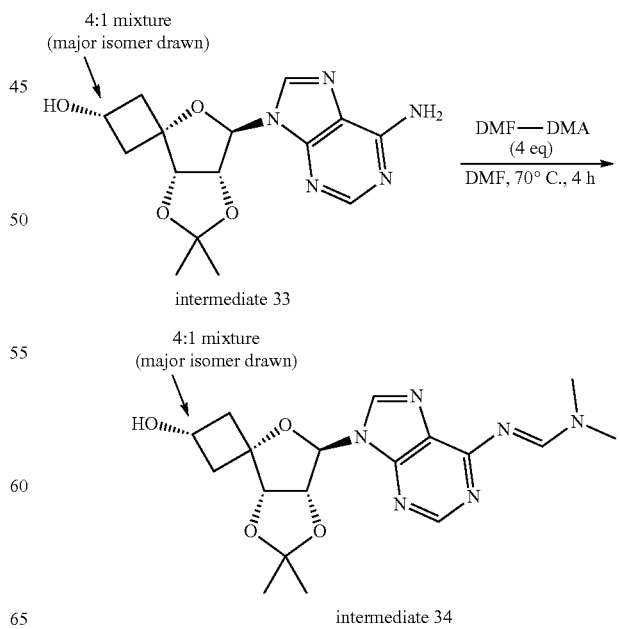

Intermediate 33 (160 mg, 0.45 mmol, 1.00 eq) was dissolved in DMF (1.60 ml) and N,N-dimethylformamide dimethyl acetal (0.25 mL, 1.81 mmol, 4.00 eq) was added. The mixture was stirred at 70° C. for 4 hours and subsequently concentrated in vacuo by coevaporation with with toluene to yield intermediate 34 (218 mg, crude).

Preparation of Intermediate 35

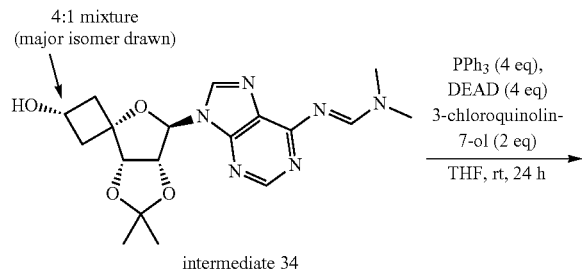

intermediate 34

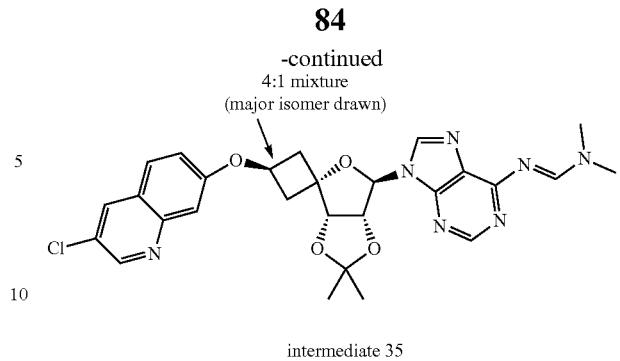

intermediate 35

Intermediate 34 (218 mg, crude) was dissolved in anhydrous THF (4.00 ml) and triphenylphosphine (477 mg, 1.80 mmol, 4.00 eq) and 3-chloroquinolin-7-ol (162 mg, 0.90 mmol, 2.00 eq) were added. Diethyl azodicarboxylate (0.28 ml, 1.80 mmol, 4.00 eq) was added dropwise and the mixture was stirred at room temperature for 24 hours. The mixture was concentrated to a minimal volume in vacuo to give intermediate 35 which was used without purification in the next step.

Preparation of Intermediate 36

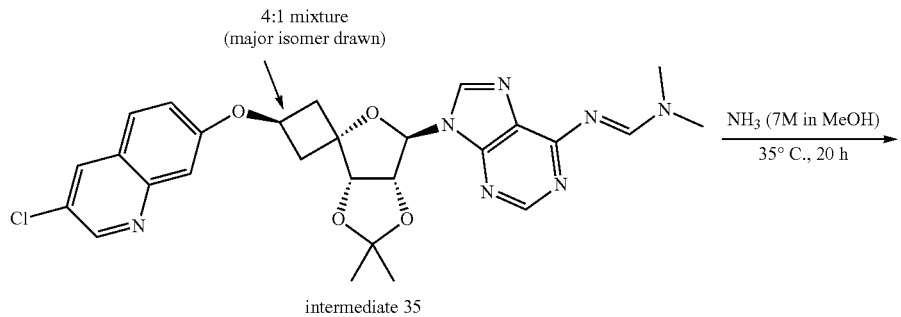

intermediate 35

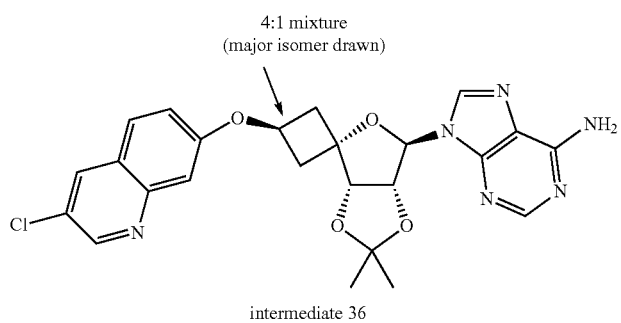

intermediate 36

Intermediate 35 (crude from previous step) was dissolved in NH$_3$ (7M in MeOH) (50 ml, 7 M) and heated to 35° C. for 20 hours. The mixture was concentrated to a minimal volume in vacuo and the residue was purified by column chromatography over silica gel (gradient elution: CH$_2$Cl$_2$/MeOH from 1:0 to 7:3). The fractions containing the product were collected and the solvent was evaporated to give the desired intermediate 36 (179 mg, 70% pure on LC). Intermediate 36 was used as such in the next step.

Preparation of Compound 9 and Compound 10

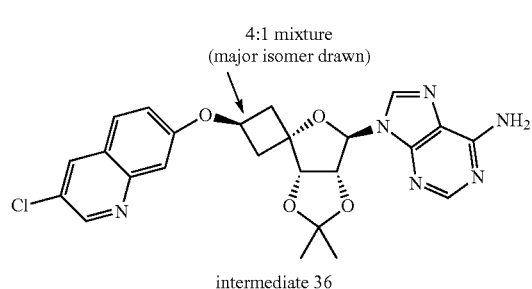

intermediate 36 (4:1 mixture, major isomer drawn)

HCl (aq. 1M in H$_2$O): EtOH (4:1) 60° C., 1 h

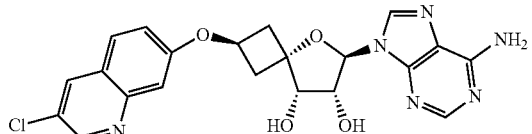

compound 9

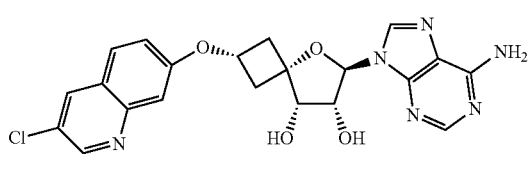

compound 10

Intermediate 36 (179 mg, crude) was dissolved in EtOH (4.00 ml) and HCl (aq. 1M in H$_2$O, 16.0 ml) was added. The mixture was stirred for 1 hour at 60° C. and subsequently cooled to room temperature, diluted with H$_2$O (50 ml) and lyophilized. The resulting brown powder was purified via Prep HPLC (Stationary phase: RP XBridge Prep C18 OBD-10 μm, 50×150 mm, Mobile phase: 0.25% NH$_4$HCO$_3$ solution in water, CH$_3$CN) followed by a purification via Prep SFC (Stationary phase: Chiralcel Diacel OJ 20×250 mm, Mobile phase: CO$_2$, EtOH+0.4% iPrNH$_2$). Pure fractions were combined and concentrated in vacuo to yield compound 9 (2.4 mg, mmol, major isomer, 1% combined yield over 4 steps) and compound 10 (0.6 mg, mmol, minor isomer).

Preparation of Intermediate 37

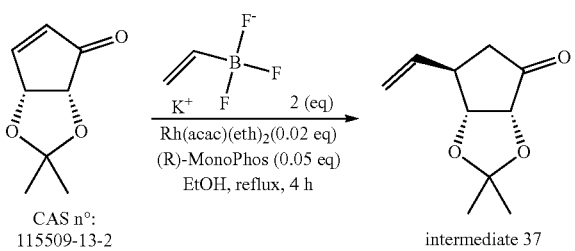

CAS n°: 115509-13-2

Rh(acac)(eth)$_2$(0.02 eq)
(R)-MonoPhos (0.05 eq)
EtOH, reflux, 4 h intermediate 37

Acetylacetonatobis(ethylene)rhodium(I) (837 mg, 3.24 mmol, 0.02 eq) and (R)—N,N-dimethyldinaphtho[2,1-D:1',2'-F][1,3,2]dioxaphosphepin-4-amine (2.91 g, 8.11 mmol, 0.05 eq) were dissolved in EtOH (625 ml) under nitrogen atmosphere. The mixture was stirred at room temperature and flushed through with nitrogen gas for 15 minutes. Then (−)—(3AR,6AR)-3A,6A-dihydro-2,2-dimethyl-4H-cyclopenta-1,3-dioxol-4-one (25.0 g, 162.16 mmol, 1.00 eq) and potassium vinyltrifluoroborate (45.7 g, 324 mmol, 2.00 eq) were added and the reaction mixture was stirred and refluxed for 4 hours. The reaction mixture (suspension) was cooled down to room temperature. The precipitate was filtered off over a pad of Celite and washed with ethanol. The solvents of the filtrate were evaporated. n-Heptane was added to the residue and the resulting suspension was filtered off over a pad of Celite and washed with heptanes resulting in a dark brown solid residue. The filtrate was washed with NH$_4$OH (3×300 ml), washed with brine, dried with MgSO$_4$, filtered and the filtrate evaporated yielding intermediate 37 (16.2 g, 51% crude yield).

Preparation of Intermediate 38

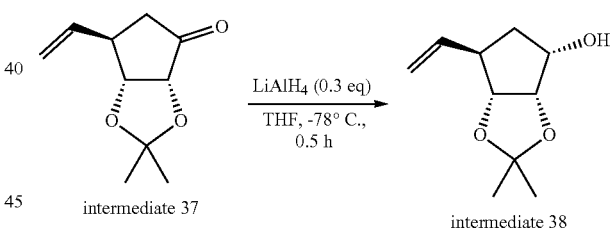

intermediate 37

LiAlH$_4$ (0.3 eq)
THF, −78° C., 0.5 h intermediate 38

A solution of intermediate 37 (16.2 g, 82.6 mmol, 1.00 eq) in THF (200 ml) was added dropwise to a stirring solution of lithium aluminum hydride (24.8 ml, 1M in THF, 24.8 mmol, 0.30 eq) in THF (400 ml) at −78° C. under nitrogen atmosphere. The reaction mixture was stirred at −78° C. under nitrogen atmosphere for 30 minutes. The reaction was quenched by the dropwise addition of acetone (6.1 mL) followed by water (50 ml) at −78° C. After addition, the reaction mixture was warmed to room temperature and EtOAc (400 ml) was added. The mixture was shaken vigorously. The organic layer was separated, washed three times with water, washed with brine, dried (MgSO$_4$), filtered and the filtrate was evaporated. The residue was purified by column chromatography over silica gel (gradient elution: n-heptane/EtOAc from 1:0 to 1:1). The fractions containing the product were collected and the solvent was evaporated to give the desired intermediate 38 (10.7 g, 71% yield).

Preparation of Intermediate 39

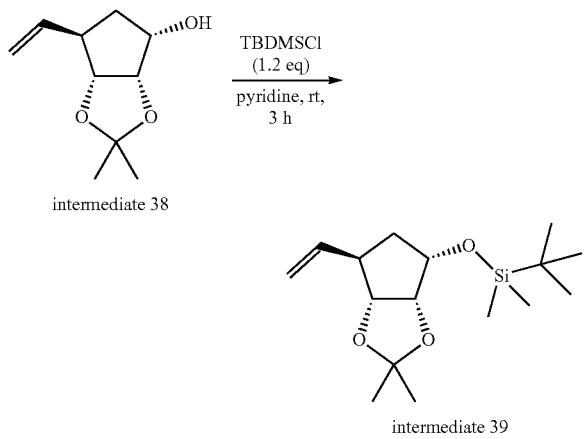

intermediate 38 intermediate 39

Intermediate 38 (3.10 g, 16.6 mmol, 1.00 eq) was dissolved in pyridine (10.3 ml) and tert-butyldimethylsilyl chloride (2.88 g, 19.1 mmol, 1.15 eq) was added portionwise at room temperature. The mixture was stirred for 17 hours at room temperature and diluted in EtOAc (250 ml). The organic layer was washed with brine (4×80 ml), dried (MgSO$_4$), filtered and the filtrate was concentrated in vacuo. The residue was purified by column chromatography over silica gel (gradient elution: n-heptane/EtOAc from 1:0 to 7:3). The fractions containing the product were collected and the solvent was evaporated to give the desired intermediate 39 (3.15 g, 63% yield) as a slightly yellow oil.

Preparation of Intermediate 40

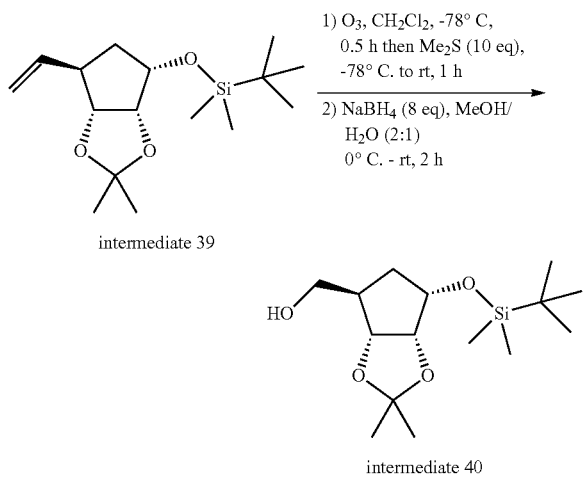

intermediate 39 intermediate 40

Intermediate 39 (20.1 g, 43.8 mmol, 1.00 eq) was dissolved in CH$_2$Cl$_2$ (400 ml) and the mixture was cooled to −78° C. Ozone was generated from oxygen gas with an ozone generator (Fischer OZ500/5) and bubbled in the cooled solution through a glass pipet. A blue color was observed after 1.5 hours and ozone was added for an additional 20 minutes at −78° C. Subsequently, the mixture was flushed with nitrogen for 5 minutes (disappearance of the blue color) and dimethyl sulfide (25.7 ml, 350 mmol, 8.00 eq) was added at −78° C. The flow of nitrogen gas was stopped and the mixture was stirred for 1 hour while the temperature was allowed to increase to −40° C. The mixture was concentrated in vacuo at 30° C. to a minimal volume and the resulting yellow oil was redissolved in methanol (220 ml) and water (110 ml). The solution was cooled to 0° C. and sodium borohydride (19.8 g, 526 mmol, 12.0 eq) was added portionwise. The ice bath was removed after 1.5 hours and stirring was continued at room temperature. After 4 hours stirring the mixture was diluted in CH$_2$Cl$_2$ (350 ml) and NH4Cl (aq. sat. 150 ml) was added. The product was extracted in CH$_2$Cl$_2$ (3×350 ml) and combined organic layers were dried (MgSO$_4$), filtered and the filtrate was concentrated in vacuo. The residue was purified by column chromatography over silica gel (gradient elution: n-heptane/EtOAc from 1:0 to 0:1). The fractions containing the product were collected and the solvent was evaporated to give the desired intermediate 40 (8.30 g, 63% yield) as a slightly yellow oil.

$^1$H NMR (400 MHz, CDCl$_3$): δ=4.37-4.42 (m, 2H), 4.10-4.15 (m, 1H), 3.55-3.62 (m, 1H), 3.45-3.53 (m, 1H), 2.16-2.26 (m, 1H), 2.01 (dt, J=12.7, 8.2 Hz, 1H), 1.86 (br s, 1H), 1.57-1.66 (m, 1H), 1.49 (s, 3H), 1.31 (s, 3H), 0.91 (s, 9H), 0.09 ppm (d, J=2.9 Hz, 6H)

$^{13}$C NMR (101 MHz, CDCl$_3$): δ=111.7, 82.0, 80.9, 72.7, 64.3, 44.7, 34.4, 26.5, 26.0, 24.9, 18.4, −4.5 ppm

Preparation of Intermediate 41

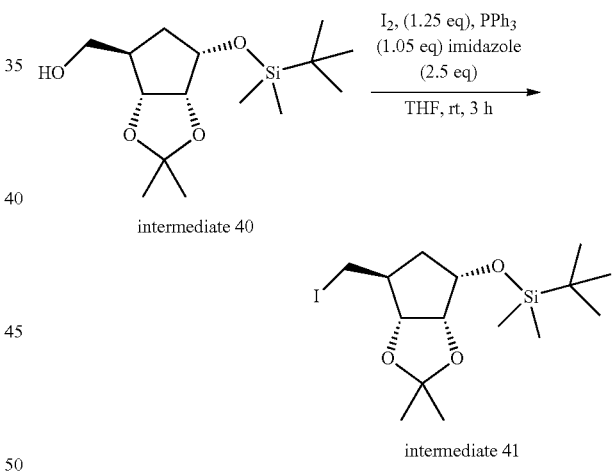

intermediate 40 intermediate 41

Intermediate 40 (8.30 g, 27.4 mmol, 1.00 eq) was dissolved in THF (140 ml). Imidazole (4.67 g, 68.6 mmol, 2.50 eq) and triphenylphosphine (8.03 g, 29.1 mmol, 1.05 eq) were added followed by the portionwise addition of iodine (8.79 g, 34.3 mmol, 1.25 eq) at room temperature. After 1 hour, additional amounts of triphenylphosphine (2.29 g, 8.31 mmol, 0.30 eq) and iodine (2.46 g, 9.60 mmol, 0.35 eq) were added. Reaction was continued for 2 hours, then, the mixture was concentrated to a minimal volume in vacuo and n-heptane (400 ml) was added. Triphenylphosphine-oxides were precipitated and the mixture was sonicated for 30 minutes. The organic layer was separated by filtration and the solids were rinsed with n-heptane (100 ml). To the filtrate was added sodiumthiosulfite (aq. sat. 150 ml) and the product was extracted in n-heptane (3×400 ml). Combined organic fractions were dried (MgSO$_4$), filtered and the filtrate was concentrated in vacuo to give intermediate 41 (9.84 g, 87% calculated yield on HNMR) as a colorless oil.

$^1$H NMR (400 MHz, CDCl$_3$): δ=4.29-4.39 (m, 1H), 4.21 (dd, J=6.1, 2.4 Hz, 1H), 4.05 (dt, J=7.8, 5.0 Hz, 1H), 2.97-3.15 (m, 2H), 2.22-2.38 (m, 1H), 1.96 (dt, J=13.0, 7.7 Hz, 1H), 1.56 (dt, J=13.0, 5.3 Hz, 1H), 1.40 (s, 3H), 1.23 (s, 3H), 0.82 (s, 9H), 0.00 ppm (d, J=2.4 Hz, 6H)

Preparation of Intermediate 42

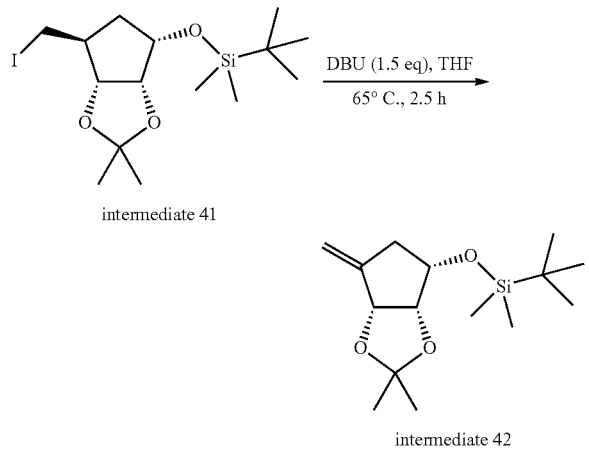

Intermediate 41 (9.84 g, 23.9 mmol, 1.00 eq) was dissolved in THF (168 ml) and 1,8-diazabicyclo [5.4.0]undec-7-ene (5.35 ml, 35.8 mmol, 1.50 eq) was added. The mixture was heated to 65° C. for 2.5 hours, then cooled to room temperature. Precipitated DBU-salts were filtered and rinsed with THF and the filtrate was concentrate to a minimal volume in vacuo. Subsequently, n-heptane (400 ml) and brine (100 ml) were added and the product was extracted in n-heptane (3×400 ml). Combined organic layers were dried (MgSO$_4$), filtered and the filtrate was concentrated in vacuo. The residue was purified by column chromatography over silica gel (gradient elution: n-heptane/EtOAc from 1:0 to 1:1). The fractions containing the product were collected and the solvent was evaporated to yield the desired intermediate 42 (6.00 g, 77% yield over 2 steps) as a colorless liquid.

$^1$H NMR (400 MHz, CDCl$_3$): δ=5.14-5.20 (m, 1H), 5.11 (dd, J=2.6, 1.0 Hz, 1H), 4.62 (d, J=5.7 Hz, 1H), 4.46 (t, J=5.1 Hz, 1H), 3.90 (ddd, J=11.2, 6.5, 4.7 Hz, 1H), 2.67 (ddtd, J=13.9, 11.1, 2.7, 1.2 Hz, 1H), 2.29-2.35 (m, 1H), 1.50 (s, 3H), 1.35 (s, 3H), 0.92 (s, 9H), 0.11 ppm (d, J=2.8 Hz, 6H)

$^{13}$C NMR (101 MHz, CDCl$_3$): δ=145.6, 113.6, 111.2, 80.8, 80.4, 72.3, 37.5, 26.4, 26.0, 24.7, 18.4, −4.5 ppm Preparation of Intermediate 43

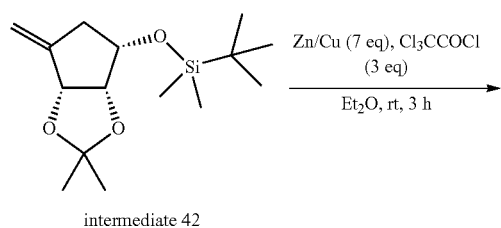

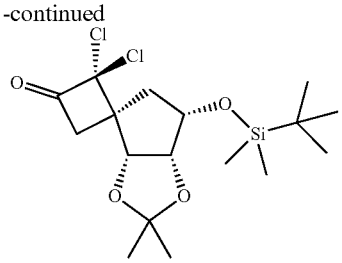

intermediate 43

Zinc powder (25.0 g, 0.38 mol, 1.00 eq) was added to a two-necked round bottomed flask (500 ml) containing demineralized water (100 ml) and the solution was degassed with nitrogen during 15 minutes. Subsequently, copper(II) sulfate (1.85 g, 11.5 mmol, 0.03 eq) was added and the stirring solution was degassed and stirred for 45 minutes. The mixture was filtered and the black solids were washed with degassed water (250 ml) and degassed acetone (250 ml), respectively. The zinc-copper couple was dried in vacuo for 12 hours.

Intermediate 42 (2.50 g, 8.79 mmol, 1.00 eq) was dissolved in anhydrous Et$_2$O (70 ml, dried over 4 Å molecular sieves and zinc-copper couple (7.93 g, 61.5 mmol, 7.00 eq) was added. Trichloroacetyl chloride (2.94 ml, 26.4 mmol, 3.00 eq) was dissolved in anhydrous Et$_2$O (20 ml), loaded in a glass syringe and added dropwise at room temperature with a rate of 6.5 ml/h. After 3 hours, the zinc-copper couple was removed via decantation and the organic layer was diluted in Et$_2$O (500 ml) and washed with NaHCO$_3$ (aq. sat. 3×150 ml) and brine (3×150 ml), dried (MgSO$_4$), filtered and the filtrate was concentrated in vacuo to yield intermediate 43 (3.36 g, crude).

$^1$H NMR (400 MHz, CDCl$_3$): δ=4.79 (dd, J=5.8, 1.0 Hz, 1H), 4.55 (t, J=5.3 Hz, 1H), 4.11 (dt, J=9.8, 5.1 Hz, 1H), 3.65 (d, J=18.3 Hz, 1H), 3.12 (d, J=18.3 Hz, 1H), 2.36 (dd, J=12.9, 5.4 Hz, 1H), 2.15 (dd, J=12.9, 9.8 Hz, 1H), 1.48 (s, 3H), 1.37 (s, 3H), 0.91-0.93 (m, 9H), 0.12 ppm (d, J=2.2 Hz, 6H)

$^{13}$C NMR (CHLOROFORM-d, 101 MHz): δ=191.8, 112.3, 80.7, 80.1, 71.5, 51.7, 26.1, 25.9, 18.4, −4.6, −4.9 ppm Preparation of Intermediate 44

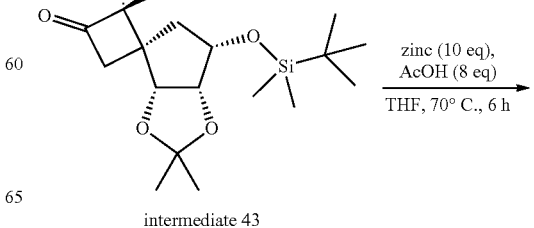

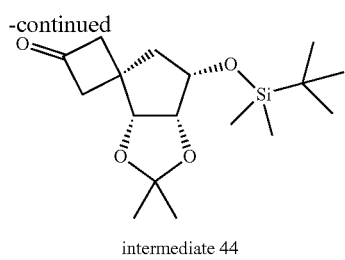

intermediate 44

Intermediate 43 (1.25 g, 3.16 mmol, 1.00 eq) was dissolved in THF (30 ml) and zinc (2.07 g, 31.6 mmol, 10.0 eq) and acetic acid (1.45 ml, 25.3 mmol, 8.00 eq) were added. The mixture was heated to 70° C. for 6 hours and then cooled to room temperature. The mixture was filtered over celite, the solids were rinsed with THF and the filtrate was concentrated to a minimal volume in vacuo. Subsequently, the oil was redissolved in $CH_2Cl_2$ (100 ml) and brine (50 ml) was added. The product was extracted in $CH_2Cl_2$ (3×100 ml) and combined organic fractions were dried ($MgSO_4$), filtered and the filtrate was concentrated in vacuo. The residue was purified by column chromatography over silica gel (gradient elution: n-heptane/EtOAc from 1:0 to 2:3). The fractions containing the product were collected and the solvent was evaporated to yield the desired intermediate 44 (0.648 mg, 63% yield over 2 steps) as a colorless oil.

$^1$H NMR (400 MHz, $CDCl_3$): δ=4.49 (t, J=5.1 Hz, 1H), 4.29-4.34 (m, 1H), 3.88 (dt, J=10.9, 5.3 Hz, 1H), 3.36 (ddd, J=18.3, 4.1, 2.4 Hz, 1H), 2.89-2.99 (m, 1H), 2.79-2.87 (m, 1H), 2.68-2.75 (m, 1H), 2.19 (t, J=11.4 Hz, 1H), 1.82 (dd, J=11.8, 5.7 Hz, 1H), 1.58 (s, 1H), 1.48 (s, 3H), 1.34 (s, 3H), 0.90-0.94 (m, 9H), 0.11 ppm (d, J=2.8 Hz, 6H)

$^{13}$C NMR (101 MHz, $CDCl_3$): δ=206.0, 111.1, 85.2, 80.2, 72.3, 56.7, 52.8, 41.3, 34.4, 26.0, 26.0, 24.5, 18.4, −4.4, −4.7 ppm Preparation of Intermediate 45

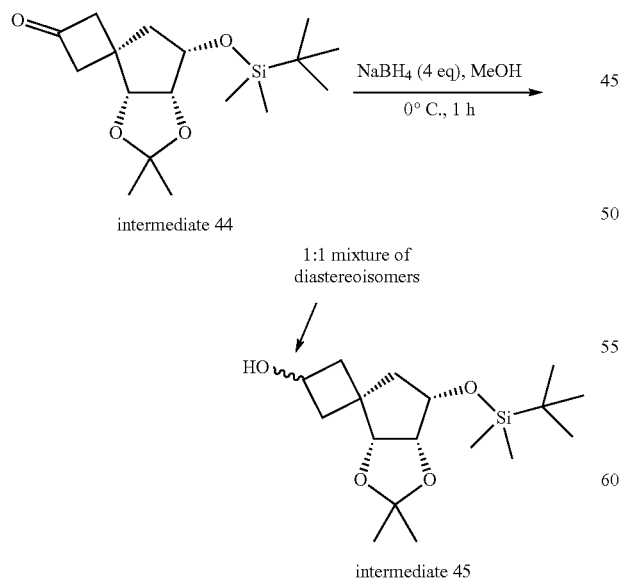

Intermediate 44 (600 mg, 1.84 mmol, 1.00 eq) was dissolved in methanol (20.0 ml) and cooled to 0° C. Sodium borohydride (282 mg, 7.35 mmol, 4.00 eq) was added portionwise and the mixture was stirred for 1 hour at 0° C. The solution was concentrated to a minimal volume in vacuo and dissolved in $CH_2Cl_2$ (100 ml) and $NH_4Cl$ (sat. aq. 50 ml) was added. The product was extracted in $CH_2Cl_2$ (3×100 ml) and combined organic layers were dried ($MgSO_4$), filtered and the filtrate was concentrated in vacuo to yield intermediate 45 (515 mg, 85% yield) in a 1:1 mixture.

Preparation of Intermediate 46a and Intermediate 46b

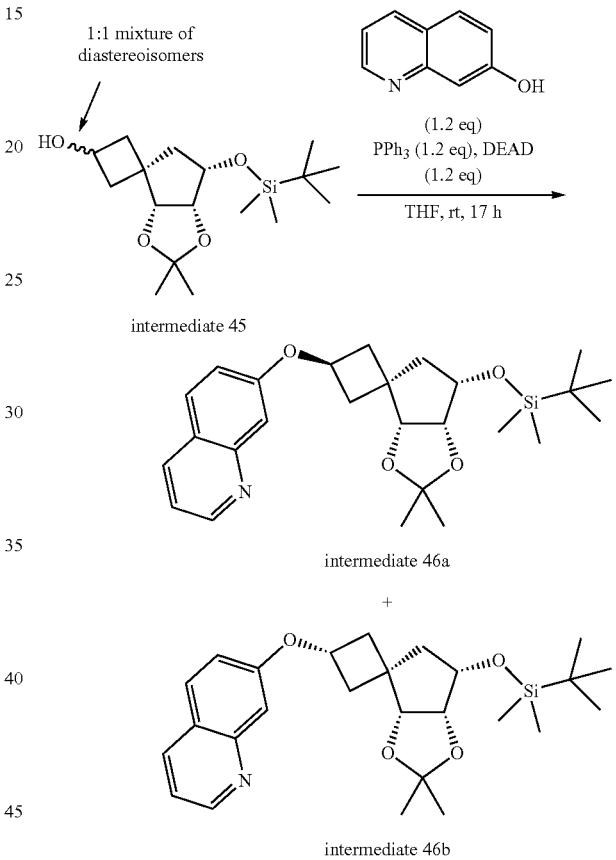

Intermediate 45 (300 mg, 0.913 mmol, 1.00 eq) was dissolved in THF (6.00 ml) and triphenylphosphine (290 mg, 1.10 mmol, 1.20 eq), 7-hydroxyquinoline (159 mg, 1.10 mmol, 1.20 eq) and diethyl azodicarboxylate (0.17 ml, 1.10 mmol, 1.20 eq) were added upon which a homogeneous solution was obtained. The mixture was stirred for 17 hours at room temperature, then concentrated to a minimal volume in vacuo. The residue was purified by column chromatography over silica gel (gradient elution: n-heptane/EtOAc from 1:0 to 0:1). The fractions containing the product were collected and the solvent was evaporated to yield the desired intermediate 46a (170 mg, 41% yield) and intermediate 46b (134 mg, 32% yield).

$^1$H NMR intermediate 46a (400 MHz, $CDCl_3$): δ=8.68 (dd, J=4.4, 1.8 Hz, 1H), 7.93 (dd, J=8.3, 1.4 Hz, 1H), 7.56 (d, J=9.0 Hz, 1H), 7.12-7.15 (m, 1H), 7.11 (s, 1H), 7.07-7.14 (m, 1H), 7.04 (dd, J=8.8, 2.4 Hz, 1H), 4.72 (quin, J=6.8 Hz, 1H), 4.25 (t, J=5.1 Hz, 1H), 4.14 (d, J=5.3 Hz, 1H), 3.76 (dt, J=10.9, 5.6 Hz, 1H), 2.31-2.44 (m, 2H), 2.17-2.31 (m, 1H), 1.85-1.94 (m, 2H), 1.70 (dd, J=11.8, 5.6 Hz, 2H), 1.31 (s, 3H), 1.18 (s, 3H), 0.81 (s, 9H), 0.00 ppm (s, 6H)

$^{13}$C NMR intermediate 46a (101 MHz, CDCl$_3$): δ=158.4, 150.5, 149.9, 135.7, 128.9, 123.5, 120.2, 119.0, 110.6, 108.8, 87.1, 79.8, 72.1, 68.8, 41.5, 40.7, 37.0, 35.9, 26.1, 24.6, 18.5, −4.4, −4.5 ppm $^1$H NMR intermediate 46b (400 MHz, CDCl$_3$): δ=8.73 (dd, J=4.3, 1.7 Hz, 1H), 7.97 (dd, J=8.1, 1.5 Hz, 1H), 7.61 (d, J=8.8 Hz, 1H), 7.18 (s, 1H), 7.14-7.22 (m, 1H), 7.08 (dd, J=8.8, 2.4 Hz, 1H), 4.75 (quin, J=6.9 Hz, 1H), 4.36 (t, J=5.2 Hz, 1H), 4.18 (s, 1H), 3.74 (dt, J=10.9, 5.4 Hz, 1H), 2.84 (ddd, J=12.2, 7.2, 4.8 Hz, 1H), 2.37 (ddd, J=11.7, 6.8, 4.8 Hz, 1H), 2.09 (dd, J=12.4, 6.9 Hz, 1H), 1.90-1.99 (m, 1H), 1.87-1.97 (m, 1H), 1.66 (dd, J=11.7, 5.7 Hz, 1H), 1.39 (s, 3H), 1.27 (s, 3H), 0.82 (s, 9H), 0.00 ppm (d, J=3.1 Hz, 6H)

$^{13}$C NMR intermediate 46b (101 MHz, CDCl$_3$): δ=158.3, 150.6, 149.9, 135.6, 128.9, 123.5, 120.0, 119.0, 110.8, 109.0, 85.1, 80.1, 71.7, 68.4, 43.0, 40.8, 37.3, 34.8, 26.1, 26.0, 24.6, 18.5, −4.4, −4.6 ppm Preparation of Intermediate 47

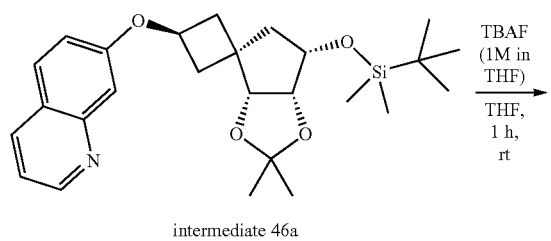

intermediate 46a intermediate 47

Intermediate 46a (170 mg, 0.37 mmol, 1.00 eq) was dissolved in THF (5.00 ml) and tert-butylammonium fluoride (1.49 ml, 1 M in THF) was added. The mixture was stirred for 1 hour at room temperature and concentrated to a minimal volume in vacuo. The residue was dissolved in EtOAc (50 ml) and washed with NaHCO$_3$ (1×25 ml) and brine (3×25 ml). The organic layer was dried (MgSO$_4$), filtered and the filtrate was concentrated to a minimal volume in vacuo to yield intermediate 47 (168 mg, crude).

Preparation of Intermediate 48

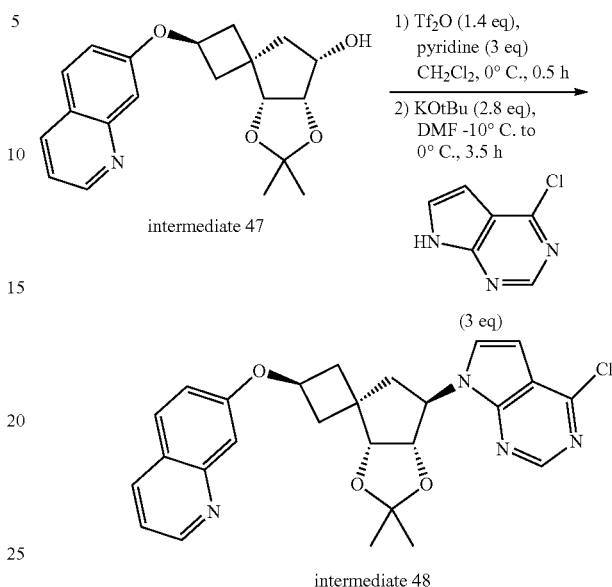

intermediate 47 intermediate 48

Intermediate 47 (127 mg, 0.37 mmol, 1.00 eq) was dissolved in anhydrous CH$_2$Cl$_2$ (3.00 ml) and anhydrous pyridine (0.09 ml, 1.12 mmol, 3.00 eq) was added. The solution was cooled to 0° C. and trifluoromethanesulfonic anhydride (0.09 ml, 0.52 mmol, 1.40 eq) was added dropwise. The mixture was stirred for 30 minutes at 0° C. and then diluted in CH$_2$Cl$_2$ (25 ml) and NaHCO$_3$ (aq. 5 ml) was added. The product was extracted in CH$_2$Cl$_2$ (3×25 ml) and combined organic layers were dried (MgSO$_4$), filtered and the filtrate concentrated in vacuo. The resulting orange residue (crude triflate) was used immediately further.

Potassium tert-butoxide (119 mg, 1.059 mmol, 2.80 eq) was dissolved in anhydrous DMF (0.50 ml) and cooled to −10° C. 4-Chloro-7H-pyrrolo[2,3-D]pyrimidine (171 mg, 1.12 mmol, 3.00 eq) was dissolved in anhydrous DMF (1.5 ml) and added dropwise followed by stirring for 45 minutes. The crude triflate (176 mg, 1.00 eq) was dissolved in anhydrous DMF (1.5 ml) and added dropwise over 30 minutes to freshly prepared solution of pyrrolopyrimidine at −10° C. The mixture was stirred for 1 hour at −10° C. and then for 2.5 hours at 0° C. The mixture was quenched with water (0.50 ml) and CH$_2$Cl$_2$ (70 ml) and brine (20 ml) was added. The product was extracted in CH$_2$Cl$_2$ (3×70 ml) and combined organic layers were dried (MgSO$_4$), filtered and the filtrate was concentrated in vacuo. The residue was dissolved in EtOAc (80 ml) and washed with brine (4×20 ml), dried (MgSO$_4$), filtered and the filtrate was concentrated in vacuo. A mixture of the desired substitution product (77%) and elimination side product (23%) was obtained (NMR). The residue was purified by column chromatography over silica gel (gradient elution: n-heptane/EtOAc from 1:0 to 0:1). The fractions containing intermediate 48 were collected and the solvent was evaporated to yield intermediate 48 (46 mg, 26% yield over 3 steps).

$^1$H NMR (400 MHz, CDCl$_3$): δ=8.81 (dd, J=4.3, 1.8 Hz, 1H), 8.66 (s, 1H), 8.06 (dd, J=8.1, 1.2 Hz, 1H), 7.69 (d, J=8.5 Hz, 1H), 7.15-7.36 (m, 5H), 6.64 (d, J=3.3 Hz, 1H), 5.10 (dd, J=6.7, 3.9 Hz, 1H), 4.89-5.01 (m, 1H), 4.69-4.85

(m, 2H), 2.78 (dd, J=12.0, 7.1 Hz, 1H), 2.34-2.63 (m, 6H), 1.86 (br s, 1H), 1.52 (s, 3H), 1.31 ppm (s, 3H)

$^{13}$C NMR (101 MHz, CDCl$_3$): δ=158.3, 152.4, 150.9, 150.6, 150.6, 149.8, 135.7, 129.0, 127.8, 123.6, 120.1, 119.1, 118.1, 113.2, 108.7, 100.0, 85.7, 83.9, 67.9, 61.5, 42.8, 40.3, 39.8, 36.6, 26.6, 24.8 ppm Preparation of Intermediate 49

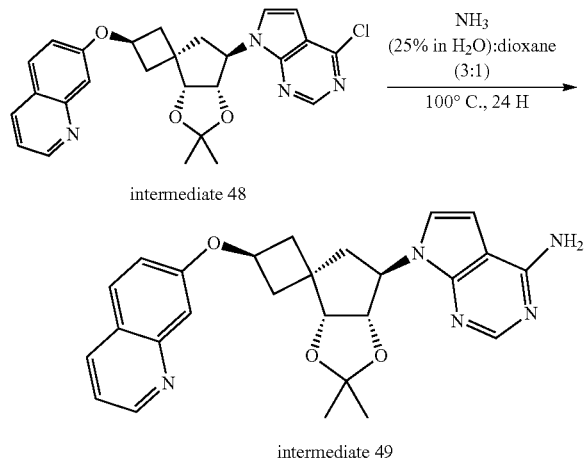

intermediate 48 intermediate 49

Intermediate 48 (46 mg, 0.10 mmol, 1.00 eq) was dissolved in 1,4-dioxane (10 ml) and NH$_3$ (25% in H$_2$O) (30 ml) was added. The mixture was heated to 100° C. in a pressure reactor for 24 hours. The mixture was concentrated to a minimal volume in vacuo and CH$_2$Cl$_2$ (30 ml) and brine (15 ml) were added. The product was extracted in CH$_2$Cl$_2$ (3×30 ml) and combined organic layers were dried (MgSO$_4$), filtered and the filtrate was concentrated in vacuo. The residue was purified by column chromatography over silica gel (gradient elution: CH$_2$Cl$_2$/MeOH from 99:1 to 85:15). The fractions containing the product were collected and the solvent was evaporated to yield the desired intermediate 49 (35.5 mg, 80% yield).

$^1$H NMR (400 MHz, CDCl$_3$): δ=8.80 (dd, J=4.3, 1.7 Hz, 1H), 8.34 (s, 1H), 8.05 (dd, J=8.3, 1.2 Hz, 1H), 7.68 (d, J=9.0 Hz, 1H), 7.21-7.28 (m, 2H), 7.16 (dd, J=8.9, 2.5 Hz, 1H), 6.90 (d, J=3.7 Hz, 1H), 6.37 (d, J=3.5 Hz, 1H), 5.36 (br s, 2H), 5.09 (dd, J=6.7, 3.4 Hz, 1H), 4.91 (td, J=7.3, 3.3 Hz, 1H), 4.77 (quin, J=7.0 Hz, 1H), 4.68 (d, J=6.6 Hz, 1H), 2.75 (dd, J=12.2, 7.2 Hz, 1H), 2.27-2.52 (m, 6H), 1.52 (s, 3H), 1.33 ppm (s, 3H)

$^{13}$C NMR (101 MHz, CDCl$_3$): δ=158.4, 156.8, 151.8, 150.5, 150.5, 149.8, 135.7, 128.9, 123.5, 123.3, 120.2, 119.0, 112.8, 108.8, 103.7, 97.9, 86.0, 84.2, 68.1, 60.8, 42.9, 40.3, 39.9, 36.6, 26.5, 24.8 ppm Preparation of Compound 11

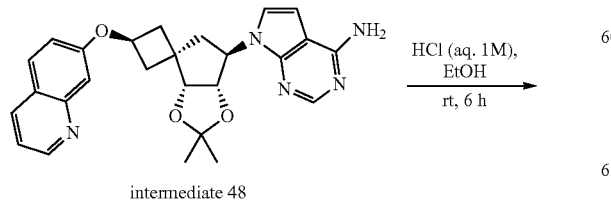

intermediate 48

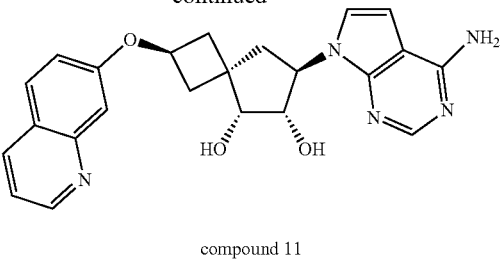

compound 11

Intermediate 49 (35.0 mg, 0.08 mmol, 1.00 eq) was dissolved in ethanol (1.00 ml) and hydrochloric acid (0.77 ml, 1M in H$_2$O) was added at room temperature. The mixture was stirred for 6 hours at room temperature and then diluted with water (8 ml) and lyophilized. The residue was purified via Prep SFC (Stationary phase: Chiralcel Diacel OJ 20×250 mm, Mobile phase: CO$_2$, EtOH+0.4% iPrNH$_2$) yielding compound 11 (10.0 mg, 31% yield)

$^1$H NMR (400 MHz, DMSO-d$_6$): δ=8.80 (dd, J=4.3, 1.7 Hz, 1H), 8.26 (dd, J=8.1, 1.3 Hz, 1H), 8.06 (s, 1H), 7.88 (d, J=8.8 Hz, 1H), 7.36 (dd, J=8.1, 4.2 Hz, 1H), 7.21-7.30 (m, 3H), 6.91 (s, 2H), 6.57 (d, J=3.5 Hz, 1H), 4.80-4.99 (m, 4H), 4.25 (q, J=5.7 Hz, 1H), 3.82 (t, J=5.0 Hz, 1H), 2.54-2.71 (m, 1H), 2.43-2.49 (m, 1H), 2.26-2.37 (m, 1H), 2.21 (dd, J=11.2, 7.0 Hz, 1H), 2.06 ppm (dd, J=13.1, 8.9 Hz, 1H)

$^{13}$C NMR (101 MHz, DMSO-d$_6$): δ=157.9, 157.4, 151.3, 150.6, 149.8, 149.4, 135.6, 129.3, 123.0, 122.5, 119.5, 119.2, 108.6, 102.8, 98.6, 77.2, 75.3, 67.8, 59.8, 40.3, 39.6, 39.2, 36.2 ppm Preparation of Intermediate 50

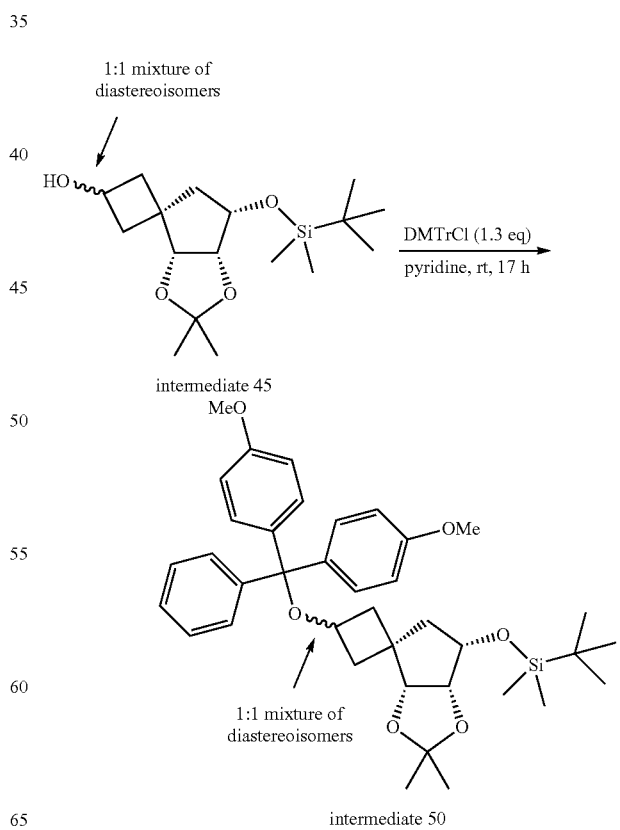

intermediate 45 intermediate 50

Intermediate 45 (470 mg, 1.43 mmol, 1.00 eq) was dissolved in pyridine (6.00 ml) and 4,4'-dimethoxytrityl chloride (630 mg, 1.86 mmol, 1.30 eq) was added portionwise. The mixture was stirred at room temperature for 17 hours and then diluted with EtOAc (100 ml) and brine (50 ml) was added. The product was extracted in EtOAc (3×100 ml), dried (MgSO$_4$), filtered and the filtrate and concentrated in vacuo. The residue was purified by column chromatography over silica gel (gradient elution: n-heptane/EtOAc from 1:0 to 0:1). The fractions containing the product were collected and the solvent was evaporated to yield the desired intermediate 50 (678 mg, 75% yield) as a 1:1 mixture of diastereoisomers.

Preparation of Intermediate 51

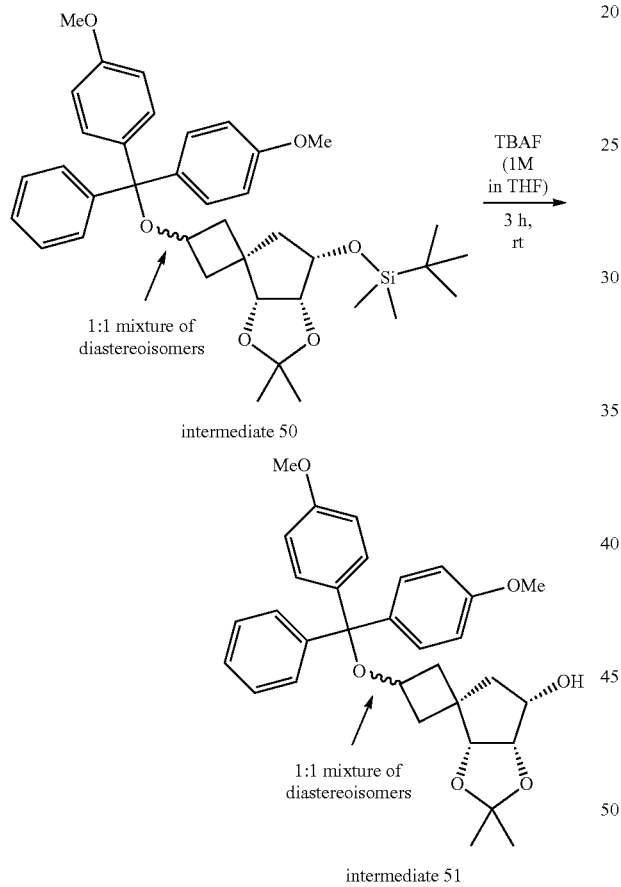

intermediate 50 intermediate 51 intermediate 51

Intermediate 50 (678 mg, 1.08 mmol, 1.00 eq) was dissolved in TBAF (10.0 ml, 1M in THF, 9.00 eq) and stirred at room temperature for 3 hours. Subsequently, the mixture was concentrated in vacuo to a minimal volume and dissolved in EtOAc (100 ml), washed with NH$_4$Cl (aq. sat. 4×50 ml) and brine (2×50 ml). The organic layer was dried (MgSO$_4$), filtered and the filtrate was concentrated in vacuo. The residue was purified by column chromatography over silica gel (gradient elution: n-heptane/EtOAc from 1:0 to 0:1). The fractions containing the product were collected and the solvent was evaporated to yield the desired intermediate 51 (455 mg, 82% yield) as a 1:1 mixture of diastereoisomers.

Preparation of Intermediate 52

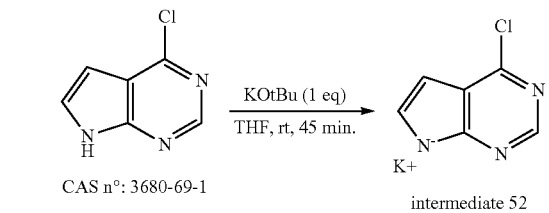 [SMILES: Clc1ncnc2[nH]ccc12 ; Clc1ncnc2[n-]ccc12 ; [K+]]

CAS n°: 3680-69-1 intermediate 52

A mixture of 4-chloro-7H-pyrrolo[2,3-D]pyrimidine (100 g, 651 mmol, 1.00 eq) and KOtBu (73.1 g, 651 mmol, 1.00 eq) in THF (1l) was stirred at room temperature for 45 minutes until a clear solution was obtained. The solvents were evaporated. The residue was triturated in DIPE. The white solids were filtered off and dried in vacuo at 30° C. yielding intermediate 52 (113 g, 90% yield).

Preparation of Intermediate 53

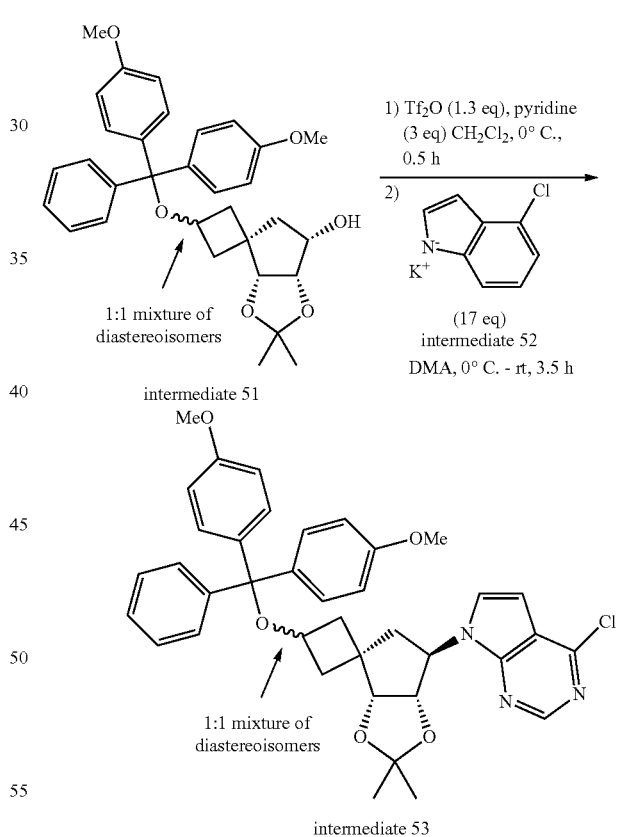

intermediate 51 intermediate 52 intermediate 53

Intermediate 51 (147 mg, 0.285 mmol, 1.00 eq) was dissolved in anhydrous CH$_2$Cl$_2$ (2.20 ml) and anhydrous pyridine (0.07 ml, 0.854 mmol, 3.00 eq) was added. The solution was cooled to 0° C. and trifluoromethanesulfonic anhydride (0.06 ml, 0.37 mmol, 1.30 eq) was added dropwise. The mixture was stirred for 30 minutes at 0° C. and then diluted in CH$_2$Cl$_2$ (40 ml) and NaHCO$_3$ (aq. 20 ml) was added. The product was extracted in CH$_2$Cl$_2$ (3×40 ml) and combined organic layers were dried (MgSO$_4$), filtered and the filtrate concentrated in vacuo. The resulting orange residue was used immediately further.

Intermediate 52 (924 mg, 4.82 mmol, 17.0 eq) was dissolved in anhydrous DMA (5.00 ml), cooled to 0° C. and stirred for 15 minutes. Subsequently, the crude triflate (184 mg, 0.28 mmol, 1.00 eq) was dissolved in anhydrous DMA (1.5 ml) and added dropwise over a period of 30 minutes to the solution at 0° C. The mixture was stirred for 1 hour at 0° C. followed and then for 30 minutes at room temperature. The mixture was poured in NH₄Cl (aq. sat. 60 ml) and the product was extracted in n-heptane (1×100 ml, 2×80 ml). Combined organic layers were washed with brine (3×50 ml), dried (MgSO₄), filtered and the filtrate was concentrated in vacuo. The residue was purified by column chromatography over silica gel (gradient elution: n-heptane/EtOAc from 1:0 to 0:1). The fractions containing the product were collected and the solvent was evaporated to yield the desired intermediate 53 (80 mg, 43% yield) as a 1:1 mixture of diastereoisomers.

Preparation of Intermediate 54 trated in vacuo. The residue was purified by column chromatography over silica gel (gradient elution: n-heptane/EtOAc from 1:0 to 0:1). The fractions containing the product were collected and the solvent was evaporated to yield the desired intermediate 54 (83 mg, 73% yield) as a 1:1 mixture of diastereoisomers.

Preparation of Intermediate 55

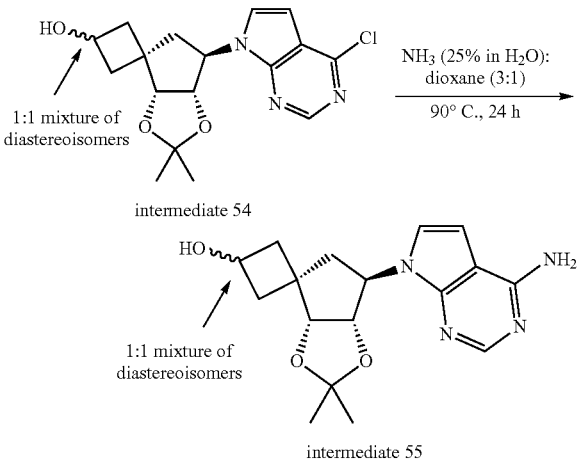

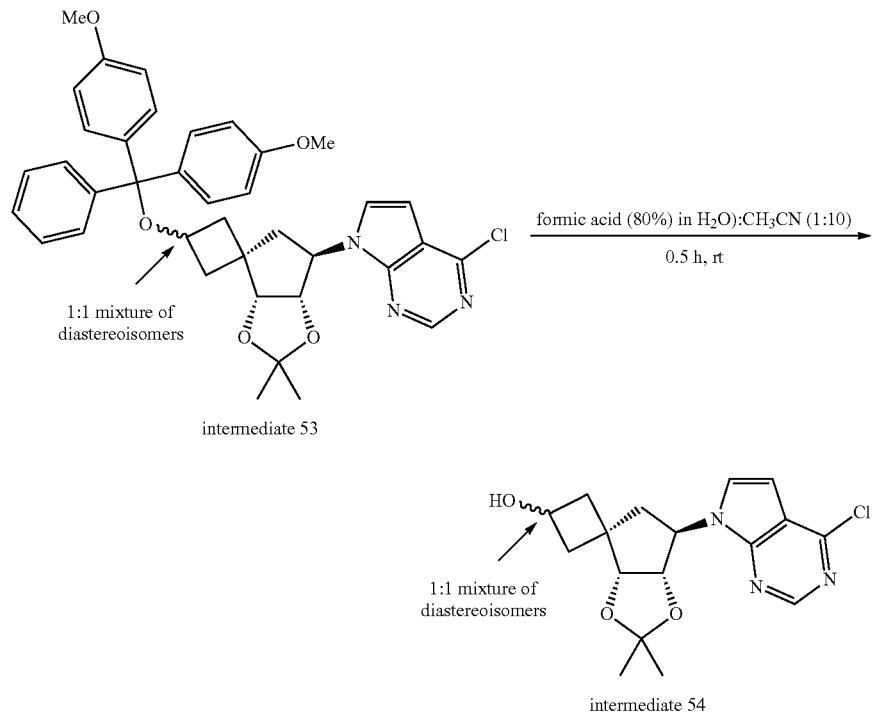

Intermediate 53 (213 mg, 0.33 mmol, 1.00 eq) was dissolved in acetonitrile (5.00 ml) and formic acid (80% in H₂O) (0.50 ml) was added. The mixture was stirred for 30 minutes and subsequently diluted with CH₂Cl₂ (50 ml) and quenched with NH₄Cl (aq. sat. 20 ml). The product was extracted in CH₂Cl₂ (3×50 ml) and combined extracts were washed with NaHCO₃ (aq. sat. 2×50 ml) and brine (1×50 ml), dried (MgSO₄), filtered and the filtrate was concen- Intermediate 54 (73.0 mg, 0.21 mmol, 1.00 eq) was dissolved in NH₃ (25% in H₂O, 30 ml) and 1,4-dioxane (10 ml). The mixture was heated to 90° C. for 24 hours in a pressure reactor and subsequently concentrated in vacuo followed by coevaporation with toluene to dryness to yield intermediate 55 (78.0 mg, 97% yield).

Preparation of Intermediate 56

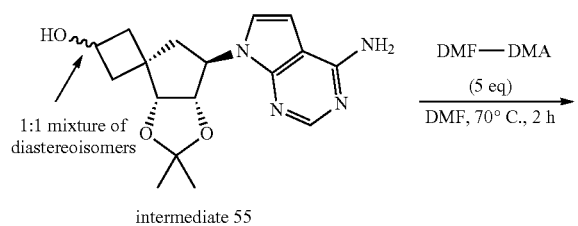

intermediate 55

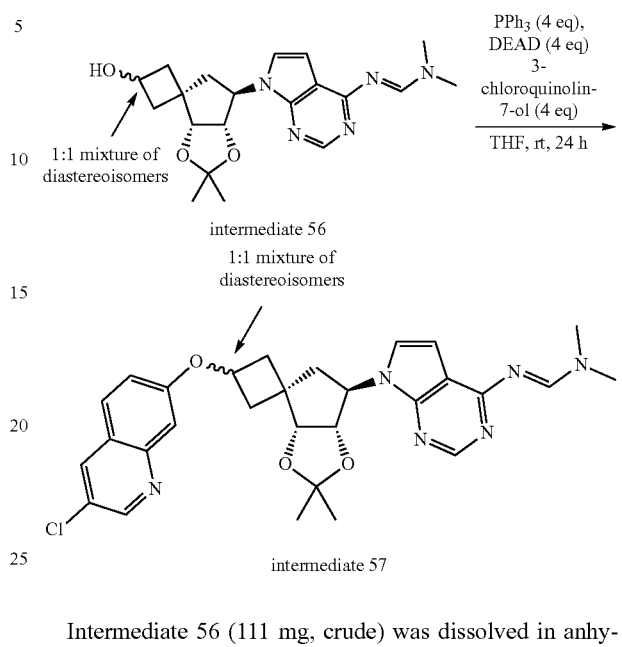

intermediate 56

Intermediate 55 (78.0 mg, 0.21 mmol, 1.00 eq) was dissolved in DMF (0.50 ml) and N,N-dimethylformamide dimethyl acetal (0.14 ml, 1.02 mmol, 5.00 eq) was added. The mixture was heated to 70° C. for 2 hours and subsequently concentrated in vacuo to a minimal volume and coevaporated with toluene to dryness to yield intermediate 56 (111 mg, crude).

Preparation of Intermediate 57

Intermediate 56 (111 mg, crude) was dissolved in anhydrous THF (1.8 ml) and triphenylphosphine (107 mg, 0.406 mmol, 2.00 eq) followed by 3-chloroquinolin-7-ol (72.9 mg, 0.406 mmol, 2.00 eq) were added. Diethyl azodicarboxylate (0.06 ml, 0.406 mmol, 2.00 eq) was added dropwise and the mixture was stirred at room temperature for 26 hours. Subsequently, the mixture was concentrated in vacuo to give intermediate 57 (303 mg, crude) which was used immediately in the next step.

Preparation of Intermediate 58

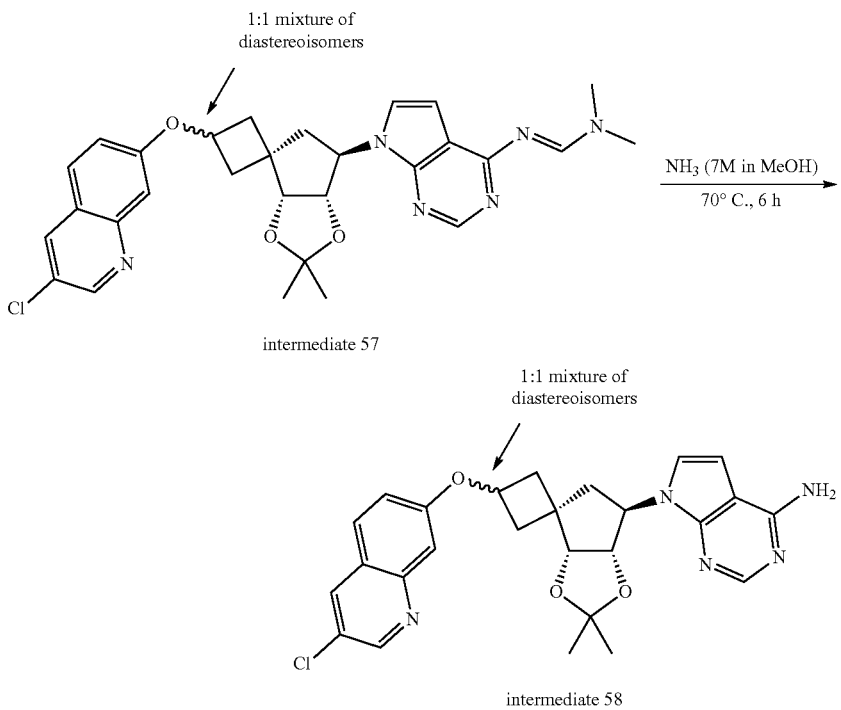

Intermediate 57(303 mg, crude) was dissolved in NH$_3$ (7M in MeOH, 35 ml) and heated to 70° C. for 6 hours. The mixture was concentrated to a minimal volume in vacuo and the residue was purified by column chromatography over silica gel (gradient elution: CH$_2$Cl$_2$/MeOH from 1:0 to 7:3). The fractions containing the product were collected and the solvent was evaporated to yield the desired intermediate 58 (271 mg, crude).

Preparation of Compound 12 and Compound 13

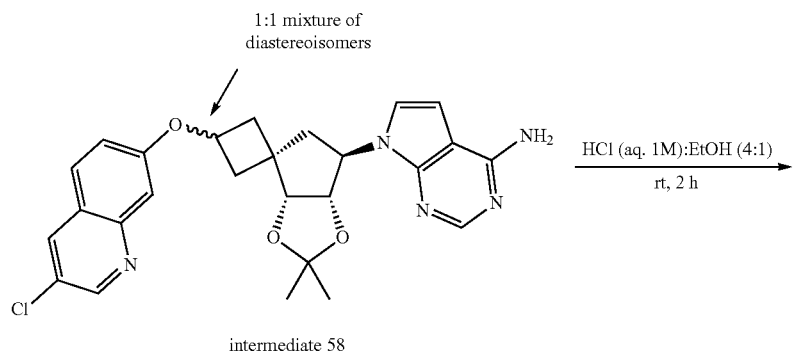

intermediate 58

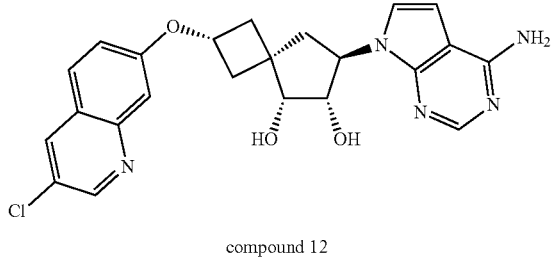

compound 12

+

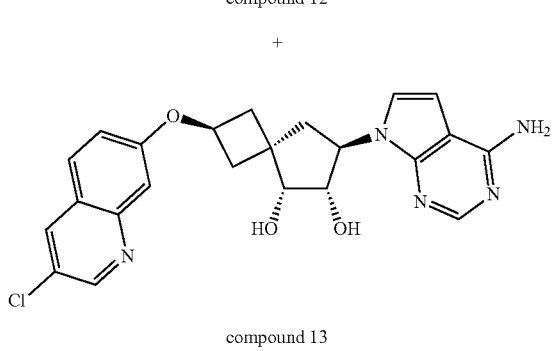

compound 13

Intermediate 58 (271 mg, crude) was dissolved in EtOH (4 ml) and HCl (16 ml, 1M in H$_2$O) was added. The mixture was stirred at room temperature for 2 hours and subsequently diluted with H$_2$O (30 ml) and lyophilized. A purification was performed via Prep SFC (Stationary phase Chiralcel Diacel OJ 20×250 mm, Mobile phase: CO$_2$, EtOH+0.4% iPrNH$_2$) to obtain compound 12 (12.7 mg, 13% yield over 5 steps) and compound 13 (20.0 mg, 22% yield over 5 steps).

Preparation of Intermediate 59

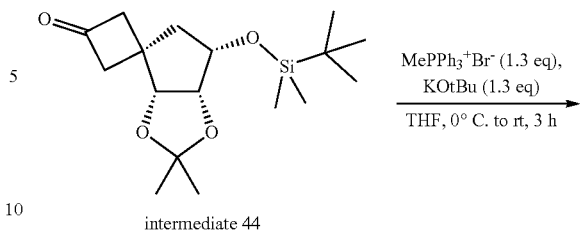

intermediate 44

-continued

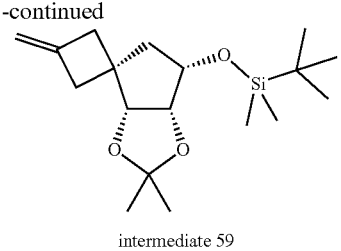

intermediate 59

Methyltriphenylphosphonium bromide (1.45 g, 3.98 mmol, 1.30 eq) was weighed in an oven dried vial and THF (12.0 ml) was added. The heterogeneous solution was cooled to 0° C. and potassium tert-butoxide (3.98 ml, 1M in THF, 3.98 mmol, 1.30 eq) was added dropwise. The mixture was stirred at 0° C. for 20 minutes. The freshly prepared wittig reagent was added dropwise via syringe to intermediate 44 (1.00 g, 3.06 mmol, 1.00 eq) dissolved in THF (12.0 ml) at 0° C. The yellow mixture was stirred for 1.5 hours at 0° C. and then 1.5 hours at room temperature. The mixture was concentrated to a minimal volume in vacuo and redissolved in n-heptane (300 ml). Triphenylphosphine-oxides were precipitated and the mixture was sonicated for 5 minutes, filtered and the filtrate was washed with NH$_4$Cl (aq. sat. 2×50 ml) and brine (2×50 ml). The organic layer was dried (MgSO$_4$), filtered and the filtrate was concentrated in vacuo. The residue was purified by column chromatography over silica gel (gradient elution: n-heptane/EtOAc from 1:0 to 7:3). The fractions containing the product were collected and the solvent was evaporated to yield the desired intermediate 59 (931 mg, 94% yield).

$^1$H NMR (400 MHz, CDCl$_3$): δ=4.81 (quin, J=2.4 Hz, 1H), 4.78 (quin, J=2.4 Hz, 1H), 4.40 (t, J=5.1 Hz, 1H), 4.26 (dd, J=5.5, 0.9 Hz, 1H), 3.80 (dt, J=11.2, 5.5 Hz, 1H), 2.87 (dd, J=16.1, 2.2 Hz, 1H), 2.54 (dq, J=15.9, 2.4 Hz, 1H), 2.31-2.46 (m, 2H), 1.95 (t, J=11.4 Hz, 1H), 1.76 (dd, J=11.7, 5.7 Hz, 1H), 1.45 (s, 3H), 1.32 (s, 3H), 0.91 (s, 9H), 0.10 ppm (d, J=2.2 Hz, 6H)

$^{13}$C NMR (101 MHz, CDCl$_3$): δ=144.7, 110.4, 106.8, 85.3, 79.9, 72.0, 42.5, 41.2, 39.2, 36.8, 26.0, 26.0, 24.5, 18.4, −4.4, −4.6 ppm Preparation of Intermediate 60

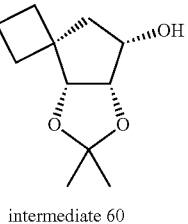

Intermediate 59 (931 mg, 2.87 mmol, 1.00 eq) was dissolved in THF (2.00 ml) and tetrabutylammonium fluoride (10.0 ml, 1M in THF, 10.0 mmol, 3.50 eq) was added. The mixture was stirred at room temperature for 3 hours. The mixture was concentrated to a minimal volume in vacuo, dissolved in EtOAc (250 ml) and washed with NH$_4$Cl (aq. sat. 3×50 ml) and brine (3×50 ml). The organic layer was dried (MgSO$_4$), filtered and the filtrate was concentrated in vacuo. The residue was purified by column chromatography over silica gel (gradient elution: n-heptane/EtOAc from 1:0 to 0:1). The fractions containing the product were collected and the solvent was evaporated to yield the desired intermediate 60 (556 mg, 92% yield)

$^1$H NMR (400 MHz, CDCl$_3$): δ=4.83 (quin, J=2.3 Hz, 1H), 4.80 (quin, J=2.4 Hz, 1H), 4.46-4.49 (m, 1H), 4.36-4.39 (m, 1H), 3.81 (br s, 1H), 2.82-2.88 (m, 1H), 2.60 (dq, J=16.1, 2.4 Hz, 1H), 2.38-2.46 (m, 2H), 2.27-2.38 (m, 1H), 1.97 (dd, J=12.0, 5.9 Hz, 1H), 1.74 (t, J=11.4 Hz, 1H), 1.47 (s, 3H), 1.36 ppm (s, 3H)

$^{13}$C NMR (101 MHz, CDCl$_3$): δ=144.1, 110.6, 107.2, 85.4, 78.7, 70.8, 41.7, 41.2, 39.5, 36.6, 25.9, 24.3 ppm Preparation of Intermediate 61

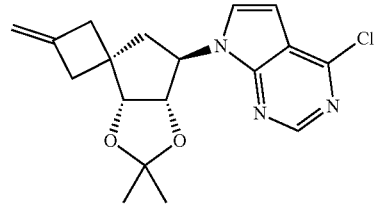

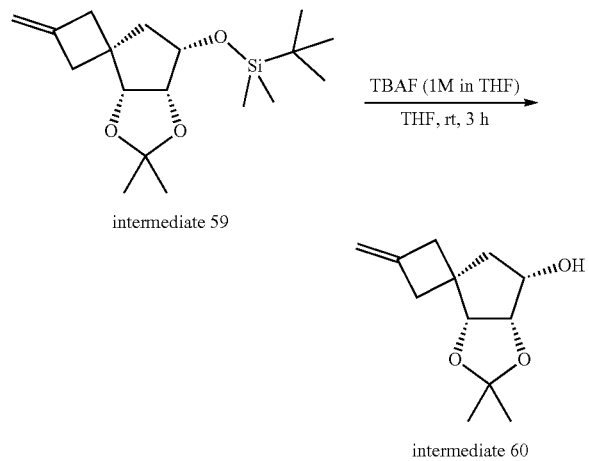

Intermediate 60 (647 mg, 3.08 mmol, 1.00 eq) was dissolved in anhydrous CH$_2$Cl$_2$ (20.0 ml) and pyridine (0.62 ml, 7.69 mmol, 2.50 eq) was added. The mixture was cooled to 0° C. and trifluoromethanesulfonic anhydride (0.57 ml, 3.39 mmol, 1.10 eq) was added dropwise. The mixture was stirred for 30 minutes at 0° C., diluted in CH$_2$Cl$_2$ (100 ml) and NaHCO$_3$ (aq. sat. 40 ml) was added. The product was extracted in CH$_2$Cl$_2$ (3×100 ml) and combined organic layers were dried (MgSO$_4$), filtered and the filtrate was concentrated in vacuo. The residue was used immediately as such in the next part of the procedure. Intermediate 52 (5.90 g, 30.8 mmol, 10.0 eq) was dissolved in anhydrous DMF (35.0 ml) and stirred for 30 minutes at 0° C. This was followed by the dropwise addition of the crude triflate (1.05 g, 3.08 mmol, 1.00 eq) dissolved in anhydrous DMF (8.00 ml) over 15 min at 0° C. The mixture was stirred for 2 hours at 0° C. and then warmed to room temperature and stirred for an additional 2 hours. The mixture was poured in NH$_4$Cl (aq. sat. 50 ml) and the product was extracted in EtOAc (3×100 ml). Combined organic layers were washed with brine (3×100 ml), dried (MgSO$_4$), filtered and the filtrate was concentrated in vacuo to a minimal volume. To the resulting powder, n-heptane (100 ml) was added and the mixture was sonicated for 10 minutes. The solids were filtered, rinsed with n-heptane and the filtrate was concentrated to a minimal volume in vacuo. The residue was purified by column chromatography over silica gel (gradient elution: n-heptane/EtOAc from 1:0 to 0:1). The fractions containing the product were collected and the solvent was evaporated to yield the desired intermediate 61 (856 mg, 80% over 2 steps).

¹H NMR (400 MHz, CDCl₃): δ=8.64-8.65 (m, 1H), 7.18 (d, J=3.7 Hz, 1H), 6.61 (d, J=3.7 Hz, 1H), 5.10 (dd, J=6.3, 3.1 Hz, 1H), 4.96 (td, J=6.8, 3.1 Hz, 1H), 4.80 (dquin, J=18.2, 2.4 Hz, 2H), 4.69 (d, J=6.5 Hz, 1H), 3.18 (dd, J=15.5, 2.4 Hz, 1H), 2.75 (dd, J=15.3, 2.6 Hz, 1H), 2.48-2.58 (m, 2H), 2.33-2.44 (m, 2H), 1.55 (s, 3H), 1.35 ppm (s, 3H)

¹³C NMR (101 MHz, CDCl₃): δ=152.3, 150.6, 143.4, 127.5, 117.9, 112.7, 107.0, 99.8, 85.7, 84.9, 61.5, 43.0, 42.3, 42.2, 38.3, 26.6, 24.7 ppm Preparation of Intermediate 62

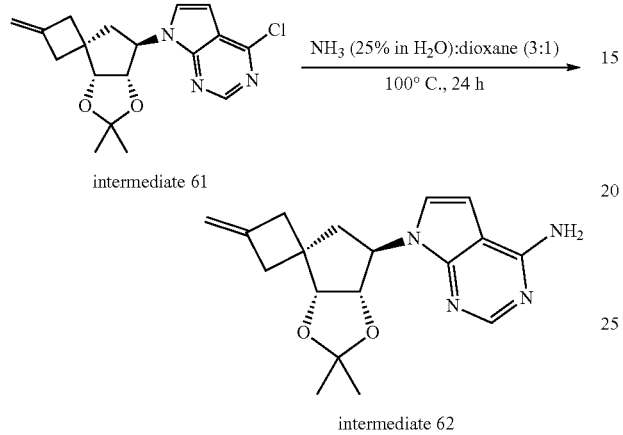

Intermediate 61 (850 mg, 2.46 mmol, 1.00 eq) was dissolved in 1,4-dioxane (20.0 ml) NH₃ (60.0 ml, 25% in H₂O) was added. The solution was heated to 100° C. for 24 hours in a pressure reactor. The mixture was concentrated to a minimal volume in vacuo and coevaporated twice with toluene. The residue was purified by column chromatography over silica gel (gradient elution: CH₂Cl₂/MeOH from 1:0 to 7:3). The fractions containing the product were collected and the solvent was evaporated to yield the desired intermediate 62 (790 mg, 98% yield).

¹H NMR (400 MHz, CDCl₃): δ=8.33 (s, 1H), 6.89 (d, J=3.7 Hz, 1H), 6.35 (d, J=3.5 Hz, 1H), 5.18 (br s, 2H), 5.09 (dd, J=6.4, 2.9 Hz, 1H), 4.93 (td, J=6.7, 2.9 Hz, 1H), 4.81 (quin, J=2.4 Hz, 1H), 4.76 (quin, J=2.4 Hz, 1H), 4.67 (d, J=6.4 Hz, 1H), 3.16 (dd, J=15.6, 2.4 Hz, 1H), 2.74 (dd, J=15.2, 2.4 Hz, 1H), 2.45-2.55 (m, 2H), 2.30-2.45 (m, 2H), 1.97 (br s, 1H), 1.55 (s, 3H), 1.35 ppm (s, 3H)

¹³C NMR (101 MHz, CDCl₃): δ=156.6, 151.7, 150.5, 143.8, 123.0, 112.4, 106.8, 103.5, 97.6, 85.9, 85.1, 60.8, 43.1, 42.5, 42.3, 38.3, 26.6, 24.7 ppm Preparation of Intermediate 63

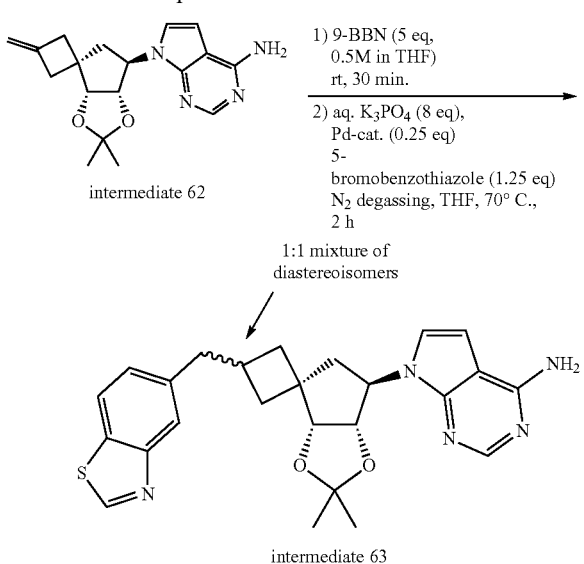

To intermediate 62 (55.0 mg, 0.17 mmol, 1.00 eq) was added 9-borabicyclo[3.3.1]nonane (0.5M in THF, 1.69 ml, 0.84 mmol, 5.00 eq) at room temperature. The mixture was stirred for 30 minutes. Subsequently, potassium phosphate (286 mg, 1.35 mmol, 8.00 eq) dissolved in water (0.53 ml, 29.3 mmol, 173 eq) was degassed with nitrogen for 10 minutes and added to the reaction mixture. The solution was stirred for 10 minutes at room temperature with degassing and 5-bromobenzothiazole (54.1 mg, 0.253 mmol, 1.25 eq) and 1,1'-bis(di-tert-butylphosphino)ferrocene palladium dichloride [CAS: 95408-45-0] (27.7 mg, 0.04 mmol, 0.25 eq) dissolved in THF (2.20 ml) was added to the mixture. Degassing with nitrogen was continued for 15 minutes before the mixture was heated to 70° C. After 2 hours, the dark brown solution was cooled to room temperature, diluted with EtOAc (90 ml), washed with NH₄OH (25% in H₂O, 2×30 ml) and brine (2×30 ml). The organic layer was dried (MgSO₄), filtered and the filtrate was concentrated in vacuo to yield intermediate 63 (196 mg, crude) as a 1:1 mixture of diastereoisomers used without purification in the next step.

Below intermediates were prepared by an analogous reaction protocol as was used for the preparation of intermediate 63 using the appropriate starting materials (Table 1—Suzuki coupling intermediates)

| Int. | Structure | Starting materials |
|---|---|---|
| 64 | 1:1 mixture of diastereoisomers | Intermediate 62 and 7-bromo-3-chloroquinoline |

-continued

| Int. | Structure | Starting materials |
|---|---|---|
| 65 | 1:1 mixture of diastereoisomers 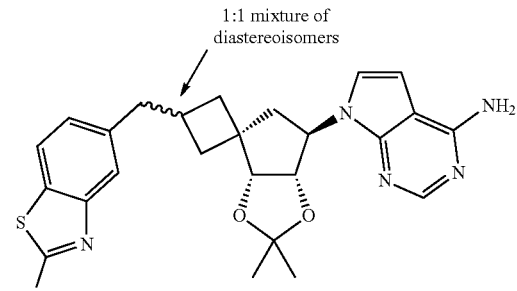 | Intermediate 62 and 2-amino-5-bromobenzothiazole |
| 66 | 1:1 mixture of diastereoisomers 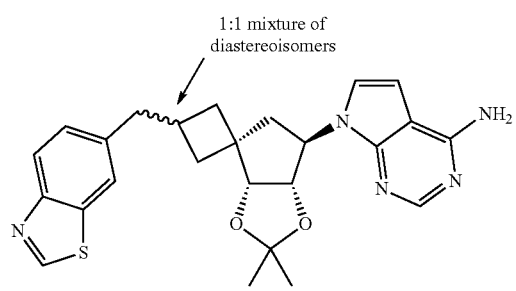 | Intermediate 62 and 6-bromobenzothiazole |
| 67 | 1:1 mixture of diastereoisomers 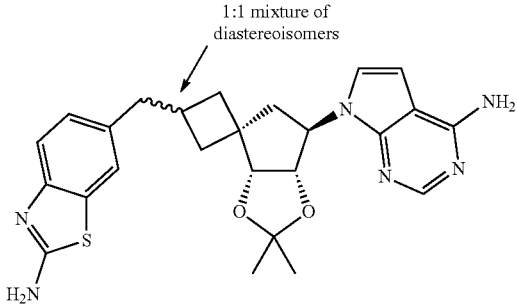 | Intermediate 62 and 2-amino-6-bromobenzothiazole |
| 68 | 1:1 mixture of diastereoisomers 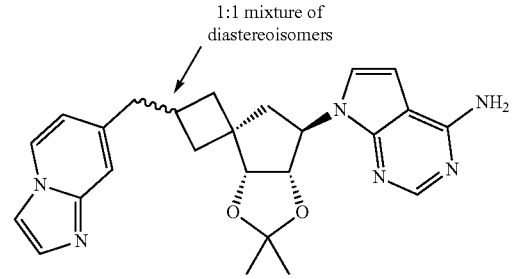 | Intermediate 62 and 7-bromoimidazo[1,2-a]pyridine |
| 69 | 1:1 mixture of diastereoisomers 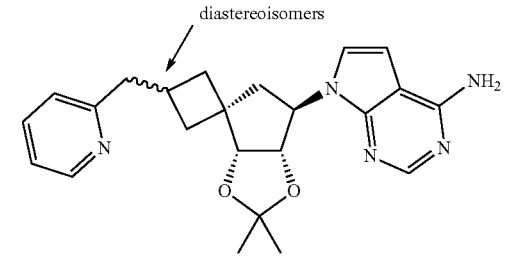 | Intermediate 62 and 2-bromopyridine |

-continued
| Int. | Structure | Starting materials |
|---|---|---|
| 70 | 1:1 mixture of diastereoisomers | Intermediate 62 and 3-bromopyridine |
| 71 | 1:1 mixture of diastereoisomers | Intermediate 62 and 3-bromo-7-iodoquinolin-2-amine |
| 79 | 1:1 mixture of diastereoisomers | Intermediate 78 and 7-bromo-3-chloroquinoline |
Preparation of Compound 16 and Compound 17
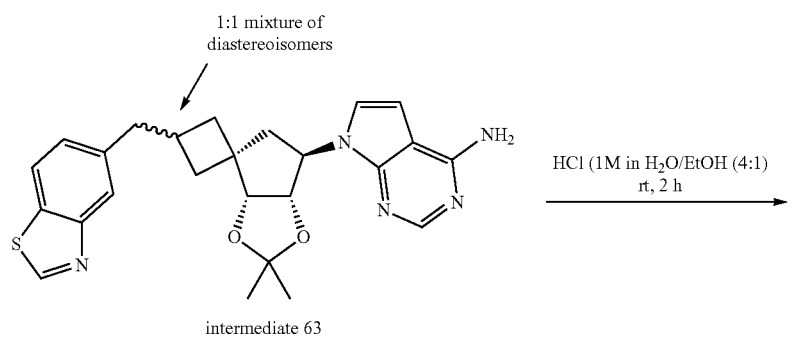
intermediate 63
HCl (1M in H₂O/EtOH (4:1)
rt, 2 h

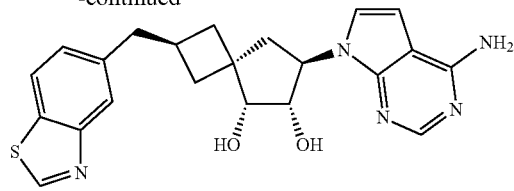

compound 16

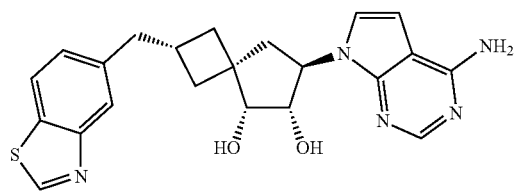

compound 17

Intermediate 63 (crude from previous step) was dissolved in EtOH (4.00 ml) and HCl (16.0 ml, 1M in $H_2O$) was added and the mixture was stirred at room temperature for 2 hours. The solution was diluted with water (20 ml), frozen and lyophilized to give a solid residue. A purification was performed via prep SFC (stationary phase: Chiralcel Diacel OJ 20×250 mm, mobile phase: $CO_2$, EtOH+0.4% $iPrNH_2$) to yield compound 16 (12.3 mg, 0.029 mmol, 17% yield over 2 steps) and compound 17(15.0 mg, 0.036 mmol, 21% yield over 2 steps).

Below compounds were prepared by an analogous reaction protocol as used for the preparation of compounds 16 & 17 using the appropriate starting materials (Table 2).

| Compound | Structure | Starting materials |
|---|---|---|
| 11 | 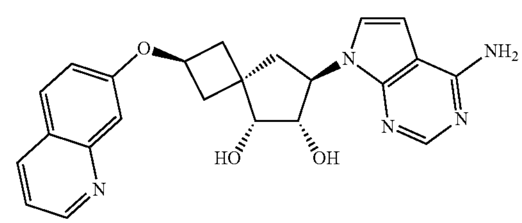 [SMILES: Nc1ncnc2c1ccn2[C@@H]1C[C@]2(C[C@H](Oc3ccc4cccnc4c3)C2)[C@@H](O)[C@H]1O] | Intermediate 49 |
| 12 | 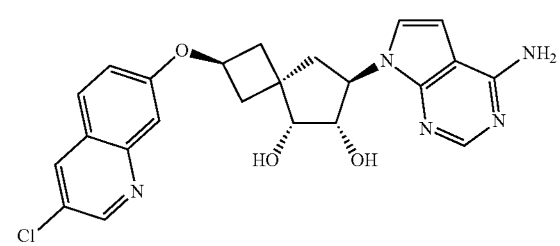 [SMILES: Nc1ncnc2c1ccn2[C@@H]1C[C@]2(C[C@H](Oc3ccc4cc(Cl)cnc4c3)C2)[C@@H](O)[C@H]1O] | Intermediate 58 |
| 13 | 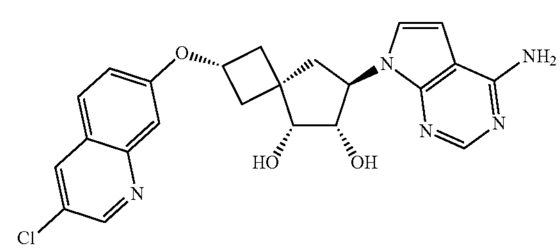 [SMILES: Nc1ncnc2c1ccn2[C@@H]1C[C@]2(C[C@@H](Oc3ccc4cc(Cl)cnc4c3)C2)[C@@H](O)[C@H]1O] | Intermediate 58 |

| Compound | Structure | Starting materials |
|---|---|---|
| 14 | 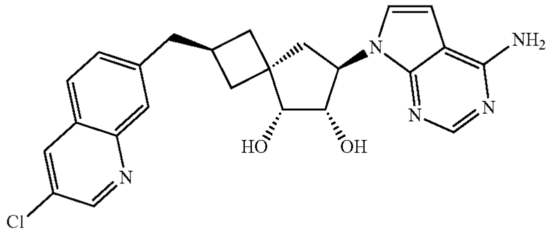 [SMILES: Nc1ncnc2c1ccn2[C@@H]1C[C@]2(C[C@H](Cc3ccc4cc(Cl)cnc4c3)C2)[C@@H](O)[C@H]1O] | Intermediate 64 |
| 15 | 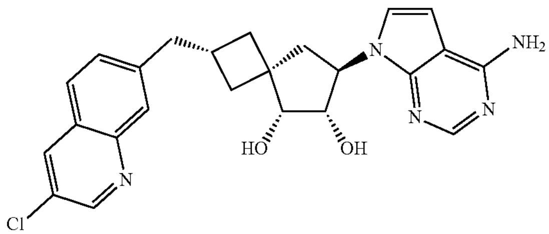 [SMILES: Nc1ncnc2c1ccn2[C@@H]1C[C@]2(C[C@@H](Cc3ccc4cc(Cl)cnc4c3)C2)[C@@H](O)[C@H]1O] | Intermediate 64 |
| 16 | 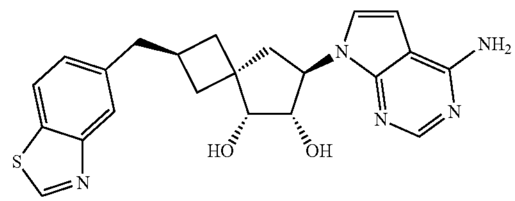 [SMILES: Nc1ncnc2c1ccn2[C@@H]1C[C@]2(C[C@H](Cc3ccc4scnc4c3)C2)[C@@H](O)[C@H]1O] | Intermediate 63 |
| 17 | 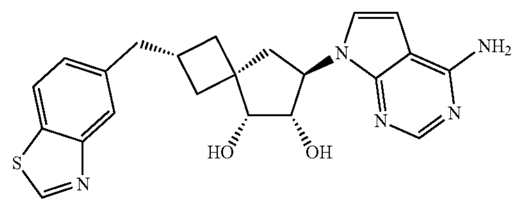 [SMILES: Nc1ncnc2c1ccn2[C@@H]1C[C@]2(C[C@@H](Cc3ccc4scnc4c3)C2)[C@@H](O)[C@H]1O] | Intermediate 63 |
| 18 | 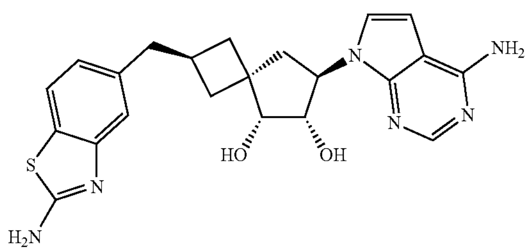 [SMILES: Nc1nc2cc(C[C@H]3C[C@]4(C[C@@H](n5ccc6c(N)ncnc65)[C@H](O)[C@@H]4O)C3)ccc2s1] | Intermediate 65 |
| 19 | 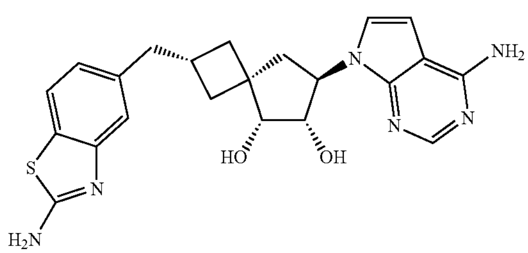 [SMILES: Nc1nc2cc(C[C@H]3C[C@@]4(C[C@@H](n5ccc6c(N)ncnc65)[C@H](O)[C@@H]4O)C3)ccc2s1] | Intermediate 65 |
| 20 | 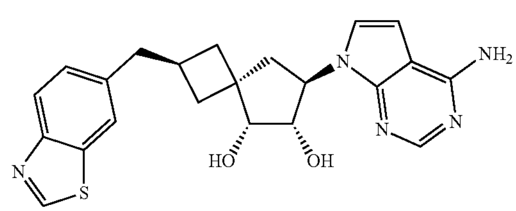 [SMILES: Nc1ncnc2c1ccn2[C@@H]1C[C@]2(C[C@H](Cc3ccc4ncsc4c3)C2)[C@@H](O)[C@H]1O] | Intermediate 66 |

| Compound | Structure | Starting materials |
|---|---|---|
| 21 | 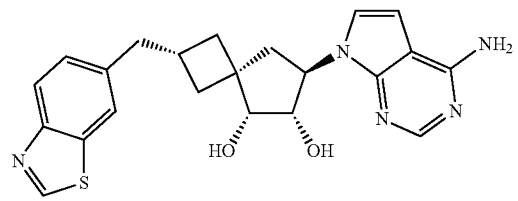 [SMILES: Nc1ncnc2c1ccn2[C@@H]1C[C@]2(C[C@@H](Cc3ccc4ncsc4c3)C2)[C@@H](O)[C@H]1O] | Intermediate 66 |
| 22 | 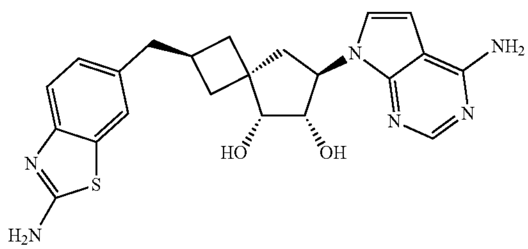 [SMILES: Nc1nc2ccc(C[C@H]3C[C@]4(C[C@@H](n5ccc6c(N)ncnc65)[C@H](O)[C@@H]4O)C3)cc2s1] | Intermediate 67 |
| 23 | 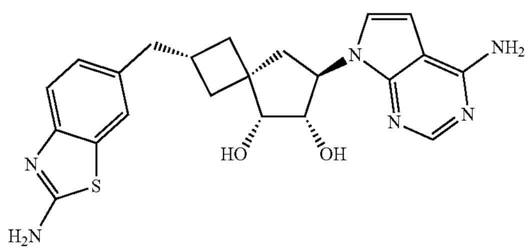 [SMILES: Nc1nc2ccc(C[C@H]3C[C@@]4(C[C@@H](n5ccc6c(N)ncnc65)[C@H](O)[C@@H]4O)C3)cc2s1] | Intermediate 67 |
| 24 | 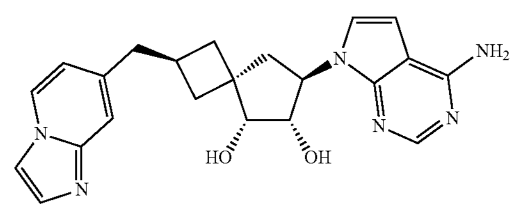 [SMILES: Nc1ncnc2c1ccn2[C@@H]1C[C@]2(C[C@H](Cc3ccn4ccnc4c3)C2)[C@@H](O)[C@H]1O] | Intermediate 68 |
| 25 | 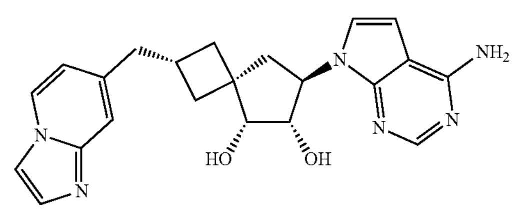 [SMILES: Nc1ncnc2c1ccn2[C@@H]1C[C@]2(C[C@@H](Cc3ccn4ccnc4c3)C2)[C@@H](O)[C@H]1O] | Intermediate 68 |
| 26 | 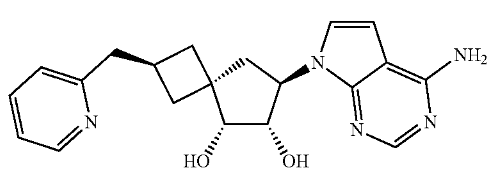 [SMILES: Nc1ncnc2c1ccn2[C@@H]1C[C@]2(C[C@H](Cc3ccccn3)C2)[C@@H](O)[C@H]1O] | Intermediate 69 |
| 27 | 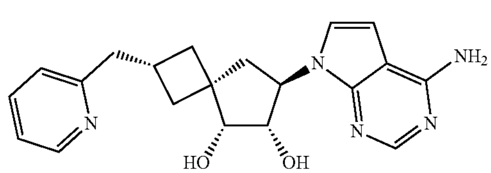 [SMILES: Nc1ncnc2c1ccn2[C@@H]1C[C@]2(C[C@@H](Cc3ccccn3)C2)[C@@H](O)[C@H]1O] | Intermediate 69 |

| Compound | Structure | Starting materials |
|---|---|---|
| 28 | 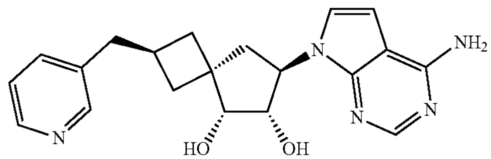 [SMILES: Nc1ncnc2c1ccn2[C@@H]1C[C@]2(C[C@H](Cc3cccnc3)C2)[C@@H](O)[C@H]1O] | Intermediate 70 |
| 29 | 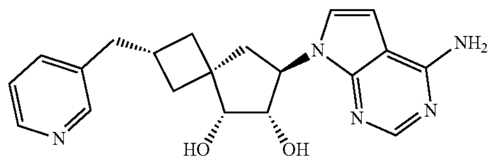 [SMILES: Nc1ncnc2c1ccn2[C@@H]1C[C@]2(C[C@@H](Cc3cccnc3)C2)[C@@H](O)[C@H]1O] | Intermediate 70 |
| 30 | 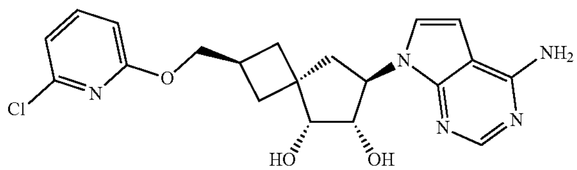 [SMILES: Nc1ncnc2c1ccn2[C@@H]1C[C@]2(C[C@H](COc3cccc(Cl)n3)C2)[C@@H](O)[C@H]1O] | Intermediate 73 |
| 31 | 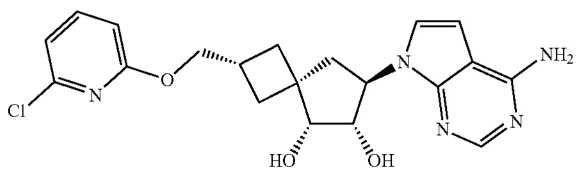 [SMILES: Nc1ncnc2c1ccn2[C@@H]1C[C@]2(C[C@@H](COc3cccc(Cl)n3)C2)[C@@H](O)[C@H]1O] | Intermediate 73 |
| 32 | 1:1 mixture of diastereoisomers<br>a HCl salt, number of equivalents not determined | Intermediate 74 |
| 33 | 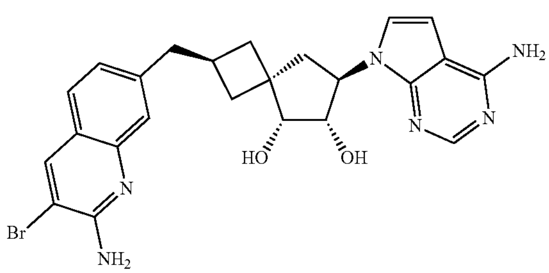 [SMILES: Nc1nc2cc(C[C@H]3C[C@]4(C[C@@H](n5ccc6c(N)ncnc65)[C@H](O)[C@@H]4O)C3)ccc2cc1Br] | Intermediate 71 |
| 34 | 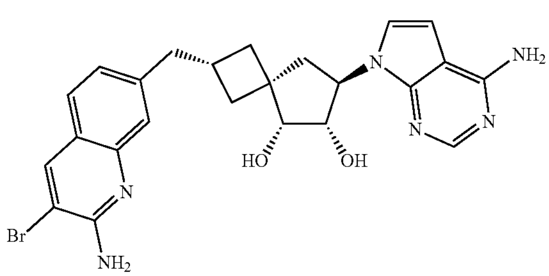 [SMILES: Nc1nc2cc(C[C@H]3C[C@@]4(C[C@@H](n5ccc6c(N)ncnc65)[C@H](O)[C@@H]4O)C3)ccc2cc1Br] | Intermediate 71 |

-continued

| Compound | Structure | Starting materials |
|---|---|---|
| 35 | (structure; a HCl salt, number of equivalents not determined) | Intermediate 72a |
| 36 | (structure; a HCl salt, number of equivalents not determined) | Intermediate 72b |
| 44 | (structure) | Intermediate 79 |
| 45 | (structure) | Intermediate 79 |

Preparation of Intermediate 72, Intermediate 72a and Intermediate 72b

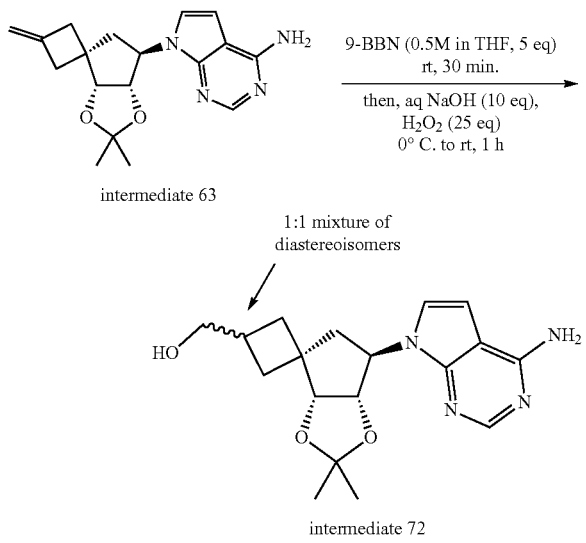

To intermediate 63 (255 mg, 0.78 mmol, 1.00 eq) was added 9-boravicyclo[3.3.1]nonane (7.81 ml, 0.5M in THF, 3.91 mmol, 5.00 eq) and the mixture was stirred for 30 minutes at room temperature. The solution was cooled to 0° C. and NaOH (7.81 ml, 1M in $H_2O$, 7.81 mmol, 10.0 eq) was added followed by the dropwise addition of hydrogenperoxide (1.99 ml, 30% in $H_2O$, 19.5 mmol, 25.0 eq). The mixture was stirred for 1 hour at room temperature, then diluted in $CH_2Cl_2$ (250 ml) and washed with $NaHCO_3$ (aq. sat. 3×50 ml) and brine (1×50 ml). The organic layer was dried ($MgSO_4$), filtered and the filtrate was concentrated in vacuo. The residue was purified by column chromatography over silica gel (gradient elution: $CH_2Cl_2$/MeOH from 1:0 to 7:3). The fractions containing the product were collected and the solvent was evaporated to yield intermediate 72 (213 mg, 79% yield) as a 1:1 mixture of diastereoisomers. A purification was performed on a sample of intermediate 72 via prep SFC (stationary phase: Chiralcel Diacel OJ 20×250 mm, mobile phase: $CO_2$, EtOH+0.4% $iPrNH_2$) to yield intermediate 72a (15 mg) and intermediate 72b (18 mg).

intermediate 72a

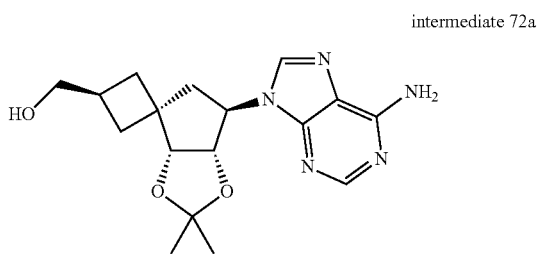 [SMILES: CC1(C)O[C@H]2[C@H](n3cnc4c(N)ncnc43)C[C@]3(C[C@H](CO)C3)[C@H]2O1]

¹H NMR (CHLOROFORM-d, 400 MHz): δ=8.31 (s, 1H), 6.89 (d, J=3.5 Hz, 1H), 6.34 (d, J=3.5 Hz, 1H), 5.24 (br s, 2H), 5.02 (dd, J=6.8, 3.5 Hz, 1H), 4.55 (d, J=6.8 Hz, 1H), 2.35-2.52 (m, 3H), 2.27 (dd, J=11.8, 8.3 Hz, 1H), 1.76-1.95 (m, 3H), 1.53 (s, 3H), 1.33 ppm (s, 3H)

¹³C NMR (CHLOROFORM-d, 101 MHz): δ=156.7, 151.7, 150.4, 123.1, 112.7, 97.7, 86.2, 84.6, 66.9, 60.3, 43.4, 43.3, 34.1, 31.6, 30.4, 26.5, 24.8 ppm intermediate 72b

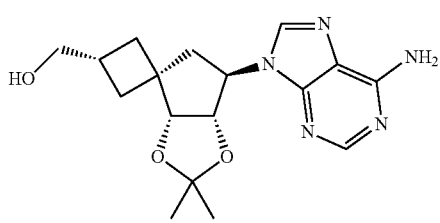

¹H NMR (CHLOROFORM-d, 400 MHz): δ=8.31 (s, 1H), 6.88 (d, J=3.7 Hz, 1H), 6.32 (d, J=3.7 Hz, 1H), 5.29 (br s, 1H), 5.00 (dd, J=6.3, 2.8 Hz, 1H), 4.86-4.94 (m, 1H), 4.66 (d, J=6.4 Hz, 1H), 3.50-3.64 (m, 2H), 2.46-2.58 (m, 1H), 2.36-2.46 (m, 2H), 2.20 (dd, J=13.6, 5.9 Hz, 1H), 2.05-2.15 (m, 2H), 1.64-1.74 (m, 2H), 1.54 (s, 3H), 1.35 ppm (s, 3H)

¹³C NMR (CHLOROFORM-d, 101 MHz): δ=156.7, 151.7, 150.4, 122.7, 112.3, 97.7, 86.6, 85.4, 66.9, 60.5, 43.7, 43.5, 35.4, 31.5, 30.2, 26.6, 24.7 ppm Preparation of Intermediate 73 and Intermediate 74

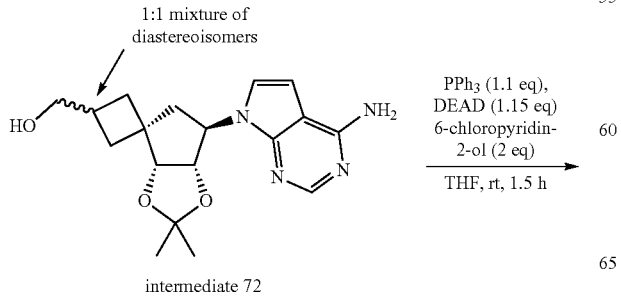

intermediate 72

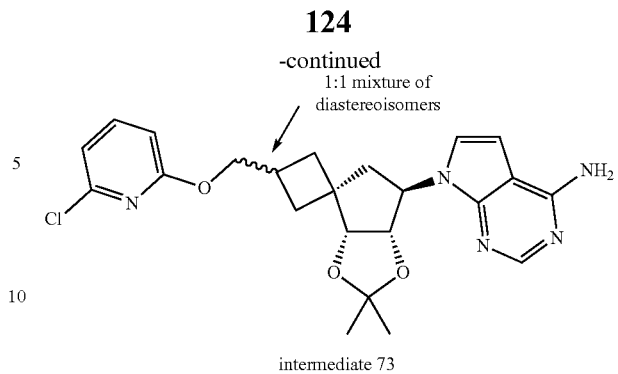

intermediate 73

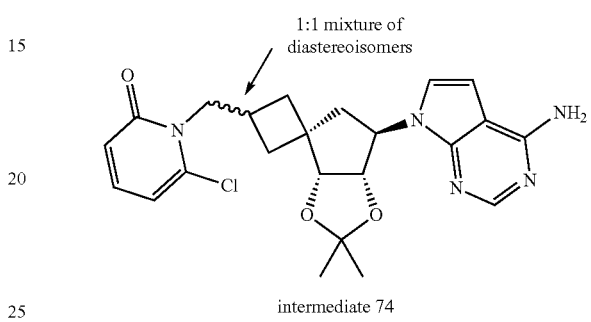

intermediate 74

Intermediate 72 (80.0 mg, 0.23 mmol, 1.00 eq) was dissolved in anhydrous THF (3.2 ml) and triphenylphosphine (67.7 mg, 0.26 mmol, 1.10 eq), 6-chloropyridin-2-ol (33.1 mg, 0.26 mmol, 1.10 eq) and diethyl azodicarboxylate (0.04 ml, 0.27 mmol, 1.15 eq) were added. The mixture was stirred at room temperature for 1.5 hours and subsequently diluted with EtOAc (50 ml) and brine (25 ml) was added. The product was extracted in EtOAc (3×50 ml), dried (MgSO₄), filtered and the filtrate was concentrated in vacuo. The crude mixture contained intermediate 73 and intermediate 74 in an 87:13 ratio, respectively. The residue was purified by column chromatography over silica gel (gradient elution: CH₂Cl₂/MeOH from 1:0 to 7:3). The fractions containing the product were collected and the solvent was evaporated to yield intermediate 73 (65 mg, 62% yield) as a 1:1 mixture of diastereoisomers. Intermediate 74 (side product, 8 mg, 8% yield) was obtained as a 1:1 mixture of diastereoisomers.

Preparation of Intermediate 75

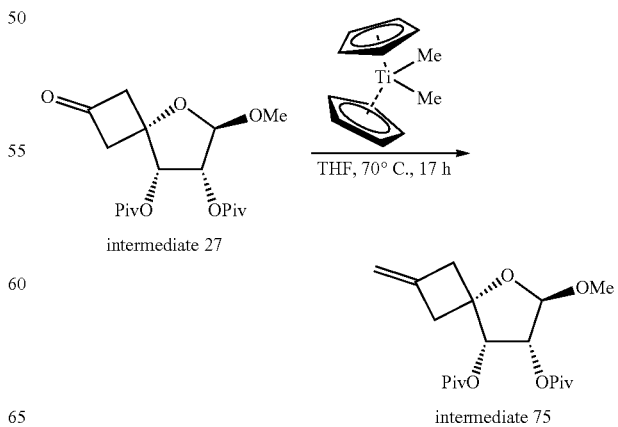

Intermediate 27(2.00 g, 5.50 mmol, 1.00 eq) was weighed in a three neck 100 ml flask equipped with a reflux condenser, thermometer and a CaCl$_2$ tube. To the substrate was added a solution (5 wt % in toluene) of bis(cyclopentadienyl)dimethyltitanium (39.4 mL, 7.97 mmol, 1.45 eq, CAS: 1271-66-5). The flask was covered from light with aluminium foil and heated to 70° C. [Note: upon heating, the active Petasis reagent is generated and 1 equivalent of methane gas relative to the titanocene is liberated. Therefore, closed systems should be avoided for reaction setup in glassware. Additionally, reaction in metal pressurized reactors did show only low conversions, as the titanocene reagent sticks to the reactor walls.] The reaction was stirred for 17 hours after which full conversion was observed. The mixture was concentrated to a minimal volume in vacuo and to the residue was added n-heptane (100 ml). The solids were sonicated for 5 minutes and removed via filtration over Celite (rinsed with n-heptane). The organic layer was concentrated to a minimal volume in vacuo. The residue was purified by column chromatography over silica gel (gradient elution: n-heptane/EtOAc from 1:0 to 3:7 in 15 column volumes). The fractions containing the product were collected and the solvent was evaporated to afford intermediate 75 (58% yield, 1.14 g; 3.19 mmol, colorless oil).

$^1$H NMR (500 MHz, CDCl$_3$): δ 5.42 (d, J=4.5 Hz, 1H), 5.17, (dd, J=4.5, 1.7 Hz, 1H), 4.85-4.83 (m, 3H), 3.39 (s, 3H), 3.09-3.05 (m, 2H), 2.94-2.85 (m, 2H), 1.21 (s, 9H), 1.20 ppm (s, 9H).

$^{13}$C NMR (125 MHz, CDCl$_3$): δ 177.4, 177.2, 139.7, 107.6, 105.7, 80.6, 75.6, 74.5, 55.6, 44.8, 41.5, 39.2, 39.0, 27.4, 27.3 ppm.

Analytical Part

NMR

For a number of compounds, $^1$H NMR and $^{13}$C NMR spectra were recorded on a Bruker DPX-360 operating at 360 MHz for $^1$H NMR and 91 Mhz for $^{13}$C NMR, on a Bruker Avance 400 operating at 400 MHz for $^1$H NMR and 101 Mhz for $^{13}$C NMR, or on a Bruker Avance III 400 operating at 400 MHz for $^1$H NMR and 101 Mhz for $^{13}$C NMR.

Alternatively, $^1$H and $^{13}$C NMR spectra for a number of compounds were recorded at 500 MHz for $^1$H NMR and 125 Mhz for $^{13}$C NMR on a Bruker Avance II 500 console, or at 250 MHz for $^1$H NMR and 63 Mhz for $^{13}$C NMR on a Bruker Avance DRX 250 console.

The solvents used and frequency are indicated in the experimental part or below. Typical solvents are CHLOROFORM-d, Methanol-d$_4$ or DMSO-d$_6$ (deuterated DMSO, dimethyl-d6 sulfoxide. Chemical shifts (δ) are reported in parts per million (ppm) relative to tetramethylsilane (TMS), which was used as internal standard. Coupling constants (J) are given in Hertz (Hz).

The following abbreviations are used in the description of spectra: singlet (s), doublet (d), triplet (t), quadruplet (q), quintet (qn), multiplet (m), doublet of doublets (dd), triplet of doublets (td), doublet of triplets (dt), doublet of doublet of doublets (ddd), pseudo (ps).

NMRs for compounds are reported in the experimental part or below (Co. No. means compound number):

Co. No. 12

$^1$H NMR (DMSO-d$_6$, 400 MHz): δ=8.78 (d, J=2.4 Hz, 1H), 8.45 (d, J=2.4 Hz, 1H), 8.06 (s, 1H), 7.88 (d, J=9.8 Hz, 1H), 7.30 (dq, J=4.8, 2.5 Hz, 2H), 7.24 (d, J=3.7 Hz, 1H), 6.92 (br s, 2H), 6.57 (d, J=3.7 Hz, 1H), 4.79-5.00 (m, 4H), 4.24 (br d, J=6.5 Hz, 1H), 3.82 (t, J=4.9 Hz, 1H), 3.33 (s, 2H), 2.58-2.68 (m, 1H), 2.41-2.48 (m, 1H), 2.27-2.36 (m, 1H), 2.21 (dd, J=11.4, 6.9 Hz, 1H), 1.98-2.10 ppm (m, 1H)

$^{13}$C NMR (DMSO-d$_6$, 101 MHz): δ=158.3, 157.4, 151.3, 149.8, 149.2, 147.5, 133.9, 128.7, 125.1, 123.2, 122.4, 120.8, 108.6, 102.8, 98.7, 77.1, 75.3, 68.0, 59.8, 40.3, 39.2, 36.1 ppm Co. No. 13

$^1$H NMR (DMSO-d$_6$, 400 MHz): δ=8.80 (d, J=2.4 Hz, 1H), 8.46 (d, J=2.4 Hz, 1H), 8.01 (s, 1H), 7.89 (d, J=9.4 Hz, 1H), 7.25-7.33 (m, 2H), 7.16 (d, J=3.7 Hz, 1H), 6.88 (s, 2H), 6.53 (d, J=3.7 Hz, 1H), 5.09 (d, J=4.5 Hz, 1H), 4.93 (d, J=6.5 Hz, 1H), 4.79-4.89 (m, 2H), 4.32-4.39 (m, 1H), 3.92 (t, J=4.5 Hz, 1H), 2.99-3.11 (m, 1H), 2.66-2.80 (m, 1H), 2.34 (dd, J=13.6, 10.0 Hz, 1H), 2.22 (dd, J=11.8, 6.9 Hz, 1H), 1.88-2.00 ppm (m, 2H)

$^{13}$C NMR (DMSO-d$_6$, 101 MHz): δ=158.2, 157.4, 151.2, 149.9, 149.2, 147.5, 133.9, 128.8, 125.1, 123.3, 122.2, 120.8, 108.5, 102.8, 98.6, 77.0, 75.7, 67.5, 59.0, 41.9, 41.5, 36.2 ppm Co. No. 14

$^1$H NMR (DMSO-d$_6$, 400 MHz): δ=8.84 (d, J=2.6 Hz, 1H), 8.51 (d, J=2.4 Hz, 1H), 8.00 (s, 1H), 7.89 (d, J=8.4 Hz, 1H), 7.82 (s, 1H), 7.52 (dd, J=8.4, 1.5 Hz, 1H), 7.15 (d, J=3.5 Hz, 1H), 6.86 (s, 2H), 6.52 (d, J=3.5 Hz, 1H), 4.79-4.85 (m, 1H), 4.75 (dd, J=10.1, 5.5 Hz, 2H), 4.17-4.24 (m, 1H), 3.71 (t, J=4.8 Hz, 1H), 2.90 (d, J=7.7 Hz, 2H), 2.53-2.67 (m, 1H), 2.27-2.40 (m, 1H), 2.14 (dd, J=11.2, 8.8 Hz, 1H), 2.00-2.10 (m, 1H), 1.91 (dd, J=13.2, 8.6 Hz, 1H), 1.85 (dd, J=10.8, 8.6 Hz, 1H), 1.73 ppm (ddd, J=11.2, 7.9, 3.5 Hz, 1H)

$^{13}$C NMR (DMSO-d$_6$, 101 MHz): δ=157.9, 151.7, 150.3, 149.5, 146.5, 143.8, 134.4, 129.9, 127.7, 127.7, 127.2, 127.0, 122.8, 103.2, 99.1, 78.4, 76.0, 60.0, 42.8, 42.7, 41.7, 38.5, 34.7, 30.8 ppm Co. No. 15

$^1$H NMR (DMSO-d$_6$, 400 MHz): δ=8.84 (d, J=2.4 Hz, 1H), 8.51 (d, J=2.2 Hz, 1H), 8.01 (s, 1H), 7.89 (d, J=8.6 Hz, 1H), 7.82 (s, 1H), 7.52 (dd, J=8.4, 1.3 Hz, 1H), 7.11 (d, J=3.5 Hz, 1H), 6.87 (s, 2H), 6.54 (d, J=3.5 Hz, 1H), 4.73-4.88 (m, 3H), 4.23-4.32 (m, 1H), 3.78 (t, J=4.1 Hz, 1H), 2.89 (d, J=7.0 Hz, 2H), 2.51-2.58 (m, 1H), 2.42-2.48 (m, J=3.7 Hz, 1H), 2.29 (dd, J=13.6, 10.3 Hz, 1H), 2.09-2.18 (m, 1H), 1.76-1.91 (m, 2H), 1.54 ppm (br dd, J=10.5, 8.0 Hz, 1H)

$^{13}$C NMR (DMSO-d$_6$, 101 MHz): δ=157.9, 151.7, 150.5, 149.5, 146.5, 143.8, 134.4, 129.9, 127.7, 127.2, 127.0, 122.4, 103.2, 99.1, 77.9, 76.2, 59.3, 43.1, 43.0, 42.4, 40.8, 34.5, 30.7 ppm Co. No. 16

$^1$H NMR (DMSO-d$_6$, 400 MHz): δ=9.35 (s, 1H), 8.05 (d, J=8.1 Hz, 1H), 8.01 (s, 1H), 7.89 (d, J=0.8 Hz, 1H), 7.32 (dd, J=8.3, 1.4 Hz, 1H), 7.16 (d, J=3.3 Hz, 1H), 6.87 (s, 2H), 6.52 (d, J=3.7 Hz, 1H), 4.78-4.86 (m, 1H), 4.76 (dd, J=12.4, 5.5 Hz, 2H), 4.18-4.25 (m, 1H), 3.71 (t, J=4.9 Hz, 1H), 2.84 (d, J=7.7 Hz, 2H), 2.53-2.61 (m, 1H), 2.28-2.40 (m, 1H), 2.13 (dd, J=11.2, 8.7 Hz, 1H), 1.99-2.09 (m, 1H), 1.91 (dd, J=13.0, 8.5 Hz, 1H), 1.84 (dd, J=10.8, 8.7 Hz, 1H), 1.72 ppm (ddd, J=11.4, 7.9, 3.5 Hz, 1H)

$^{13}$C NMR (DMSO-d$_6$, 101 MHz): δ=157.4, 155.9, 153.4, 151.2, 149.9, 139.3, 130.8, 126.5, 122.4, 122.2, 122.0, 102.7, 98.6, 77.9, 75.5, 59.4, 42.1, 42.1, 41.2, 38.1, 34.1, 30.8 ppm Co. No. 17

$^1$H NMR (DMSO-d$_6$, 400 MHz): δ=9.34 (s, 1H), 8.04 (d, J=8.5 Hz, 1H), 8.02 (s, 1H), 7.88 (d, J=1.2 Hz, 1H), 7.31 (dd, J=8.1, 1.6 Hz, 1H), 7.14-7.16 (m, 1H), 7.12 (d, J=3.7 Hz, 1H), 6.87 (s, 2H), 6.54 (d, J=3.7 Hz, 1H), 4.75-4.89 (m, 2H), 4.73-4.75 (m, 1H), 4.23-4.32 (m, 1H), 3.77 (t, J=4.1 Hz, 1H), 2.83 (br d, J=6.9 Hz, 2H), 2.46 (br d, J=4.5 Hz, 1H), 2.29 (dd, J=13.6, 10.4 Hz, 1H), 2.04-2.19 (m, 1H), 1.82 (td, J=13.3, 7.5 Hz, 2H), 1.47-1.60 ppm (m, 1H)

<sup>13</sup>C NMR (DMSO-d<sub>6</sub>, 101 MHz): δ=157.4, 155.9, 153.4, 151.2, 150.0, 139.3, 130.8, 126.5, 122.3, 122.0, 121.9, 102.7, 98.7, 77.4, 75.8, 58.7, 42.6, 42.3, 41.8, 40.3, 33.9, 30.7 ppm Co. No. 18

<sup>1</sup>H NMR (DMSO-d<sub>6</sub>, 400 MHz): δ=8.01 (s, 1H), 7.50 (d, J=8.1 Hz, 1H), 7.37 (br s, 2H), 7.13 (d, J=1.2 Hz, 1H), 7.11 (d, J=3.7 Hz, 1H), 6.87 (br s, 2H), 6.81 (dd, J=8.1, 1.2 Hz, 1H), 6.53 (d, J=3.7 Hz, 1H), 4.74-4.86 (m, 3H), 4.23-4.31 (m, 1H), 3.76 (t, J=4.1 Hz, 1H), 2.66 (br d, J=6.9 Hz, 2H), 2.34-2.47 (m, 2H), 2.27 (dd, J=13.6, 10.4 Hz, 1H), 2.03-2.14 (m, 1H), 1.73-1.82 (m, 2H), 1.42-1.53 ppm (m, 1H)

$^{13}$C NMR (DMSO-d$_6$, 101 MHz): δ=166.5, 157.4, 153.0, 151.2, 150.0, 138.2, 128.1, 121.9, 121.4, 120.3, 117.7, 102.7, 98.7, 77.5, 75.8, 58.7, 42.6, 41.8, 40.5, 39.9, 34.0, 30.8 ppm Co. No. 19

$^{1}$H NMR (DMSO-d$_6$, 400 MHz): δ=8.01 (s, 1H), 7.51 (d, J=7.7 Hz, 1H), 7.38 (s, 3H), 7.16 (d, J=3.7 Hz, 1H), 7.14 (d, J=1.2 Hz, 1H), 6.88 (s, 2H), 6.82 (dd, J=7.9, 1.4 Hz, 1H), 6.53 (d, J=3.7 Hz, 1H), 4.78-4.88 (m, 1H), 4.77 (d, J=6.1 Hz, 1H), 4.73 (d, J=4.9 Hz, 1H), 4.17-4.22 (m, 1H), 3.69 (t, J=4.9 Hz, 1H), 3.41-3.49 (m, 1H), 3.18 (d, J=4.9 Hz, 1H), 2.62-2.74 (m, 3H), 2.39-2.49 (m, 1H), 2.33 (dd, J=13.0, 9.8 Hz, 1H), 1.98-2.13 (m, 3H), 1.91 (dd, J=13.0, 8.5 Hz, 1H), 1.79 (dd, J=10.6, 8.5 Hz, 1H), 1.66-1.74 ppm (m, 1H)

$^{13}$C NMR (DMSO-d$_6$, 101 MHz): δ=166.5, 157.4, 153.0, 151.2, 149.9, 138.3, 128.1, 122.2, 121.4, 120.4, 117.7, 102.7, 98.6, 78.0, 75.5, 59.4, 42.4, 42.1, 41.3, 38.2, 34.3, 30.9 ppm Co. No. 20

$^{1}$H NMR (DMSO-d$_6$, 400 MHz): δ=9.30 (s, 1H), 8.03 (s, 1H), 7.99 (d, J=8.5 Hz, 1H), 7.94 (d, J=1.2 Hz, 1H), 7.36 (dd, J=8.5, 1.6 Hz, 1H), 7.17 (d, J=3.7 Hz, 1H), 6.90 (s, 2H), 6.54 (d, J=3.7 Hz, 1H), 4.73-4.91 (m, 3H), 4.22 (br d, J=6.5 Hz, 1H), 3.72 (br s, 1H), 3.19 (d, J=5.3 Hz, 2H), 2.83 (br d, J=7.7 Hz, 2H), 2.47-2.59 (m, 2H), 2.34 (dd, J=13.0, 9.8 Hz, 1H), 2.13 (dd, J=11.4, 9.0 Hz, 1H), 2.01-2.08 (m, 1H), 1.92 (dd, J=13.0, 8.5 Hz, 1H), 1.83 (dd, J=10.8, 8.7 Hz, 1H), 1.73 ppm (ddd, J=11.4, 7.9, 3.5 Hz, 1H)

$^{13}$C NMR (DMSO-d$_6$, 101 MHz): δ=157.4, 151.4, 151.2, 149.9, 138.6, 133.6, 127.1, 122.6, 122.3, 121.4, 102.7, 98.6, 77.9, 75.5, 59.5, 42.2, 42.1, 41.2, 38.1, 34.2, 30.8 ppm Co. No. 21

$^{1}$H NMR (DMSO-d$_6$, 400 MHz): δ=9.29 (s, 1H), 8.02 (s, 1H), 7.97 (d, J=8.5 Hz, 1H), 7.92 (s, 1H), 7.34 (dd, J=8.3, 1.4 Hz, 1H), 7.12 (d, J=3.7 Hz, 1H), 6.89 (br s, 2H), 6.55 (d, J=3.3 Hz, 1H), 4.79-4.89 (m, 3H), 4.28 (br d, J=3.7 Hz, 1H), 3.77 (br s, 1H), 3.17 (d, J=4.1 Hz, 1H), 2.80 (br d, J=6.9 Hz, 2H), 2.45 (br dd, J=6.5, 4.1 Hz, 2H), 2.28 (dd, J=13.6, 10.4 Hz, 1H), 2.07-2.15 (m, 1H), 1.75-1.85 (m, 2H), 1.46-1.56 ppm (m, J=2.0 Hz, 1H)

$^{13}$C NMR (DMSO-d$_6$, 101 MHz): δ=157.4, 151.4, 151.2, 150.0, 138.6, 133.6, 127.1, 122.5, 121.9, 121.4, 102.7, 98.7, 77.4, 75.8, 58.7, 42.6, 42.4, 41.8, 40.3, 34.0, 30.7 ppm Co. No. 22

$^{1}$H NMR (DMSO-d$_6$, 400 MHz): δ=8.02 (s, 1H), 7.43 (d, J=1.2 Hz, 1H), 7.33 (s, 2H), 7.23 (d, J=8.1 Hz, 1H), 7.16 (d, J=3.7 Hz, 1H), 7.00 (dd, J=8.1, 1.6 Hz, 1H), 6.89 (br s, 2H), 6.54 (d, J=3.7 Hz, 1H), 4.70-4.89 (m, 3H), 4.18-4.25 (m, 1H), 3.69 (t, J=4.7 Hz, 1H), 2.66 (br d, J=7.3 Hz, 2H), 2.45 (dt, J=16.0, 8.1 Hz, 1H), 2.33 (dd, J=13.0, 9.8 Hz, 1H), 1.98-2.13 (m, 2H), 1.91 (br dd, J=13.2, 8.3 Hz, 1H), 1.78 (br dd, J=10.6, 9.0 Hz, 1H), 1.67-1.74 ppm (m, 1H)

$^{13}$C NMR (DMSO-d$_6$, 101 MHz): δ=165.7, 157.4, 151.2, 150.9, 149.9, 133.6, 130.9, 125.9, 122.2, 120.3, 117.4, 102.7, 98.6, 78.0, 75.5, 59.4, 42.2, 42.1, 41.3, 38.2, 34.3, 34.2, 30.9 ppm Co. No. 23

$^{1}$H NMR (DMSO-d$_6$, 400 MHz): δ=8.01 (s, 1H), 7.42 (d, J=1.2 Hz, 1H), 7.31 (s, 2H), 7.22 (d, J=8.1 Hz, 1H), 7.11 (d, J=3.3 Hz, 1H), 6.99 (dd, J=8.1, 1.6 Hz, 1H), 6.87 (s, 2H), 6.53 (d, J=3.3 Hz, 1H), 4.74-4.90 (m, 3H), 4.23-4.32 (m, 1H), 3.76 (br s, 1H), 2.65 (br d, J=6.9 Hz, 2H), 2.31-2.46 (m, 2H), 2.27 (dd, J=13.6, 10.4 Hz, 1H), 2.05-2.15 (m, 1H), 1.72-1.83 (m, 2H), 1.39-1.51 ppm (m, 1H)

$^{13}$C NMR (DMSO-d$_6$, 101 MHz): δ=165.7, 157.4, 151.2, 150.9, 150.0, 133.5, 130.9, 125.9, 121.9, 120.3, 117.4, 102.7, 98.7, 77.5, 75.8, 58.7, 42.7, 42.4, 41.7, 40.4, 34.0, 30.8 ppm Co. No. 24

$^{1}$H NMR (DMSO-d$_6$, 400 MHz): δ=8.42 (d, J=6.9 Hz, 1H), 8.01 (s, 1H), 7.84 (s, 1H), 7.49 (s, 1H), 7.30 (s, 1H), 7.16 (d, J=3.3 Hz, 1H), 6.88 (s, 2H), 6.73 (d, J=6.9 Hz, 1H), 6.53 (d, J=3.3 Hz, 1H), 4.71-4.88 (m, 3H), 4.17-4.25 (m, 1H), 3.71 (br t, J=4.3 Hz, 1H), 2.71 (br d, J=7.7 Hz, 2H), 2.52-2.59 (m, 1H), 2.35 (dd, J=13.0, 9.8 Hz, 1H), 2.01-2.17 (m, 2H), 1.92 (dd, J=13.0, 8.5 Hz, 1H), 1.77-1.86 (m, 1H), 1.68-1.77 ppm (m, 1H)

$^{13}$C NMR (DMSO-d$_6$, 101 MHz): δ=157.4, 151.2, 149.8, 144.8, 137.8, 132.8, 126.2, 122.3, 114.6, 113.7, 112.3, 102.7, 98.6, 77.9, 75.5, 59.4, 42.2, 41.6, 41.2, 38.0, 34.1, 29.7 ppm Co. No. 25

$^{1}$H NMR (DMSO-d$_6$, 400 MHz): δ=8.42 (d, J=6.9 Hz, 1H), 8.01 (s, 1H), 7.84 (s, 1H), 7.49 (s, 1H), 7.29 (s, 1H), 7.12 (d, J=3.3 Hz, 1H), 6.88 (s, 2H), 6.73 (d, J=6.9 Hz, 1H), 6.54 (d, J=3.7 Hz, 1H), 4.77-4.89 (m, 3H), 4.24-4.33 (m, 1H), 3.79 (t, J=3.9 Hz, 1H), 3.18 (d, J=4.5 Hz, 1H), 2.70 (br d, J=6.5 Hz, 2H), 2.47 (br d, J=4.1 Hz, 1H), 2.29 (dd, J=13.6, 10.4 Hz, 1H), 2.08-2.19 (m, 1H), 1.74-1.88 (m, 2H), 1.45-1.56 ppm (m, 1H)

$^{13}$C NMR (DMSO-d$_6$, 101 MHz): δ=157.4, 151.2, 150.0, 144.9, 137.8, 132.8, 126.2, 121.9, 114.6, 113.8, 112.3, 102.7, 98.7, 77.4, 75.7, 58.7, 42.6, 41.9, 40.3, 33.9, 29.6 ppm Co. No. 26

$^{1}$H NMR (DMSO-d$_6$, 400 MHz): δ=8.45 (d, J=4.0 Hz, 1H), 8.01 (s, 1H), 7.66 (td, J=7.6, 1.8 Hz, 1H), 7.11-7.23 (m, 3H), 6.87 (br s, 2H), 6.53 (d, J=3.5 Hz, 1H), 4.66-4.88 (m, 3H), 4.14-4.24 (m, 1H), 3.67-3.73 (m, 1H), 3.17 (d, J=3.5 Hz, 1H), 2.81 (d, J=7.7 Hz, 2H), 2.54-2.69 (m, 1H), 2.33 (dd, J=13.0, 9.7 Hz, 1H), 2.10 (dd, J=11.2, 8.8 Hz, 1H), 1.98-2.05 (m, 1H), 1.90 (dd, J=13.0, 8.6 Hz, 1H), 1.81 (br dd, J=10.7, 8.7 Hz, 1H), 1.71 ppm (ddd, J=11.3, 7.9, 3.5 Hz, 1H)

$^{13}$C NMR (DMSO-d$_6$, 101 MHz): δ=160.9, 157.9, 151.7, 150.4, 149.4, 136.7, 123.1, 122.7, 121.6, 103.2, 99.1, 78.4, 76.0, 59.9, 45.1, 42.8, 41.7, 38.6, 34.7, 29.8 ppm Co. No. 27

$^{1}$H NMR (DMSO-d$_6$, 400 MHz): δ=8.45 (d, J=4.0 Hz, 1H), 8.01 (s, 1H), 7.66 (td, J=7.6, 1.8 Hz, 1H), 7.14-7.24 (m, 2H), 7.10 (d, J=3.5 Hz, 1H), 6.86 (s, 2H), 6.53 (d, J=3.5 Hz, 1H), 4.73-4.90 (m, 3H), 4.24-4.33 (m, 1H), 3.77 (t, J=4.0 Hz, 1H), 2.80 (d, J=7.5 Hz, 2H), 2.51-2.60 (m, 1H), 2.43 (tt, J=7.4, 4.0 Hz, 1H), 2.26 (dd, J=13.6, 10.3 Hz, 1H), 2.11 (ddd, J=11.2, 7.6, 4.1 Hz, 1H), 1.73-1.85 (m, 2H), 1.50 ppm (dd, J=11.0, 8.6 Hz, 1H)

$^{13}$C NMR (DMSO-d$_6$, 101 MHz): δ=160.9, 157.9, 151.7, 150.5, 149.4, 136.7, 123.2, 122.4, 121.6, 103.2, 99.2, 77.9, 76.2, 59.3, 55.4, 45.4, 43.1, 42.4, 40.9, 34.4, 29.7 ppm Co. No. 28

$^1$H NMR (DMSO-$d_6$, 400 MHz): δ=8.35-8.46 (m, 2H), 8.00 (s, 1H), 7.58 (dt, J=7.8, 2.0 Hz, 1H), 7.29 (dd, J=7.7, 4.5 Hz, 1H), 7.15 (d, J=3.7 Hz, 1H), 6.87 (s, 2H), 6.52 (d, J=3.3 Hz, 1H), 4.62-4.88 (m, 3H), 4.15-4.28 (m, 1H), 3.68 (t, J=4.7 Hz, 1H), 2.67 (d, J=7.7 Hz, 2H), 2.40-2.49 (m, 1H), 2.32 (dd, J=13.0, 9.8 Hz, 1H), 1.97-2.11 (m, 2H), 1.90 (dd, J=13.0, 8.5 Hz, 1H), 1.79 (dd, J=10.8, 8.7 Hz, 1H), 1.70 ppm (ddd, J=11.5, 8.0, 3.7 Hz, 1H)

$^{13}$C NMR (DMSO-$d_6$, 101 MHz): δ=157.4, 151.2, 149.8, 149.6, 147.1, 136.1, 135.8, 123.4, 122.3, 102.7, 98.6, 77.8, 75.5, 59.5, 42.1, 41.1, 37.9, 34.0, 30.3 ppm Co. No. 29

$^1$H NMR (DMSO-$d_6$, 400 MHz): δ=8.40 (br s, 2H), 8.01 (s, 1H), 7.58 (br d, J=7.7 Hz, 1H), 7.29 (br s, 1H), 7.11 (d, J=3.5 Hz, 1H), 6.86 (br s, 2H), 6.54 (d, J=3.5 Hz, 1H), 4.69-4.92 (m, 3H), 4.16-4.39 (m, 1H), 3.76 (t, J=3.9 Hz, 1H), 2.85-2.87 (m, 1H), 2.67 (br d, J=6.6 Hz, 2H), 2.33-2.46 (m, 2H), 2.26 (dd, J=13.4, 10.3 Hz, 1H), 2.03-2.16 (m, 1H), 1.73-1.84 (m, 2H), 1.42-1.54 ppm (m, 1H)

$^{13}$C NMR (DMSO-$d_6$, 101 MHz): δ=157.9, 151.7, 150.5, 150.0, 147.6, 136.6, 136.3, 123.9, 122.4, 103.2, 99.2, 77.9, 76.2, 59.3, 43.1, 42.2, 40.6, 34.3, 30.7 ppm Co. No. 30

$^1$H NMR (DMSO-$d_6$, 400 MHz): δ=8.02 (s, 1H), 7.74 (dd, J=8.1, 7.3 Hz, 1H), 7.17 (d, J=3.7 Hz, 1H), 7.06 (d, J=7.7 Hz, 1H), 6.88 (s, 2H), 6.81 (d, J=7.7 Hz, 1H), 6.53 (d, J=3.3 Hz, 1H), 4.75-4.88 (m, 3H), 4.21 (d, J=6.9 Hz, 3H), 3.71 (t, J=4.9 Hz, 1H), 2.57-2.71 (m, 1H), 2.37 (dd, J=13.0, 9.8 Hz, 1H), 2.19 (dd, J=11.6, 7.9 Hz, 1H), 2.07-2.15 (m, 1H), 1.96 (dd, J=13.0, 8.5 Hz, 1H), 1.89 (dd, J=11.4, 7.7 Hz, 1H), 1.78 ppm (ddd, J=11.6, 8.7, 2.8 Hz, 1H)

$^{13}$C NMR (DMSO-$d_6$, 101 MHz): δ=163.2, 157.4, 151.2, 149.8, 147.1, 142.0, 122.3, 116.4, 109.4, 102.8, 98.6, 77.8, 75.5, 70.5, 59.4, 42.5, 41.5, 35.1, 30.9, 27.7 ppm Co. No. 31

$^1$H NMR (DMSO-$d_6$, 400 MHz): δ=8.01 (s, 1H), 7.73 (t, J=7.9 Hz, 1H), 7.12 (d, J=3.7 Hz, 1H), 7.05 (d, J=7.7 Hz, 1H), 6.87 (s, 2H), 6.80 (d, J=8.1 Hz, 1H), 6.53 (d, J=3.7 Hz, 1H), 4.78-4.91 (m, 3H), 4.25-4.35 (m, 1H), 4.20 (d, J=6.9 Hz, 2H), 3.81 (s, 1H), 2.59 (dt, J=15.3, 7.4 Hz, 1H), 2.47 (br d, J=3.3 Hz, 1H), 2.28 (dd, J=13.4, 10.2 Hz, 1H), 2.11-2.22 (m, 1H), 1.91 (dd, J=11.4, 8.1 Hz, 1H), 1.83 (dd, J=13.6, 7.5 Hz, 1H), 1.58 ppm (dd, J=11.2, 7.9 Hz, 1H)

$^{13}$C NMR (DMSO-$d_6$, 101 MHz): δ=163.2, 157.4, 151.2, 149.9, 147.1, 142.0, 122.0, 116.4, 109.4, 102.7, 98.6, 77.5, 75.7, 70.6, 58.9, 42.4, 42.1, 36.9, 30.7, 27.7 ppm Co. No. 33

$^1$H NMR (DMSO-$d_6$, 400 MHz): δ=8.31 (s, 1H), 8.00 (s, 1H), 7.56 (d, J=8.1 Hz, 1H), 7.27 (s, 1H), 7.15 (d, J=3.5 Hz, 1H), 7.05 (dd, J=8.1, 1.5 Hz, 1H), 6.86 (br s, 2H), 6.53 (br s, 2H), 6.52 (d, J=3.7 Hz, 1H), 4.77-4.88 (m, 1H), 4.76 (br d, J=6.2 Hz, 1H), 4.72 (br d, J=4.6 Hz, 1H), 4.16-4.26 (m, 1H), 3.69 (t, J=4.6 Hz, 1H), 3.17 (d, J=4.4 Hz, 1H), 2.77 (br d, J=7.3 Hz, 2H), 2.51-2.58 (m, 1H), 2.33 (dd, J=13.0, 9.7 Hz, 1H), 2.11 (dd, J=11.0, 8.8 Hz, 1H), 1.99-2.08 (m, 1H), 1.91 (dd, J=13.2, 8.6 Hz, 1H), 1.78-1.85 (m, 1H), 1.67-1.77 ppm (m 1H)

$^{13}$C NMR (DMSO-$d_6$, 101 MHz): δ=157.9, 154.8, 151.7, 150.4, 147.2, 143.3, 139.5, 127.0, 124.3, 124.1, 122.7, 122.7, 106.1, 103.2, 99.1, 78.4, 76.0, 59.9, 43.1, 42.7, 41.7, 38.7, 34.8, 30.9 ppm Co. No. 34

$^1$H NMR (DMSO-$d_6$, 400 MHz): δ=8.31 (s, 1H), 8.01 (s, 1H), 7.56 (d, J=8.4 Hz, 1H), 7.27 (s, 1H), 7.11 (d, J=3.5 Hz, 1H), 7.05 (dd, J=8.3, 1.4 Hz, 1H), 6.87 (s, 2H), 6.54 (d, J=3.3 Hz, 3H), 4.69-4.96 (m, 3H), 4.22-4.36 (m, 1H), 3.77 (br s, 1H), 2.76 (br d, J=6.6 Hz, 2H), 2.41-2.46 (m, J=5.5 Hz, 1H), 2.28 (dd, J=13.6, 10.3 Hz, 1H), 2.08-2.18 (m, 1H), 1.76-1.87 (m, 2H), 1.43-1.57 ppm (m, 1H)

$^{13}$C NMR (DMSO-$d_6$, 101 MHz): δ=157.9, 154.8, 151.7, 150.5, 147.2, 143.3, 139.5, 127.0, 124.3, 124.1, 122.7, 122.4, 106.1, 103.2, 99.2, 77.9, 76.2, 59.2, 43.3, 43.1, 42.4, 41.0, 34.6, 30.8 ppm Co. No. 35

$^1$H NMR (DMSO-$d_6$, 400 MHz): δ=13.75 (br s, 1H), 9.25 (br s, 1H), 8.58 (br s, 1H), 8.35 (s, 1H), 7.56 (d, J=3.5 Hz, 1H), 7.00 (d, J=3.5 Hz, 1H), 4.93 (br d, J=9.9 Hz, 1H), 4.19 (dd, J=8.4, 4.6 Hz, 1H), 3.64 (d, J=4.4 Hz, 1H), 3.35 (d, J=6.8 Hz, 2H), 2.38 (dd, J=13.4, 9.9 Hz, 1H), 2.23-2.34 (m, 1H), 1.90-2.11 (m, 3H), 1.76 (dd, J=11.2, 7.9 Hz, 1H), 1.64 ppm (ddd, J=11.3, 8.4, 2.8 Hz, 1H)

$^{13}$C NMR (DMSO-$d_6$, 101 MHz): δ=151.3, 147.5, 126.3, 102.5, 102.0, 78.7, 76.3, 66.0, 60.5, 42.4, 42.4, 36.3, 31.5, 31.5 ppm Co. No. 36

$^1$H NMR (DMSO-$d_6$, 400 MHz): δ=13.75 (br s, 1H), 9.29 (br s, 1H), 8.67 (br s, 1H), 8.35 (s, 1H), 7.51 (d, J=3.5 Hz, 1H), 7.01 (d, J=3.5 Hz, 1H), 6.88-7.09 (m, 1H), 4.87-5.00 (m, 1H), 4.28 (dd, J=8.6, 4.2 Hz, 1H), 3.78 (d, J=4.0 Hz, 1H), 3.58 (br s, 2H), 3.33 (d, J=6.2 Hz, 2H), 2.33-2.41 (m, 1H), 2.19-2.32 (m, 2H), 1.99-2.07 (m, 1H), 1.73-1.83 (m, 2H), 1.46 ppm (dd, J=11.3, 7.8 Hz, 1H)

$^{13}$C NMR (DMSO-$d_6$, 101 MHz): δ=151.3, 147.5, 126.1, 102.6, 102.0, 78.2, 76.5, 65.9, 60.2, 43.0, 42.2, 37.6, 31.5, 30.8 ppm Co. No. 44

$^{13}$C NMR (DMSO-$d_6$, 101 MHz): δ=156.4, 153.0, 150.1, 149.6, 146.4, 143.8, 134.4, 129.9, 127.9, 127.8, 127.3, 127.0, 119.8, 87.3, 85.2, 76.6, 73.2, 41.6, 39.1, 34.7, 27.8 ppm.

Co. No. 45

$^1$H NMR (DMSO-$d_6$, 400 MHz): δ=8.84 (d, J=2.8 Hz, 1H), 8.51 (d, J=2.0 Hz, 1H), 8.27 (s, 1H), 8.13 (s, 1H), 7.89 (d, J=8.5 Hz, 1H), 7.82 (s, 1H), 7.52 (dd, J=8.1, 1.6 Hz, 1H), 7.24 (s, 2H), 5.84 (d, J=7.3 Hz, 1H), 5.38 (d, J=6.9 Hz, 1H), 5.34 (d, J=4.5 Hz, 1H), 4.99 (dt, J=6.9, 3.5 Hz, 1H), 3.99 (t, J=4.1 Hz, 1H), 2.91 (br d, J=7.3 Hz, 2H), 2.56-2.67 (m, 1H), 2.30-2.41 (m, 1H), 2.07-2.24 (m, 1H), 1.94 (dd, J=11.0, 9.4 Hz, 1H), 1.78 ppm (dd, J=11.0, 9.8 Hz, 1H).

$^{13}$C NMR (DMSO-$d_6$, 101 MHz): δ=156.0, 152.5, 149.8, 149.1, 145.9, 143.0, 139.8, 133.9, 129.4, 127.2, 126.7, 126.5, 119.3, 86.6, 82.2, 74.5, 72.6, 42.0, 41.1, 35.9, 26.4 ppm.

LCMS (Liquid Chromatography/Mass Spectrometry)

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software. Compounds are described by their experimental retention times ($R_t$) and ions. If not specified differently in the table of data, the reported molecular ion corresponds to the [M+H]$^+$ (protonated molecule) and/or [M−H]$^-$ (deprotonated molecule). In case the compound was not directly ionizable the type of adduct is specified (i.e. [M+NH$_4$]$^+$, [M+HCOO]$^-$, etc. . . . ). For molecules with multiple isotopic patterns (Br, Cl), the reported value is the one obtained for the lowest isotope mass. All results were obtained with experimental uncertainties that are commonly associated with the method used.

Hereinafter, "SQD" means Single Quadrupole Detector, "MSD" Mass Selective Detector, "RT" room temperature, "BEH" bridged ethylsiloxane/silica hybrid, "DAD" Diode Array Detector, "HSS" High Strength silica., "Q-Tof" Quadrupole Time-of-flight mass spectrometers, "CLND", ChemiLuminescent Nitrogen Detector, "ELSD" Evaporative Light Scanning Detector,

TABLE

LCMS Method codes (Flow expressed in mL/min; column temperature (T) in ° C.; Run time in minutes).

| Method code | Instrument | Column | Mobile phase | Gradient | Flow Col T | Run time |
|---|---|---|---|---|---|---|
| 1 | Waters: Acquity ® UPLC ® - DAD and SQD | Waters:HSS T3 (1.8 μm, 2.1*100 mm) | A: 10 mM $CH_3COONH_4$ in 95% $H_2O$ + 5% $CH_3CN$ B: $CH_3CN$ | From 100% A to 5% A in 2.10 min, to 0% A in 0.90 min, to 5% A in 0.5 min | 0.7 55 | 3.5 |
| 2 | Waters: Acquity ® UPLC ® - DAD and SQD | Waters:BEH C18 (1.7 μm, 2.1*50 mm) | A: 10 mM $CH_3COONH_4$ in 95% $H_2O$ + 5% $CH_3CN$ B: $CH_3CN$ | From 95% A to 5% A in 1.3 min, held for 0.7 min. | 0.8 55 | 2 |
| 4 | Waters: Acquity ® UPLC ® - DAD and SQD | Waters:BEH (1.8 μm, 2.1*100 mm) | A: 10 mM $CH_3COONH_4$ in 95% $H_2O$ + 5% $CH_3CN$ B: CH3CN | From 100% A to 5% A in 2.10 min, to 0% A in 0.90 min, to 5% A in 0.5 min | 0.7 55 | 3.5 |
| 5 | Waters: Acquity ® UPLC ® - DAD and SQD | Waters:HSS T3 (1.8 μm, 2.1*100 mm) | A: 10 mM $CH_3COONH_4$ in 95% $H_2O$ + 5% $CH_3CN$ B: CH3CN | From 100% A to 5% A in 2.10 min, to 0% A in 0.90 min, to 5% A in 0.5 min | 0.7 55 | 3.5 |
| 6 | Waters: Acquity ® UPLC ® - DAD and SQD | Waters:BEH (1.8 μm, 2.1*100 mm) | A: 10 mM $CH_3COONH_4$ in 95% $H_2O$ + 5% $CH_3CN$ B: CH3CN | From 100% A to 5% A in 2.10 min, to 0% A in 0.90 min, to 5% A in 0.5 min | 0.7 55 | 3.5 |
| 7 | Waters: Acquity ® UPLC ® - DAD, SQD and ELSD | Waters:HSS T3 (1.8 μm, 2.1*100 mm) | A: 10 mM $CH_3COONH_4$ in 95% $H_2O$ + 5% $CH_3CN$ B: $CH_3CN$ | From 100% A to 5% A in 2.10 min, to 0% A in 0.90 min, to 5% A in 0.5 min | 0.6 55 | 3.5 |

TABLE

LCMS of compounds (Co. No. means compound number; Rt expressed in minutes)

| Co. No. | $R_t$ | $[M + H]^+$ | LCMS method |
|---|---|---|---|
| 1 | / | / | / |
| 2 | 1.16 | 436.3 | 1 |
| 3 | 1.48 | 455.3 | 1 |
| 4 | 1.50 | 499.2 | 1 |
| 5 | 1.10 | 436.3 | 1 |
| 6 | 0.77 | 499.2 | 2 |
| 7 | 0.25 | 294.2 | 2 |
| 8 | 0.25 | 294.2 | 2 |
| 9 | 1.44 | 455.3 | 4 |
| 10 | 1.42 | 455.3 | 4 |
| 11 | 1.37 | 418.2 | 4 |
| 12 | 1.58 | 452.3 | 4 |
| 13 | 1.55 | 452.3 | 4 |
| 14 | 1.70 | 450.3 | 4 |
| 15 | 1.70 | 450.3 | 4 |
| 16 | 1.46 | 422.3 | 4 |
| 17 | 1.49 | 422.3 | 4 |
| 18 | 1.29 | 437.4 | 4 |
| 19 | 1.30 | 437.4 | 4 |
| 20 | 1.44 | 422.4 | 5 |
| 21 | 1.44 | 422.4 | 5 |
| 22 | 1.24 | 437.4 | 4 |
| 23 | 1.24 | 437.3 | 4 |
| 24 | 1.15 | 405.4 | 4 |
| 25 | 1.13 | 405.4 | 4 |
| 26 | 1.20 | 366.3 | 4 |
| 27 | 1.20 | 366.3 | 4 |
| 28 | 1.17 | 366.3 | 4 |
| 29 | 1.17 | 366.3 | 4 |
| 30 | 1.58 | 416.3 | 5 |
| 31 | 1.57 | 416.3 | 5 |
| 32 | 0.59; 0.61 | 416.3 | 2 |
| 33 | 1.57 | 509.3 | 6 |
| 34 | 1.56 | 509.3 | 6 |
| 35 | 0.43 | 305.2 | 2 |
| 36 | 0.40 | 305.2 | 2 |
| 39 | / | / | / |
| 40 | 2.36 | 558.2 | 1 |
| 41 | 2.29 | 602.2 | 1 |
| 42 | 1.11 | 558.2 | 2 |

TABLE-continued

LCMS of compounds (Co. No. means compound number; Rt expressed in minutes)

| Co. No. | R$_t$ | [M + H]$^+$ | LCMS method |
|---|---|---|---|
| 43 | 1.13 | 602.2 | 2 |
| 44 | 1.59 | 453.3 | 7 |
| 45 | 1.63 | 453.3 | 7 |

Experimental Procedures In Vitro Assay

Reagents. PRMT5-MEP50 Oenzyme was purchased from Charles River (Argenta). The enzyme complex was produced in insect cells (Sf9) infected simultaneously with two baculoviruses. One virus expresses full length human PRMT5 with Flag-tag at N-terminus, the second virus expresses full length MEP50 with His6-TEV cleavage at N-terminus. The protein was affinity purified using anti-Flag (M2) beads eluted with 3×FLAG peptide, followed by His-Select eluted with 0.5M imidazole. Eluted protein was then dialysed against tris-buffered saline (TBS) (pH 8.0) containing 20% glycerol and 3mM dithiothreitol (DTT).

Full-length untagged human recombinant histone H2A (residues 1-130, Genbank Accession #NM_021052, MW=14.1 kDa) expressed in *E. coli* was purchased from Reaction Biology Corporation, Cat #HMT-11-146. Reagents used for making reaction buffer or stopping reaction were purchased including Tris base (Sigma Cat #1-1503), NaCl (Sigma Cat #RGF-3270), MgCl$_2$ (Sigma Cat #M0250), DTT (Invitrogen Cat #15508-013) and Formic Acid (Riedel deHaen, Cat #33015)

High Throughput Mass Spectrometer Assay PRMT5 catalyzes the sequential methylations of the terminal nitrogen atoms on the guanidine groups of arginine residues within proteins using co-substrate S-adenosyl-L-methionine (AdoMet, SAM), forming mono-methyl (MMA), symmetric-dimethyl arginine (sDMA) and S-adenosyl-L-homocysteine (AdoHcy, SAH). The enzyme activity was determined by following the product SAH formation using high throughput mass spectrometry (Agilent Rapidfire 300 System coupled to a Sciex 4000 series QTrap® triple-quad MS/MS). The reaction buffer was 20 mM Tris-HCl, pH 8.5, 50 mM NaCl, 5 mM MgCl$_2$ and 1 mM DTT. The reaction activity was stopped using 1% formic acid (final concentration).

Inhibition Studies. The IC$_{50}$ Studies were performed using eleven point dosing series made for each compound by serially diluted 1:2 in dimethyl sulfoxide (DMSO), with point 12 being a DMSO control. Compounds were first spotted to plates, and followed by addition of 2 µM SAM and 0.6 µM H2A (histone H2A) solution mixture. The same volume of enzyme solution was added to initiate the enzymatic reactions. The final concentrations of the reaction are at 1 µM SAM, 0.3 µM H2A and 1.25 nM enzyme. The reaction was incubated at 30° C. for 60 minutes (min) when 10 nM enzyme was used and for 120 min when 1.25 nM enzyme was used. Subsequently, the reaction was quenched by addition of formic acid to a final concentration of 1%. The inhibitions of SAH formation in the presence of compounds were calculated as a percentage of the control relative to the uninhibited reaction as a function of inhibitor concentration. The data were fit as follows:

$$Y=\text{Bottom}+(\text{Top}-\text{Bottom})/(1+10^{((\log IC_{50}-X)*h)})$$

where IC$_{50}$ is the inhibitor concentration (same unit as X) at 50% inhibition and h is the Hill slope. Y is percent of inhibition, X is log of compound concentration. Bottom and Top are the plateaus in same units as Y.

The pIC$_{50}$ values in the Table below are averaged values (Co. No. means compound number; n.d. means not determined)

| Co. No. | pIC$_{50}$ | Co. No. | pIC$_{50}$ | Co. No. | pIC$_{50}$ |
|---|---|---|---|---|---|
| 8 | 5.45 | 11 | 7.04 | 18 | 7.45 |
| 7 | 5.30 | 15 | 5.96 | 26 | 5.61 |
| 1 | 5.52 | 14 | 5.70 | 27 | 5.25 |
| 4 | 5.52 | 16 | 6.31 | 10 | n.d. |
| 2 | 7.51 | 17 | 6.41 | 9 | 6.59 |
| 5 | 8.03 | 35 | 6.03 | 22 | 5.80 |
| 6 | 6.92 | 36 | 5.85 | 23 | 6.53 |
| 3 | 5.09 | 19 | 6.88 | 20 | 6.31 |
| 21 | 6.84 | 33 | 6.61 | 42 | n.d. |
| 31 | 5.46 | 29 | 6.77 | 43 | n.d. |
| 30 | 5.79 | 28 | 6.84 | 39 | n.d. |
| 32 | 5.69 | 25 | 7.99 | 45 | 5.26 |
| 12 | 5.62 | 24 | 8.04 | 44 | 5.34 |
| 13 | 6.19 | 40 | n.d. | | |
| 34 | n.d. | 41 | n.d. | | |

Composition Examples

"Active ingredient" (a.i.) as used throughout these examples relates to compounds of Formula (I), and pharmaceutically acceptable addition salts, and solvates thereof; in particular to any one of the exemplified compounds.

Typical examples of recipes for the formulation of the invention are as follows:

1. Tablets

| | |
|---|---|
| Active ingredient | 5 to 50 mg |
| Di-calcium phosphate | 20 mg |
| Lactose | 30 mg |
| Talcum | 10 mg |
| Magnesium stearate | 5 mg |
| Potato starch | ad 200 mg |

2. Suspension

An aqueous suspension is prepared for oral administration so that each milliliter contains 1 to 5 mg of active ingredient, 50 mg of sodium carboxymethyl cellulose, 1 mg of sodium benzoate, 500 mg of sorbitol and water ad 1 ml.

3. Injectable

A parenteral composition is prepared by stirring 1.5% (weight/volume) of active ingredient in 0.9% NaCl solution or in 10% by volume propylene glycol in water.

4. Ointment

| | |
|---|---|
| Active ingredient | 5 to 1000 mg |
| Stearyl alcohol | 3 g |
| Lanoline | 5 g |
| White petroleum | 15 g |
| Water | ad 100 g |

In this Example, active ingredient can be replaced with the same amount of any of the compounds according to the present invention, in particular by the same amount of any of the exemplified compounds.

The invention claimed is:
1. A compound of Formula (I)

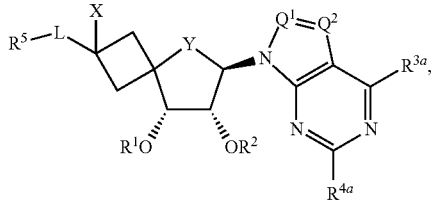 (I)

wherein
R$^1$ represents hydrogen or —C(=O)—C$_{1-4}$alkyl;
R$^2$ represents hydrogen or —C(=O)—C$_{1-4}$ alkyl;
X represents hydrogen;
Y represents —O—, —CH$_2$— or —CF$_2$—;
Q$^1$ represents CR$^{6a}$;
Q$^2$ represents N or CR$^{6b}$;
R$^{6a}$ and R$^{6b}$ each independently represent hydrogen, halogen, C$_{1-4}$ alkyl, —NR$^{9a}$R$^{9b}$, or C$_{1-4}$ alkyl substituted with one, two or three halo atoms;
R$^{9a}$ and R$^{9b}$ each independently represent hydrogen or C$_{1-4}$ alkyl;
R$^{3a}$ represents hydrogen, halo, —NR$^{7a}$R$^{7b}$, C$_{1-4}$ alkyl, C$_{2-4}$alkenyl, C$_{3-6}$ cycloalkyl, —OH, or —O—C$_{1-4}$ alkyl;
R$^{7a}$ represents hydrogen;
R$^{7b}$ represents hydrogen, C$_{3-6}$ cycloalkyl, or C$_{1-4}$ alkyl;
R$^{4a}$ represents hydrogen, halo, —NR$^{8a}$R$^{8b}$, or C$_{1-4}$ alkyl;
L represents —CH$_2$—, —O—CH$_2$—, —CH$_2$—O—, or —O—;
R$^5$ represents Ar or Het; and in case L represents —O— or —O—CH$_2$—, R$^5$ can also represent hydrogen;
Ar represents phenyl optionally substituted with one or more halo substituents; and
Het represents a monocyclic or bicyclic ring system selected from the group consisting of (a-1), (a-2), (a-3), (a-4), (a-5), (a-6) and (a-7):

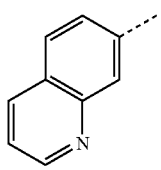 (a-1)

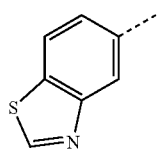 (a-2)

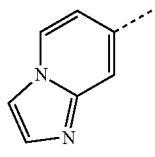 (a-3)

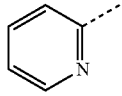 (a-4)

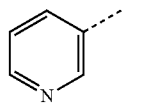 (a-5)

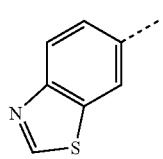 (a-6)

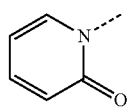 (a-7)

wherein said monocyclic or bicyclic aromatic ring system is optionally substituted with one or more substituents each independently selected from the group consisting of halo and —NH$_2$;
or a pharmaceutically acceptable addition salt or a solvate thereof.

2. The compound according to claim 1, wherein
Y represents —O— or —CH$_2$—;
R$^{6a}$ and R$^{6b}$ represent hydrogen;
R$^{3a}$ represents halo or —NR$^{7a}$R$^{7b}$;
R$^{7b}$ represents hydrogen;
R$^{4a}$ represents hydrogen;
R$^5$ represents Ar or Het; and in case L represents —O— or —O—CH$_2$—, R$^5$ can also represent hydrogen; and
Ar represents phenyl.

3. The compound according to claim 1, wherein
R$^1$ represents hydrogen;
R$^2$ represents hydrogen;
Y represents —O—;
Q$^2$ represents N;
R$^{6a}$ represents hydrogen;
R$^{3a}$ represents —NR$^{7a}$R$^{7b}$;
R$^{7b}$ represents hydrogen;
R$^{4a}$ represents hydrogen;
L represents —O—;
R$^5$ represents Het; and
Het represents (a-1), optionally substituted with one or more substituents each independently selected from the group consisting of halo and —NH$_2$.

4. The compound according to claim 1, wherein R$^1$ and R$^2$ represent hydrogen.

5. The compound according to claim 1, wherein R$^1$ represents —C(=O)—C$_{1-4}$ alkyl; and R$^2$ represents —C(=O)—C$_{1-4}$ alkyl.

6. The compound according to claim 1, wherein Y represents —O—.

7. The compound according to claim 1, wherein Y represents —CH$_2$— or —CF$_2$—.

8. The compound according to claim 1, wherein R$^5$ represents Het.

9. The compound according to claim 1, wherein R$^{3a}$ represents halo or —NR$^{7a}$R$^{7b}$.

10. The compound according to claim 1, wherein R$^{3a}$ represents —NR$^{7a}$R$^{7b}$; and R$^{7a}$ and R$^{7b}$ represent hydrogen.

11. The compound according to claim 1, wherein Q$^2$ represents N.

12. A pharmaceutical composition comprising a pharmaceutically acceptable carrier and, as active ingredient, a therapeutically effective amount of a compound according to claim 1.

13. A method of treating a disease or condition selected from a blood disorder, metabolic disorders, autoimmune disorders, cancer, inflammatory diseases, cardiovascular diseases, neurodegenerative diseases, pancreatitis, multiorgan failure, kidney diseases, platelet aggregation, sperm motility, transplantation rejection, graft rejection, and lung injuries: comprising administering to a subject a compound of claim 1 or a pharmaceutically acceptable salt thereof.

14. The method according to claim 13 wherein the disease or condition is cancer.

15. A compound of Formula (XXX)

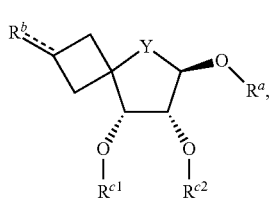

(XXX)

wherein
Y represents —O—, —CH$_2$— or —CF$_2$—;
R$^a$ represents hydrogen or a hydroxyl protecting group;
R$^b$ represents —OH, =O, —CH$_2$—OH, or =CH$_2$;
wherein the bond towards R$^b$ represents a single bond in case R$^b$ represents —OH or —CH$_2$—OH, or a double bond in case R$^b$ represents =O or =CH$_2$;
R$^{c1}$ and R$^{c2}$ represent —C(=O)—C$_{1-4}$ alkyl, benzoyl optionally substituted with one or two substituents each independently selected from —CH$_3$ and —OCH$_3$, benzyl optionally substituted with one or two substituents each independently selected from —CH$_3$ and —OCH$_3$, or —CH$_2$—napthyl optionally substituted with one or two substituents each independently selected from —CH$_3$ and —OCH$_3$;
or R$^{c1}$ and R$^{c2}$ taken together represent —C(C$_{1-4}$ alkyl)$_2$-;
or a pharmaceutically acceptable addition salt or a solvate thereof.

16. The compound of claim 15, wherein the hydroxyl protecting group is C$_{1-4}$ alkyl, t-butyldimethylsilyl, C$_{1-4}$ alkyl—O—C$_{1-4}$ alkyl, tetrahydropyranyl, allyl, t-butyldiphenylsilyl, benzyl, —C(=O)—C$_{1-4}$ alkyl, or —C(=O)—phenyl.

17. A method of making a compound of Formula I of claim 1, comprising contacting a compound of Formula XXX with a suitable acid;
wherein the compound of Formula XXX has the structure

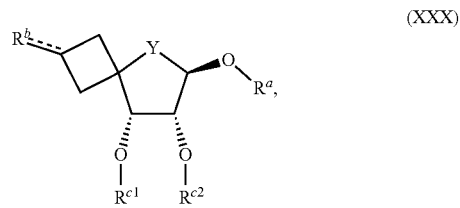

(XXX)

wherein
Y represents —O—, —CH$_2$— or —CF$_2$—;
R$^a$ represents hydrogen or a hydroxyl protecting group;
R$^b$ represents —OH, =O, —CH$_2$—OH, or =CH$_2$;
wherein the bond towards R$^b$ represents a single bond in case R$^b$ represents —OH or —CH$_2$—OH, or a double bond in case R$^b$ represents =O or =CH$_2$;
R$^{c1}$ and R$^{c2}$ represent —C(=O)—C$_{1-4}$ alkyl, benzoyl optionally substituted with one or two substituents each independently selected from —CH$_3$ and —OCH$_3$, benzyl optionally substituted with one or two substituents each independently selected from —CH$_3$ and —OCH$_3$, or —CH$_2$—napthyl optionally substituted with one or two substituents each independently selected from —CH$_3$ and —OCH$_3$;
or R$^{c1}$ and R$^{c2}$ taken together represent —C(C$_{1-4}$ alkyl)$_2$-;
or a pharmaceutically acceptable addition salt or a solvate thereof.

18. The method of claim 17, comprising contacting the compound of Formula XXX with an acid anhydride after contacting with the suitable acid.

19. The method of claim 18, wherein the acid anhydride has the formula (C$_{1-4}$ alkylC=O)$_2$O.

20. The method of claim 17, wherein the suitable acid is HCl.

21. The method of claim 17, wherein the hydroxyl protecting group is C$_{1-4}$ alkyl, t-butyldimethylsilyl, C$_{1-4}$ alkyl—O—C$_{1-4}$ alkyl, tetrahydropyranyl, allyl, t-butyldiphenylsilyl, benzyl, —C(=O)—C$_{1-4}$ alkyl, or —C(=O)—phenyl.

* * * * *